United States Patent
Cheung et al.

(10) Patent No.: US 9,545,404 B2
(45) Date of Patent: *Jan. 17, 2017

(54) 1,4-DISUBSTITUTED PYRIDAZINE ANALOGS THERE OF AND METHODS FOR TREATING SMN-DEFICIENCY-RELATED CONDITIONS

(71) Applicant: NOVARTIS AG, Basel (CH)

(72) Inventors: Atwood Kim Cheung, Arlington, MA (US); Donovan Noel Chin, Lexington, MA (US); Natalie Dales, Arlington, MA (US); Aleem Fazal, Burlington, MA (US); Timothy Hurley, Boston, MA (US); John Kerrigan, Wakefield, MA (US); Gary O'Brien, Maynard, MA (US); Lei Shu, Woburn, MA (US); Robert Sun, Natick, MA (US); Moo Je Sung, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/242,282

(22) Filed: Apr. 1, 2014

(65) Prior Publication Data

US 2014/0213570 A1    Jul. 31, 2014

Related U.S. Application Data

(63) Continuation of application No. 13/960,917, filed on Aug. 7, 2013, now Pat. No. 8,729,263.

(60) Provisional application No. 61/682,448, filed on Aug. 13, 2012.

(51) Int. Cl.

| | |
|---|---|
| C07D 401/12 | (2006.01) |
| C07D 401/14 | (2006.01) |
| C07D 413/14 | (2006.01) |
| C07D 471/04 | (2006.01) |
| C07D 471/10 | (2006.01) |
| C07D 487/04 | (2006.01) |
| A61K 31/551 | (2006.01) |
| A61K 31/5377 | (2006.01) |
| A61K 31/501 | (2006.01) |
| A61K 31/502 | (2006.01) |
| A61K 31/506 | (2006.01) |
| A61K 45/06 | (2006.01) |
| C07D 237/20 | (2006.01) |
| C07D 401/04 | (2006.01) |
| C07D 403/10 | (2006.01) |
| C07D 403/12 | (2006.01) |
| C07D 403/14 | (2006.01) |
| C07D 405/14 | (2006.01) |
| C07D 409/14 | (2006.01) |
| C07D 417/14 | (2006.01) |
| C07D 471/08 | (2006.01) |
| C07D 487/10 | (2006.01) |

(52) U.S. Cl.
CPC ........... *A61K 31/501* (2013.01); *A61K 31/502* (2013.01); *A61K 31/506* (2013.01); *A61K 31/5377* (2013.01); *A61K 31/551* (2013.01); *A61K 45/06* (2013.01); *C07D 237/20* (2013.01); *C07D 401/04* (2013.01); *C07D 401/12* (2013.01); *C07D 401/14* (2013.01); *C07D 403/10* (2013.01); *C07D 403/12* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 471/08* (2013.01); *C07D 471/10* (2013.01); *C07D 487/04* (2013.01); *C07D 487/10* (2013.01)

(58) Field of Classification Search
None
See application file for complete search history.

(56) References Cited

U.S. PATENT DOCUMENTS

| | | | |
|---|---|---|---|
| 8,729,263 B2 * | 5/2014 | Cheung | A61K 31/501 540/575 |
| 2008/0247964 A1 | 10/2008 | Xu et al. | |
| 2008/0275048 A1 * | 11/2008 | Frost | A61K 31/4178 514/242 |
| 2010/0267721 A1 | 10/2010 | Hohlweg et al. | |
| 2010/0305089 A1 | 12/2010 | Ji et al. | |
| 2012/0232078 A1 | 9/2012 | Hohlweg et al. | |

(Continued)

FOREIGN PATENT DOCUMENTS

| | | |
|---|---|---|
| WO | 2004014370 A2 | 2/2004 |
| WO | 2004014881 A2 | 2/2004 |

(Continued)

OTHER PUBLICATIONS

Xiao et al. J Med Chem. Sep. 22, 2011; 54(18): 6215-6233.*
Wadman et al. Drug treatment for spinal muscular atrophy types II and III (Review) from the Cochrane Collaboration Issue 4,p. 1-53 Published by JohnWiley & Sons, Ltd. (2012).*
Wadman et al. Drug treatment for spinal muscular atrophy type I (Review) from The Cochran Collaboration Issue 12, p. 1-22 Published by JohnWiley & Sons, Ltd. (2011).*

(Continued)

*Primary Examiner* — Emily Bernhardt
(74) *Attorney, Agent, or Firm* — Joshua Roth

(57) ABSTRACT

The present invention provides a compound of formula I or a pharmaceutically acceptable salt thereof;

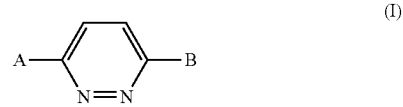

(I)

a method for manufacturing the compounds of the invention, and its therapeutic uses. The present invention further provides a combination of pharmacologically active agents and a pharmaceutical composition.

10 Claims, No Drawings

(56) References Cited

U.S. PATENT DOCUMENTS

2013/0096160 A1    4/2013    Marugan et al.
2013/0143862 A1    6/2013    Ashcraft et al.

FOREIGN PATENT DOCUMENTS

| | | |
|---|---|---|
| WO | 2004014902 A2 | 2/2004 |
| WO | 2004043960 A1 | 5/2004 |
| WO | 2004110351 A2 | 12/2004 |
| WO | 2005077368 A2 | 8/2005 |
| WO | 2005077373 A2 | 8/2005 |
| WO | 2006034341 A2 | 3/2006 |
| WO | 2006044860 A2 | 4/2006 |
| WO | 2008107677 A2 | 9/2008 |
| WO | 2011107530 A2 | 9/2011 |

OTHER PUBLICATIONS

Akio Ohsawa et al., "Cross-Coupling Reaction of Chloropyridazines and Grignard Reagents with Nickel-phosphine Complexes: Alkylation and Arylation of Pyridazines," Chemical and Pharmaceutical Bulletin 26(8):2550-2554 (1978).

Database Registry, Chemical Abstracts Service, Columbus, Ohio, US XP002716119, Database Accession No. 1330184-80-9 Abstract, (2011).

Database Registry, Chemical Abstracts Service, Columbus, Ohio, US Petrenko et al., "Effect of an intramolecular hydrogen bond on the rate of nucleophilic substituion in a series of haloazines," XP002716255, Database Accession No. 1981:191211 abstract Compound with the Registry No. 77585-98-9.

\* cited by examiner

1,4-DISUBSTITUTED PYRIDAZINE ANALOGS THERE OF AND METHODS FOR TREATING SMN-DEFICIENCY-RELATED CONDITIONS

BACKGROUND OF THE INVENTION

Proximal spinal muscular atrophy (SMA) is an inherited, clinically heterogeneous group of neuromuscular disorders characterized by degeneration of the anterior horn cells of the spinal cord. Patients suffer from symmetrical weakness of trunk and limb muscles, the legs being more affected than the arms and the proximal muscles weaker than the distal ones; diaphragm, facial and ocular muscles are spared. There are three forms of childhood-onset SMA (types I, II and III), and a relatively recently categorized adult-onset form IV, all of which can be distinguished on the basis of age of onset and severity of the clinical course assessed by clinical examination, muscle biopsy and electromyography (EMG)(Munsat T L, Davies K E (1992)).

Type I (Werdnig-Hoffmann disease) is the most acute and severe form, with onset before six months and death usually before two years; children are never able to sit without support. Symptoms of the disease can be present in utero, as reduction of fetal movements; at birth; or more often, within the first four months of life. Affected children are particularly floppy, experience feeding difficulties and diaphragmatic breathing, and are characterized by a general weakness in the intercostals and accessory respiratory muscles. Affected children never sit or stand and usually die before the age of 2; death is generally due to respiratory insufficiency.

Type II (intermediate, chronic form) has onset between six and eighteen months of age; muscular fasciculations are common, and tendon reflexes progressively reduce. Children are unable to stand or walk without aid. Feeding and swallowing problems are not usually present in Type II SMA, although in some patients a feeding tube may become necessary. Most patients generally develop a progressive muscular scoliosis which can require surgical correction. Like patients with type I disease, clearing of tracheal secretions and coughing might become difficult because of poor bulbar function and weak intercostal muscles. These patients have profound hypotonia, symmetrical flaccid paralysis, and no control of head movement.

Type III (Kugelberg-Welander disease, or Juvenile Spinal Muscular Atrophy) is a mild, chronic form, with onset after the age of 18 months; motor milestones achievement is normal, and deambulation can be preserved until variable ages. These patients often develop scoliosis, and symptoms of joint overuse, generally caused by weakness, are frequently seen. Life expectancy is almost normal but quality of life is markedly compromised.

Types I, II and III progress over time, accompanied by deterioration of the patient's condition.

Adult-onset type IV is characterized by weakness in the second or third decade of life, with mild motor impairment not accompanied by respiratory or nutritional problems. Adult SMA is characterized by insidious onset and very slow progression. The bulbar muscles are rarely affected in Type IV. It is not clear that Type IV SMA is etiologically related to the Type I-III forms.

Other forms of spinal muscular atrophy include X-linked disease, spinal muscular atrophy with respiratory distress (SMARD), spinal and bulbar muscular atrophy (Kennedy's disease, or Bulbo-Spinal Muscular Atrophy), and distal spinal muscular atrophy.

SMA is due to mutations in the Survival of Motor Neuron (SMN) gene, which exists in two forms in humans (SMN1 and SMN2). Loss of SMN is deleterious to motor neurons and results in neuromuscular insufficiency, a hallmark of the disease. From a genetic point of view, SMA is an autosomal recessive condition, caused by disruption of SMN1 gene, located in 5q13 (Lefebvre S., et al. (1995) Cell 80: 155-165). More than 98% of patients with spinal muscular atrophy have a homozygous disruption of SMN1 by deletion, rearrangement, or mutation. All these patients, however, retain at least one copy of SMN2.

At the genomic level, only five nucleotides have been found that differentiate the SMN1 gene from the SMN2 gene. Furthermore, the two genes produce identical mRNAs, except for a silent nucleotide change in exon 7, i.e., a C→T change six base pairs inside exon 7 in SMN2. This mutation modulates the activity of an exon splicing enhancer (Lorson and Androphy (2000) Hum. Mol. Genet. 9:259-265). The result of this and the other nucleotide changes in the intronic and promoter regions is that most SMN2 are alternatively spliced, and their transcripts lack exons 3, 5, or 7. In contrast, the mRNA transcribed from the SMN1 gene is generally a full-length mRNA with only a small fraction of its transcripts spliced to remove exon 3, 5, or 7 (Gennarelli et al. (1995) Biochem. Biophys. Res. Commun. 213:342-348; Jong et al. (2000) J. Neurol. Sci. 173:147-153). All SMA subjects have at least one, and generally two to four copies of the SMN2 gene, which encodes the same protein as SMN1; however, the SMN2 gene produces only low levels of full-length SMN protein.

The SMNΔ7 protein is non-functional and thought to be rapidly degraded. About 10% of SMN2 pre-mRNA is properly spliced and subsequently translated into full length SMN protein (FL-SMN), and the rest being the SMNΔ7 copy. The efficiency of SMN2 splicing might be dependent on severity of disease, and production of a full length transcript of SMN2 could range from 10% to 50%. Furthermore, presence or absence of the SMN1 gene, roughly 90% of which becomes the FL-SMN gene product and protein, influences the severity of SMA by whether or not it can compensate for the truncated SMNΔ7 copies. A low level of SMN protein allows embryonic development, but is not sufficient to sustain the survival of motor neurons of the spinal cord.

The clinical severity of SMA patients inversely correlates with the number of SMN2 genes and with the level of functional SMN protein produced (Lorson C L, et al. (1999) PNAS; 96:6307-6311) (Vitali T. et al. (1999) Hum Mol Genet; 8:2525-2532)(Brahe C. (2000) Neuromusc. Disord.; 10:274-275)(Feldkotter M, et al. (2002) Am J Hum Genet; 70:358-368)(Lefebvre S, et al. (1997) Nature Genet; 16:265-269)(Coovert D D, et al. (1997) Hum Mol Genet; 6:1205-1214)(Patrizi A L, et al. (1999) Eur J Hum Genet; 7:301-309).

Current therapeutic strategies for SMA are mostly centered on elevating full length (wild type) SMN protein levels, modulating splicing towards exon 7 inclusion, stabilizing the wild type protein, and to a lesser extent, on restoring muscle function in SMA by providing trophic support or by inhibiting skeletal muscle atrophy.

The mechanism leading to motorneuron loss and to muscular atrophy still remains obscure, although the availability of animal models of the disease is rapidly increasing knowledge in this field (Frugier T, et al. (2000) Hum Mol. Genet. 9:849-58; Monani U R, et al. (2000) Hum Mol Genet 9:333-9; Hsieh-Li H M, et al. (2000) Nat Genet 24:66-70; Jablonka S, et al. (2000) Hum Mol. Genet. 9:341-6). Also the function of SMN protein is still partially unknown, and studies indicate that it can be involved in mRNA metabolism (Meister G, et al. (2002). Trends Cell Biol. 12:472-8; Pellizzoni L, et al. (2002). Science. 298: 1775-9), and probably in transport of proteins/mRNA to neuromuscular junctions (Ci-fuentes-Diaz C, et al. (2002) Hum Mol. Genet. 11: 1439-47; Chan Y B, et al. (2003) Hum Mol. Genet. 12:1367-76; McWhorter M L, et al. (2003) J. Cell Biol. 162:919-31; Rossoll W, et al. (2003) J. Cell Biol. 163:801-812).

In addition to the SMAs, a subclass of neurogenic-type arthrogryposis multiplex congenita (congenital AMC) has separately been reported to involve SMN1 gene deletion, suggesting that some degree of pathology in those afflicted is likely due to low levels of motor neuron SMN. (L. Burgien et al., (1996) J. Clin. Invest. 98(5):1130-32. Congenital AMC affects humans and animals, e.g., horses, cattle, sheep, goats, pigs, dogs, and cats. (M. Longeri et al., (2003) Genet. Sel. Evol. 35:S167-S175). Also, the risk of development or the severity of amyotrophic lateral sclerosis (ALS) has been found to be correlated with low levels of motor neuron SMN.

There is no cure for SMA available to date and therefore it would be advantageous to provide novel methods for modulating SMN in order to treat those afflicted with SMA, with neurogenic congenital AMC, ALS, or with other SMN-deficiency-related conditions. It would further be advantageous to provide novel drug targets that could be used as a basis for developing effective therapeutics or diagnostics for such neuronal conditions.

SUMMARY OF THE INVENTION

There remains a need for new treatments and therapies for Spinal Muscular Atrophy. The invention provides compounds, salts thereof, pharmaceutical formulations thereof and combinations thereof which compounds are Spinal uscular Atrophy modulators. The invention further provides methods of treating, preventing, or ameliorating Spinal Muscular Atrophy, comprising administering to a subject in need thereof an effective amount of an SMN modulator (e.g., a compound of the invention).

Various embodiments of the invention are described herein. It will be recognized that features specified in each embodiment may be combined with other specified features to provide further embodiments.

Within certain aspects, SMN modulators provided herein are compounds of Formula I and salts thereof:

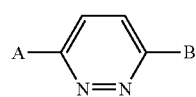

(I)

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more therapeutically active.

One embodiment of the invention is to provide a method for treating, preventing, or ameliorating an SMN-deficiency-related condition, comprising administering to a subject in need thereof an effective amount of an SMN modulator, or a pharmaceutical composition comprising the same.

Another embodiment of the invention is a method of modulating SMN protein through the administration of an SMN modulator. In another embodiment, said SMN modulator is capable of increasing one or more of FL-SMN or SMNΔ7 levels. In still another embodiment, said SMN modulator is capable of preventing exon 7 from being spliced from the SMN transcript.

The present invention is based on the discovery that the SMN modulators of the invention (e.g., compounds of formula (I) and/or compounds of formula (I-A) are capable of modulating SMN proteins, e.g., through SMN promoter activation, splicing modulation (e.g., preventing exon7 from being spliced out of the SMN gene), and/or SMN protein stability modulation.

DETAILED DESCRIPTION OF THE INVENTION

As noted above, the present invention provides compounds that modulate SMN activity. Such compounds may be used in vitro or in vivo to modulate (preferably increase) SMN production and activity in a variety of contexts.

In a first embodiment, the invention provides compounds of Formula I and pharmaceutically acceptable salts thereof, which modulate SMN activity. Compounds of Formula I are represented by the structure:

In a first embodiment, the invention provides compounds, or salts thereof (preferably pharmaceutically acceptable salts thereof) according to Formula (I).

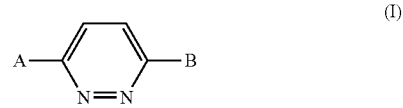

(I)

A is 2-hydroxy-phenyl which is substituted with 0, 1, 2, or 3 substituents independently selected from $C_1$-$C_4$alkyl, wherein 2 $C_1$-$C_4$alkyl groups can combine with the atoms to which they are bound to form a 5-6 membered ring and is substituted with 0 or 1 substituents selected from oxo, oxime and hydroxy, halo$C_1$-$C_4$alkyl, dihalo$C_1$-$C_4$alkyl, trihalo$C_1$-$C_4$alkyl, $C_1$-$C_4$alkoxy, $C_1$-$C_4$alkoxy-$C_3$-$C_7$cycloalkyl, halo$C_1$-$C_4$alkoxy, dihalo$C_1$-$C_4$alkoxy, trihalo$C_1$-$C_4$alkoxy, hydroxy, cyano, halogen, amino, mono- and di-$C_1$-$C_4$alkylamino, heteroaryl, $C_1$-$C_4$alkyl substituted with hydroxy, $C_1$-$C_4$alkoxy substituted with aryl, amino, —C(O)NH $C_1$-$C_4$alkyl-heteroaryl, —NHC(O)—$C_1$-$C_4$alkyl-heteroaryl, $C_1$-$C_4$alkyl C(O)NH— heteroaryl, $C_1$-$C_4$alkyl NHC(O)-heteroaryl, 3-7 membered cycloalkyl, 5-7 membered cycloalkenyl or 5, 6 or 9 membered heterocycle containing 1 or 2 heteroatoms, independently, selected from S, O and N, wherein heteroaryl has 5, 6 or 9 ring atoms, 1, 2 or 3 ring heteroatoms selected from N, O and S and substituted with 0, 1, or 2 substituents independently selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, trihalo$C_1$-$C_4$alkyl, mono- and di-$C_1$-$C_4$alkylamino, —C(O)NH$_2$, —NH$_2$, —NO$_2$, hydroxy$C_1$-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl; or A is 2-naphthyl optionally substituted at the 3 position with hydroxy and additionally substituted with 0, 1, or 2 substituents selected from hydroxy, cyano, halogen, $C_1$-$C_4$alkyl, $C_2$-$C_4$alkenyl, $C_1$-$C_5$alkoxy, wherein the alkoxy is unsubstituted or substituted with hydroxy, $C_1$-$C_4$alkoxy, amino, $N(H)C(O)C_1$-$C_4$alkyl, $N(H)C(O)_2$ $C_1$-$C_4$alkyl, alkylene 4 to 7 member heterocycle, 4 to 7 member heterocycle and mono- and di-$C_1$-$C_4$alkylamino; or A is 6 member heteroaryl having 1-3 ring nitrogen atoms, which 6 member heteroaryl is substituted by phenyl or a heteroaryl having 5 or 6 ring atoms, 1 or 2 ring heteroatoms independently selected from N, O and S and substituted with 0, 1, or 2 substituents independently selected from $C_1$-$C_4$alkyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl; or A is bicyclic heteroaryl having 9 to 10 ring atoms and 1, 2, or 3 ring heteroatoms independently selected from N, O or S, which bicyclic heteroaryl is substituted with 0, 1, or 2 substituents independently selected from cyano, halogen, hydroxy, $C_1$-$C_4$alkyl, $C_2$-$C_4$alkenyl, $C_2$-$C_4$alkynyl, $C_1$-$C_4$alkoxy and $C_1$-$C_4$alkoxy substituted with hydroxy, $C_1$-$C_4$alkoxy, amino and mono- and di-$C_1$-$C_4$alkylamino; or A is tricyclic heteroaryl having 12 or 13 ring atoms and 1, 2, or 3 ring heteroatoms independently selected from N, O or S, which tricyclic heteroaryl is substituted with 0, 1, or 2 substituents independently selected from cyano, halogen, hydroxy, $C_1$-$C_4$alkyl, $C_2$-$C_4$alkenyl, $C_2$-$C_4$alkynyl, $C_1$-$C_4$alkoxy, $C_1$-$C_4$alkoxy substituted with hydroxy, $C_1$-$C_4$alkoxy, amino, mono- and di-$C_1$-$C_4$alkylamino and heteroaryl, wherein said heteroaryl has 5, 6 or 9 ring atoms, 1, 2 or 3 ring heteroatoms selected from N, O and S and substituted with 0, 1, or 2 substituents independently selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, trihalo$C_1$-$C_4$alkyl, mono- and di-$C_1$-$C_4$alkylamino, —$C(O)NH_2$, —$NH_2$, —$NO_2$, hydroxy$C_1$-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl; B is a group of the formula:

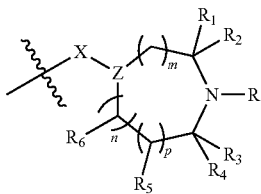

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$akylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_B$, O, $NR_7$ or a bond; $R_7$ is hydrogen, or $C_1$-$C_4$alkyl; $R_A$ and $R_B$ are independently selected from hydrogen and $C_1$-$C_4$alkyl, or $R_A$ and $R_B$, taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

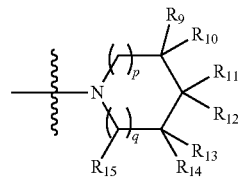

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$akylamino and $C_1$-$C_4$alkyl, which alkyl is optionally substituted with hydroxy, amino or mono- and di-$C_1$-$C_4$akylamino; $R_{11}$ is hydrogen, $C_1$-$C_4$alkyl, amino or mono- and di-$C_1$-$C_4$akylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a second embodiment, the invention is a compound according to the first embodiment, or a salt thereof, wherein A is 6 member heteroaryl having 1-3 ring nitrogen atoms, which 6 member heteroaryl is substituted by phenyl or a heteroaryl having 5 or 6 ring atoms, 1 or 2 ring heteroatoms independently selected from N, O and S and substituted with 0, 1, or 2 substituents independently selected from $C_1$-$C_4$alkyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl; or A is bicyclic heteroaryl having 9 to 10 ring atoms and 1, 2, or 3 ring heteroatoms independently selected from N, O or S, which heteroaryl is substituted with 0, 1, or 2 substituents independently selected from cyano, halogen, hydroxy, $C_1$-$C_4$alkyl, $C_2$-$C_4$alkenyl, $C_2$-$C_4$alkynyl, $C_1$-$C_4$alkoxy and $C_1$-$C_4$alkoxy substituted with hydroxy, $C_1$-$C_4$alkoxy, amino and mono- and di-$C_1$-$C_4$alkylamino.

In a third embodiment, the invention is a compound according to the first embodiment, or a salt thereof, wherein A is 2-hydroxy-phenyl which is substituted with 0, 1, 2, or 3 substituents independently selected from $C_1$-$C_4$alkyl, halo$C_1$-$C_4$alkyl $C_1$-$C_4$alkoxy, hydroxy, cyano, halogen, amino, mono- and di-$C_1$-$C_4$alkylamino, heteroaryl and $C_1$-$C_4$alkyl substituted with hydroxy or amino, which heteroaryl has 5 or 6 ring atoms, 1 or 2 ring heteroatoms selected from N, O and S and substituted with 0, 1, or 2 substituents independently selected from $C_1$-$C_4$alkyl, mono- and di-$C_1$-$C_4$alkylamino, hydroxy$C_1$-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl.

In a fourth embodiment, the invention is a compound according to the first embodiment, or a salt thereof, wherein A is 2-naphthyl optionally substituted at the 3 position with hydroxy and additionally substituted with 0, 1, or 2 substituents selected from hydroxy, cyano, halogen, $C_1$-$C_4$alkyl, $C_2$-$C_4$alkenyl, $C_1$-$C_4$alkoxy, wherein the alkoxy is unsubstituted or substituted with hydroxy, $C_1$-$C_4$alkoxy, amino, $N(H)C(O)C_1$-$C_4$alkyl, $N(H)C(O)_2$ $C_1$-$C_4$alkyl, 4 to 7 member heterocycle and mono- and di-$C_1$-$C_4$alkylamino; or In a fifth embodiment, the invention is a compound according to the first through fourth embodiments, or a salt thereof, wherein B is a group of the formula:

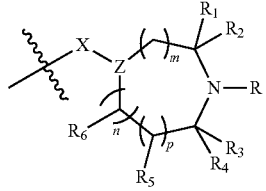

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$akylamino; $R_5$ and $R_6$ are hydrogen; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_B$, O, $NR_7$ or a bond; $R_A$ and $R_B$ are independently selected from hydrogen and $C_1$-$C_4$alkyl, or $R_A$ and $R_B$, taken in combination, form a divalent $C_2$-$C_5$alkylene group; Z is $CR_8$ or N; when Z is N, X is a bond; $R_8$ is hydrogen or taken in combination with $R_8$ form a double bond.

In a sixth embodiment, the invention is a compound according to the first through fourth embodiments, or a salt thereof, wherein B is a group of the formula:

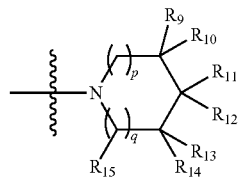

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$akylamino and $C_1$-$C_4$alkyl, which alkyl is optionally substituted with hydroxy, amino or mono- and di-$C_1$-$C_4$akylamino; $R_{11}$ is hydrogen, $C_1$-$C_4$alkyl, amino or mono- and di-$C_1$-$C_4$akylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a seventh embodiment, the invention the invention is a compound according to the first or third embodiments, or a salt thereof, which compound is represented by Formula (II):

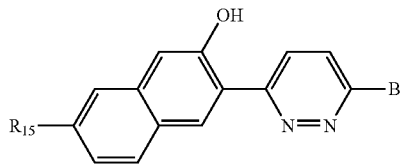

wherein $R_{15}$ is hydrogen, hydroxyl, $C_1$-$C_4$alkoxy, which alkoxy is optionally substituted with hydroxy, methoxy, amino, mono- and di-methylamino or morpholine.

In an eighth embodiment, the invention is a compound of the first or fourth embodiments, or a salt thereof, which compound is represented by Formula (III):

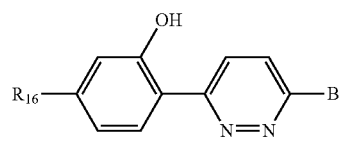

wherein $R_{16}$ is a 5 member heteroaryl having one ring nitrogen atom and 0 or 1 additional ring heteroatom selected from N, O or S, wherein the heteroaryl is optionally substituted with $C_1$-$C_4$alkyl.

In a ninth embodiment, the invention is a compound of the first through fourth, seventh and eighth embodiments, or salt thereof, wherein B is selected from the group consisting of

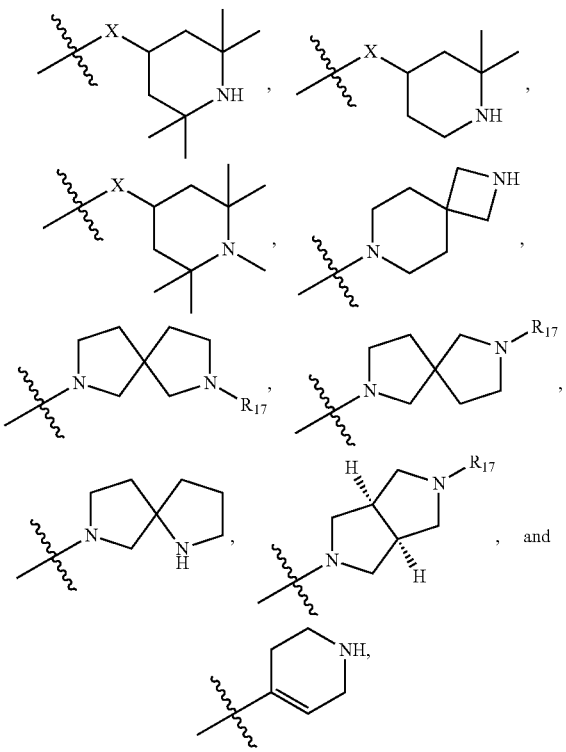

wherein X is O or N(Me); and $R_{17}$ is hydrogen or methyl.

In a tenth embodiment, the invention is a compound according to the first through fifth and seventh through ninth embodiments, or salt thereof, wherein X is —O—.

In an eleventh embodiment, the invention is a compound according to the first through fifth and seventh through ninth embodiments, or salt thereof, wherein B is:

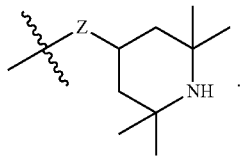

In a twelfth embodiment, the invention is a compound of the eighth through eleventh embodiments, or salt thereof, wherein $R_{16}$ is:

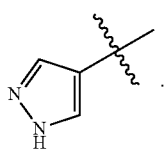 [SMILES: *c1cn[nH]c1]

In a thirteenth embodiment, the invention is a compound of the first embodiment, or salt thereof, wherein the compound is of formula (IV):

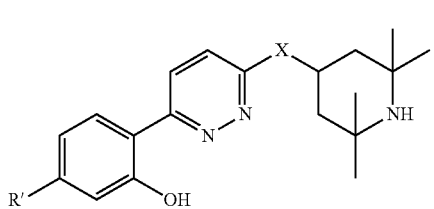

wherein X is —O— or

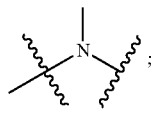 [SMILES: *N(*)C]

R' is a 5-membered heteroaryl optionally substituted with 0, 1, or 2 groups selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, trihalo$C_1$-$C_4$alkyl, mono- and di-$C_1$-$C_4$alkylamino, —C(O)NH$_2$, —NH$_2$, —NO$_2$, hydroxyC1-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl.

In a fourteenth embodiment, the invention is a compound, or salt thereof, selected from the group consisting of:
6-(naphthalen-2-yl)-N-(2,2,6,6-tetramethylpiperidin-4-yl) pyridazin-3-amine;
6-(benzo[b]thio-phen-2-yl)-N-methyl-N-(2,2,6,6-tetra-methylpiperidin-4-yl)pyridazin-3-amine;
2-(6-(2,2,6,6-tetramethylpiperidin-4-ylamino)-pyridazin-3-yl)phenol;
2-(6-(methyl-(2,2,6,6-tetra-methylpiperidin-4-yl)amino) pyridazin-3-yl)benzo[b]-thiophene-5-carbonitrile;
6-(quinolin-3-yl)-N-(2,2,6,6-tetramethyl-piperidin-4-yl) pyridazin-3-amine;
3-(benzo[b]-thiophen-2-yl)-6-(2,2,6,6-tetra-methylpiperidin-4-yloxy)pyridazine;
2-(6-(methyl-(2,2,6,6-tetra-methylpiperidin-4-yl)amino)-pyridazin-3-yl)phenol;
6-(6-(methyl-(2,2,6,6-tetra-methylpiperidin-4-yl)amino)-pyridazin-3-yl)naphthalen-2-ol;
6-(benzo[b]-thiophen-2-yl)-N-(2,2,6,6-tetra-methylpiperidin-4-yl)pyridazin-3-amine;
7-(6-((2,2,6,6-tetramethylpiperidin-4-yl)oxy)pyridazin-3-yl)isoquinoline;
6-(6-((2,2,6,6-tetramethylpiperidin-4-yl)oxy)pyridazin-3-yl)isoquinoline;
N-methyl-6-(quinolin-7-yl)-N-(2,2,6,6-tetramethyl-piperidin-4-yl)pyridazin-3-amine;
N-methyl-6-(quinolin-6-yl)-N-(2,2,6,6-tetramethylpiperidin-4-yl)pyridazin-3-amine;
6-(isoquinolin-7-yl)-N-methyl-N-(2,2,6,6-tetramethylpiperidin-4-yl)pyridazin-3-amine;
6-(isoquinolin-6-yl)-N-methyl-N-(2,2,6,6-tetramethylpiperidin-4-yl)pyridazin-3-amine;
6-(imidazo[1,2-a]pyridin-6-yl-pyridazin-3-yl)-methyl-(2,2,6,6-tetramethyl-piperidin-4-yl)-amine;
methyl-[6-(6-phenyl-pyridin-3-yl)-pyridazin-3-yl]-(2,2,6,6-tetramethyl-piperidin-4-yl)-amine;
methyl-[6-(6-pyrrol-1-yl-pyridin-3-yl)-pyridazin-3-yl]-(2,2,6,6-tetramethyl-piperidin-4-yl)-amine;
methyl-[6-(6-pyrazol-1-yl-pyridin-3-yl)-pyridazin-3-yl]-(2,2,6,6-tetramethyl-piperidin-4-yl)-amine;
methyl-(6-quinoxalin-2-yl-pyridazin-3-yl)-(2,2,6,6-tetramethyl-piperidin-4-yl)-amine;
methyl-(6-quinolin-3-yl-pyridazin-3-yl)-(2,2,6,6-tetramethyl-piperidin-4-yl)-amine;
N-methyl-6-(phthalazin-6-yl)-N-(2,2,6,6-tetramethylpiperidin-4-yl)pyridazin-3-amine;
6-(benzo[c][1,2,5]oxa-diazol-5-yl)-N-(2,2,6,6-tetramethyl-piperidin-4-yl)pyridazin-3-amine;
6-(benzo[d]thiazol-5-yl)-N-(2,2,6,6-tetramethyl-piperidin-4-yl)pyridazin-3-amine;
6-(2-methylbenzo-[d]oxazol-6-yl)-N-(2,2,6,6-tetramethyl-piperidin-4-yl)pyridazin-3-amine;
3-(6-(methyl(2,2,6,6-tetramethylpiperidin-4-yl)amino) pyridazin-3-yl)naphthalen-2-ol;
5-chloro-2-(6-(methyl(1,2,2,6,6-pentamethylpiperidin-4-yl) amino)pyridazin-3-yl)phenol;
3-(6-(2,2,6,6-tetramethylpiperidin-4-ylamino)pyridazin-3-yl)naphthalen-2-ol;
5-chloro-2-(6-(1,2,2,6,6-pentamethylpiperidin-4-ylamino) pyridazin-3-yl)phenol;
4-hydroxy-3-(6-(methyl(2,2,6,6-tetramethylpiperidin-4-yl) amino)pyridazin-3-yl)benzonitrile;
3-[6-(2,2,6,6-tetramethyl-piperidin-4-yloxy)-pyridazin-3-yl]-naphthalen-2-ol;
2-{6-[methyl-(2,2,6,6-tetramethyl-piperidin-4-yl)-amino]-pyridazin-3-yl}-4-trifluoromethyl-phenol;
2-fluoro-6-{6-[methyl-(2,2,6,6-tetramethyl-piperidin-4-yl)-amino]-pyridazin-3-yl}-phenol;
3,5-dimethoxy-2-{6-[methyl-(2,2,6,6-tetramethyl-piperidin-4-yl)-amino]-pyridazin-3-yl}-phenol;
4,5-dimethoxy-2-{6-[methyl-(2,2,6,6-tetramethyl-piperidin-4-yl)-amino]-pyridazin-3-yl}-phenol;
5-methoxy-2-{6-[methyl-(2,2,6,6-tetramethyl-piperidin-4-yl)-aminol-pyridazin-3-yl}-phenol;
4,5-difluoro-2-{6-[methyl-(2,2,6,6-tetramethyl-piperidin-4-yl)-amino]-pyridazin-3-yl}-phenol;
5-fluoro-2-{6-[methyl-(2,2,6,6-tetramethyl-piperidin-4-yl)-amino]-pyridazin-3-yl}-phenol;

3-hydroxy-4-(6-(methyl(2,2,6,6-tetramethylpiperidin-4-yl)
amino)pyridazin-3-yl)benzonitrile;
1-allyl-6-(6-(methyl(2,2,6,6-tetramethylpiperidin-4-yl)
amino)pyridazin-3-yl)naphthalen-2-ol;
6-(benzo[b]thiophen-2-yl)-N-(1,2,2,6,6-pentamethylpiperi-
din-4-yl)pyridazin-3-amine;
N-allyl-3-hydroxy-4-(6-(methyl(2,2,6,6-tetramethylpiperi-
din-4-yl)amino)pyridazin-3-yl)benzamide;
2-(6-(methyl(2,2,6,6-tetramethylpiperidin-4-yl)amino)
pyridazin-3-yl)-5-(1H-pyrazol-1-yl)phenol;
5-(5-methyl-oxazol-2-yl)-2-{6-[methyl-(2,2,6,6-tetram-
ethyl-piperidin-4-yl)-amino]-pyridazin-3-yl}-phenol;
5-(4-hydroxymethyl)-1H-pyrazole-1-yl)-2-(6-(methyl(2,2,
6,6-tetramethylpiperidin-4-yl)amino)pyridazin-3-yl)phe-
nol;
5-(1H-imidazole-1-yl)-2-(6-(methyl(2,2,6,6-tetramethyl-pi-
peridin-4-yl)amino)pyridazin-3-yl)phenol;
5-(4-amino-1H-pyrazole-1-yl)-2-(6-(methyl(2,2,6,6-tetram-
ethylpiperidin-4-yl)amino)pyridazin-3-yl)phenol;
5-(4-amino-1H-pyrazol-1-yl)-2-(6-(methyl(2,2,6,6-tetram-
ethylpiperidin-4-yl)amino)pyridazin-3-yl)phenol;
5-(3-amino-pyrazol-1-yl)-2-{6-[methyl-(2,2,6,6-tetram-
ethyl-piperidin-4-yl)-amino]-pyridazin-3-yl}-phenol;
2-(6-(methyl(2,2,6,6-tetramethylpiperidin-4-yl)amino)
pyridazin-3-yl)-5-(1-(2-morpholino-ethyl)-1H-pyrazol-4-
yl)phenol;
2-(6-(methyl(2,2,6,6-tetramethylpiperidin-4-yl)amino)
pyridazin-3-yl)-5-(1-methyl-1H-pyrazol-4-yl)phenol;
5-(5-amino-1H-pyrazol-1-yl)-2-(6-(methyl-(2,2,6,6-tetram-
ethyl-piperidin-4-yl)amino)pyridazin-3-yl)phenol;
2-(6-(methyl(2,2,6,6-tetramethylpiperidin-4-yl)amino)
pyridazin-3-yl)-4-(1H-pyrazol-1-yl)phenol;
2-{6-[(2-hydroxy-ethyl)-(2,2,6,6-tetramethyl-piperidin-4-
yl)-amino]-pyridazin-3-yl}-5-pyrazol-1-yl-phenol;
2-(6-(piperidin-4-yloxy)pyridazin-3-yl)-5-(1H-pyrazol-1-
yl)phenol;
2-(6-(((2S,4R,6R)-2,6-dimethylpiperidin-4-yl)oxy)
pyridazin-3-yl)-5-(1H-pyrazol-1-yl)phenol;
2-(6-((-2,6-dimethylpiperidin-4-yl)oxy)pyridazin-3-yl)-5-
(1H-pyrazol-1-yl)phenol;
2-(6-((-2,6-dimethylpiperidin-4-yl)oxy)pyridazin-3-yl)-5-
(1H-pyrazol-1-yl)phenol;
5-(1H-pyrazol-1-yl)-2-(6-(pyrrolidin-3-yloxy)pyridazin-3-
yl)phenol;
2-(6-((-2-methylpiperidin-4-yl)oxy)pyridazin-3-yl)-5-(1H-
pyrazol-1-yl)phenol;
(S)-5-(1H-Pyrazol-1-yl)-2-(6-(pyrrolidin-3-ylmethoxy)
pyridazin-3-yl)phenol;
(R)-5-(1H-pyrazol-1-yl)-2-(6-(pyrrolidin-3-ylmethoxy)
pyridazin-3-yl)phenol;
2-(6-((3-fluoropiperidin-4-yl)oxy)pyridazin-3-yl)-5-(1H-
pyrazol-1-yl)-phenol;
2-[6-(1,2,2,6,6-pentamethyl-piperidin-4-yloxy)-pyridazin-
3-yl]-5-pyrazol-1-yl-phenol;
5-pyrazol-1-yl-2-[6-(2,2,6,6-tetramethyl-piperidin-4-
yloxy)-pyridazin-3-yl]-phenol;
5-(1H-Pyrazol-4-yl)-2-(6-((2,2,6,6-tetramethylpiperidin-4-
yl)oxy)pyridazin-3-yl)phenol;
2-(6-piperazin-1-yl-pyridazin-3-yl)-5-pyrazol-1-yl-phenol;
3-[6-(azetidin-3-ylamino)-pyridazin-3-yl]-naphthalen-2-ol;
2-[6-(azetidin-3-ylamino)-pyridazin-3-yl]-5-pyrazol-1-yl-
phenol;
2-[6-(3,5-dimethyl-piperazin-1-yl)-pyridazin-3-yl]-5-pyra-
zol-1-yl-phenol;
2-[6-(7-methyl-2,7-diaza-spiro[4.4]non-2-yl)-pyridazin-3-
yl]-5-pyrazol-1-yl-phenol;
2-(6-[1,4]diazepan-1-yl-pyridazin-3-yl)-5-pyrazol-1-yl-
phenol;
2-{6-[4-(2-hydroxy-ethyl)-piperazin-1-yl]-pyridazin-3-yl}-
5-pyrazol-1-yl-phenol;
2-[6-(3,6-diaza-bicyclo[3.2.1]oct-3-yl)-pyridazin-3-yl]-5-
pyrazol-1-yl-phenol;
2-[6-(2,7-diaza-spiro[3.5]non-7-yl)-pyridazin-3-yl]-5-pyra-
zol-1-yl-phenol;
2-[6-(3-hydroxy-methyl-piperazin-1-yl)-pyridazin-3-yl]-5-
pyrazol-1-yl-phenol;
2-[6-(1,7-diaza-spiro[4.4]non-7-yl)-pyridazin-3-yl]-5-pyra-
zol-1-yl-phenol;
2-[6-(4-amino-4-methyl-piperidin-1-yl)-pyridazin-3-yl]-5-
pyrazol-1-yl-phenol;
2-[6-(3-dimethyl-amino-piperidin-1-yl)-pyridazin-3-yl]-5-
pyrazol-1-yl-phenol;
2-[6-(1,2,2,6,6-pentamethyl-piperidin-4-ylamino)-
pyridazin-3-yl]-5-pyrazol-1-yl-phenol;
2-[6-(3,3-di methyl-piperazin-1-yl)-pyridazin-3-yl]-5-pyra-
zol-1-yl-phenol;
2-(6-(7-(2-hydroxyethyl)-2,7-diazaspiro[4.4]-nonan-2-yl)
pyridazin-3-yl)-5-(1H-pyrazol-1-yl)phenol;
2-(6-((3aR,6aS)-hexahydropyrrolo[3,4-c]pyrrol-2(1H)-yl)
pyridazin-3-yl)-5-(1H-pyrazol-1-yl)phenol;
3-(6-(piperazin-1-yl)pyridazin-3-yl)naphthalene-2,7-diol;
5-pyrazol-1-yl-2-[6-(1,2,3,6-tetrahydro-pyridin-4-yl)-
pyridazin-3-yl]-phenol;
2-(6-piperidin-4-yl-pyridazin-3-yl)-5-pyrazol-1-yl-phenol;
3-(6-(1,2,3,6-tetra-hydropyridin-4-yl)pyridazin-3-yl)naph-
thalen-2-ol;
3-(6-(1,2,3,6-tetrahydropyridin-4-yl)pyridazin-3-yl)naph-
thalene-2,7-diol;
3-(6-(2,2,6,6-tetramethyl-1,2,3,6-tetrahydropyridin-4-yl)
pyridazin-3-yl)naphthalene-2,7-diol;
3-(6-(1-methyl-1,2,3,6-tetrahydropyridin-4-yl)pyridazin-3-
yl)naphthalene-2,7-diol;
3-(6-(piperidin-4-yl)pyridazin-3-yl)naphthalene-2,7-diol;
3-(6-((2,2,6,6-tetramethylpiperidin-4-yl)oxy)pyridazin-3-
yl)naphthalene-2,7-diol;
3-(6-(methyl(2,2,6,6-tetramethylpiperidin-4-yl)amino)
pyridazin-3-yl)naphthalene-2,7-diol;
3-(6-((2,2,6,6-tetramethylpiperidin-4-yl)amino)pyridazin-3-
yl)naphthalene-2,7-diol;
[3-(7-hydroxy-6-{6-[methyl-(2,2,6,6-tetramethyl-piperidin-
4-yl)-amino]-pyridazin-3-yl}-naphthalen-2-yloxy)-pro-
pyl]-carbamic acid tert-butyl ester;
7-(3-amino-propoxy)-3-{6-[methyl-(2,2,6,6-tetramethyl-pi-
peridin-4-yl)-amino]-pyridazin-3-yl}-naphthalen-2-ol;
N-[3-(7-hydroxy-6-{6-[methyl-(2,2,6,6-tetramethyl-piperi-
din-4-yl)-amino]-pyridazin-3-yl}-naphthalen-2-yloxy)-
propyl]-acetamide;
7-(3-hydroxypropoxy)-3-(6-(methyl(2,2,6,6-tetramethylpi-
peridin-4-yl)amino)pyridazin-3-yl)naphthalen-2-ol;
7-(3-methoxypropoxy)-3-(6-(methyl(2,2,6,6-tetramethylpi-
peridin-4-yl)amino)pyridazin-3-yl)naphthalen-2-ol;
7-(2-morpholinoethoxy)-3-(6-((2,2,6,6-tetramethylpiperi-
din-4-yl)oxy)pyridazin-3-yl)naphthalen-2-ol;
3-(6-(piperidin-4-ylmethyl)pyridazin-3-yl)naphthalen-2-ol;
5-(1H-pyrazol-1-yl)-2-(6-((2,2,6,6-tetramethylpiperidin-4-
yl)methyl)pyridazin-3-yl)phenol;
3-methoxy-2-(6-(methyl(2,2,6-trimethylpiperidin-4-yl)
amino)pyridazin-3-yl)-5-(5-methyloxazol-2-yl)phenol;
2-(6-((6S)-6-((S)-1-hydroxyethyl)-2,2-dimethylpiperidin-4-
yloxy)pyridazin-3-yl)-5-(1H-pyrazol-1-yl)phenol;
7-hydroxy-6-(6-(methyl(2,2,6,6-tetramethylpiperidin-4-yl)
amino)pyridazin-3-yl)-2-naphthonitrile;

3-(6-(methyl(2,2,6,6-tetramethylpiperidin-4-yl)amino)
pyridazin-3-yl)-7-(piperidin-1-ylmethyl)naphthalen-2-ol;
3-(6-(methyl(2,2,6,6-tetramethylpiperidin-4-yl)amino)
pyridazin-3-yl)-7-(pyrrolidin-1-ylmethyl)naphthalen-2-ol;
1-bromo-6-(6-(methyl(2,2,6,6-tetramethylpiperidin-4-yl)
amino)pyridazin-3-yl)naphthalene-2,7-diol;
1-chloro-6-(6-(methyl(2,2,6,6-tetramethylpiperidin-4-yl)
amino)pyridazin-3-yl)naphthalene-2,7-diol;
7-methoxy-3-(6-(methyl(2,2,6,6-tetramethylpiperidin-4-yl)
amino)pyridazin-3-yl)naphthalen-2-ol;
7-methoxy-3-(6-(methyl(1,2,2,6,6-pentamethylpiperidin-4-yl)amino)pyridazin-3-yl)naphthalen-2-ol;
7-(3,6-dihydro-2H-pyran-4-yl)-3-(6-(methyl(2,2,6,6-tetramethylpiperidin-4-yl)amino)pyridazin-3-yl)naphthalen-2-ol;
3-(6-(methyl(2,2,6,6-tetramethylpiperidin-4-yl)amino)
pyridazin-3-yl)-7-(tetrahydro-2H-pyran-4-yl)naphthalen-2-ol;
7-(difluoromethyl)-3-(6-(methyl(2,2,6,6-tetramethylpiperidin-4-yl)amino)pyridazin-3-yl)naphthalen-2-ol;
7-((4-hydroxy-2-methylbutan-2-yl)oxy)-3-(6-(methyl(2,2,6,6-tetramethylpiperidin-4-yl)amino)pyridazin-3-yl)naphthalen-2-ol;
7-(3-hydroxy-3-methylbutoxy)-3-(6-(methyl(2,2,6,6-tetramethylpiperidin-4-yl)amino)pyridazin-3-yl)naphthalen-2-ol;
2-(6-(methyl(2,2,6,6-tetramethylpiperidin-4-yl)amino)
pyridazin-3-yl)-5-(1H-pyrazol-4-yl)benzene-1,3-diol;
3-methoxy-2-(6-(methyl(2,2,6,6-tetramethylpiperidin-4-yl)amino)pyridazin-3-yl)-5-(1H-pyrazol-4-yl)phenol;
5-(1H-pyrazol-4-yl)-2-(64(2,2,6,6-tetramethylpiperidin-4-yl)amino)pyridazin-3-yl)-3-(trifluoromethoxy)phenol;
2-(6-(methyl(2,2,6,6-tetramethylpiperidin-4-yl)amino)
pyridazin-3-yl)-5-(1-methyl-1H-pyrazol-4-yl)-3-(trifluoromethoxy)phenol;
2-(6-(methyl(2,2,6,6-tetramethylpiperidin-4-yl)amino)
pyridazin-3-yl)-5-(1H-pyrazol-4-yl)-3-(trifluoromethoxy)phenol;
4-(3-hydroxy-4-(6-(methyl(2,2,6,6-tetramethylpiperidin-4-yl)amino)pyridazin-3-yl)-5-(trifluoromethoxy)phenyl)-1-methylpyridin-2(1H)-one;
3-methoxy-2-(6-(methyl(2,2,6,6-tetramethylpiperidin-4-yl)amino)pyridazin-3-yl)-5-(1-methyl-1H-pyrazol-4-yl)phenol;
3-methoxy-2-(6-(methyl(2,2,6,6-tetramethylpiperidin-4-yl)amino)pyridazin-3-yl)-5-(5,6,7,8-tetrahydroimidazo[1,2-a]pyridin-3-yl)phenol;
3-methoxy-2-(6-(methyl(2,2,6,6-tetramethylpiperidin-4-yl)amino)pyridazin-3-yl)-5-(pyridin-3-yl)phenol;
5-(1-cyclopentyl-1H-pyrazol-4-yl)-3-methoxy-2-(6-(methyl(2,2,6,6-tetramethylpiperidin-4-yl)amino)pyridazin-3-yl)phenol;
3',5-dimethoxy-4-(6-(methyl(2,2,6,6-tetramethylpiperidin-4-yl)amino)pyridazin-3-yl)[1,1'-biphenyl]-3-ol;
3-(benzyloxy)-2-(6-(methyl(2,2,6,6-tetramethylpiperidin-4-yl)amino)pyridazin-3-yl)-5-(5-methyloxazol-2-yl)phenol;
3-ethoxy-2-(6-(methyl(2,2,6,6-tetramethylpiperidin-4-yl)amino)pyridazin-3-yl)-5-(5-methyloxazol-2-yl)phenol;
3-(cyclopropylmethoxy)-2-(6-(methyl(2,2,6,6-tetramethylpiperidin-4-yl)amino)-pyridazin-3-yl)-5-(5-methyloxazol-2-yl)phenol;
2-methyl-5-(6-(methyl(2,2,6,6-tetramethylpiperidin-4-yl)amino)pyridazin-3-yl)-1H-benzo[d]imidazol-6-ol;
5-chloro-2-(6-(methyl(2,2,6,6-tetramethylpiperidin-4-yl)amino)pyridazin-3-yl)phenol;
5-(1H-pyrazol-1-yl)-2-(6-((2,2,6,6-tetramethylpiperidin-4-yl)amino)pyridazin-3-yl)phenol;
3-hydroxy-4-(6-((2,2,6,6-tetramethylpiperidin-4-yl)amino)pyridazin-3-yl)benzonitrile;
2-(6-((2,2-dimethylpiperidin-4-yl)oxy)pyridazin-3-yl)-5-(1H-pyrazol-1-yl)phenol;
2-(6-(methyl(2,2,6,6-tetramethylpiperidin-4-yl)amino)
pyridazin-3-yl)-4-(1H-pyrazol-4-yl)phenol;
2-(6-(methyl(2,2,6,6-tetramethylpiperidin-4-yl)amino)
pyridazin-3-yl)-4-(4,5,6,7-tetrahydropyrazolo[1,5-a]pyridin-3-yl)phenol;
2-(6-(methyl(2,2,6,6-tetramethylpiperidin-4-yl)amino)
pyridazin-3-yl)-4-(4,5,6,7-tetrahydropyrazolo[1,5-a]pyrazin-3-yl)phenol;
4-(1H-indol-2-yl)-2-(6-(methyl(2,2,6,6-tetramethylpiperidin-4-yl)amino)pyridazin-3-yl)phenol;
4-(cyclopent-1-en-1-yl)-2-(6-(methyl(2,2,6,6-tetramethylpiperidin-4-yl)amino)pyridazin-3-yl)phenol;
2-(6-(methyl(2,2,6,6-tetramethylpiperidin-4-yl)amino)
pyridazin-3-yl)-4-(1H-pyrazol-3-yl)phenol;
4-(4-hydroxy-3-(6-(methyl(2,2,6,6-tetramethylpiperidin-4-yl)amino)pyridazin-3-yl)phenyl)pyridin-2-ol;
4-(4-hydroxy-3-(6-((2,2,6,6-tetramethylpiperidin-4-yl)oxy)pyridazin-3-yl)phenyl)-1-methylpyridin-2(1H)-one;
4-(4-hydroxy-3-(6-((2,2,6,6-tetramethylpiperidin-4-yl)oxy)pyridazin-3-yl)phenyl)pyridin-2-ol;
5-(1H-indazol-7-yl)-2-(6-(methyl(2,2,6,6-tetramethylpiperidin-4-yl)amino)pyridazin-3-yl)phenol;
4-chloro-2-(6-(methyl(2,2,6,6-tetramethylpiperidin-4-yl)amino)pyridazin-3-yl)-5-(1H-pyrazol-4-yl)phenol;
4-fluoro-2-(6-(methyl(2,2,6,6-tetramethylpiperidin-4-yl)amino)pyridazin-3-yl)-5-(1H-pyrazol-4-yl)phenol;
5-fluoro-4-(1H-imidazol-4-yl)-2-(6-(methyl(2,2,6,6-tetramethylpiperidin-4-yl)amino)pyridazin-3-yl)phenol;
5-fluoro-2-(6-(methyl(2,2,6,6-tetramethylpiperidin-4-yl)amino)pyridazin-3-yl)-4-(1H-pyrazol-4-yl)phenol;
5-fluoro-2-(6-(methyl(2,2,6,6-tetramethylpiperidin-4-yl)amino)pyridazin-3-yl)-4-(1H-pyrazol-5-yl)phenol;
6-hydroxy-5-(6-(methyl(2,2,6,6-tetramethylpiperidin-4-yl)amino)pyridazin-3-yl)-2,3-dihydro-1H-inden-1-one;
6-(6-(methyl(2,2,6,6-tetramethylpiperidin-4-yl)amino)
pyridazin-3-yl)-1,4-dihydroindeno[1,2-c]pyrazol-7-ol;
6-hydroxy-5-(6-(methyl(2,2,6,6-tetramethylpiperidin-4-yl)amino)pyridazin-3-yl)-2,3-dihydro-1H-inden-1-one oxime hydrochloride salt;
5-(6-(methyl(2,2,6,6-tetramethylpiperidin-4-yl)amino)
pyridazin-3-yl)-2,3-dihydro-1H-indene-1,6-diol;
2-amino-6-(6-(methyl(2,2,6,6-tetramethylpiperidin-4-yl)
amino)pyridazin-3-yl)-8H-indeno[1,2-d]thiazol-5-ol
hydrochloride salt;
9-(6-(methyl(2,2,6,6-tetramethylpiperidin-4-yl)amino)
pyridazin-3-yl)-5,6-dihydroimidazo[5,1-a]isoquinolin-8-ol hydrochloride salt;
4-hydroxy-3-(6-(methyl(2,2,6,6-tetramethylpiperidin-4-yl)amino)pyridazin-3-yl)-N-((1-methyl-1H-pyrazol-4-yl)methyl)benzamide;
4-(4-(hydroxymethyl)-1H-pyrazol-1-yl)-2-(6-(methyl(2,2,6,6-tetramethylpiperidin-4-yl)amino)pyridazin-3-yl)phenol;
5-(1H-pyrazol-4-yl)-2-(64(2,2,6,6-tetramethylpiperidin-4-yl)methyl)pyridazin-3-yl)phenol;
6-(3-(benzyloxy)isoquinolin-6-yl)-N-methyl-N-(2,2,6,6-tetramethylpiperidin-4-yl)pyridazin-3-amine;
6-(1-(benzyloxy)isoquinolin-7-yl)-N-methyl-N-(2,2,6,6-tetramethylpiperidin-4-yl)pyridazin-3-amine;

3-fluoro-5-(2-methoxypyridin-4-yl)-2-(6-(methyl(2,2,6,6-tetramethylpiperidin-4-yl)amino)pyridazin-3-yl)phenol hydrochloride salt;
4-(3-fluoro-5-hydroxy-4-(6-(methyl(2,2,6,6-tetramethylpiperidin-4-yl)amino)pyridazin-3-yl)phenyl)pyridin-2(1H)-one hydrochloride salt;
4-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt;
5-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt;
3-fluoro-5-(1H-pyrazol-4-yl)-2-(64(2,2,6,6-tetramethylpiperidin-4-yl)oxy)pyridazin-3-yl)phenol hydrochloride salt;
5-chloro-3-fluoro-2-(6-(methyl(2,2,6,6-tetramethylpiperidin-4-yl)amino)pyridazin-3-yl)phenol hydrochloride salt;
3-fluoro-2-(6-(methyl(2,2,6,6-tetramethylpiperidin-4-yl)amino)pyridazin-3-yl)-5-(1H-pyrazol-4-yl)phenol hydrochloride salt;
3-fluoro-2-(6-(methyl(2,2,6,6-tetramethylpiperidin-4-yl)amino)pyridazin-3-yl)-5-(1-methyl-1H-pyrazol-4-yl)phenol hydrochloride salt;
5-(5-methoxypyridin-3-yl)-2-(6-(methyl(2,2,6,6-tetramethylpiperidin-4-yl)amino)pyridazin-3-yl)phenol;
5-(3-hydroxy-4-(6-methyl(2,2,6,6-tetramethylpiperidin-4-yl)amino)pyridazin-3-yl)phenyl)pyridin-2-ol;
4-(3-hydroxy-4-(6-methyl(2,2,6,6-tetramethylpiperidin-4-yl)amino)pyridazin-3-yl)phenyl)pyridin-2-ol;
5-(6-methoxypyridin-3-yl)-2-(6-(methyl(2,2,6,6-tetramethylpiperidin-4-yl)amino)pyridazin-3-yl)phenol;
5-(3-hydroxy-4-(6-(methyl(2,2,6,6-tetramethylpiperidin-4-yl)amino)pyridazin-3-yl)phenyl)-3-(trifluoromethyl)pyridin-2-ol;
5-(3-hydroxy-4-(6-(methyl(2,2,6,6-tetramethylpiperidin-4-yl)amino)pyridazin-3-yl)phenyl)-1-methylpyridin-2(1H)-one;
4-(3-hydroxy-4-(6-(methyl(2,2,6,6-tetramethylpiperidin-4-yl)amino)pyridazin-3-yl)phenyl)-1-methylpyridin-2(1H)-one;
5-(2-methoxypyridin-4-yl)-2-(6-(methyl(2,2,6,6-tetramethylpiperidin-4-yl)amino)pyridazin-3-yl)phenol;
4-(3-hydroxy-4-(6-((2,2,6,6-tetramethylpiperidin-4-yl)oxy)pyridazin-3-yl)phenyl)pyridin-2-ol;
5-(6-(dimethylamino)pyridin-3-yl)-2-(6-(methyl(2,2,6,6-tetramethylpiperidin-4-yl)amino)pyridazin-3-yl)phenol;
4-(3-hydroxy-4-(6-((2,2,6,6-tetramethylpiperidin-4-yl)oxy)pyridazin-3-yl)phenyl)-1-methylpyridin-2(1H)-one;
2-(6-(methyl(2,2,6,6-tetramethylpiperidin-4-yl)amino)pyridazin-3-yl)-5-(pyrimidin-5-yl)phenol;
5-(3-hydroxy-4-(6-(methyl(2,2,6,6-tetramethylpiperidin-4-yl)amino)pyridazin-3-yl)phenyl)pyridin-3-ol;
1-cyclopropyl-4-(3-hydroxy-4-(6-(methyl(2,2,6,6-tetramethylpiperidin-4-yl)amino)pyridazin-3-yl)phenyl)pyridin-2(1H)-one;
2-(6-(methyl(2,2,6,6-tetramethylpiperidin-4-yl)amino)pyridazin-3-yl)-5-(1,2,3,6-tetrahydropyridin-4-yl)phenol;
5-(cyclopent-1-en-1-yl)-2-(6-(methyl(2,2,6,6-tetramethylpiperidin-4-yl)amino)pyridazin-3-yl)phenol;
5-(3,6-dihydro-2H-pyran-4-yl)-2-(6-(methyl(2,2,6,6-tetramethylpiperidin-4-yl)amino)pyridazin-3-yl)phenol;
5-(imidazo[1,5-a]pyridin-7-yl)-2-(6-(methyl(2,2,6,6-tetramethylpiperidin-4-yl)amino)pyridazin-3-yl)phenol;
5-(imidazo[1,2-a]pyridin-7-yl)-2-(6-(methyl(2,2,6,6-tetramethylpiperidin-4-yl)amino)pyridazin-3-yl)phenol;
2-(6-(methyl(2,2,6,6-tetramethylpiperidin-4-yl)amino)pyridazin-3-yl)-5-(2-methylpyridin-4-yl)phenol;
5-(1H-imidazol-2-yl)-2-(6-(methyl(2,2,6,6-tetramethylpiperidin-4-yl)amino)pyridazin-3-yl)phenol;
5-(1H-imidazol-4-yl)-2-(6-(methyl(2,2,6,6-tetramethylpiperidin-4-yl)amino)pyridazin-3-yl)phenol;
5-(imidazo[1,2-a]pyrazin-3-yl)-2-(6-(methyl(2,2,6,6-tetramethylpiperidin-4-yl)amino)pyridazin-3-yl)phenol;
2-(6-(methyl(2, 2,6,6-tetramethylpiperidin-4-yl)amino)pyridazin-3-yl)-5-(5,6,7,8-tetrahydroimidazo[1,2-a]pyrazin-3-yl)phenol;
2-(6-(methyl(2,2,6,6-tetramethylpiperidin-4-yl)amino)pyridazin-3-yl)-5-(4-methyl-1H-imidazol-2-yl)phenol;
2-(6-(methyl(2,2,6,6-tetramethylpiperidin-4-yl)amino)pyridazin-3-yl)-5-(1-methyl-1H-imidazol-4-yl)phenol;
2-(6-(methyl(2,2,6,6-tetramethylpiperidin-4-yl)amino)pyridazin-3-yl)-5-(1-methyl-1H-imidazol-5-yl)phenol;
2-(6-(methyl(2,2,6,6-tetramethylpiperidin-4-yl)amino)pyridazin-3-yl)-5-(4-nitro-1H-imidazol-2-yl)phenol;
2-(6-(methyl(2,2,6,6-tetramethylpiperidin-4-yl)amino)pyridazin-3-yl)-5-(2-methyl-1H-imidazol-4-yl)phenol;
5-(1,2-dimethyl-1H-imidazol-4-yl)-2-(6-(methyl(2,2,6,6-tetramethylpiperidin-4-yl)amino)pyridazin-3-yl)phenol;
1-(3-hydroxy-4-(6-(methyl(2,2,6,6-tetramethylpiperidin-4-yl)amino)pyridazin-3-yl)phenyl)-1H-pyrazole-4-carboxamide;
2-(6-((3aR,6aS)-5-(2-hydroxyethyl)hexahydropyrrolo[3,4-c]pyrrol-2(1H)-yl)pyridazin-3-yl)-5-(1H-pyrazol-4-yl)phenol;
2-(6-((3aR,6aS)-hexahydropyrrolo[3,4-c]pyrrol-2(1H)-yl)pyridazin-3-yl)-5-(1H-pyrazol-4-yl)phenol;
2-(6-((3aR,6aS)-5-methylhexahydropyrrolo[3,4-c]pyrrol-2(1H)-yl)pyridazin-3-yl)-5-(1H-pyrazol-4-yl)phenol;
4-(3-hydroxy-4-(6-(5-methylhexahydropyrrolo[3,4-c]pyrrol-2(1H)-yl)pyridazin-3-yl)phenyl)-1-methylpyridin-2(1H)-one;
4-(3-hydroxy-4-(6-((3aR,6aR)-1-methylhexahydropyrrolo[3,4-b]pyrrol-5(1H)-yl)pyridazin-3-yl)phenyl)-1-methylpyridin-2(1H)-one;
2-(6-(2,7-diazaspiro[4.5]decan-2-yl)pyridazin-3-yl)-5-(1H-pyrazol-4-yl)phenol; and
4-(4-(6-(2,7-diazaspiro[4.5]decan-2-yl)pyridazin-3-yl)-3-hydroxyphenyl)-1-methylpyridin-2(1H)-one.

In a fifteenth embodiment, the invention is a pharmaceutical composition comprising a therapeutically effective amount of a compound according to any one of the first through fourteenth embodiments, or a pharmaceutically acceptable salt thereof and one or more pharmaceutically acceptable carriers.

In a sixteenth embodiment, the invention is a combination comprising a therapeutically effective amount of a compound according to any one of the first through fourteenth embodiments or a pharmaceutically acceptable salt thereof and one or more therapeutically active co-agents.

In a seventeenth embodiment, the invention is a method to treat, prevent or ameliorate an SMN-deficiency-related condition, comprising administering to a subject in need thereof an effective amount of a compound or salt thereof of any one of the first through fourteenth embodiments.

In an eighteenth embodiment, the invention is the method of the seventeenth embodiment, wherein said SMN-deficiency-related condition is Spinal Muscular Atrophy.

In a nineteenth embodiment, the invention is a compound according to any one of the first through fourteenth embodiments or a pharmaceutically acceptable salt thereof, for use as a medicament.

In a twentieth embodiment, the invention is a compound according to any one of the first through fourteenth embodiments or a pharmaceutically acceptable salt thereof, for use in the treatment of an SMN-deficiency-related condition.

In a twentyfirst embodiment, the invention is the compound according to the twentieth embodiment, or pharmaceutically acceptable salt thereof, for use in the treatment of spinal muscular atrophy.

In a twentysecond embodiment, the invention is use of a compound according to any one of the first through fourteenth embodiments, or a pharmaceutically acceptable salt thereof, in the manufacture of a medicament for the treatment of spinal muscular atrophy.

For purposes of interpreting this specification, the following definitions will apply and whenever appropriate, terms used in the singular will also include the plural and vice versa.

As used herein, the term "SMN modulator" includes agents, such as the compounds of the invention, which possess the ability to modulate, e.g., increase, SMN protein levels by at least one of multiple possible mechanisms. A non-limiting set of mechanisms includes SMN promoter activation, splicing modulation (e.g., preventing exon7 from being spliced out of the SMN gene), and SMN protein stability modulation. SMN modulators can modulate, e.g., increase FL-SMN and/or SMNΔ7 levels via any of said mechanisms, and/or can prevent SMNΔ7 from being degraded.

As used herein, the term "compounds of the invention" include but are not limited to the compounds of formula (I) and the compounds of formula (I-A) As used herein, the term "SMN-deficiency-related conditions" includes but is not limited to Spinal Muscular Atrophy (SMA), neurogenic-type arthrogryposis multiplex congenita (congenital AMC), and amyotrophic lateral sclerosis (ALS).

As used herein, the term "Spinal Muscular Atrophy", "SMA," include three forms of childhood-onset SMA: Type I (Werdnig-Hoffmann disease); Type II (intermediate, chronic form), Type III (Kugelberg-Welander disease, or Juvenile Spinal Muscular Atrophy); Adult-onset type IV; as well as other forms of SMA, including X-linked disease, spinal muscular atrophy with respiratory distress (SMARD), spinal and bulbar muscular atrophy (Kennedy's disease, or Bulbo-Spinal Muscular Atrophy), and distal spinal muscular atrophy.

For purposes of interpreting this specification, the following definitions will apply and whenever appropriate, terms used in the singular will also include the plural and vice versa.

As used herein, the term "$C_{1-10}$alkyl" refers to a fully saturated branched or unbranched hydrocarbon moiety having 1 to 10 carbon atoms. The terms "$C_{1-6}$alkyl" and "$C_{1-4}$alkyl" are to be construed accordingly. Representative examples of $C_{1-10}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

As used herein, the term "$C_{1-10}$alkylene" refers to divalent alkyl group as defined herein above having 1 to 10 carbon atoms. The terms "$C_{1-6}$alkylene" and "$C_{1-4}$alkylene" are to be construed accordingly. Representative examples of $C_{1-10}$alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

As used herein, the term "halo$C_{1-10}$alkyl" refers to a $C_{1-10}$alkyl group as defined herein, wherein at least one of the hydrogen atoms is replaced by a halo atom. The halo$C_{1-10}$alkyl group can be monohalo$C_{1-10}$alkyl, dihalo$C_{1-10}$alkyl or polyhalo$C_{1-10}$alkyl including perhalo$C_{1-10}$alkyl. A monohalo$C_{1-10}$alkyl can have one iodo, bromo, chloro or fluoro within the alkyl group. Dihalo$C_{1-10}$alkyl and polyhalo$C_{1-10}$alkyl groups can have two or more of the same halo atoms or a combination of different halo groups within the alkyl. Typically the polyhalo$C_{1-10}$alkyl group contains up to 12, or 10, or 8, or 6, or 4, or 3, or 2 halo groups. Non-limiting examples of halo$C_{1-10}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-10}$alkyl group refers to an $C_{1-10}$alkyl group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-10}$alkoxy" refers to $C_{1-10}$alkyl-O—, wherein $C_{1-10}$alkyl is defined herein above. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy- and decyloxy-.

As used herein, the term "heterocyclyl" or "heterocyclo" refers to a saturated or unsaturated non-aromatic ring or ring system, which is a 4-, 5-, 6-, or 7-membered monocyclic ring containing 1, 2 or 3 heteroatoms selected from O, S and N, a 7-, 8-, 9-, 10-, 11-, or 12-membered bicyclic ring system containing 1, 2, 3, 4 or 5 heteroatoms selected from O, S and N, or a 10-, 11-, 12-, 13-, 14- or 15-membered tricyclic ring system and containing 1, 2, 3, 4, 5, 6 or 7 heteroatoms selected from O, S and N, where the N and S can also optionally be oxidized to various oxidation states. The heterocyclic group can be attached via a heteroatom or a carbon atom. The heterocyclyl can include fused or bridged rings as well as spirocyclic rings. Examples of heterocycles include tetrahydrofuran (THF), dihydrofuran, 1, 4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane and thiomorpholine.

As used herein, the term "$C_{3-12}$cycloalkyl" refers to saturated or unsaturated monocyclic, bicyclic or tricyclic hydrocarbon groups of 3-12 carbon atoms. The term "$C_{3-18}$cycloalkyl" refers to a fully saturated or unsaturated monocyclic hydrocarbon group of 3-8 carbon atoms. Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic hydrocarbon groups include, for example, adamantyl.

As used herein the term "$C_{3-12}$cycloalklyoxy" refers to $C_{3-12}$cycloalkyl-O—, wherein $C_{3-12}$cycloalkyl is defined herein above. Representative examples of $C_{3-12}$cycloalklyoxy include, but are not limited to monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyl oxy, decahydronaphthyloxy, bicyclo[2.1.1]hexyloxy, bicyclo[2.2.1] heptyloxy, bicyclo[2.2.1]heptenyloxy, 6,6-dimethylbicyclo [3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

As used herein, the term "aryloxy" refers to both an —O-aryl and an —O-heteroaryl group, wherein aryl and heteroaryl are defined herein.

As used herein, the term "heteroaryl" refers to a 5-, 6-, or 7-membered monocyclic aromatic ring containing 1, 2, 3 or 4 heteroatoms selected from O, S and N, an 8-, 9-, or 10-membered fused bicyclic ring system containing 1, 2, 3, 4 or 5 heteroatoms selected from O, S and N, or an 11-, 12-, 13-, or 14-membered fused tricyclic ring system containing 1, 2, 3, 4, 5 or 6 heteroatoms selected from O, S and N, wherein at least one of the rings of the bicyclic or tricyclic ring systems is fully aromatic. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl, 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6- , or 7-indazolyl, 2-, 4-, 5-, 6-, 7-, or 8-purinyl, 1-, 2-, 3-, 4-, 6-, 7-, 8-, or 9-quinolizinyl, 2-, 3-, 4- , 5-, 6-, 7-, or 8-quinoliyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8- carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H- pyrido[2,3-d]-o-oxazinyl, 1-, 3-, or 5-1H-pyrazolo [4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo [2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c] carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H- pyrrolo[1,2-b][2]benzazapinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b] thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts." The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}C$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, de-acetone, de-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Survival of Motor Neuron (SMN) gene or gene product, or by SMNΔ7 degradation, or by the relative levels of FL-SMN and SMNΔ7 (ii) associated with SMN activity, or (iii) characterized by activity (normal or abnormal) of SMN; or (2) reducing or inhibiting the activity of SMN; or (3) reducing or inhibiting the expression of SMN1 or SMN2.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SMN; or at least partially reducing or inhibiting the expression of SMN, in both cases by modulating the relative levels of FL-SMN and SMNΔ7.

The phrases "therapeutically effective amount" and "effective amount" are used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of an SMN-deficiency-related condition. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat", "treating" or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with diluents, e.g., lactose, dextrose, sucrose, mannitol, sorbitol, cellulose and/or glycine;

lubricants, e.g., silica, talcum, stearic acid, its magnesium or calcium salt and/or polyethyleneglycol; for tablets also binders, e.g., magnesium aluminum silicate, starch paste, gelatin, tragacanth, methylcellulose, sodium carboxymethylcellulose and/or polyvinylpyrrolidone; if desired disintegrants, e.g., starches, agar, alginic acid or its sodium salt, or effervescent mixtures; and/or absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host.

For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. full length SMN protein production modulating properties, e.g. as indicated in in vitro and in vivo tests as provided in the next sections, and are therefore indicated for therapy or for use as research chemicals, e.g. as tool compounds.

Thus, as a further embodiment, the present invention provides the use of a compound of formula (I) or a salt thereof in therapy. In a further embodiment, the therapy is selected from a disease which may be treated by modulating full length SMN protein production. In another embodiment, the disease is selected from the afore-mentioned list, suitably spinal muscular atrophy.

In another embodiment, the invention provides a method of treating a disease which is treated by modulating full length SMN protein production comprising administration of a therapeutically acceptable amount of a compound of formula (I) or salt thereof to a patient in need of such therapy. In a further embodiment, the disease is selected from the afore-mentioned list, suitably spinal muscular atrophy.

Thus, as a further embodiment, the present invention provides the use of a compound of formula (I) or salt thereof for the manufacture of a medicament. In a further embodiment, the medicament is for treatment of a disease which may be treated by modulation of SMN protein production. In another embodiment, the disease is selected from the afore-mentioned list, suitably spinal muscular atrophy.

The pharmaceutical composition or combination of the present invention can be in unit dosage of about 0.01-1000 mg of active ingredient(s) for a subject of about 0.05-70 kg or about 1-20 kg, or about 1-500 mg or about 1-250 mg or about 1-150 mg or about 0.5-100 mg, or about 0.01-1 mg or about 0.01-0.1 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a spinal muscular atrophy. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Preparations of Compounds

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1999), 3rd Ed., Wiley. The protecting group may also be a polymer resin, such as a Wang resin or a 2-chlorotrityl-chloride resin.

It will also be appreciated by those skilled in the art, although such protected derivatives of compounds of this invention may not possess pharmacological activity as such, they may be administered to a subject and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this invention. A, B, X, R, $R^1$, $R^2$, $R^3$, $R^4$, are defined as in the Specification unless specifically defined.

In general, pyridazine compounds of Formula (I) of this invention can be synthesized following the general procedure described in Scheme 1.

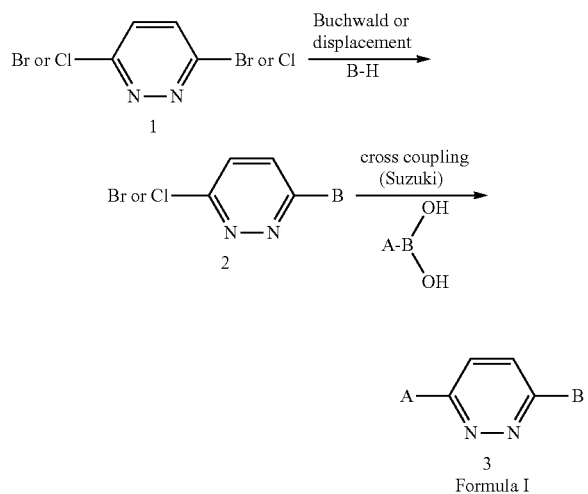

The starting materials for the above reaction scheme are commercially available or can be prepared according to methods known to one skilled in the art or by methods disclosed herein. In general, the compounds of the invention are prepared in the above reaction Scheme 1 as follows:

Di-halopyridazine (1) reacts in a displacement reaction or a metal-mediated cross coupling reaction (Buchwald) with an alcohol or an amine (B) to provide pyridazine intermediate (2). Transition metal-mediated cross coupling reaction, such as a Suzuki reaction, between halide compound (2) and a substituted aryl or heteroaryl compound A, such as a boronate acid or boronate ester, provides compound (3) of Formula (I) of the invention.

In a complementary manner, compounds of Formula (I) can be synthesized following the general procedure described in Scheme 2.

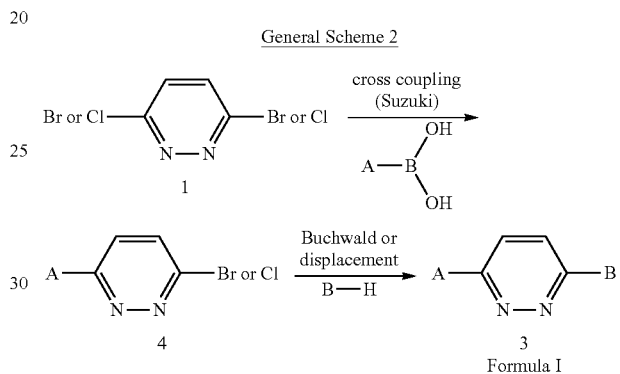

The starting materials for the above reaction scheme are commercially available or can be prepared according to methods known to one skilled in the art or by methods disclosed herein. In general, the compounds of the invention are prepared in the above reaction Scheme 2 as follows:

Di-halopyridazine (1) reacts in a transition metal-mediated cross coupling reaction, such as a Suzuki reaction, with a substituted aryl or heteroaryl compound A, such as a boronate acid or ester, to provide pyridazine intermediate (4). Pyridazine intermediate (4) reacts via a displacement reaction with an alcohol or an amine (B) to provide pyridazine (3) of Formula (I) of the invention.

Compounds of Formula (I) can also be prepared following the general procedure described in Scheme 3.

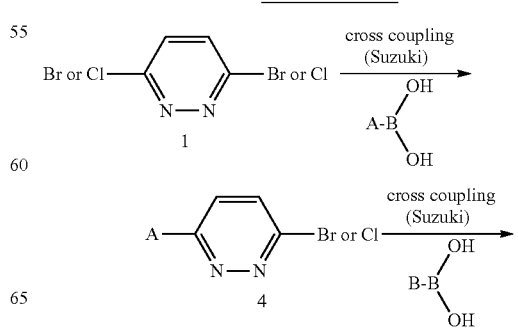

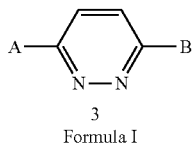

Formula I

The starting materials for the above reaction scheme are commercially available or can be prepared according to methods known to one skilled in the art or by methods disclosed herein. In general, the compounds of the invention are prepared in the above reaction Scheme 3 as follows:

Di-halopyridazine (1) reacts in a transition metal-mediated cross coupling reaction, such as a Suzuki reaction, with a substituted aryl or heteroaryl compound A, such as a boronate acid or ester, to provide pyridazine intermediate (4). Pyridazine intermediate (4) reacts via second metal-mediated cross coupling, such as a Suzuki reaction, to provide pyridazine (3) of Formula (I) of the invention.

General Schemes 1, 2 and 3 can be followed for a variety of aromatic A groups such as substituted phenols, naphthyls, heteroaryls, and the like, and for a variety of amine or alcohol B groups such as substituted aminopiperdines, piperazines, homopiperazines, 4-hydroxy piperidines, and the like, to provide compounds of Formula (I) of the invention. Routine protecting group strategies may be required to achieve final compounds of Formula (I).

All starting materials, building blocks, reagents, acids, bases, dehydrating agents, solvents, catalysts and scavengers utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., LCMS, NMR, CHN. Abbreviations used are those conventional in the art, a list of which is provided at the end of the experimental section.

Preparation 1

Intermediate 1-1: Synthesis of 6-chloro-N-methyl-N-(2,2,6,6-tetramethylpiperidin-4-yl)pyridazin-3-amine

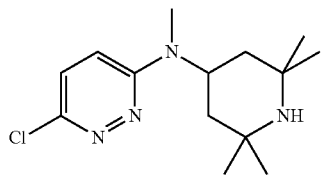 [SMILES: CN(c1ccc(Cl)nn1)C1CC(C)(C)NC(C)(C)C1]

To 3,6-dichloropyridazine (4 g, 26.8 mmol) and N,2,2,6,6-pentamethylpiperidin-4-amine (7.32 g, 43.0 mmol) in a 300 mL round bottom flask was added butan-1-ol (67 mL) to give a colorless solution. The mixture was heated to 120° C. for 72 h. Butan-1-ol was removed using a rotary evaporator. The residue was partitioned between water and DCM, and the water layer was further extracted with DCM. The combined organic layers were washed with water and brine, dried over MgSO$_4$, and concentrated in vacuo. The black crude material was stirred in small amount of EtOAc overnight, and the resulting off-white solid was collected to provide 6-chloro-N-methyl-N-(2,2,6,6-tetramethylpiperidin-4-yl)pyridazin-3-amine, Intermediate 1-1 (4.18 g, 14.78 mmol, 55.0% yield). LCMS Rt=0.8 min (condition B), MS (M+1)=283.5. $^1$H NMR (400 MHz, METHANOL-d4) δ ppm 7.40 (d, J=9.60 Hz, 1H), 7.14 (d, J=9.60 Hz, 1H), 4.96-5.13 (m, 1H), 2.93 (s, 3H), 1.59-1.68 (m, 2H), 1.51 (t, J=12.38 Hz, 2H), 1.20 (s, 6H), 1.33 (s, 6H).

Preparation 2

Intermediate 1-2: Synthesis of 6-chloro-N-(2,2,6,6-tetramethylpiperidin-4-yl)pyridazin-3-amine

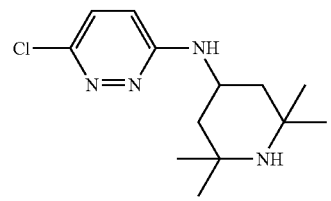 [SMILES: CC1(C)CC(Nc2ccc(Cl)nn2)CC(C)(C)N1]

A mixture of 3,6-dichloropyridazine (6.26 g, 42 mmol) and 2,2,6,6-tetramethylpiperidin-4-amine (14.7 mL, 84 mmol) was stirred at 120° C. for 1 h, neat. To this crude mixture was added n-butanol (40 mL), and the reaction was stirred at 120° C. for 1 h. The crude reaction mixture was cooled to room temperature and diluted in water and CH$_2$Cl$_2$. The organic layer was dried over MgSO$_4$, filtered, and concentrated. The crude material was recrystallized from CH$_3$CN to give 6-chloro-N-(2,2,6,6-tetramethylpiperidin-4-yl)pyridazin-3-amine, Intermediate 1-2 (7.3 g) as an off-white solid. LCMS Rt=1.10 min (condition B), MS (M+1)=269.2. $^1$H NMR (400 MHz, CHLOROFORM-d) δ ppm 7.08 (d, J=9.3 Hz, 1H), 6.54 (d, J=9.3 Hz, 1H), 4.53 (d, J=7.6 Hz, 1H), 4.05-4.26 (m, 1H), 1.98 (dd, J=12.6, 3.8 Hz, 2H), 1.22 (s, 6H), 1.08 (s, 6H), 0.93 (apparent t, J=12.1 Hz, 2H).

Preparation 3

Intermediate 1-3: Synthesis of 3-chloro-6-(2,2,6,6-tetramethylpiperidin-4-yloxy)pyridazine

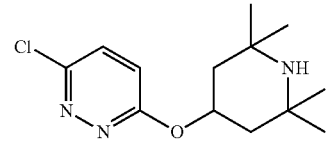 [SMILES: CC1(C)CC(Oc2ccc(Cl)nn2)CC(C)(C)N1]

To a solution of 2,2,6,6-tetramethylpiperidin-4-ol (106 mg, 0.67 mmol) in DMF (6.7 mL) was added 60% wt NaH (35 mg, 0.87 mmol). The solution was stirred at RT for 30 min, then 3,6-dichloropyridazine (100 mg, 0.67 mmol) was added and the reaction was stirred for 1 h. The crude reaction mixture was diluted in EtOAc. The organic layer was washed with water (5×), brine, dried over Na₂SO₄, filtered and concentrated under reduced pressure to give 3-chloro-6-(2,2,6,6-tetramethylpiperidin-4-yloxy)pyridazine, intermediate 1-3 (135 mg). The crude material used without further purification. LCMS Rt=1.22 min (condition B); MS (M+1)=270.2. ¹H NMR (400 MHz, CHLOROFORM-d) δ ppm 7.53 (s, 1H), 7.37 (d, J=9.1 Hz, 1H), 6.91 (d, J=9.1 Hz, 1H), 5.68-5.78 (m, 1H), 2.20 (dd, J=12.4, 4.0 Hz, 2H), 1.32 (s, 6H), 1.27-1.29 (m, 2H), 1.20 (s, 6H).

Preparation 4

Intermediate 1-4: Synthesis of 6-chloro-N-methyl-N-(1,2,2,6,6-pentamethylpiperidin-4-yl)pyridazin-3-amine

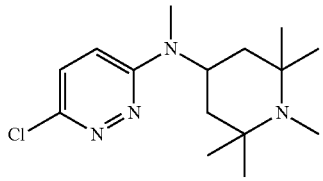 [SMILES: CN(c1ccc(Cl)nn1)C1CC(C)(C)N(C)C(C)(C)C1]

To a suspension of 6-chloro-N-(1,2,2,6,6-pentamethylpiperidin-4-yl)pyridazin-3-amine, Intermediate 1-5, (4.0 g, 14.1 mmol) in DMF (140 mL) cooled to 0° C. was added 60% wt NaH (735 mg, 18.39 mmol) portionwise. The reaction was warmed to RT and stirred for 60 minutes. After 60 minutes methyl iodide (0.88 mL, 14.1 mmol) was added and the reaction was stirred an additional 3 h, then slowly quenched with water at room temperature. The crude reaction mixture was diluted in EtOAc. The organic layer was washed with water (5×), brine, dried over MgSO₄, filtered and concentrated under reduced pressure to give 6-chloro-N-methyl-N-(1,2,2,6,6-pentamethylpiperidin-4-yl)pyridazin-3-amine, Intermediate 1-4 (3.98 g). The crude material was carried on without further purification. LCMS Rt=1.16 min (condition B), MS (M+1)=297.0. ¹H NMR (400 MHz, CHLOROFORM-d) δ ppm 7.10 (d, J=9.6 Hz, 1H), 6.69 (d, J=9.6 Hz, 1H), 4.79-5.00 (m, 1H), 2.86 (s, 3H), 2.22 (s, 3H), 1.61-1.73 (m, 2H), 1.48-1.57 (m, 2H), 1.14 (s, 6H), 1.10 (s, 6H).

Intermediate 1-5: Synthesis of 6-chloro-N-(1,2,2,6,6-pentamethylpiperidin-4-yl)pyridazin-3-amine

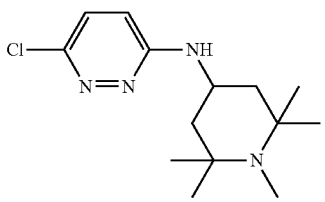 [SMILES: CN1C(C)(C)CC(Nc2ccc(Cl)nn2)CC1(C)C]

This material was prepared in two batches.

Batch 1: A mixture of 1,2,2,6,6-pentamethylpiperidin-4-amine (15.1 g, 89.0 mmol) and 3,6-dichloropyridazine (6.6 g, 44.3 mmol) was heated neat at 120° C. for 30 min. The crude material solidified and was re-suspended in n-butanol (45 mL). The crude mixture was stirred at 120° C. for an additional 2 h, then heated to 160° C. for 1 h, then cooled, and combined with batch 2 for workup.

Batch 2: A mixture of 1,2,2,6,6-pentamethylpiperidin-4-amine (14.2 g, 83 mmol) and 3,6-dichloropyridazine (6.2 g, 41.6 mmol) in n-butanol (10 mL) was heated at 120° C. for 120 min. The crude material solidified and was re-suspended in n-butanol (15 mL) and heated at 120° C. for 1 h. This crude material was combined with batch 1 for workup and purification. Water and CH₂Cl₂ were added to the combined crude material and the organic layer was separated, washed with water and brine, dried over MgSO₄, filtered and concentrated. The crude material was recyrstallized from CH₃CN (400 mL) to give 6-chloro-N-(1,2,2,6,6-pentamethylpiperidin-4-yl)pyridazin-3-amine, Intermediate 1-5 (15.5 g, first crop). Recrystalization was repeated using CH₃CN to give a 2nd crop of 6-chloro-N-(1,2,2,6,6-pentamethylpiperidin-4-yl)pyridazin-3-amine Intermediate 1-5 (3.98 g). LCMS Rt=1.10 min (condition B); MS (M+1)=283.0. ¹H NMR (400 MHz, CHLOROFORM-d) δ ppm 7.15 (d, J=9.3 Hz, 1H), 6.65 (d, J=9.3 Hz, 1H), 4.70 (d, J=7.3 Hz, 1H), 4.08-4.26 (m, 1H), 2.31 (s, 3H), 1.89-2.09 (m, 2H), 1.42 (apparent t, J=12.1 Hz, 2H), 1.21 (s, 6H), 1.15 (s, 6H).

Preparation 5

Intermediate 2-1: Synthesis of 3-chloro-6-(2-methoxy-4-(1H-pyrazol-1-yl)phenyl)pyridazine

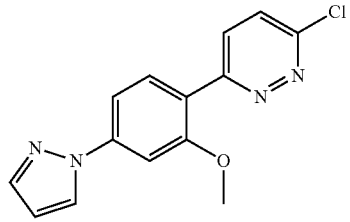 [SMILES: COc1cc(-n2cccn2)ccc1-c1ccc(Cl)nn1]

Step 1: (4-Bromo-3-methoxyphenyl)hydrazine

4-Bromo-3-methoxyaniline (3.0 g, 14.85 mmol) was suspended in concentrated HCl (50 mL) and the mixture was cooled to 0° C. in the ice-water bath. A solution of sodium nitrite (1.23 g, 17.82 mmol) in 10 mL water was added very slowly to the reaction mixture. The mixture turned yellow, then brown with a yellow haze indicating diazotization. The diazonium salt was held at 0° C. for an hour and then a solution of tin(II) chloride dihydrate (10.05 g, 44.5 mmol) in concentrated HCl (20 mL) was added very slowly (caution, extremely exothermic). The reaction was stirred for 2 h at 0° C. then at RT overnight. The reaction was filtered and the filter cake was washed with cold H₂O to afford (4-bromo-3-methoxyphenyl)hydrazine as a tan solid (3.1 g, MS: 218 [M+H⁺]).

Step 2: 1-(4-Bromo-3-methoxyphenyl)-1H-pyrazole

To a solution of (4-bromo-3-methoxyphenyl)hydrazine (62 g, 245 mmol) in ethanol (310 mL) was added tetramethoxypropane (40.2 g, 245 mmol) over a few minutes, and the mixture was heated to an internal temperature of 70° C. The mixture was stirred at 70° C. for 1.5 h then slowly cooled to RT. Ethanol was removed in vacuo and the residue was slurried in EtOAc. The residue was neutralized with 1 M aqueous sodium hydroxide (~700 mL) to cause precipitation. The biphasic mixture was filtered and the filtrate was extracted with EtOAC, dried over sodium sulfate and concentrated to provide 30 g of 1-(4-bromo-3-methoxyphenyl)-1H-pyrazole as a black solid (30 g, MS: 254 [M+H$^+$].).

Step 3: 1-(3-Methoxy-4-(4,4,5,5-tetramethyl-1,3,2-dioxaborolan-2-yl)phenyl)-1H-pyrazole 1-(4-bromo-3-methoxyphenyl)-1H-pyrazole (28.5 g, 113 mmol), bis(pinacolato)diboron (42.9 g, 169 mmol), potassium carbonate (15.56 g, 113 mmol), and PdCl$_2$(dppf).CH$_2$Cl$_2$ adduct (9.20 g, 11.26 mmol) were added to a 2 L round bottom flask, followed by addition of dioxane (700 mL). The reaction mixture was purged by N$_2$ and stirred under N$_2$ at an internal temp of 84° C. overnight. The reaction mixture was filtered through a disposable filter funnel and concentrated onto silica gel. The mixture was purified using column chromotagraphy (20% EtOAc in heptanes). The desired fractions were collected and concentrated to provide 13.5 g of 1-(3-methoxy-4-(4,4,5,5-tetramethyl-1,3,2-dioxaborolan-2-yl)phenyl)-1H-pyrazole.

Step 4: 3-chloro-6-(2-methoxy-4-(1H-pyrazol-1-yl)phenyl)pyridazine 3,6-Dichloropyridizine (11.99 g, 80 mmol), 1-(3-methoxy-4-(4,4,5,5-tetramethyl-1,3,2-dioxaborolan-2-yl)phenyl)-1H-pyrazole (16.1 g, 53.6 mmol), sodium carbonate (17.06 g, 161 mmol), and 1,1'-bis(diphenylphosphino)ferrocene palladium dichloride dichloromethane adduct (3.07 g, 3.75 mmol) were charged to a 3-neck 250 mL round bottom flask fitted with a magnetic stir bar and nitrogen inlet. 1,4-Dioxane (274 mL) and deionized water (46 mL) were added and the reaction mixture was evacuated and backfilled with nitrogen three times. The reaction mixture was heated in a teflon heating block to 85° C. for 16 h. After removing the 1,4-dioxane in vacuo, the residue was slurried in ethyl acetate and filtered through a celite-packed glass fritted funnel. The filtrate was concentrated onto silica gel and purified on a 330 g Silica gel column, eluting with 10-35% ethyl acetate in heptanes. The product-containing fractions were concentrated down to 10% volume, slurried in 3:1 ethyl acetate:heptanes (100 mL), stirred at RT for 1 h, and then filtered to provide 7 g (46%) of 3-chloro-6-(2-methoxy-4-(1H-pyrazol-1-yl)phenyl)pyridazine as a solid. $^1$H NMR (600 MHz, CHLOROFORM-d) δ 8.12 (dd, J=8.80, 11.30 Hz, 2H), 8.05 (d, J=1.88 Hz, 1H), 7.80 (s, 1H), 7.61 (d, J=1.25 Hz, 1H), 7.54 (d, J=9.03 Hz, 1H), 7.35 (dd, J=1.44, 8.22 Hz, 1H), 6.55 (s, 1H), 4.00 (s, 3H).

Preparation 6

Intermediate 2-2: Synthesis of 2-(6-chloropyridazin-3-yl)-5-(1H-pyrazol-1-yl)phenol

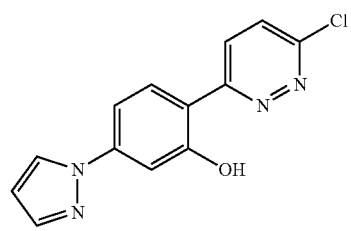 [SMILES: Oc1cc(-n2cccn2)ccc1-c1ccc(Cl)nn1]

BCl$_3$ (1 M in DCM, 91 mL, 91 mmol) was added to a solution of 3-chloro-6-(2-methoxy-4-(1H-pyrazol-1-yl)phenyl)pyridazine (Intermediate 2-1, 8.6 g, 30 mmol) in DCM (150 mL) at 0° C. and the reaction was stirred for 5 h at RT. MeOH (50 mL) was added to the reaction at 0° C., then the reaction was warmed to RT and the solvent was evaporated under reduced pressure. The crude material was treated with hot CH$_3$CN then cooled to 5° C. The mixture was filtered and 2-(6-chloropyridazin-3-yl)-5-(1H-pyrazol-1-yl)phenol Intermediate 2-2 (7.6 g, 86%) was afforded as yellow solid. MS [M+H]: 273.2; $^1$H NMR (400 MHz, DMSO-d6) δ 11.95 (s, 1H), 8.59 (d, J=2.0 Hz, 1H), 8.49 (d, J=9.0 Hz, 1H), 8.09 (d, J=8.5 Hz, 1H), 8.04 (d, J=9.0 Hz, 1H), 7.80 (d, J=2.0 Hz, 1H), 7.56 (d, J=2.0 Hz, 1H), 7.51 (dd, J=8.5, 2.0 Hz, 1H), 6.59 (t, J=2.0 Hz, 1H).

Preparation 7

Intermediate 3-1: Synthesis of 7-(benzyloxy)-6-(4,4,5,5-tetramethyl-1,3,2-dioxaborolan-2-yl)naphthalen-2-ol

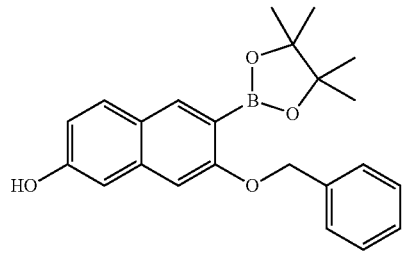 [SMILES: CC1(C)OB(c2cc3ccc(O)cc3cc2OCc2ccccc2)OC1(C)C]

Bis(pinacolato)diboron (3.13 g, 12.33 mmol), KOAc (3.63 g, 37.0 mmol), and PdCl$_2$(dppf).CH$_2$Cl$_2$ adduct (0.504 g, 0.617 mmol) were added to a 250 mL flask containing 7-(benzyloxy)-6-bromonaphthalen-2-ol (2.03 g, 6.17 mmol). DMSO (30.8 mL) was then added, and a reflux condenser attached. The reaction mixture was evacuated then filled with N$_2$ (2x), then heated at 100° C. overnight. The reaction mixture was cooled to room temperature, filtered through celite (pre-packed filter funnel) using EtOAc, and concentrated in vacuo to a crude oil. Flash chromatography, eluting with 5-30% EtOAc/heptane, afforded the product, 7-(benzyloxy)-6-(4,4,5,5-tetramethyl-1,3,2-dioxaborolan-2-yl)naphthalen-2-ol, (58% yield) as a colorless oil. LCMS Rt=1.72 min (condition C), MS (M+1)= 377.6. $^1$H NMR (400 MHz, METHANOL-d4) δ ppm 8.07 (s, 1H), 7.68 (t, J=8.91 Hz, 3H), 7.36-7.43 (m, 2H), 7.28-7.34 (m, 1H), 7.09 (s, 1H), 7.02 (d, J=2.51 Hz, 1H), 6.92 (dd, J=8.78, 2.51 Hz, 1H), 5.21 (s, 2H), 1.40 (s, 12H).

Preparation 8

Intermediate 4-1: Synthesis of (6S)-6-((S)-1-(tert-Butyldimethylsilyloxy)ethyl)-2,2-dimethylpiperidin-4-ol

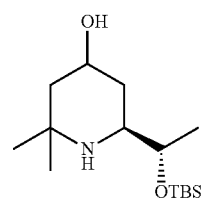 [SMILES: C[C@H](O[Si](C)(C)C(C)(C)C)[C@@H]1CC(O)CC(C)(C)N1]

Step 1. (S)-Ethyl 2-(tert-butyldimethylsilyloxy)propanoate

To a solution of (S)-ethyl lactate (11.8 g, 100 mmol) in DMF (50 mL) was added imidazole (10.2 g, 150 mmol). The mixture was cooled in an ice bath and tert-butyldimethylsilyl chloride (15.8 g, 105 mmol) was added in three portions, at intervals of 30 min between each addition. The reaction mixture was stirred overnight. The reaction mixture was diluted with water (30 mL) and extracted with Et$_2$O (50 mL×2). The combined extracts were washed with brine, dried over MgSO$_4$ and concentrated in vacuo. The residue was distilled under vacuum (bp 70-78° C., 0.5 mmHg) to afford 22.07 g (95%) of (S)-ethyl 2-(tert-butyldimethylsilyloxy)propanoate: $^1$H NMR (400 MHz, CHLOROFORM-d) δ 4.32 (q, J=6.6 Hz, 1H), 4.11-4.25 (m, 2H), 1.40 (d, J=6.6 Hz, 3H), 1.29 (t, J=7.1 Hz, 3H), 0.93 (s, 9H), 0.12 (s, 3H), 0.09 (s, 3H).

Step 2. (S)-2-(tert-Butyldimethylsilyloxy)propanal

To a solution of (S)-ethyl 2-(tert-butyldimethylsilyloxy)propanoate (6.3 g, 27.1 mmol) in CH$_2$Cl$_2$ (22 mL) was added 54.2 mL of DIBAL (1.0 M in CH$_2$Cl$_2$, 54.2 mmol) over 20 min at −78° C. After stirring for 2 h at −78° C., methanol (3 mL) was added to the solution at the same temperature. The mixture was allowed to warm to RT and saturated aqueous potassium sodium tartrate (60 mL) was added to the solution. The resulting mixture was vigorously stirred for 3 h. The mixture was extracted with dichloromethane (30 mL×2), and the combined extracts were washed with brine (20 mL), dried over sodium sulfate, and concentrated in vacuo. The residue was distilled under vacuum (bp 50-52° C., 0.5 mmHg) to afford 2.5 g (49%) of (S)-2-(tert-butyldimethylsilyloxy)propanal: $^1$H NMR (400 MHz, CHLOROFORM-d) δ 9.59 (d, J=1.3 Hz, 1H), 4.07 (dq, J=6.9, 1.3 Hz, 1H), 1.26 (d, J=6.9 Hz, 3H), 0.93 (s, 9H), 0.08 (s, 3H), 0.07 (s, 3H).

Step 3. (S,E)-N-(2-(tert-Butyldimethylsilyloxy)propylidene)-1-(4-methoxyphenyl) methanamine To a solution of (S)-2-(tert-butyldimethylsilyloxy)propanal (2.07 g, 11.0 mmol) in dichloromethane (60 mL) was added (4-methoxyphenyl)methanamine (1.51 g, 11.0 mmol) and MgSO$_4$ (3.97 g, 33.0 mmol). After stirring overnight, the mixture was filtered through the celite and washed with dichloromethane. The solvent was removed under reduced pressure whereuopon 3.38 g (100%) of (S,E)-N-(2-(tert-butyldimethylsilyloxy)propylidene)-1-(4-methoxyphenyl) methanamine was obtained as a pale yellow oil which was used in the next step without purification: $^1$H NMR (400 MHz, CHLOROFORM-d) δ 7.56 (d, J=5.1 Hz, 1H), 7.09 (d, J=8.6 Hz, 2H), 6.80 (d, J=8.6 Hz, 2H), 4.44 (s, 2H), 4.24-4.34 (m, 1H), 3.73 (s, 3H), 1.23 (d, J=6.6 Hz, 3H), 0.82 (s, 9H), 0.00 (s, 3H), −0.02 (s, 3H).

Step 4. (S)-6-((S)-1-Hydroxyethyl)-1-(4-methoxybenzyl)-2, 2-dimethylpiperidin-4-one To a solution of (S,E)-N-(2-(tert-butyldimethylsilyloxy)propylidene)-1-(4-methoxyphenyl)methanamine (3.38 g, 11 mmol) in dichloromethane (90 mL) was added TMSOTf (2.2 mL, 12.1 mmol) and tert-butyldimethyl(4-methylpenta-1,3-dien-2-yloxy)silane (9.35 g, 44 mmol) at 0° C. After stirring for 2 days at 0° C., the reaction mixture was poured into aq. NaHCO$_3$ solution (100 mL), followed by extraction with dichloromethane (100 mL×2). The combined organic layers were dried over MgSO$_4$, and the solvent was evaporated. The residue was dissolved in THF (60 mL) and then 41.8 mL of TBAF (1 M in THF, 41.8 mmol) was added to the solution. The mixture was stirred for 12 h, quenched with water (100 mL), extracted with dichloromethane (100 mL×2), and the combined extracts were dried over Na$_2$SO$_4$. After the solvent was concentrated in vacuo, the product was purified by column chromatography (Et2O/Heptane) to give 1.3 g (41%) of (S)-6-((S)-1-hydroxyethyl)-1-(4-methoxybenzyl)-2,2-dimethylpiperidin-4-one and 1.0 g (31%) of (R)-6-((S)-1-hydroxyethyl)-1-(4-methoxybenzyl)-2,2-dimethylpiperidin-4-one.

(S)-6-((S)-1-hydroxyethyl)-1-(4-methoxybenzyl)-2, 2-dimethylpiperidin-4-one

LCMS (m/z, MH$^+$): 292.4; $^1$H NMR (400 MHz, CHLOROFORM-d) δ 7.13 (d, J=8.6 Hz, 2H), 6.74 (d, J=8.6 Hz, 2H), 3.84 (d, J=15.2 Hz, 1H), 3.63-3.70 (m, 1H), 3.65 (s, 3H), 3.56 (d, J=15.2 Hz, 1H), 3.36 (qd, J=8.5, 5.9 Hz, 1H), 2.93 (dt, J=8.2, 4.8 Hz, 1H), 2.40 (d, J=15.2 Hz, 1H), 2.29-2.36 (m, 1H), 2.08-2.17 (m, 2H), 1.17 (s, 3H), 1.14 (s, 3H), 0.81 (d, J=6.1 Hz, 3H).

(R)-6-((S)-1-hydroxyethyl)-1-(4-methoxybenzyl)-2, 2-dimethylpiperidin-4-one

LCMS (m/z, MH$^+$): 292.4; $^1$H NMR (400 MHz, CHLOROFORM-d) δ 7.30 (d, J=8.1 Hz, 2H), 6.84 (d, J=8.1 Hz, 2H), 4.09 (d, J=16.7 Hz, 1H), 3.82-3.92 (m, 1H), 3.74 (s, 3H), 3.26 (d, J=16.7 Hz, 1H), 2.71-2.78 (m, 1H), 2.55-2.66 (m, 2H), 2.23 (ddd, J=14.7, 4.5, 2.5 Hz, 1H), 2.15 (dd, J=13.6, 2.5 Hz, 1H), 1.70 (br., s, 1H), 1.29 (s, 3H), 1.00 (s, 3H), 0.89 (d, J=6.6 Hz, 3H).

Step 5. (S)-6-((S)-1-Hydroxyethyl)-2, 2-dimethylpiperidin-4-one

To a solution of (S)-6-((S)-1-hydroxyethyl)-1-(4-methoxybenzyl)-2,2-dimethylpiperidin-4-one (0.28 g, 0.96 mmol) in MeOH (40 mL) was added acetic acid (0.055 mL, 0.96 mmol) and palladium hydroxide (0.13 g, 0.96 mmol). After degassing, the mixture was stirred overnight under hydrogen.

The mixture was filtered through the celite, washed with MeOH (20 mL), and concentrated in vacuo to give 0.11 g (67%) of (S)-6-((S)-1-hydroxyethyl)-2,2-dimethylpiperidin-4-one which was used in the next step without purification.

Step 6. (S)-6-((S)-1-(tert-Butyldimethylsilyloxy) ethyl)-2,2-dimethylpiperidin-4-one To a solution of (S)-6-((S)-1-hydroxyethyl)-2,2-dimethylpiperidin-4-one (0.11 g, 0.64 mmol) in DMF (3 mL) were added imidazole (0.13 g, 1.93 mmol) and TBSCl (0.14 g, 0.96 mmol). The mixture was stirred overnight. The reaction mixture was diluted with water (10 mL) and extracted with EtOAc (20 mL). The extract was washed with brine, dried over Na$_2$SO$_4$, and concentrated in vacuo. The residue was purified by column chromatography (EtOAc/Heptane) to afford 65 mg (35%) of (S)-6-((S)-1-(tert-butyldimethylsilyloxy)ethyl)-2,2-dimethylpiperidin-4-one: $^1$H NMR (400 MHz, CHLOROFORM-d) δ 3.99 (dq, J=6.3, 2.8 Hz, 1H), 2.96-3.04 (m, 1H), 2.21-2.32 (m, 3H), 2.13 (d, J=13.1 Hz, 1H), 1.26 (s, 3H), 1.12 (d, J=6.1 Hz, 3H), 1.05 (s, 3H), 0.91 (s, 9H), 0.12 (s, 3H), 0.09 (s, 3H).

Step 7. (6S)-6-((S)-1-(tert-Butyldimethylsilyloxy) ethyl)-2,2-dimethylpiperidin-4-ol To a solution of (S)-6-((S)-1-(tert-butyldimethylsilyloxy) ethyl)-2,2-dimethylpiperidin-4-one (42 mg, 0.15 mmol) in MeOH (3 mL) was added NaBH$_4$ (5.6 mg, 0.15 mmol) at 0° C. After the mixture was stirred for 1 h, the mixture was diluted with water (5 mL) and extracted with EtOAc (20 mL). The extract was washed with brine, dried over Na$_2$SO$_4$, and concentrated in vacuo. Purification by column chromatography (EtOAc/Heptane) gave 32 mg (76%) of (6S)-6-((S)-1-(tert-butyldimethylsilyloxy)ethyl)-2,2-dimethylpiperidin-4-ol (a 5:1 mixture of diastereomers): $^1$H NMR (400 MHz, CHLOROFORM-d) δ 4.17-4.27 (m, 1H), 3.71-3.78 (m, 1H), 2.92-3.02 (m, 1H), 1.56-1.67 (m, 2H), 1.30-1.37 (m, 2H), 1.25 (s, 3H), 1.07 (d, J=6.1 Hz, 3H), 1.02 (s, 3H), 0.83 (s, 9H), 0.01 (s, 3H), 0.00 (s, 3H).

General Method 1-1

Representative Procedure for Suzuki Cross-Coupling (Conventional Heating)

The boronic ester (2 equivalents), Na$_2$CO$_3$ (3 equivalents), and Pd(PPh$_3$)$_4$ (0.1 equivalents) were added to a vial containing the chloropyridazine (1 equivalent). DME (0.2 M) and H$_2$O (0.8 M) were added and the reaction mixture was evacuated, and filled with N$_2$ (2×). The reaction was heated at 90° C. for 18 h, cooled to RT, then filtered through celite (pre-packed funnel) with a MeOH wash. The filtrate was acidified to pH 3 using 1 M HCl, then adsorbed onto a MeOH conditioned SCX column. The column was washed several times (5-7 column volumes) with MeOH, then eluted with 2 N NH$_3$ in MeOH. The residue was purified by silica gel chromatography to provide the desired product.

General Method 1-2

Representative Procedure for Suzuki Coupling

SiliaCat® DPP-Pd (0.05 equivalents) was added to a microwave vial containing a mixture of the chloropyridazine intermediate, such as 1-1, (1 equivalent), boronic acid (1.6 equivalents), and Na$_2$CO$_3$ (3 equivalents) in wet EtOH (0.2 M). The reaction mixture was sealed, then heated via microwave irradiation at 130° C. for 35 min. The reaction mixture was filtered through a small celite plug with a MeOH/DCM wash, then concentrated to dryness in vacuo. The resulting brown residue was partitioned between 5% MeOH/DCM and sat. aq. NaHCO$_3$ solution. After separation, the aqueous layer was extracted with 5% MeOH/DCM. The combined organic layers were washed with brine, dried over MgSO$_4$, filtered, and concentrated to dryness in vacuo. The resulting residue was dissolved in MeOH then adsorbed onto a MeOH conditioned SCX column. The column was washed several times with MeOH then eluted with 3 N NH$_3$/MeOH. Evaporation of the solvent afforded a the crude product. The crude product was dissolved in MeOH/DCM then 3 g of Siliabond® DMT (palladium scavenger) was added and the mixture was stirred at RT for 1 h. The mixture was filtered then concentrated to dryness in vacuo affording the desired product.

General Method 1-3

Representative procedure for Suzuki Coupling

Chloropyridazine intermediate, such as 1-1, (1 equivalent), boronic acid reagent (2 equivalents), and Na$_2$CO$_3$ (3 equivalents) were added to a microwave vial. Pd(PPh$_3$)$_4$ (0.1 equivalents) was then added to the reaction mixture followed by addition of DME (0.2 M) and H$_2$O (0.8 M). The reaction mixture was sealed, then evacuated and filled with N$_2$ (2×), and heated via microwave irradiation at 125° C. for 30 min. The reaction mixture was filtered through celite and washed with DCM. The resulting filtrate was washed with 1 M aq. Na$_2$CO$_3$ solution. The organic layer was dried over MgSO$_4$, filtered, and concentrated to afford the crude product. The crude product was purified by flash chromatography affording the product as an off-white solid.

General Method 1-4

Representative procedure for Suzuki Coupling

Boronic ester (0.36 mmol), pyridazine intermediate (0.36 mmol), Na$_2$CO$_3$ (1.08 mmol), DME (0.58 mL), and H$_2$O (0.14 mL) were added to a 5 mL microwave vial. The vial was degassed for 5 min with N$_2$, then PdCl$_2$(dppf)CH$_2$Cl$_2$ adduct (29.4 mg, 0.04 mmol) was added. The reaction mixture was heated via microwave irradiation at 120° C. for 45 min. The crude mixture was diluted with EtOAc and filtered through celite, then concentrated in vacuo. Flash chromatography, eluting with 0-100% EtOAc/heptane, afforded the product.

General Method 2-1

Representative Procedure for Boronate Ester Formation.

Bis(pinacolato) diboron (12.3 mmol), KOAc (37.0 mmol), and PdCl$_2$(dppf).CH$_2$Cl$_2$ (0.617 mmol) were added to a 250 mL round bottom flask containing an aryl bromide (6.17 mmol). DMSO (31 mL) was then added, and reflux condenser attached. The reaction mixture was evacuated then filled with N$_2$ (2×), then heated at 100° C. overnight. The reaction mixture was cooled to RT, then filtered through celite (pre-packed filter funnel) using EtOAc, and concentrated in vacuo to a crude oil. Flash chromatography, eluting with 5-30% EtOAc/heptane, afforded the product.

General Method 3-1

Representative Procedure for Methoxy Deprotection (Thiophenol)

Thiophenol (1 equivalent) and potassium carbonate (1 equivalent) were added to the methoxy substrate in NMP (0.2 M) and the reaction was stirred at 190° C. for 15 min in a Biotage® Initiator microwave reactor. The reaction mixture was purified by catch and release using SiliaBond Propylsulfonic Acid® (2 g, MeOH as eluent and a 2 N ammonia solution in MeOH to release the material). After evaporation, the material was purified via reverse phase HPLC.

General Method 3-2

Representative Procedure for Methoxy Deprotection (BBr$_3$)

The methoxy substrate (1 equivalent) was dissolved in CH$_2$Cl$_2$ (0.03 M) and cooled in an ice bath. A 1 M solution of BBr$_3$ in CH$_2$Cl$_2$ (3 equivalents) was added dropwise. The crude reaction mixture as stirred at RT overnight then diluted with CH$_2$Cl$_2$ and water. The organic layer was diluted in EtOAc and washed with sat NaHCO$_3$ aq (2×), water, brine and dried over Na$_2$SO$_4$. The crude product was purified via HPLC, column chromatography or recystallization.

General Method 3-3

Representative Procedure for Methoxy Deprotection (LiI, Collidine)

To a solution of the methoxy substrate (1 equivalent) in 2,4,6 collidine (0.03 M, dried over MgSO$_4$, and filtered), was added anhydrous LiI (9 equivalents). The reaction was stirred at 170° C. for 4 hrs, then cooled and diluted with small amounts of MeOH, EtOAc and H$_2$O. The organic layer was washed with brine, dried over Na$_2$SO$_4$, filtered and concentrated under reduced pressure. The crude product was purified via HPLC.

General Method 4-1

Representative Procedure for Hydrogenolysis of Benzyl Group.

In a 25 mL round-bottomed flask, Pd/C (1.6 mg, 0.016 mmol) or Pd(OH)$_2$ (2.2 mg, 0.016 mmol) was added to the benzyl-protected substrate (75 mg, 0.155 mmol) in EtOH (1.5 mL). 1 M HCl solution (0.25 mL, 0.25 mmol) was added and the reaction vessel was evacuated. H$_2$ was bubbled through the solution for 5 min, then reaction was stirred under H$_2$ at RT. After 18 h, the reaction mixture was filtered through celite and washed with MeOH/DCM. The solvent was removed in vacuo and the crude material was dissolved in MeOH, and purified by preparative HPLC (10-30% ACN/H$_2$O with 0.1% TFA). The residue was dissolved in MeOH/DCM, acidified to ca. pH 3 using 1 M HCl then adsorbed onto a MeOH conditioned SCX column. The column was washed several times (3-4 column volumes) with MeOH then eluted with 2 N NH$_3$/MeOH. Evaporation of the solvent afforded the desired product.

General Method 4-2

Representative Procedure for Hydrogenation

To a 25 mL round-bottomed flask containing 10% Pd/C (0.026 mmol), was added the substrate (0.52 mmol) in MeOH (2.5 mL). H$_2$ was bubbled through the solution for 5 min, then reaction was stirred under H$_2$ at 55 psi at RT. After 18 h, the reaction mixture was filtered through celite and washed with MeOH. The solvent was removed in vacuo. The resulting oil was dissolved in MeOH then adsorbed onto a MeOH conditioned SCX column. The column was washed several times (5-7 column volumes) with MeOH then eluted with 2 N NH$_3$ in MeOH to provide the desired product.

General Method 5-1

Representative Procedure for Phenol Alkylation

Cs$_2$CO$_3$ (1.489 mmol) was added to a solution of the phenol (1.489 mmol) in acetone (15 mL) at RT. The reaction mixture was stirred for 5 min then the bromide (682 mg, 2.98 mmol) was added all at once, followed by addition of NaI (446 mg, 2.98 mmol). The reaction mixture was stirred at 60° C. overnight, filtered with acetone, then concentrated in vacuo. The resulting residue was partitioned between Et$_2$O (60 mL) and water (20 mL). After separation, the organic layer was washed with saturated aq. sodium sulfite solution (20 mL), 2 M Na$_2$CO$_3$, and brine. The organic layer was then dried over MgSO$_4$, filtered, and concentrated in vacuo. Flash chromatography afforded the desired product.

General Method 6-1

Representative Procedure for SnAr Reaction

Intermediate 2-2 (50 mg, 0.174 mmol), tert-butyl piperazine-1-carboxylate (59 mg, 0.314 mmol), DIPEA (0.06 mL, 0.349 mmol), and n-butanol (0.1 mL) were combined in a 4 mL reaction vial and heated to 120° C. overnight. The reaction was cooled to RT and EtOAc was added. The white solid was filtered and washed with EtOAc, dissolved in DCM and washed with H$_2$O. The organic layer was dried over sodium sulfate, filtered, and concentrated in vacuo to afford desired product. Purification by flash column or HPLC provided the desired compound.

Example 1-1

Synthesis of 6-(naphthalen-2-yl)-N-(2,2,6,6-tetramethylpiperidin-4-yl)pyridazin-3-amine

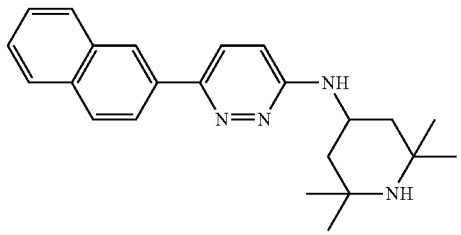 [SMILES: CC1(C)CC(Nc2ccc(-c3ccc4ccccc4c3)nn2)CC(C)(C)N1]

To a 2 mL microwave vial was added 6-chloro-N-(2,2,6,6-tetramethylpiperidin-4-yl)pyridazin-3-amine Intermediate 1-2 (100 mg, 0.37 mmol), naphthalen-2-ylboronic acid (96 mg, 0.56 mmol), Na$_2$CO$_3$ (118 mg, 1.17 mmol), water (0.25 mL), DME (1 mL), and PdCl$_2$(dppf).CH$_2$Cl$_2$ (30 mg, 0.037 mmol). The reaction vessel was sealed and heated in a microwave at 120° C. for 45 mins. The crude mixture was diluted with EtOAc, then the organic layer was washed with water, brine, dried over MgSO$_4$, filtered and concentrated. The crude product was purified via silica chromatography to give 6-(naphthalen-2-yl)-N-(2,2,6,6-tetramethylpiperdin-4-yl)pyridazin-3-amine (86 mg). LCMS Rt=1.39 min (condition B); MS (M+1)=361.3. $^1$H NMR (400 MHz, CHLOROFORM-d) δ ppm 8.30 (s, 1H), 8.12 (dd, J=8.6, 1.8 Hz, 1H), 7.86 (d, J=8.8 Hz, 1H), 7.76-7.84 (m, 2H), 7.67 (d, J=9.3 Hz, 1H), 7.37-7.48 (m, 2H), 6.69 (d, J=9.1 Hz, 1H), 4.82 (br. m, 1H), 4.31-4.51 (m, 2H), 2.07 (dd, J=12.9, 3.5 Hz, 2H), 1.35 (s, 6H), 1.22 (s, 6H).

The following compounds were prepared using similar procedures as in Example 1-1:

| Example | Compound | LCMS M + 1, Rt, conditions | $^1$H NMR 400 MHz |
|---|---|---|---|
| 1-2 | 6-(benzo[b]thio-phen-2-yl)-N-methyl-N-(2,2,6,6-tetramethylpiperidin-4-yl)pyridazin-3-amine | 381.3 0.58 min Q | CHLOROFORM-d δ ppm 7.88-7.92 (m, 1H), 7.78-7.83 (m, 1H), 7.71 (d, J = 9.6 Hz, 1H), 7.67 (s, 1H), 7.34-7.44 (m, 2H), 6.87 (d, J = 9.6 Hz, 1H), 5.06-5.34 (m, 1H), 3.05 (s, 3H), 1.74 (dd, J = 12.3, 3.2 Hz, 2H), 1.43-1.50 (m, 2H), 1.42 (s, 6H), 1.23 (s, 6H) |

| Example | Compound | LCMS M + 1, Rt, conditions | ¹H NMR 400 MHz |
|---|---|---|---|
| 1-3 | 2-(6-(2,2,6,6-tetramethylpiperidin-4-ylamino)-pyridazin-3-yl)phenol | 327.2 0.42 min Q | CHLOROFORM-d δ ppm 13.64 (br. s, 1H), 7.85 (d, J = 9.6 Hz, 1H), 7.61 (d, J = 7.6 Hz, 1H), 7.30-7.35 (m, 1H), 7.10 (d, J = 8.1 Hz, 1H), 6.90-6.99 (m, 1H), 6.84 (d, J = 9.3 Hz, 1H), 4.66 (d, J = 6.3 Hz, 1H), 4.17-4.46 (m, 1H), 2.13 (dd, J = 12.3, 3.2 Hz, 2H), 1.38 (s, 6H), 1.23 (s, 6H), 1.03-1.16 (m, 2H) |
| 1-4 | 2-(6-(methyl-(2,2,6,6-tetra-methylpiperidin-4-yl)amino)pyridazin-3-yl)benzo[b]-thio-phene-5-carbonitrile | 406.3 0.55 min Q | DMSO-d6 δ ppm 8.34 (d, J = 1.0 Hz, 1H), 8.22 (d, J = 8.3 Hz, 1H), 8.11 (d, J = 9.6 Hz, 1H), 8.06 (s, 1H), 7.72 (dd, J = 8.3, 1.8 Hz, 1H), 7.20 (d, J = 9.9 Hz, 1H), 5.05-5.23 (m, 1H), 2.95 (s, 3H), 1.51 (dd, J = 11.9, 3.5 Hz, 2H), 1.38-1.47 (m, 2H), 1.25 (s, 6H), 1.09 (s, 6H) |
| 1-5 | 6-(quinolin-3-yl)-N-(2,2,6,6-tetramethyl-piperidin-4-yl)pyridazin-3-amine | 362.2 0.41 min Q | CHLOROFORM-d δ ppm 9.59 (d, J = 2.3 Hz, 1H), 8.74 (d, J = 2.0 Hz, 1H), 8.18 (d, J = 8.3 Hz, 1H), 7.94 (d, J = 8.1 Hz, 1H), 7.72-7.83 (m, 2H), 7.57-7.65 (m, 1H), 6.79 (d, J = 9.3 Hz, 1H), 4.71 (d, J = 7.6 Hz, 1H), 4.37-4.53 (m, 1H), 2.16 (dd, J = 12.6, 3.8 Hz, 2H), 1.38 (s, 6H), 1.22 (s, 6H), 1.06-1.16 (m, 2H) |
| 1-6 | 3-benzo[b]-thiophen-2-yl)-6-(2,2,6,6-tetra-methylpiperidin-4-yloxy)pyridazine | 368.1 0.56 min Q | CHLOROFORM-d δ ppm 7.90-7.96 (m, 1H), 7.88 (d, J = 9.1 Hz, 1H), 7.81-7.86 (m, 1H), 7.79 (s, 1H), 7.33-7.47 (m, 2H), 7.01 (d, J = 9.3 Hz, 1H), 5.77-6.02 (m, 1H), 2.28 (dd, J = 12.5, 4.2 Hz, 2H), 1.39 (s, 6H), 1.31-1.38 (m, 2H), 1.27 (s, 6H) |
| 1-7 | 2-(6-(methyl-(2,2,6,6-tetra-methylpiperidin-4-yl)amino)-pyridazin-3-yl)phenol | 341.3 1.02 min B | METHANOL-d4 δ ppm 8.09 (d, J = 9.9 Hz, 1H), 7.74 (dd, J = 8.0, 1.4 Hz, 1H), 7.30 (d, J = 9.9 Hz, 1H), 7.21-7.27 (m, 1H), 6.88-6.98 (m, 2H), 4.99-5.13 (m, 1H), 3.00 (s, 3H), 1.67 (dd, J = 12.6, 3.8 Hz, 2H), 1.48-1.61 (m, 2H), 1.37 (s, 6H), 1.22 (s, 6H) |

| Example | Compound | LCMS M + 1, Rt, conditions | 1H NMR 400 MHz |
|---|---|---|---|
| 1-8 | 6-(6-(methyl-(2,2,6,6-tetra-methylpiperidin-4-yl)amino)-pyridazin-3-yl)naphthalen-2-ol | 391.0 0.48 min Q | METHANOL-d4 δ ppm 8.23 (d, J = 1.0 Hz, 1H), 8.00 (dd, J = 8.6, 1.8 Hz, 1H), 7.94 (d, J = 9.6 Hz, 1H), 7.81 (d, J = 8.6 Hz, 1H), 7.73 (d, J = 8.6 Hz, 1H), 7.18 (d, J = 9.6 Hz, 1H), 7.13 (s, 1H), 7.07-7.12 (m, 1H), 5.13-5.31 (m, 1H), 2.99 (s, 3H), 1.69 (dd, J = 12.6, 3.5 Hz, 2H), 1.52-1.62 (m, 2H), 1.39 (s, 6H), 1.23 (s, 6H) |
| 1-9 | 6-(benzo[b]-thiophen-2-yl)-N-(2,2,6,6-tetra-methylpiperidin-4-yl)pyridazin-3-amine | 367.4 0.54 min Q | CHLOROFORM-d δ ppm 7.89-7.83 (m, 1H), 7.80-7.75 (m, 1H), 7.67 (s, 1H), 7.65 (s, 1H), 7.38-7.31 (m, 2H), 6.67 (d, J = 9.60 Hz, 1H), 4.56 (d, J = 6.57 Hz, 1H), 4.48-4.36 (m, 1H), 2.13 (dd, J = 12.63, 3.54 Hz, 2H), 1.35 (s, 6H), 1.19 (s, 6H), 1.06-1.05 (m, 2H) |
| 1-10 | 7-(6-((2,2,6,6-tetramethylpiperidin-4-yl)oxy)pyridazin-3-yl)isoquinoline | 363.1 0.43 min Q | DMSO-d6 δ ppm 9.43 (s, 1H), 8.84-8.90 (m, 1H), 8.55-8.59 (m, 2H), 8.38 (d, J = 9.29 Hz, 1H), 8.12 (d, J = 8.78 Hz, 1H), 7.90 (d, J = 5.77 Hz, 1H), 7.35 (d, J = 9.29 Hz, 1H), 5.75 (tt, J = 11.26, 4.05 Hz, 1H), 2.12 (d, J = 8.78 Hz, 2H), 1.26 (br. s, 8H), 1.12 (br. s, 6H) |
| 1-11 | 6-(6-((2,2,6,6-tetramethylpiperidin-4-yl)oxy)pyridazin-3-yl)isoquinoline | 363.1 0.41 min Q | METHANOL-d4 δ ppm 9.33 (s, 1H), 8.55 (s, 1H), 8.52 (d, J = 5.77 Hz, 1H), 8.40 (dd, J = 8.66, 1.63 Hz, 1H), 8.25-8.31 (m, 2H), 7.97 (d, J = 5.77 Hz, 1H), 7.29 (d, J = 9.29 Hz, 1H), 5.85 (tt, J = 11.23, 4.20 Hz, 1H), 2.28 (dd, J = 12.80, 4.02 Hz, 2H), 1.47 (t, J = 11.92 Hz, 2H), 1.40 (s, 6H), 1.28 (s, 6H) |
| 1-12 | N-methyl-6-(quinolin-7-yl)-N-(2,2,6,6-tetramethyl-piperidin-4-yl)pyridazin-3-amine | 376.2 0.46 min Q | DMSO-d6 δ ppm 8.94 (dd, J = 4.27, 1.76 Hz, 1H), 8.58 (d, J = 0.75 Hz, 1H), 8.35-8.46 (m, 2H), 8.18 (d, J = 9.54 Hz, 1H), 8.08 (d, J = 8.53 Hz, 1H), 7.55 (dd, J = 8.28, 4.27 Hz, 1H), 7.19 (d, J = 9.79 Hz, 1H), 5.17 (br. s, 1H), 2.96 (s, 3H), 1.35-1.59 (m, 4H), 1.27 (s, 6H), 1.10 (s, 6H) |

-continued

| Example | Compound | LCMS M + 1, Rt, conditions | ¹H NMR 400 MHz |
|---|---|---|---|
| 1-13 | N-methyl-6-(quinolin-6-yl)-N-(2,2,6,6-tetramethylpiperidin-4-yl)pyridazin-3-amine | 376.7 0.45 min Q | DMSO-d6 δ ppm 8.91 (dd, J = 4.02, 1.76 Hz, 1H), 8.62 (d, J = 2.01 Hz, 1H), 8.52 (dd, J = 8.78, 2.01 Hz, 1H), 8.45 (dd, J = 8.41, 0.88 Hz, 1H), 8.11 (dd, J = 9.29, 5.27 Hz, 2H), 7.58 (dd, J = 8.28, 4.27 Hz, 1H), 7.20 (d, J = 9.79 Hz, 1H), 5.20 (br. s, 1H), 3.35 (s, 1H), 2.95 (s, 3H), 1.49-1.57 (m, 2H), 1.39-1.48 (m, 2H), 1.26 (s, 6H), 1.09 (s, 6H) |
| 1-14 | 6-(isoquinolin-7-yl)-N-methyl-N-(2,2,6,6-tetramethylpiperidin-4-yl)pyridazin-3-amine | 376.24 0.42 min Q | DMSO-d6 δ ppm 9.40 (s, 1H), 8.76 (s, 1H), 8.48-8.58 (m, 2H), 8.14 (d, J = 9.54 Hz, 1H), 8.07 (d, J = 8.78 Hz, 1H), 7.86 (d, J = 5.77 Hz, 1H), 7.21 (d, J = 9.79 Hz, 1H), 5.21 (br. s, 1H), 3.35 (s, 1H), 2.95 (s, 3H), 1.49-1.58 (m, 2H), 1.39-1.48 (m, 2H), 1.27 (s, 6H), 1.10 (s, 6H) |
| 1-15 | 6-(isoquinolin-6-yl)-N-methyl-N-(2,2,6,6-tetramethylpiperidin-4-yl)pyridazin-3-amine | 376.25 0.40 min Q | METHANOL-d4 δ ppm 9.28 (s, 1H), 8.46-8.50 (m, 2H), 8.38 (dd, J = 8.66, 1.63 Hz, 1H), 8.24 (d, J = 8.78 Hz, 1H), 8.13 (d, J = 9.54 Hz, 1H), 7.93 (d, J = 5.77 Hz, 1H), 7.30 (d, J = 9.54 Hz, 1H), 5.54 (dt, J = 10.73, 5.55 Hz, 1H), 3.05 (s, 3H), 1.91-1.98 (m, 4H), 1.63 (s, 6H), 1.48 (s, 6H) |
| 1-16 | 6-(imidazo[1,2-a]pyridin-6-yl-pyridazin-3-yl)-methyl-(2,2,6,6-tetramethyl-piperidin-4-yl)-amine | 0.34 min 365.2 Q | DMSO-d6 δ ppm 9.18-9.21 (m, 1H), 7.87-7.99 (m, 3H), 7.58-7.66 (m, 2H), 7.15 (d, J = 9.60 Hz, 1H), 5.07-5.16 (m, 1H), 2.94 (s, 3H), 1.50-1.64 (m, 2H), 1.45 (br. s, 2H), 1.28 (br. s, 6H), 1.11 (br. s, 6H) |
| 1-17 | methyl-[6-(6-phenyl-pyridin-3-yl)-pyridazin-3-yl]-(2,2,6,6-tetramethyl-piperidin-4-yl)-amine | 402.2 0.55 min Q | CHLOROFORM-d δ ppm 9.21 (d, J = 1.52 Hz, 1H), 8.43-8.56 (m, 1H), 8.08 (dd, J = 8.34, 1.26 Hz, 2H), 7.79-7.93 (m, 1H), 7.69 (d, J = 9.60 Hz, 1H), 7.47-7.54 (m, 2H), 7.44 (d, J = 7.58 Hz, 1H), 6.90 (d, J = 9.60 Hz, 1H), 5.16-5.10 (m, 1H), 3.05 (s, 3H), 1.75 (dd, J = 12.13, 3.54 Hz, 2H), 1.46 (t, J = 12.13 Hz, 2H), 1.39 (s, 6H), 1.21 (s, 6H) |

| Example | Compound | LCMS M + 1, Rt, conditions | ¹H NMR 400 MHz |
|---|---|---|---|
| 1-18 | methyl-[6-(6-pyrrol-1-yl-pyridin-3-yl)-pyridazin-3-yl]-(2,2,6,6-tetramethyl-piperidin-4-yl)-amine | 391.26 0.54 min Q | CHLOROFORM-d δ ppm 8.74-8.87 (m, 1H), 8.40 (d, J = 8.59 Hz, 1H), 7.53 (d, J = 9.60 Hz, 1H), 7.45-7.50 (m, 2H), 7.26-7.36 (m, 1H), 6.78 (d, J = 10.11 Hz, 1H), 6.28 (t, J = 2.27 Hz, 2H), 5.04-4.98 (m, 1H), 2.94 (s, 3H), 1.62 (d, J = 3.54 Hz, 2H), 1.35 (br. s, 2H), 1.28 (s, 6H), 1.10 (s, 6H) |
| 1-19 | methyl-[6-(6-pyrazol-1-yl-pyridin-3-yl)-pyridazin-3-yl]-(2,2,6,6-tetramethyl-piperidin-4-yl)-amine | 392.25 0.52 min Q | CHLOROFORM-d δ ppm 8.87 (d, J = 1.52 Hz, 1H), 8.52 (d, J = 3.54 Hz, 1H), 8.40 (dd, J = 8.59, 2.02 Hz, 1H), 7.99 (d, J = 8.59 Hz, 1H), 7.66 (d, J = 1.01 Hz, 1H), 7.54 (d, J = 9.60 Hz, 1H), 6.79 (d, J = 9.60 Hz, 1H), 6.39 (dd, J = 2.53, 1.52 Hz, 1H), 5.12-4.98 (m, 1H), 2.94 (s, 3H), 1.64 (dd, J = 12.63, 3.54 Hz, 2H), 1.36 (br. s, 2H), 1.24-1.33 (m, 6H), 1.11 (br. s, 6H) |
| 1-20 | methyl-(6-quinoxalin-2-yl-pyridazin-3-yl)-(2,2,6,6-tetramethyl-piperidin-4-yl)-amine | 377.2 0.88 min Q | CHLOROFORM-d δ ppm 10.03 (s, 1H), 8.36 (d, J = 9.60 Hz, 1H), 7.92-8.12 (m, 2H), 7.64 (ddd, J = 7.58, 5.31, 1.77 Hz, 2H), 6.87 (d, J = 9.60 Hz, 1H), 5.12-5.06 (m, 1H), 3.00 (s, 3H), 1.66 (dd, J = 12.38, 3.28 Hz, 2H), 1.38 (m, 2H), 1.30 (s, 6H), 1.11 (s, 6H) |
| 1-21 | methyl-(6-quinolin-3-yl-pyridazin-3-yl)-(2,2,6,6-tetramethyl-piperidin-4-yl)-amine | 376.3 0.50 min Q | DMSO-d6 δ ppm 9.60 (d, J = 2.53 Hz, 1 H), 8.87 (d, J = 2.02 Hz, 1 H), 8.02-8.13 (m, 3 H), 7.76 (ddd, J = 8.34, 6.82, 1.52 Hz, 1 H), 7.59-7.68 (m, 1 H), 7.18 (d, J = 10.11 Hz, 1 H), 5.09-5.21 (m, 1 H), 2.97 (s, 3 H), 1.56 (dd, J = 12.38, 3.79 Hz, 2 H), 1.45 (t, J = 12.13 Hz, 2 H), 1.26-1.32 (m, 6 H) 1.10 (s, 6 H) |

Example 1-22

Synthesis of N-methyl-6-(phthalazin-6-yl)-N-(2,2,6,6-tetramethylpiperidin-4-yl)pyridazin-3-amine

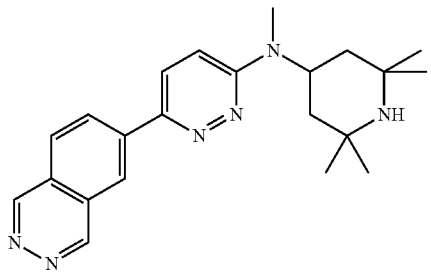 [SMILES: CN(c1ccc(-c2ccc3cnncc3c2)nn1)C1CC(C)(C)NC(C)(C)C1]

A mixture of 6-bromophthalazine (0.11 g, 0.50 mmol), 6-chloro-N-methyl-N-(2,2,6,6-tetramethylpiperidin-4-yl)pyridazin-3-amine (0.16 g, 0.58 mmol), 4,4,4',4',5,5,5',5'-octamethyl-2,2'-bi(1,3,2-dioxaborolane) (0.14 g, 0.55 mmol), potassium acetate (0.15 g, 1.5 mmol) and [1,1'-bis(diphenylphosphino)ferrocene]dichloropalladium(II), complex with dichloromethane (0.04 g, 0.05 mmol) in dioxane (3 mL) was heated at 80° C. for 3 h. Potassium carbonate (0.20 g, 1.5 mmol) and water (0.4 mL) were added and the mixture was stirred for 48 h at 90° C. After cooling, the reaction was purified by solid phase extraction (SiliaBond Carbonates, MeOH as eluent). After evaporation of the solvent under reduced pressure, the material afforded was purified via reverse phase preparative HPLC using 5 to 95% acetonitrile in water modified with 3% n-PrOH. LCMS: Rt=0.43 min [M+H] (LCMS method Q); 377.245; $^1$H NMR (400 MHz, DMSO-d6) δ 9.74-9.62 (m, 2H), 8.75 (s, 1H), 8.74 (dd, J=8.5, 2.0 Hz, 1H), 8.23 (d, J=8.5 Hz, 1H), 8.12 (d, J=9.5 Hz, 1H), 7.19 (d, J=9.5 Hz, 1H), 5.19 (tt, J=12.0, 3.5 Hz, 1H), 2.98 (s, 3H), 1.56 (dd, J=12.0, 3.5 Hz, 2H), 1.45 (t, J=12.0 Hz, 2H), 1.27 (s, 6H), 1.10 (s, 6H).

The following compounds are prepared using similar procedures as in Example 1-1 utilizing high throughput parallel solution phase synthesis technology.

| Example | Product | LCMS M + 1, Rt, conditions |
|---|---|---|
| 2-1 | 6-(benzo[c][1,2,5]oxa-diazol-5-yl)-N-(2,2,6,6-tetramethyl-piperidin-4-yl)pyridazin-3-amine | 353.2 0.51 min Q |
| 2-2 | 6-(benzo[d]thiazol-5-yl)-N-(2,2,6,6-tetramethyl-piperidin-4-yl)pyridazin-3-amine | 368.2 1.26 min B |
| 2-3 | 6-(2-methylbenzo-[d]oxazol-6-yl)-N-(2,2,6,6-tetramethyl-piperidin-4-yl)pyridazin-3-amine | 366.3 2.87 min B |

The following final compounds were prepared using similar procedures as in Example 1-1, followed by methoxy deprotection as outlined in GENERAL METHODS 3-1 and 3-2 when appropriate.

| Example | Compound | LCMS M + 1, Rt, conditions | $^1$H NMR 400 MHz, |
|---|---|---|---|
| 3-1 | 3-(6-(methyl(2,2,6,6-tetramethylpiperidin-4-yl)amino)pyridazin-3-yl)naphthalen-2-ol | 391.1 0.56 min Q | DMSO-d6 δ ppm 13.33 (br. s, 1H), 8.51 (s, 1H), 8.37 (d, J = 9.9 Hz, 1H), 7.88 (d, J = 8.1 Hz, 1H), 7.71 (d, J = 8.3 Hz, 1H), 7.37-7.48 (m, 2H), 7.30 (s, 1H), 7.27-7.34 (m, 1H), 4.92-5.14 (m, 1H), 2.98 (s, 3H), 1.54 (dd, J = 11.9, 3.3 Hz, 2H), 1.45 (m, J = 12.1 Hz, 2H), 1.27 (s, 6H), 1.10 (s, 6H) |

-continued

| Example | Compound | LCMS M + 1, Rt, conditions | ¹H NMR 400 MHz, |
|---|---|---|---|
| 3-2 | 5-chloro-2-(6-(methyl(1,2,2,6,6-pentamethylpiperidin-4-yl)amino)pyridazin-3-yl)phenol | 389.1 1.30 min B | DMSO-d6 δ ppm 14.05 (br. s, 1H), 8.20 (d, J = 9.9 Hz, 1H), 7.91 (d, J = 8.6 Hz, 1H), 7.37 (d, J = 9.9 1H), 7.01 (d, J = 2.0 Hz, 1H), 6.97 (dd, J = 8.5, 2.1 Hz, 1H), 4.75-4.95 (m, 1H), 2.97 (s, 3H), 2.20 (s, 3H), 1.62-1.74 (m, 2H), 1.49-1.60 (m, 2H), 1.13 (s, 6H), 1.11 (s, 6H) |
| 3-3 | 3-(6-(2,2,6,6-tetramethylpiperidin-4-ylamino)pyridazin-3-yl)naphthalen-2-ol | 377.3 1.06 min B | CHLOROFORM-d δ ppm 13.42 (br. s, 1H), 8.12 (s, 1H), 8.04 (d, J = 9.6 Hz, 1H), 7.80 (d, J = 8.3 Hz, 1H), 7.73 (d, J = 8.3 Hz, 1H), 7.41-7.49 (m, 1H), 7.43 (s, 1H), 7.31-7.35 (m, 1H), 6.90 (d, J = 9.6 Hz, 1H), 4.75 (br. s, 1H), 4.33-4.51 (m, 1H), 2.15 (dd, J = 12.3, 2.1 Hz, 2H), 1.42 (s, 6H), 1.27 (s, 6H), 1.10-1.19 (m, 2H) |
| 3-4 | 5-chloro-2-(6-(1,2,2,6,6-pentamethylpiperidin-4-ylamino)pyridazin-3-yl)phenol | 375.1 0.55 min Q | DMSO-d6 δ ppm 14.36 (br. s, 1H), 8.10 (d, J = 9.6 Hz, 1H), 7.84 (d, J = 8.6 Hz, 1H), 7.13 (d, J = 7.6 Hz, 1H), 7.03 (d, J = 9.6 Hz, 1H), 7.00 (d, J = 2.0 Hz, 1H), 6.96 (dd, J = 8.5, 2.1 Hz, 1H), 4.14-4.36 (m, 1H), 2.20 (s, 3H), 1.83-1.96 (m, 2H), 1.25-1.35 (m, 2H), 1.10 (s, 6H), 1.08 (s, 6H) |
| 3-5 | 4-hydroxy-3-(6-(methyl(2,2,6,6-tetramethyl-piperidin-4-yl)amino)pyridazin-3-yl)benzonitrile | 366.0 0.51 min Q | CHLOROFORM-d δ ppm 7.91 (d, J = 2.02 Hz, 1 H), 7.83 (d, J = 9.85 Hz, 1 H), 7.54 (dd, J = 8.59, 2.02 Hz, 1 H), 7.12 (d, J = 8.59 Hz, 1 H), 7.06 (d, J = 9.85 Hz, 1 H), 5.06 (br. s, 1 H), 3.05 (s, 3 H), 1.73 (dd, J = 12.51, 3.41 Hz, 2 H), 1.43-1.58 (m, 3 H), 1.41 (s, 6 H), 1.25 (s, 6 H) |
| 3-6 | 3-[6-(2,2,6,6-tetramethyl-piperidin-4-yloxy)-pyridazin-3-yl]-naphthalen-2-ol | 378.21 0.57 min Q | CHLOROFORM-d δ ppm 8.00-8.21 (m, 2H), 7.69 (d, J = 8.08 Hz, 1H), 7.61 (d, J = 8.08 Hz, 1H), 7.28-7.43 (m, 2H), 7.18-7.25 (m, 1H), 7.04 (d, J = 9.60 Hz, 1H), 5.72 (tt, J = 10.99, 4.42 Hz, 1H), 2.17 (dd, J = 12.63, 4.04 Hz, 2H), 1.48 (br. s, 2H), 1.36 (br. s, 6H), 1.28 (br. s, 6H) |

-continued

| Example | Compound | LCMS M + 1, Rt, conditions | ¹H NMR 400 MHz, |
|---|---|---|---|
| 3-7 | 2-{6-[methyl-(2,2,6,6-tetramethyl-piperidin-4-yl)-amino]-pyridazin-3-yl}-4-trifluoromethyl-phenol•HCl | 409.1 0.58 min Q | CHLOROFORM-d δ ppm 14.41 (br. s, 1H), 7.87 (d, J = 10.04 Hz, 1H), 7.82 (d, J = 1.76 Hz, 1H), 7.50 (dd, J = 8.53, 1.76 Hz, 1H), 7.12 (d, J = 8.53 Hz, 1H), 7.03 (d, J = 9.79 Hz, 1H), 4.99 (t, J = 11.17 Hz, 1H), 3.03 (s, 3H), 1.72 (dd, J = 12.55, 3.26 Hz, 2H), 1.45 (t, J = 12.30 Hz, 2H), 1.38 (s, 6H), 1.22 (s, 6H) |
| 3-8 | 2-fluoro-6-{6-[methyl-(2,2,6,6-tetramethyl-piperidin-4-yl)-amino]-pyridazin-3-yl}-phenol | 359.1 0.51 min Q | CHLOROFORM-d δ ppm 14.13 (br. s, 1H), 7.82 (d, J = 9.79 Hz, 1H), 7.36 (d, J = 8.03 Hz, 1H), 7.10 (ddd, J = 10.60, 8.09, 1.38 Hz, 1H), 7.01 (d, J = 10.04 Hz, 1H), 6.83 (td, J = 8.09, 4.89 Hz, 1H), 4.97 (br. s, 1H), 3.03 (s, 3H), 1.72 (dd, J = 12.30, 3.01 Hz, 2H), 1.40 (br. s, 8H), 1.23 (br. s, 6H) |
| 3-9 | 3,5-dimethoxy-2-{6-[methyl-(2,2,6,6-tetramethyl-piperidin-4-yl)-amino]-pyridazin-3-yl}-phenol | 401.3 0.48 min Q | DMSO-d6 δ ppm 13.86 (br. s, 1H), 8.12 (d, J = 9.60 Hz, 1H), 7.23 (d, J = 10.11 Hz, 1H), 6.17 (d, J = 2.53 Hz, 1H), 6.15 (d, J = 2.53 Hz, 1H), 4.95-4.80 (m, 1H), 3.82 (s, 3H), 3.77 (s, 3H), 2.93 (s, 3H), 1.61-1.44 (m, 4H), 1.28 (s, 6H), 1.13 (br. s, 6H) |
| 3-10 | 4,5-dimethoxy-2-{6-[methyl-(2,2,6,6-tetramethyl-piperidin-4-yl)-amino]-pyridazin-3-yl}-phenol | 401.3 0.48 min Q | DMSO-d6 δ ppm 13.38 (s, 1H), 8.11 (d, J = 10.10 Hz, 1H), 7.33 (s, 1H), 7.26 (d, J = 10.11 Hz, 1H), 6.56 (s, 1H), 4.95-4.83 (m, 1H), 3.79 (s, 3H), 3.77 (s, 3H), 2.94 (s, 3H), 1.58-1.51 (m, 2H), 1.43 (t, J = 12.13 Hz, 2H), 1.26 (s, 6H), 1.09 (s, 6H) |
| 3-11 | 5-methoxy-2-{6-[methyl-(2,2,6,6-tetramethyl-piperidin-4-yl)-amino]-pyridazin-3-yl}-phenol | 371.7 0.52 min Q | DMSO-d6 ppm δ 13.91 (s, 1H), 8.18 (d, J = 10.04 Hz, 1H), 7.82 (d, J = 8.53 Hz, 1H), 7.45 (d, J = 10.04 Hz, 1H), 6.54-6.48 (m, 2H), 5.07 (t, J = 12.30 Hz, 1H), 3.77 (s, 3H), 2.96 (s, 3H), 1.99 (t, J = 12.80 Hz, 2H), 1.75 (d, J = 11.04 Hz, 1H), 1.53 (s, 6H), 1.47 (s, 6H) |

| Example | Compound | LCMS M + 1, Rt, conditions | ¹H NMR 400 MHz, |
|---|---|---|---|
| 3-12 | 4,5-difluoro-2-{6-[methyl-(2,2,6,6-tetramethyl-piperidin-4-yl)-amino]-pyridazin-3-yl}-phenol | 377.2 0.56 min Q | DMSO-d6 ppm δ 8.14 (d, J = 9.60 Hz, 1H), 7.94 (dd, J = 12.13, 9.09 Hz, 1H), 7.33 (d, J = 10.11 Hz, 1H), 6.95 (dd, J = 12.13, 7.07 Hz, 1H), 5.08-4.88 (m, 1H), 2.96 (s, 3H), 1.63-1.48 (m, 4H), 1.31 (s, 6H), 1.17 (br. s, 6H) |

Example 4-1

Synthesis of 5-fluoro-2-{6-[methyl-(2,2,6,6-tetramethyl-piperidin-4-yl)-amino]-pyridazin-3-yl}-phenol

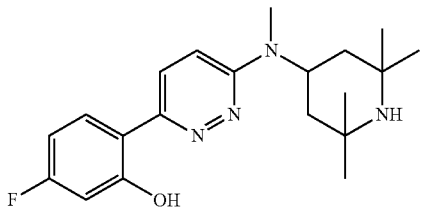

Step 1: 6-(2-(Benzyloxy)-4-fluorophenyl)-N-methyl-N-(2,2,6,6-tetramethylpiperidin-4-yl)pyridazin-3-amine Intermediate 1-1 and (2-(benzyloxy)-4-fluorophenyl)boronic acid were reacted according to GENERAL METHOD 1-1 for Suzuki coupling. A tan solid (94% yield) was obtained after SCX purification. No further chromatography was needed. MS (M+1)=449.2. ¹H NMR (400 MHz, DMSO-d6) δ ppm 7.79-7.67 (m, 2H) 7.43-7.27 (m, 5H) 7.10 (dd, J=11.37, 2.27 Hz, 1H) 6.99 (d, J=9.60 Hz, 1H) 6.88 (td, J=8.46, 2.27 Hz, 1H) 5.20 (s, 2H) 5.10-4.98 (m, 1H) 2.90 (s, 3H) 1.51 (dd, J=12.13, 3.54 Hz, 2H) 1.41 (t, J=12.13 Hz, 2H) 1.24 (s, 6H) 1.11 (s, 1H) 1.08 (s, 6H)

Step 2: 5-Fluoro-2-{6-[methyl-(2,2,6,6-tetramethyl-piperidin-4-yl)-amino]-pyridazin-3-yl)}-phenol Following GENERAL METHOD 4-1, Pd/C (10% wt, 47.0 mg, 0.044 mmol) was added to a solution of 6-(2-(benzyloxy)-4-fluorophenyl)-N-methyl-N-(2,2,6,6-tetramethylpiperidin-4-yl)pyridazin-3-amine (198 mg, 0.441 mmol) in MeOH (2 mL)/EtOAc (2 mL) at RT. The reaction mixture was evacuated and filled with H₂ (2×), then stirred under H₂ atmosphere for 4 h and filtered through celite using MeOH. The filtrate was concentrated in vacuo affording a yellow oil, which was redissolved in DCM and concentrated in vacuo affording the title compound as a yellow solid (129 mg, 82% yield). LCMS Rt=0.49 min (LCMS method Q); MS (M+1)=359.2. ¹H NMR (400 MHz, DMSO-d6) δ ppm 14.10 (br. s, 1H), 8.11 (d, J=9.60 Hz, 1H), 7.83-7.92 (m, 1H), 7.32 (d, J=10.11 Hz, 1H), 6.67-6.77 (m, 2H), 4.83-4.98 (m, 1H), 2.95 (s, 3H), 1.54 (dd, J=12.13, 3.54 Hz, 2H), 1.43 (t, J=12.13 Hz, 2H), 1.25 (s, 6H), 1.09 (s, 6H).

Example 5-1

Synthesis of 3-hydroxy-4-(6-(methyl(2,2,6,6-tetramethylpiperidin-4-yl)amino)pyridazin-3-yl)benzonitrile

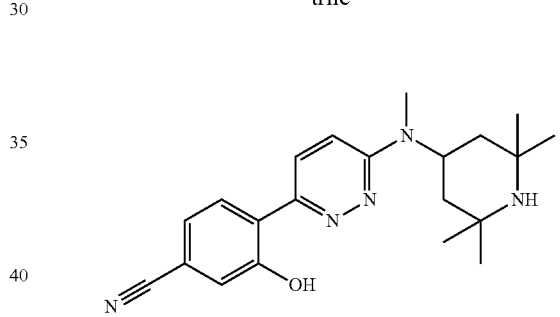

Step 1: 3-Methoxy-4-(6-(methyl(2,2,6,6-tetramethylpiperidin-4-yl)amino)pyridazin-3-yl)benzonitrile To a flask containing 6-(4-chloro-2-methoxyphenyl)-N-methyl-N-(2,2,6,6-tetramethylpiperidin-4-yl)pyridazin-3-amine (1.1 g, 2.88 mmol), Pd₂(dba)₃ (0.26 g, 0.29 mmol), dppf (0.32 g, 0.58 mmol), zinc dust (75 mg, 1.15 mmol), and zinc cyanide (1.0 g, 8.63 mmol) was added DMA (8.99 mL). The reaction was stirred at 150° C. for 18 h. The crude reaction mixture was cooled to RT, then diluted with EtOAc and filtered through celite. The filtrate was washed with 1 M NaOH (4×), water (6×), and brine. The organic layer was dried over Na₂SO₄, filtered, and concentrated under reduced pressure. The crude product was purified via column chromatography to give 3-methoxy-4-(6-(methyl(2,2,6,6-tetramethylpiperidin-4-yl)amino)pyridazin-3-yl)benzonitrile (1.1 g). LCMS Rt=1.02 min (condition B); MS (M+1)=380.4. ¹H NMR (400 MHz, CHLOROFORM-d) δ ppm 8.09 (d, J=8.1 Hz, 1H), 7.80 (d, J=9.6 Hz, 1H), 7.38 (dd, J=7.8, 1.5 Hz, 1H), 7.21 (d, J=1.5 Hz, 1H), 6.81 (d, J=9.6 Hz, 1H), 5.12-5.28 (m, 1H), 3.90 (s, 3H), 3.00 (s, 3H), 1.71 (dd, J=12.5, 3.4 Hz, 2H), 1.42-1.51 (m, 2H), 1.38 (s, 6H), 1.23 (s, 6H).

Step 2: 3-Hydroxy-4-(6-(methyl(2,2,6,6-tetramethylpiperidin-4-yl)amino)pyridazin-3-yl)benzonitrile Following GENERAL METHOD 3-3 for methoxy deprotection using LiI and collidine, 3-hydroxy-4-(6-(methyl(2,2,6,6-tetramethylpiperidin-4-yl)amino)pyridazin-3-yl)benzonitrile was prepared. LCMS Rt=0.52 min (LCMS method Q); MS (M+1)=366.2. NMR: $^1$H NMR (400 MHz, DMSO-d6) δ ppm 8.27 (d, J=9.85 Hz, 1H), 8.08 (d, J=8.08 Hz, 1H), 7.28-7.46 (m, 3H), 4.99 (br. s, 1H), 2.97 (s, 3H), 1.37-1.60 (m, 4H), 1.25 (s, 6H), 1.08 (s, 6H).

Example 6-1

Synthesis of 1-allyl-6-(6-(methyl(2,2,6,6-tetramethylpiperidin-4-yl)amino)pyridazin-3-yl)naphthalen-2-ol

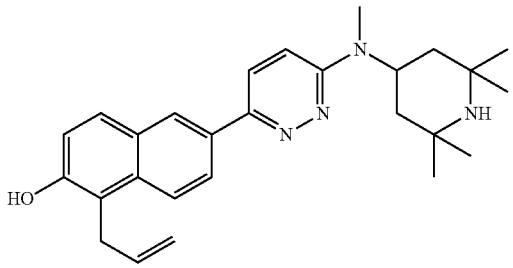 [SMILES: C=CCc1c(O)ccc2cc(-c3ccc(N(C)C4CC(C)(C)NC(C)(C)C4)nn3)ccc12]

Step 1: 6-(6-(Allyloxy)naphthalen-2-yl)-N-methyl-piperidin-4-yl)pyridazin-3-amine To a solution of 6-(6-(methyl(2,2,6,6-tetramethylpiperidin-4-yl)amino)pyridazin-3-yl)naphthalen-2-ol (208 mg, 0.53 mmol) in DMF (5.3 mL) was added 60% wt NaH (47 mg, 1.17 mmol) followed by allyl iodide (54 μL, 0.59 mmol). The reaction was stirred at RT for 10 min. The crude reaction mixture was diluted with EtOAc. The organic layer was washed with water (5×) and brine, then dried over Na$_2$SO$_4$, filtered and concentrated under reduced pressure. The crude product was purified via HPLC to give 6-(6-(allyloxy)naphthalen-2-yl)-N-methyl-N-(2,2,6,6-tetramethylpiperidin-4-yl)pyridazin-3-amine (85 mg). LCMS Rt=1.46 min (condition B); MS (M+1)=431.1. $^1$H NMR (400 MHz, CHLOROFORM-d) δ ppm 8.37 (d, J=1.5 Hz, 1H), 8.20 (dd, J=8.6, 1.8 Hz, 1H), 7.84 (d, J=8.8 Hz, 1H), 7.83 (d, J=8.6 Hz, 1H), 7.79 (d, J=9.9 Hz, 1H), 7.20-7.25 (m, 1H), 7.19 (d, J=2.3 Hz, 1H), 6.92 (d, J=9.6 Hz, 1H), 6.09-6.23 (m, 1H), 5.51 (dd, J=17.2, 1.5 Hz, 1H), 5.36 (dd, J=10.5, 1.4 Hz, 1H), 5.16-5.31 (m, 1H), 4.66-4.74 (m, 2H), 3.03 (s, 3H), 1.76 (dd, J=12.5, 3.4 Hz, 2H), 1.45-1.53 (m, 2H), 1.41 (s, 6H), 1.24 (s, 6H).

Step 2: 1-Allyl-6-(6-(methyl(2,2,6,6-tetramethylpiperidin-4-yl)amino)pyridazin-3-yl)naphthalen-2-ol A flask containing 6-(6-(allyloxy)naphthalen-2-yl)-N—N-methy-N-(2,2,6,6-tetramethylpiperidin-4-yl)pyridazin-3-amine (40 mg, 0.09 mmol) was placed into a preheated oil bath at 220° C. for 10 min. After 10 min, the flask was allowed to cool to RT. The crude product was purified via HPLC (XBridge C$_8$, H$_2$O (0.1% NH$_4$OH aq. as modifier/CH$_3$CN) to give 1-allyl-6-(6-(methyl(2,2,6,6-tetramethylpiperidin-4-yl)amino)pyridazin-3-yl)naphthalen-2-ol (25 mg). LCMS Rt=1.20 min (condition B); MS (M+1)=431.0. $^1$H NMR (400 MHz, CHLOROFORM-d) δ ppm 8.40 (d, J=1.8 Hz, 1H), 8.21 (dd, J=9.0, 1.9 Hz, 1H), 8.01 (d, J=9.1 Hz, 1H), 7.71-7.86 (m, 2H), 7.17 (d, J=8.8 Hz, 1H), 6.92 (d, J=9.6 Hz, 1H), 6.03-6.21 (m, 1H), 5.18-5.39 (m, 1H), 5.15 (dd, J=6.9, 1.6 Hz, 1H), 5.11 (dd, J=13.9, 1.8 Hz, 1H), 3.88 (d, J=5.6 Hz, 2H), 3.03 (s, 3H), 1.76 (dd, J=12.4, 3.3 Hz, 2H), 1.43-1.57 (m, 2H), 1.41 (s, 6H), 1.25 (s, 6H).

Example 7-1

Synthesis of 6-(benzo[b]thiophen-2-yl)-N-(1,2,2,6,6-pentamethylpiperidin-4-yl)pyridazin-3-amine

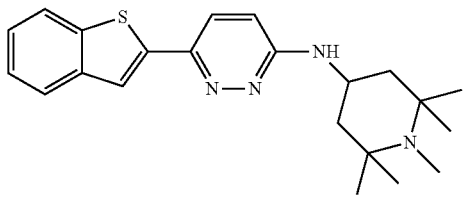 [SMILES: CN1C(C)(C)CC(Nc2ccc(-c3cc4ccccc4s3)nn2)CC1(C)C]

Step 1: 3-(Benzo[b]thiophen-2-yl)-6-chloropyridazine

To 3,6-dichloropyridazine (4.18 g, 28.1 mmol) and Na$_2$CO$_3$ (8.93 g, 84 mmol) in DME (100 mL) and water (25 mL) was added benzo[b]thiophen-2-ylboronic acid (5 g, 28.1 mmol) and PdCl$_2$(dppf).CH$_2$Cl$_2$ (0.69 g, 0.84 mmol). The reaction was evacuated under vacuum and purged with N$_2$ 3×. The reaction was heated at 85° C. for 18 h and cooled to RT. The crude product was filtered through celite and was rinsed with EtOAc followed by CH$_2$Cl$_2$. The crude filtrate was concentrated under vacuum and diluted in CH$_2$Cl$_2$ and water. The organic layer was separated, and the remaining emulsion was acidified with 1 M HCl and extracted with EtOAc. The combined organic layers were washed with water, brine, dried over MgSO$_4$, filtered, and concentrated. The crude product was purified by silica gel chromatography. The product was partially concentrated to provide a precipitate which was filtered to give 3-(benzo[b]thiophen-2-yl)-6-chloropyridazine (2.36 g) as a light yellow solid. The filtrate was recrystallized from CH$_3$CN to give 3-(benzo[b]thiophen-2-yl)-6-chloropyridazine (0.46 g). LCMS Rt=1.57 minutes (condition B); (M+1)=247.1.

Step 2: 6-(benzo[b]thiophen-2-yl)-N-(1,2,2,6,6-pentamethylpiperidin-4-yl)pyridazin-3-amine To a suspension of 3-(benzo[b]thiophen-2-yl)-6-chloropyridazine (100 mg, 0.41 mmol) in n-butanol (2 mL) in a 2 mL microwave vial was added 1,2,2,6,6-pentamethylpiperidin-4-amine (276 mg, 1.62 mmol) and DIPEA (0.14 mL, 0.81 mmol). The reaction vessel was sealed and heated via microwave radiation for 180 min at 180° C. The crude reaction mixture was diluted in EtOAc. The organic layer was washed with water (5×), brine, dried over MgSO$_4$, filtered and concentrated. The crude product was purified via HPLC to give 25 mg of 6-(benzo[b]thiophen-2-yl)-N-(1,2,2,6,6-pentamethylpiperidin-4-yl)pyridazin-3-amine. LCMS Rt=0.54 min (LCMS method Q); (M+1)=381.1. $^1$H NMR (400 MHz, CHLOROFORM-d) δ ppm 7.73-7.82 (m, 1H), 7.64-7.73 (m, 1H), 7.54 (d, J=9.1 Hz, 1H), 7.53 (s, 1H), 7.21-7.34 (m, 2H), 6.56 (d, J=9.3 Hz, 1H), 4.55 (d, J=7.8 Hz, 1H), 4.14-4.32 (m, 1H), 2.20 (s, 3H), 1.93 (dd, J=12.4, 3.8 Hz, 2H), 1.30 (apparent t, J=12.1 Hz, 2H), 1.07 (s, 6H), 1.10 (s, 6H).

Example 8-1

Synthesis of N-allyl-3-hydroxy-4-(6-(methyl(2,2,6,6-tetramethylpiperidin-4-yl)amino)pyridazin-3-yl)benzamide

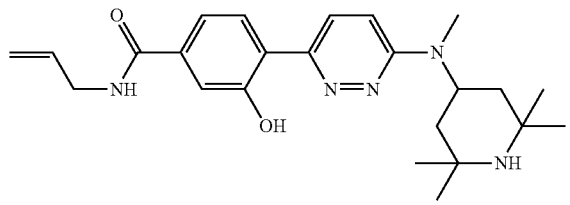 [SMILES: C=CCNC(=O)c1ccc(-c2ccc(N(C)C3CC(C)(C)NC(C)(C)C3)nn2)c(O)c1]

Step 1: 3-Methoxy-4-(6-(methyl(2,2,6,6 tetramethylpiperidin-4-yl)amino)pyridazin-3-yl)benzoic acid To a microwave vial was added 6-chloro-N-methyl-N-(2,2,6,6-tetramethylpiperidin-4-yl)pyridazin-3-amine (Intermediate 1-1, 100 mg, 0.35 mmol), 4-borono-3-methoxybenzoic acid (76 mg, 0.39 mmol), PdCl$_2$(dppf).CH$_2$Cl$_2$ (29 mg, 0.035 mmol), Na$_2$CO$_3$ (112 mg, 1.06 mmol), DMF (2 mL) and water (0.5 mL). The microwave vial was sealed and heated in a microwave at 120° C. for 45 min. The crude reaction mixture was cooled and diluted in water and ether. The aqueous layer was extracted with ether. The resultant emulsion was diluted in water and 1 M NaOH. The aqueous layer was acidified with 1 M HCl slowly and extracted again with ether. The organic layer was concentrated under reduced pressure, and the resulting precipitate was suspended in 10 mL MeOH and filtered. The filtrate was concentrated and used without further purification. LCMS Rt=0.63 min (condition B); MS (M+1)=399.0

Step 2: Synthesis of N-allyl-3-methoxy-4-(6-(methyl(2,2,6,6-tetramethylpiperidin-4-yl)amino)pyridazin-3-yl)benzamide To a solution of crude 3-methoxy-4-(6-(methyl(2,2,6,6 tetramethylpiperidin-4-yl)amino)pyridazin-3-yl)benzoic acid (0.354 mmol) in DMF (4 mL) and CH$_2$Cl$_2$ (4 mL) was added TEA (0.40 mL, 2.83 mmol), allyl amine (0.053 mL, 0.71 mmol), and HATU (202 mg, 0.53 mmol). The crude reaction was allowed to stir at RT overnight. The crude mixture was quenched with sat aq NaHCO$_3$ and diluted with CH$_2$Cl$_2$. The organic layer is washed with water (6×), brine, dried over MgSO$_4$, filtered, and concentrated. The crude product was purified via HPLC to give N-allyl-3-methoxy-4-(6-(methyl(2,2,6,6-tetramethylpiperidin-4-yl)amino)pyridazin-3-yl)benzamide (8.2 mg). LCMS Rt=1.08 min (condition B); MS (M+1)=438.1

Step 3

Following GENERAL METHOD 3-2 for methoxy deprotection using boron tribromide, N-allyl-3-hydroxy-4-(6-(methyl(2,2,6,6-tetramethylpiperidin-4-yl)amino)pyridazin-3-yl)benzamide was prepared. NMR: $^1$H NMR (400 MHz, METHANOL-d4) δ ppm 8.14 (d, J=10.10 Hz, 1H), 7.85 (d, J=8.08 Hz, 1H), 7.42 (d, J=1.77 Hz, 1H), 7.39 (dd, J=8.21 Hz, 1.89 Hz, 1H), 7.31 (d, J=9.85 Hz, 1H), 5.95 (ddt, J=17.18 Hz, 10.36 Hz, 5.43 Hz, 5.43 Hz, 1H), 5.25 (dq, J=17.18 Hz, 1.60 Hz, 1H), 5.15 (dq, J=10.33 Hz, 1.44 Hz, 1H), 5.11 (br. s, 1H), 4.00 (dt, J=5.49 Hz, 1.55 Hz, 2H), 3.02 (s, 3H), 1.65-1.74 (m, 2H), 1.52-1.63 (m, 2H), 1.39 (s, 6H), 1.24 (s, 6H).

Example 9-1

Synthesis of 2-(6-(methyl(2,2,6,6-tetramethylpiperidin-4-yl)amino)pyridazin-3-yl)-5-(1H-pyrazol-1-yl)phenol

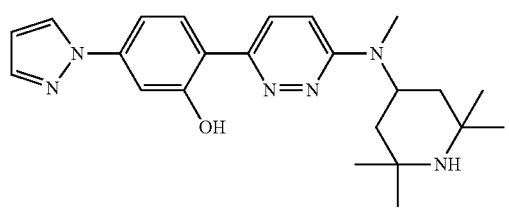 [SMILES: CN(c1ccc(-c2ccc(-n3cccn3)cc2O)nn1)C1CC(C)(C)NC(C)(C)C1]

Step 1: 6-(2-Methoxy-4-(1H-pyrazol-1-yl)phenyl)-N-methy-N-(2,2,6,6-tetramethyl-piperidin-4-yl)pyridazin-3-amine 1-(3-methoxy-4-(4,4,5,5-tetramethyl-1,3,2-dioxaborolan-2-yl)phenyl)-1H-pyrazole from Step 3 of Intermediate 2-1, was coupled with Intermediate 1-1 under standard Suzuki coupling methods as described in GENERAL METHOD 1-2 to provide 6-(2-methoxy-4-(1H-pyrazol-1-yl)phenyl)-N-methyl-N-(2,2,6,6-tetramethyl-piperidin-4-yl)pyridazin-3-amine.

Step 2: 2-(6-(Methyl(2,2,6,6-tetramethylpiperidin-4-yl)amino)pyridazin-3-yl)-5-(1H-pyrazol-1-yl)phenol As described in GENERAL METHOD 3-1, thiophenol (0.127 mL, 1.24 mmol) was added to a microwave vial containing 6-(2-methoxy-4-(1H-pyrazol-1-yl)phenyl)-N-methyl-N-(2,2,6,6-tetramethylpiperidin-4-yl)pyridazin-3-amine (520 mg, 1.24 mmol) and K$_2$CO$_3$ (171 mg, 1.24 mmol) in NMP (5 mL). The microwave vial was evacuated and filled with N$_2$ (2×). The reaction mixture was heated in the microwave at 190° C. for 30 min. The reaction mixture was filtered through celite (pre-packed filter funnel) washing with MeOH. The filtrate was acidified to pH 3 using 1 M HCl aqueous solution and then adsorbed onto a methanol conditioned SCX (10 g) column. The column was washed several times with methanol then eluted with 2 N ammonia in methanol solution. The product was collected and concentrated in vacuo to afford the crude product which was purified by preparative HPLC under basic conditions to provide 2-(6-(methyl(2,2,6,6-tetramethylpiperidin-4-yl)amino)pyridazin-3-yl)-5-(1H-pyrazol-1-yl)phenol (198 mg, MS: 407.25 [M+H$^+$], LC/MS Rt=0.53 min (LCMS method Q); $^1$H NMR (400 MHz, CHLOROFORM-d) δ ppm 7.86 (d, J=2.02 Hz, 1H), 7.71 (d, J=10.11 Hz, 1H), 7.63 (d, J=1.52 Hz, 1H), 7.54 (d, J=8.59 Hz, 1H), 7.21-7.30 (m, 2H), 6.91 (d, J=9.60 Hz, 1H) 6.31-6.41 (m, 1H), 4.76-4.95 (m, 1H), 2.89-3.01 (m, 3H), 1.62 (dd, J=12.13, 3.54 Hz, 2H), 1.34 (br. s, 2H), 1.27 (s, 6H), 1.10 (s, 6H).

Example 10-1

Synthesis of 5-(5-methyl-oxazol-2-yl)-2-{6-[methyl-(2,2,6,6-tetramethyl-piperidin-4-yl)-amino]-pyridazin-3-yl}-phenol

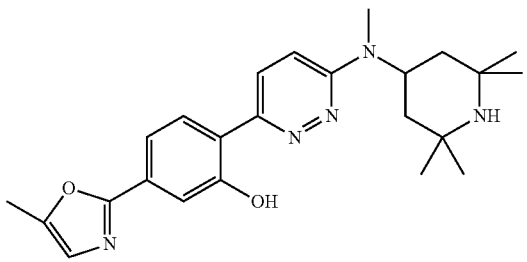

Step 1: 3-Methoxy-4-(6-(methyl(2,2,6,6-tetramethylpiperidin-4-yl)amino)pyridazin-3-yl)-N-(prop-2-yn-1-yl)benzamide To a crude solution of 3-methoxy-4-(6-(methyl-(2,2,6,6-tetramethylpiperidin-4-yl)amino)pyridazin-3-yl)benzoic acid (620 mg, 1.56 mmol) in DMF (10 mL) and CH$_2$Cl$_2$ (10 mL) was added propargyl amine (129 mg, 2.33 mmol), DIPEA (0.82 mL, 4.67 mmol) and HATU (887 mg, 2.33 mmol). The reaction was stirred at RT overnight, then diluted with water and EtOAc. The layers were separated and the aqueous layer was concentrated and partially dissolved in MeOH. The resultant white precipitate was filtered, and the MeOH filtrate was concentrated. The filtrate was dissolved in MeOH and the resultant precipitate filtered. The filtrate was concentrated and purified via HPLC (C18 sunfire column, 20% CH$_3$CN/H$_2$O to 100% CH$_3$CN, 0.1% NH$_4$OH aq. as modifier to give 3-methoxy-4-(6-(methyl(2,2,6,6-tetramethylpiperidin-4-yl)amino)pyridazin-3-yl)-N-(prop-2-yn-1-yl)benzamide (190 mg). LCMS Rt=0.86 min (condition B); MS (M+1)=436.3. $^1$H NMR (400 MHz, METHANOL-d$_4$) δ ppm 7.82 (d, J=9.6 Hz, 1H), 7.73 (d, J=8.1 Hz, 1H), 7.58 (d, J=1.5 Hz, 1H), 7.52 (dd, J=7.8, 1.5 Hz, 1H), 7.10 (d, J=9.6 Hz, 1H), 5.15-5.27 (m, 1H), 4.18 (d, J=2.3 Hz, 2H), 3.93 (s, 3H), 2.99 (s, 3H), 2.63 (t, J=2.5 Hz, 1H), 1.67 (dd, J=12.5, 3.4 Hz, 2H), 1.54 (t, J=12.5 Hz, 2H), 1.33 (s, 6H), 1.20 (s, 6H).

Step 2: 6-(2-Methoxy-4-(5-methyloxazol-2-yl)phenyl)-N-methyl-N-(2,2,6,6-tetramethyl-piperidin-4-yl)pyridazin-3-amine To a solution of 3-methoxy-4-(6-(methyl(2,2,6,6-tetramethylpiperidin-4-yl)amino)pyridazin-3-yl)-N-(prop-2-yn-1-yl)benzamide (190 mg, 0.44 mmol) in dioxane (8 mL) was added 60% wt NaH (52 mg, 1.31 mmol). The reaction was refluxed for 5 h, then cooled to RT and diluted in EtOAc and water. The organic layer was washed with water, brine, dried over Na$_2$SO$_4$, filtered, and concentrated under reduced pressure. The crude material was purified via HPLC to give 6-(2-methoxy-4-(5-methyloxazol-2-yl)phenyl)-N-methyl-N-(2,2,6,6-tetramethylpiperidin-4-yl)pyridazin-3-amine (106 mg). LCMS Rt=0.97 min (condition B); MS (M+1)= 436.3. $^1$H NMR (400 MHz, CHLOROFORM-d) δ ppm 8.08 (d, J=8.1 Hz, 1H), 7.85 (d, J=9.6 Hz, 1H), 7.72 (dd, J=8.1, 1.5 Hz, 1H), 7.65 (d, J=1.3 Hz, 1H), 6.88 (s, 1H), 6.82 (d, J=9.6 Hz, 1H), 5.20-5.39 (m, 1H), 3.96 (s, 3H), 2.99 (s, 3H), 2.43 (s, 3H), 1.74 (dd, J=12.4, 3.3 Hz, 2H), 1.47-1.59 (m, 2H), 1.43 (s, 6H), 1.31 (s, 6H).

Step 3. 5-(5-Methyl-oxazol-2-yl)-2-{6-[methyl-(2,2,6,6-tetramethyl-piperidin-4-yl)-amino]-pyridazin-3-yl}-phenol To a solution of 6-(2-methoxy-4-(5-methyloxazol-2-yl)phenyl)-N-methyl-N-(2,2,6,6-tetramethylpiperidin-4-yl)pyridazin-3-amine (106 mg, 0.24 mmol) in 2,4,6 collidine (8 mL, dried over MgSO$_4$, and filtered), was added anhydrous LiI (292 mg, 2.18 mmol). The reaction was stirred at 170° C. for 4 h, then cooled and diluted with small amounts of MeOH and EtOAc (150 mL) and H$_2$O (30 mL). The organic layer was washed with brine, dried over Na$_2$SO$_4$, filtered and concentrated under reduced pressure. The crude product was purified via HPLC to provide 2-(6-(methyl(2,2,6,6-tetramethylpiperidin-4-yl)amino)pyridazin-3-yl)-5-(5-methyloxazol-2-yl)phenol (49 mg). LCMS Rt=0.55 min (LCMS method Q); MS (M+1)=422.3. $^1$H NMR (400 MHz, METHANOL-d4) δ ppm 8.12 (d, J=9.9 Hz, 1H), 7.86 (d, J=8.8 Hz, 1H), 7.53 (dd, J=6.1, 1.8 Hz, 1H), 7.51 (s, 1H), 7.30 (d, J=10.1 Hz, 1H), 6.92 (d, J=1.0 Hz, 1H), 5.03-5.14 (m, 1H), 3.01 (s, 3H), 2.43 (d, J=1.2 Hz, 3H), 1.68 (dd, J=12.6, 3.5 Hz, 2H), 1.56 (t, J=12.3 Hz, 2H), 1.37 (s, 6H), 1.21 (s, 6H).

Example 11-1

Synthesis of 5-(4-hydroxymethyl)-1H-pyrazole-1-yl)-2-(6-(methyl(2,2,6,6-tetramethylpiperidin-4-yl)amino)pyridazin-3-yl)phenol

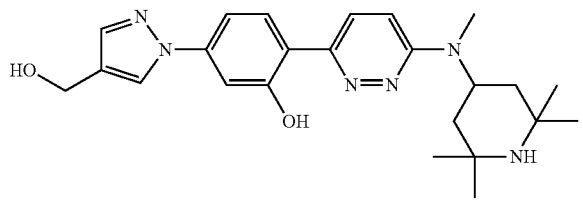 [SMILES: CN(c1ccc(-c2ccc(-n3cc(CO)cn3)cc2O)nn1)C1CC(C)(C)NC(C)(C)C1]

Step 1. (1-(4-Bromo-3-methoxyphenyl)-1H-pyrazol-4-yl)methanol

A mixture of 4-(hydroxymethyl)pyrazole (500 mg, 5.10 mmol), salicylaldoxime (140 mg, 1.019 mmol), cesium carbonate (4.98 g, 15.29 mmol), cuprous oxide (58.2 mg, 0.306 mmol), iodobromoanisole (1.59 g, 5.10 mmol) and N,N-dimethyl-formamide (10 mL) were combined in a microwave vial fitted with an N$_2$ inlet and magnetic stir bar. The reaction mixture was stirred under a nitrogen atmosphere at 90° C. overnight. The reaction mixture was cooled to RT, then filtered through celite, and the filtrate was concentrated in vacuo. The crude material was purified by column chromotography (10% to 60% EtOAc in heptanes) to give (1-(4-bromo-3-methoxyphenyl)-1H-pyrazol-4-yl)methanol (800 mg, MS: 285.3 [M+H$^+$].)

Step 2. (1-(3-Methoxy-4-(4,4,5,5-tetramethyl-1,3,2-dioxaborolan-2-yl)phenyl)-1H-pyrazol-4-yl)methanol To a microwave vial was added (1-(4-bromo-3-methoxyphenyl)-1H-pyrazol-4-yl)methanol (400 mg, 1.41 mmol), bis(pinacolato)diboron (538 mg, 2.12 mmol), potassium acetate (415 mg, 4.24 mmol), PdCl$_2$(dppf) (103 mg, 0.14 mmol), and dppf (78 mg, 0.14 mmol), followed by addition of 1,4-dioxane (6 mL). The reaction mixture was purged with N$_2$ and stirred under an N$_2$ atmosphere at 90° C. overnight. The reaction mixture was filtered through a disposable filter funnel and concentrated in vacuo. Purification by column chromotography (10% to 60% EtOAc in heptane) afforded (1-(3-methoxy-4-(4,4,5,5-tetramethyl-1,3,2-dioxaborolan-2-yl)phenyl)-1H-pyrazol-4-yl)methanol (300 mg, MS: 331.2 [M+H$^+$].).

Step 3. (1-(3-Methoxy-4-(6-(methyl(2,2,6,6-tetramethylpiperidin-4-yl)amino)pyridazin-3-yl)phenyl)-1H-pyrazol-4-yl)methanol To a microwave vial was added (1-(3-methoxy-4-(4,4,5-tetramethyl-1,3,2-dioxaborolan-2-yl)phenyl)-1H-pyrazol-4-yl)methanol (87 mg, 0.26 mmol), 6-chloro-N-methyl-N-(2,2,6,6-tetramethylpiperidin-4-yl)pyridazin-3-amine Intermediate 1-1 (74.5 mg, 0.26 mmol), potassium phosphate (168 mg, 0.79 mmol), Pd$_2$(dba)$_3$ (12.06 mg, 0.01 mmol), and SPhos (10.82 mg, 0.03 mmol), followed by addition of 1,4-dioxane (5 mL)/H$_2$O (1 mL). The vial was purged with N$_2$ for 10 min and the reaction mixture was heated at 100° C. in the microwave for one hour. The reaction mixture was concentrated in vacuo. The crude material was adjusted to pH 3 using 1 M HCl aqueous solution and loaded on an SCX column. The crude material was washed with methanol then eluted with 2 N ammonia in methanol. The product-containing fractions were concentrated to afford (1-(3-methoxy-4-(6-(methyl(2,2,6,6-tetramethylpiperidin-4-yl)amino)pyridazin-3-yl)phenyl)-1H-pyrazol-4-yl)methanol (100 mg, MS: 451.4 [M+H$^+$].).

Step 4 5-(4-(Hydroxymethyl)-1H-pyrazol-1-yl)-2-(6-(methyl(2,2,6,6-tetramethylpiperidin-4-yl)amino)pyridazin-3-yl)phenol Following standard GENERAL METHOD 3-1 for methoxy deprotection, the title compound was afforded as pale yellow powder (30 mg). MS: 437.2 [M+H$^+$], LCMS Rt=0.48 min (LCMS method Q); $^1$H NMR (400 MHz, CHLOROFORM-d) δ ppm 7.88 (s, 1H), 7.73 (d, J=10.11 Hz, 1H), 7.65 (s, 1H), 7.55 (d, J=8.08 Hz, 1H), 7.20-7.27 (m, 2H), 6.93 (d, J=10.11 Hz, 1H), 4.86 (t, J=12.13 Hz, 1H), 4.61 (s, 2H), 2.91-2.98 (m, 3H), 1.62 (dd, J=12.38, 3.28 Hz, 2H), 1.32-1.37 (m, 2H), 1.28 (s, 6H), 1.11 (s, 6H).

Example 12-1

Synthesis of 5-(1H-imidazole-1-yl)-2-(6-(methyl(2,2,6,6-tetramethyl-piperidin-4-yl)amino)pyridazin-3-yl)phenol

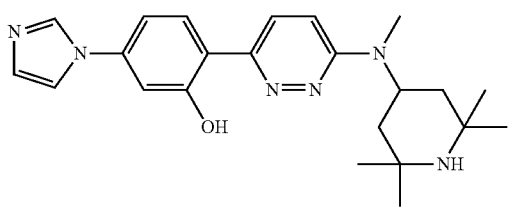 [SMILES: CN(c1ccc(-c2ccc(-n3ccnc3)cc2O)nn1)C1CC(C)(C)NC(C)(C)C1]

Step 1.
1-(4-Bromo-3-methoxyphenyl)-1H-imidazole

A mixture of 2-(2-pyridyl)benzimidazole (287 mg, 1.469 mmol), cesium carbonate (5.98 g, 18.36 mmol), copper(I) iodide (280 mg, 1.469 mmol) and DMF (5 mL) were combined in a microwave vial fitted with an N$_2$ inlet and magnetic stir bar. The slurry was heated at 60° C. for 1 h, followed by addition of imidazole (500 mg, 7.34 mmol) and 1-bromo-4-iodo-2-methoxybenzene (2.3 g, 7.34 mmol). The reaction mixture was heated at 90° C. for 2 days. The reaction mixture was filtered through celite, washed with EtOAc, and concentrated in vacuo. The crude material was purified by silica gel chromatography (10% to 40% EtOAc in heptanes) to give 1-(4-bromo-3-methoxyphenyl)-1H-imidazole (1.25 g, MS: 255.2 [M+H$^+$])

Step 2.
(4-(1H-Imidazol-1-yl)-2-methoxyphenyl)boronic acid

To a stirred solution of 1-(4-bromo-3-methoxyphenyl)-1H-imidazole in THF (5 mL) was added 2.5 M n-butyl lithium in hexanes (0.348 ml, 0.869 mmol) dropwise at −78° C. over 15 min.
After addition was complete, the reaction solution was stirred at −78° C. for 15 min, and trimethyl borate (0.353 mL, 3.16 mmol) was added. The reaction was allowed to warm to RT, and continued to stir overnight. The reaction was quenched with 1 M HCl aqueous solution to pH 2, diluted with water and extracted with DCM (3×). The product remained in the aqueous solution which was concentrated in vacuo to give crude (4-(1H-imidazol-1-yl)-2-methoxyphenyl)boronic acid (120 mg, MS: 219.2 [M+H$^+$]).

Step 3. 6-(4-(1H-Imidazol-1-yl)-2-methoxyphenyl)-N-methyl-N-(2,2,6,6-tetramethylpiperidin-4-yl)pyridazin-3-amine To a microwave vial was added (4-(1H-imidazol-1-yl)-2-methoxyphenyl)boronic acid (120 mg, 0.55 mmol), 6-chloro-N-methyl-N-(2,2,6,6-tetramethylpiperidin-4-yl)pyridazin-3-amine Intermediate 1-1 (156 mg, 0.55 mmol), potassium phosphate (351 mg, 1.65 mmol), Pd$_2$(dba)$_3$ (25.2 mg, 0.028 mmol), and SPhos (22.6 mg, 0.05 mmol), followed by addition of 1,4-dioxane (2 mL)/H$_2$O (0.5 mL). The vial was purged with N$_2$ for 10 minutes and the reaction mixture was heated at 100° C. in the microwave for 40 min. The reaction mixture was concentrated in vacuo and adjusted to pH 3 by 1 M HCl aqueous solution, then loaded on an SCX column. The column was washed with methanol and eluted with 2 N NH$_3$ in methanol. The product-containing fractions were concentrated to afford 6-(4-(1H-imidazol-1-yl)-2-methoxyphenyl)-N-methyl-N-(2,2,6,6-tetramethyl-piperidin-4-yl)pyridazin-3-amine (90 mg, MS: 421.4 [M+H$^+$]).

Step 4: 5-(1H-Imidazole-1-yl)-2-(6-(methyl(2,2,6,6-tetramethyl-piperidin-4-yl)amino)pyridazin-3-yl)phenol Followed GENERAL METHOD 3-1 for methoxy deprotection using thiophenol, 5-(1H-imidazole-1-yl)-2-(6-(methyl(2,2,6,6-tetramethyl-piperidin-4-yl)amino-)pyridazin-3-yl)phenol was afforded as pale yellow powder (8 mg, MS: 407.2 [M+H$^+$], LCMS Rt=0.40 min (LCMS method Q); $^1$H NMR (400 MHz, CHLOROFORM-d) δ ppm 7.82 (br. s, 1H), 7.70 (d, J=10.11 Hz, 1H), 7.55 (d, J=8.59 Hz, 1H), 7.23 (br. s, 1H), 7.12 (br. s, 1H), 7.02 (d, J=2.02 Hz, 1H), 6.92 (d, J=10.11 Hz, 1H), 6.85 (dd, J=8.59, 2.02 Hz, 1H), 4.86-4.92 (m, 1H), 2.94 (s, 3H), 1.62 (dd, J=12.63, 3.54 Hz, 2H), 1.36 (br. s, 2H), 1.28 (s, 6H), 1.11 (s, 6H).

Example 13-1

Synthesis of 5-(4-amino-H-pyrazole-1-yl)-2-(6-(methyl(2,2,6,6-tetramethylpiperidin-4-yl)amino)pyridazin-3-yl)phenol

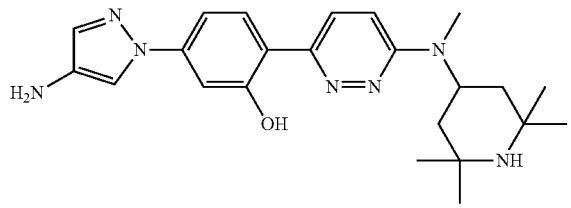 [SMILES: CN(c1ccc(-c2ccc(-n3cc(N)cn3)cc2O)nn1)C1CC(C)(C)NC(C)(C)C1]

Step 1: 1-(4-Bromo-3-methoxyphenyl)-1H-pyrazol-4-amine

A mixture of pyrazole-4-amine dihydrochloride (0.75 g, 4.79 mmol), salicylaldoxime (0.131 g, 0.96 mmol), cesium carbonate (4.69 g, 14.38 mmol), cuprous oxide (0.06 g, 0.29 mmol), 1-bromo-4-iodo-2-methoxybenzene (1.5 g, 4.79 mmol) and N,N-dimethyl-formamide (5 mL) were combined in a microwave vial fitted with an $N_2$ inlet and magnetic stir bar. The reaction mixture was stirred under a nitrogen atmosphere at 90° C. overnight. The solution obtained was allowed to cool to RT, then filtered through celite and the filtrate was concentrated in vacuo. The crude material was purified by silica gel chromatography (10% to 60% EtOAc in heptanes) to give 1-(4-bromo-3-methoxyphenyl)-1H-pyrazol-4-amine (250 mg, MS: 270.2 [M+H$^+$].)

Step 2: 1-(3-Methoxy-4-(4,4,5,5-tetramethyl-1,3,2-dioxaborolan-2-yl)phenyl)-1H-pyrazol-4-amine To a microwave vial was added 1-(4-bromo-3-methoxyphenyl)-1H-pyrazol-4-amine (250 mg, 0.93 mmol), bis(pinacolato)diboron (355 mg, 1.39 mmol), potassium acetate (543 mg, 5.59 mmol), PdCl$_2$(dppf) (68.20 mg, 0.09 mmol), and dppf (51.70 mg, 0.09 mmol), followed by addition of 1,4-dioxane (2 mL). The reaction mixture was purged with $N_2$ and stirred under $N_2$ protection at 90° C. overnight. The reaction mixture was filtered through a disposable filter funnel, concentrated in vacuo, and purified by column chromatography (10% to 60% EtOAc in heptane) to afford 1-(3-methoxy-4-(4,4,5,5-tetramethyl-1,3,2-dioxaborolan-2-yl)phenyl)-1H-pyrazol-4-amine (160 mg, MS: 316.2 [M+H$^+$].)

Step 3: 6-(4-(4-Amino-1H-pyrazol-1-yl)-2-methoxyphenyl)-N-methyl-N-(2,2,6,6-tetramethylpiperidin-4-yl)pyridazin-3-amine To a microwave vial was added 1-(3-methoxy-4-(4,4,5,5-tetramethyl-1,3,2-dioxaborolan-2-yl)phenyl)-1H-pyrazol-4-amine (92 mg, 0.29 mmol), 6-chloro-N-methyl-N-(2,2,6,6-tetramethylpiperidin-4-yl)pyridazin-3-amine Intermediate 1-1 (75 mg, 0.27 mmol), potassium phosphate (169 mg, 0.78 mmol), Pd$_2$(dba)$_3$ (12.14 mg, 0.01 mmol), and SPhos (10.89 mg, 0.03 mmol), followed by addition of 1,4-dioxane (1 mL)/H$_2$O (0.2 mL). The vial was purged with $N_2$ for 10 minutes and the reaction mixture was heated at 100° C. in a microwave reactor for one hour. The reaction mixture was concentrated in vacuo, then the crude material was adjusted to pH 3 using 1 M HCl aqueous solution, then loaded on an SCX column. The column was washed with methanol then eluted with 2 N ammonia in methanol. The product-containing fractions concentrated to afford 6-(4-(4-amino-1H-pyrazol-1-yl)-2-methoxyphenyl)-N-methyl-N-(2,2,6,6-tetramethylpiperidin-4-yl)pyridazin-3-amine (100 mg, MS: 436.4 [M+H$^+$].).

Step 4: 5-(4-Amino-1H-pyrazol-1-yl)-2-(6-(methyl(2,2,6,6-tetramethylpiperidin-4-yl)amino)pyridazin-3-yl)phenol As described in GENERAL METHOD 3-1, thiophenol (0.02 mL, 0.23 mmol) was added to a microwave vial containing 6-(4-(4-amino-1H-pyrazol-1-yl)-2-methoxyphenyl)-N-methyl-N-(2,2,6,6-tetramethylpiperidin-4-yl)pyridazin-3-amine (100 mg, 0.23 mmol) and K$_2$CO$_3$ (31.7 mg, 0.23 mmol) and NMP (2 mL). The microwave vial was evacuated and filled with $N_2$ (2×). The reaction mixture was heated in a microwave reactor at 190° C. for 20 min, then filtered through celite (pre-packed filter funnel) with methanol. The filtrate was acidified to pH 3 using 1 M HCl aqueous solution and then adsorbed onto a methanol conditioned SCX column. The column was washed several times with methanol then eluted with 2 N ammonia in methanol solution. The eluent was collected, concentrated in vacuo, then purified by preparative HPLC under basic conditions to give 5-(4-amino-1H-pyrazol-1-yl)-2-(6-(methyl(2,2,6,6-tetramethylpiperidin-4-yl)amino)pyridazin-3-yl)phenol (50 mg, MS: 422.26 [M+H$^+$]; LCMS Rt=0.43 min (LCMS method Q); $^1$H NMR (400 MHz, CHLOROFORM-d) δ ppm 7.68 (d, J=10.11 Hz, 1H), 7.49 (d, J=8.59 Hz, 1H), 7.43 (s, 1H), 7.29 (s, 1H), 7.18 (dd, J=8.59, 2.53 Hz, 1H), 7.12 (d, J=2.02 Hz, 1H), 6.89 (d, J=9.60 Hz, 1H), 4.77-4.93 (m, 1H), 2.92 (s, 3H), 1.61 (dd, J=12.38, 3.28 Hz, 2H), 1.33 (t, J=12.38 Hz, 2H), 1.27 (s, 6H), 1.10 (s, 6H).

Example 14-1

2-(6-(methyl(2,2,6,6-tetramethylpiperidin-4-yl)amino)pyridazin-3-yl)-5-(1H-pyrazol-4-yl)phenol

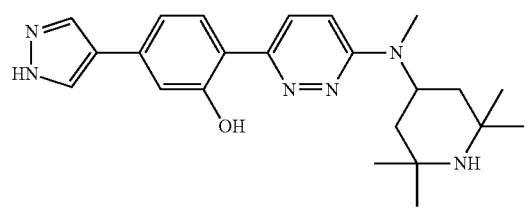 [SMILES: CN(c1ccc(-c2ccc(-c3cn[nH]c3)cc2O)nn1)C1CC(C)(C)NC(C)(C)C1]

Step 1: 3-Methoxy-4-(4,4,5,5-tetramethyl-1,3,2-dioxaborolan-2-yl)phenol

To a 25 mL microwave vial was added 4-bromo-3-methoxyphenol (1.0 g, 4.93 mmol), bis(pinacolato)diboron (1.88 g, 7.39 mmol), potassium acetate (2.41 g, 24.63 mmol), PdCl$_2$(dppf) (0.36 g, 0.49 mmol), dppf (0.27 g, 0.49 mmol), and 1,4-dioxane (10 mL). The reaction solution was purged with nitrogen (3×) and stirred at 90° C. overnight. The reaction mixture was filtered through Celite and the filter cake was washed with EtOAC. The filtrate was concentrated in vacuo to give a brown liquid which was purified by silica gel chromotography (10%-50% EtOAc/Heptane) to afford 3-methoxy-4-(4,4,5,5-tetramethyl-1,3,2-dioxaborolan-2-yl)phenol (700 mg, MS: 251.4 [M+H$^+$].).

Step 2: 3-methoxy-4-(6-(methyl(2,2,6,6-tetramethyl-piperidin-4-yl)amino)pyridazin-3-yl)phenol To a microwave vial was added 3-methoxy-4-(6-(methyl (2,2,6,6-tetramethylpiperidin-4-yl)amino)pyridazin-3-yl) phenol (500 mg, 2.0 mmol), 6-chloro-N-methyl-N-(2,2,6,6-tetramethylpiperidin-4-yl)pyridazin-3-amine Intermediate 1-1 (565 mg, 2.0 mmol), potassium phosphate (1.27 g, 6.0 mmol), Pd$_2$(dba)$_3$ (92 mg, 0.1 mmol), and SPhos (82 mg, 0.2 mmol), followed by addition of 1,4-dioxane (5 mL)/H$_2$O (1 mL). The vial was purged with N$_2$ for 10 min and the reaction mixture was heated at 100° C. in a microwave reactor for one hour. The reaction mixture was concentrated in vacuo and the crude material was adjusted to pH 3 using 1 M aqueous HCl, then loaded on an SCX column. The crude material was washed with methanol then eluted with 2 N ammonia in methanol. The product fractions were collected and dried to afford 3-methoxy-4-(6-(methyl(2,2,6, 6-tetramethylpiperidin-4-yl)amino)pyridazin-3-yl)phenol which was used without further purification.

Step 3: 3-Methoxy-4-(6-(methyl(2,2,6,6-tetramethylpiperidin-4-yl)amino)pyridazin-3-yl)phenyl trifluoromethanesulfonate To a solution of 3-methoxy-4-(6-(methyl(2,2,6,6-tetramethylpiperidin-4-yl)amino)pyridazin-3-yl)phenol (120 mg, 0.32 mmol) in DCM (2 mL) was added triethylamine (0.113 mL, 0.810 mmol) at RT. The reaction mixture was cooled to 0° C., followed by addition of N-phenyltrifluoromethanesulfonimide (116 mg, 0.32 mmol). The reaction mixture was warmed to RT and stirred for 2 h. The reaction was quenched with aqueous sodium bicarbonate solution and extracted with DCM. The organic layer was dried over sodium sulfate, filtered and concentrated to give the crude product which was adjusted to pH 3 using 1 M HCl aqueous solution and loaded on an SCX column. The crude product was washed with methanol then eluted with 2 N ammonia in methanol. The product fractions were collected and dried to afford 3-methoxy-4-(6-(methyl(2,2,6,6-tetramethylpiperidin-4-yl) amino)pyridazin-3-yl)phenyl trifluoromethanesulfonate (140 mg, MS: 503.4 [M+H$^+$].).

Step 4: 6-(2-Methoxy-4-(1H-pyrazol-4-yl)phenyl)-N-methyl-N-(2,2,6,6-tetramethylpiperidin-4-yl)pyridazin-3-amine To a microwave vial was added 3-methoxy-4-(6-(methyl (2,2,6,6-tetramethylpiperidin-4-yl)amino)pyridazin-3-yl) phenyl trifluoromethanesulfonate (60 mg, 0.12 mmol), 1H-pyrazole-4-boronic acid (25.5 mg, 0.13 mmol), potassium phosphate (76 mg, 0.36 mmol), Pd$_2$(dba)$_3$ (6 mg, 5.9 umol), and SPhos (5 mg, 0.012 mmol), followed by addition of 1,4-dioxane (1 mL)/H$_2$O (0.2 mL). The vial was purged with N$_2$ for 10 minutes and the reaction mixture was heated at 100° C. in the microwave for one hour. The reaction mixture was concentrated in vacuo, and the crude product was adjusted to pH 3 using 1 M aqueous HCl, then loaded on an SCX column. The crude product was washed with methanol then eluted with 2 N ammonia in methanol. The product fractions were collected and dried to afford 6-(2-methoxy-4-(1H-pyrazol-4-yl)phenyl)-N-methyl-N-(2,2,6,6-tetramethylpiperidin-4-yl)pyridazin-3-amine (MS: 421.4 [M+H$^+$].).

Step 5: 2-(6-(Methyl(2,2,6,6-tetramethylpiperidin-4-yl)amino)pyridazin-3-yl)-5-(1H-pyrazol-4-yl)phenol Following GENERAL METHOD 3-1 for methoxy deprotection using thiophenol, 2-(6-(methyl(2,2,6,6-tetramethylpiperidin-4-yl)amino)pyridazin-3-yl)-5-(1H-pyrazol-4-yl) phenol was afforded as pale yellow powder (8 mg, MS: 407.2 [M+H$^+$]; LCMS Rt=0.48 min (LCMS method Q); $^1$H NMR (400 MHz, CHLOROFORM-d) δ ppm 7.83 (s, 2H), 7.75 (d, J=10.11 Hz, 1H), 7.51 (d, J=8.08 Hz, 1H), 7.13-7.17 (m, 1H), 7.01 (d, J=8.08 Hz, 1H), 6.93 (d, J=10.11 Hz, 1H), 4.85 (t, J=12.38 Hz, 1H), 2.94 (s, 3H), 1.63 (dd, J=12.13, 3.03 Hz, 2H), 1.36 (t, J=12.38 Hz, 2H), 1.29 (s, 6H), 1.13 (s, 6H).

Example 15-1

Synthesis of 5-(3-amino-pyrazol-1-yl)-2-{6-[methyl-(2,2,6,6-tetramethyl-piperidin-4-yl)-amino]-pyridazin-3-yl}-phenol

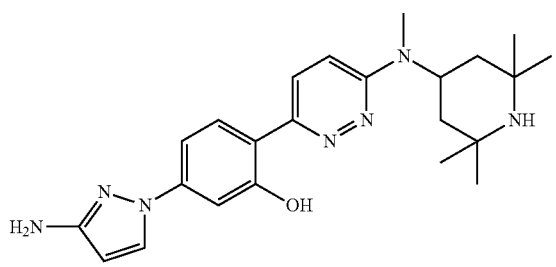 [SMILES: CN(c1ccc(-c2ccc(-n3ccc(N)n3)cc2O)nn1)C1CC(C)(C)NC(C)(C)C1]

Step 1: 1-(4-Bromo-3-methoxyphenyl)-3-nitro-1H-pyrazole

A mixture of 1-bromo-4-iodo-2-methoxybenzene (3.99 g, 12.75 mmol), 3-nitro-1H-pyrazole (1.730 g, 15.30 mmol), Salicylaldoxime (0.350 g, 2.55 mmol), Cu$_2$O (0.146 g, 1.020 mmol) and Cs$_2$CO$_3$ (6.23 g, 19.13 mmol) in DMF (13 mL) was degassed with N$_2$ and heated at 95° C. overnight. After cooling to RT, the mixture was filtered through celite and rinsed with EtOAc. The filtrate was washed with water and brine. The organic solution was dried over Na$_2$SO$_4$, filtered and concentrated in vacuo. The residue was suspended in 5% MeOH/DCM, and the precipitate filtered, rinsed with 5% MeOH/DCM, and dried to give 2.3 g of 1-(4-bromo-3-methoxyphenyl)-3-nitro-1H-pyrazole as a white solid. The filtrate from the above work up was purified by silica gel chromatography (EtOAc/Heptane=10:90 to 50:50) to give an additional 760 mg of 1-(4-bromo-3-methoxyphenyl)-3-nitro-1H-pyrazole as a light yellow solid.

Step 2: 1-(4-Bromo-3-methoxyphenyl)-1H-pyrazol-3-amine

To a mixture of 1-(4-bromo-3-methoxyphenyl)-3-nitro-1H-pyrazole (2.3 g, 7.72 mmol) in DCM (24 mL) and acetic acid (6.18 mL, 108 mmol) was added zinc dust (2.52 g, 38.6 mmol) at 0° C. The reaction mixture was stirred at 0° C. to RT overnight. The reaction mixture was filtered through celite, rinsed with EtOAc and concentrated in vacuo. The residue was purified by silica chromatagraphy (EtOAc/heptane=10:90 to 50:50) to give a white foam which was dissolved in 6 mL of toluene, concentrated and dried to give 1.9 g of 1-(4-bromo-3-methoxyphenyl)-1H-pyrazol-3-amine as a white powder.

Step 3. 1-(3-Methoxy-4-(4,4,5,5-tetramethyl-1,3,2-dioxaborolan-2-yl)phenyl)-1H-pyrazol-3-amine A degassed reaction mixture of 1-(4-bromo-3-methoxyphenyl)-1H-pyrazol-3-amine (1 g, 3.73 mmol), bis(pinacolato) diboron (1.989 g, 7.83 mmol), Pd(dppf)Cl$_2$ (0.273 g, 0.373 mmol), dppf (0.207 g, 0.373 mmol) and potassium acetate (2.56 g, 26.1 mmol) in 1,4-dioxane (10 mL) was heated at 88° C. overnight. After cooling to RT, the mixture was filtered through celite and washed with EtOAc. The filtrate was concentrated and the residue was purified by silica gel chromatagraphy (EtOAc/heptane=10:90 to 50:50, then 50:50 to 60:40) to give 930 mg of 1-(3-methoxy-4-(4,4,5,5-tetramethyl-1,3,2-dioxaborolan-2-yl)phenyl)-1H-pyrazol-3-amine as a white solid.

Step 4. 6-(4-(3-Amino-1H-pyrazol-1-yl)-2-methoxyphenyl)-N-methyl-N-(2, 2,6,6-tetramethylpiperidin-4-yl)pyridazin-3-amine A degassed reaction mixture of 1-(3-methoxy-4-(4,4,5,5-tetramethyl-1,3,2-dioxaborolan-2-yl)phenyl)-1H-pyrazol-3-amine (474 mg, 1.505 mmol), 6-chloro-N-methyl-N-(2,2,6,6-tetramethylpiperidin-4-yl)pyridazin-3-amine Intermediate 1-1 (370 mg, 1.308 mmol) tetrakis(triphenylphosphine)palladium(0) (76 mg, 0.065 mmol) and 1 M NaHCO$_3$ (330 mg, 3.92 mmol) in 1,4-dioxane (7 mL) and water (2.3 mL) was heated at 100° C. for 14 h. After cooling to RT, the mixture was filtered through celite, washed with EtOAc, and the filtrate was concentrated. The residue was suspended in MeOH, acidified to pH 2-3 using 1 M aqueous HCl and loaded on a 10 g SCX column. The column was washed with MeOH, then eluted with 2 N NH$_3$ in MeOH. The collected fractions were concentrated to give a light brown oil, which was treated with ether and concentrated to give 570 mg of 6-(4-(3-amino-1H-pyrazol-1-yl)-2-methoxyphenyl)-N-methyl-N-(2,2,6,6-tetramethylpiperidin-4-yl)pyridazin-3-amine as a light brown solid.

Step 5. 5-(3-Amino-1H-pyrazol-1-yl)-2-(6-(methyl(2,2,6,6-tetramethylpiperidin-4-yl)amino)pyridazin-3-yl)phenol A degassed mixture of 6-(4-(3-amino-1H-pyrazol-1-yl)-2-methoxyphenyl)-N-methyl-N-(2,2,6,6-tetramethylpiperidin-4-yl)pyridazin-3-amine (135 mg, 0.310 mmol), K$_2$CO$_3$ (42.8 mg, 0.310 mmol) and thiophenol (0.032 mL, 0.310 mmol) in NMP (2 mL) was heated at 190° C. under microwave radiation for 20 min. After addition of another 0.05 mmol of thiophenol and K$_2$CO$_3$, the mixture was heated at 190° C. under microwave radiation for another 10 min. The mixture was acidified to pH 2-3 with 1 M HCl aqueous solution, then loaded on a 5 g SCX column. The column was washed with MeOH and eluted with 2 N NH$_3$ in MeOH. The collected fractions were concentrated and dissolved in a mixture of MeOH and DMSO, then purified by preparative HPLC to give 95 mg of 5-(3-amino-1H-pyrazol-1-yl)-2-(6-(methyl(2,2,6,6-tetramethylpiperidin-4-yl)amino)pyridazin-3-yl)phenol as a dark yellow solid. LCMS Rt=0.47 min (LCMS method Q), MS (M+1)=422.3, HRMS: 422.2672 [M+H$^+$].

$^1$H NMR (400 MHz, METHANOL-d4) δ ppm 8.08 (d, J=10.10 Hz, 1H), 7.98 (d, J=3.03 Hz, 1H), 7.80 (d, J=9.09 Hz, 1H), 7.31 (d, J=10.10 Hz, 1H), 7.15-7.22 (m, 2H), 5.91 (d, J=2.53 Hz, 1H), 5.06 (m, 1H), 3.01 (s, 3H), 1.70 (m, 2H), 1.51-1.65 (m, 2H), 1.39 (s, 6H), 1.24 (s, 6H).

The following final compounds were prepared using similar procedures as in Examples 9-1 through 15-1, and general methods as outlined in the GENERAL METHODS section.

| Example | Compound | LCMS M + 1, Rt, conditions | $^1$H NMR 400 MHz |
|---|---|---|---|
| 16-1 | 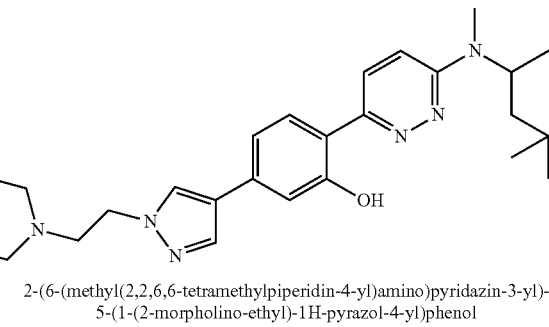 2-(6-(methyl(2,2,6,6-tetramethylpiperidin-4-yl)amino)pyridazin-3-yl)-5-(1-(2-morpholino-ethyl)-1H-pyrazol-4-yl)phenol | 520.6 0.43 min Q | CHLOROFORM-d δ 13.75 (s, 1H), 7.71-7.80 (m, 2H), 7.68 (s, 1H), 7.49 (d, J = 8.6 Hz, 1H), 7.11 (d, J = 2.0 Hz, 1H), 6.89-7.01 (m, 2H), 5.00 (m, 1H), 4.20 (t, J = 6.6 Hz, 2H), 3.58-3.69 (m, 4H), 2.93 (s, 3H), 2.77 (t, J = 6.6 Hz, 2H), 2.39-2.48 (m, 4H), 1.65 (dd, J = 12.4, 3.3 Hz, 2H), 1.51 (br. s., 2H), 1.36 (br. s, 6H), 1.18-1.31 (m, 6H) |

-continued

| Example | Compound | LCMS M + 1, Rt, conditions | ¹H NMR 400 MHz |
|---|---|---|---|
| 16-2 | 2-(6-(methyl(2,2,6,6-tetramethylpiperidin-4-yl)amino)pyridazin-3-yl)-5-(1-methyl-1H-pyrazol-4-yl)phenol | 421.4 0.51 min Q | CHLOROFORM-d d 13.75 (br. s., 1H), 7.70-7.77 (m, 2H), 7.56 (s, 1H), 7.48 (d, J = 8.6 Hz, 1H), 7.06-7.12 (m, 1H), 6.89-7.00 (m, 2H), 4.82 (t, J = 12.4 Hz, 1H), 3.87 (s, 3H), 2.91-2.98 (m, 3H), 1.63 (dd, J = 12.4, 3.3 Hz, 2H), 1.34 (t, J = 12.4 Hz, 2H), 1.28 (s, 6H), 1.09-1.14 (m, 6H) |
| 16-3 | 5-(5-amino-1H-pyrazol-1-yl)-2-(6-(methyl-(2,2,6,6-tetramethyl-piperidin-4-yl)pyridazin-3-yl)phenol | 422.3 0.43 min Q | METHANOL-d4 δ 8.08 (d, J = 10.11 Hz, 1H), 7.87 (d, J = 8.59 Hz, 1H), 7.36 (d, J = 2.02 Hz, 1H), 7.29 (d, J = 9.60 Hz, 1H), 7.06-7.21 (m, 2H), 7.06-7.21 (m, 2H), 5.62 (d, J = 2.02 Hz, 1H), 4.97-5.19 (m, 1H), 3.02 (s, 3H), 1.70 (dd, J = 12.63, 3.54 Hz, 2H), 1.56 (t, J = 12.13 Hz, 2H), 1.38 (s, 6H), 1.22 (s, 6H) |
| 16-4 | 2-(6-(methyl(2,2,6,6-tetramethylpiperidin-4-yl)amino)pyridazin-3-yl)-4-(1H-pyrazol-1-yl)phenol·HCl | 407.2 0.51 min Q | CHLOROFORM-d δ 8.69 (d, J = 11.8 Hz, 1H), 8.51 (d, J = 2.0 Hz, 1H), 8.41 (d, J = 9.8 Hz, 1H), 8.24 (d, J = 2.8 Hz, 1H), 7.65-7.80 (m, 3H), 7.52 (d, J = 9.8 Hz, 1H), 7.08 (d, J = 8.8 Hz, 1H), 6.48-6.59 (m, 1H), 5.09-5.22 (m, 1H), 3.01 (s, 3H), 1.79-1.98 (m, 4H), 1.53 (s, 6H), 1.42 (s, 6H) |
| 16-5 | 2-{6-[(2-hydroxy-ethyl)-(2,2,6,6-tetramethyl-piperidin-4-yl)-amino]-pyridazin-3-yl}-5-pyrazol-1-yl-phenol | 437.4 0.51 min Q | METHANOL-d4 δ 7.99 (s, 1H), 7.91 (d, J = 9.6 Hz, 1H), 7.70 (d, J = 8.6 Hz, 1H), 7.63 (s, 1H), 7.20-7.29 (m, 3H), 6.40-6.44 (m, 1H), 5.08-5.24 (m, 1H), 3.66 (t, J = 6.1 Hz, 2H), 3.47-3.56 (m, 2H), 2.13 (t, J = 12.9 Hz, 2H), 1.82-1.94 (m, 2H), 1.56 (s, 6H), 1.48 (s, 6H) |

Example 17-1

Synthesis of 2-(6-(piperidin-4-yloxy)pyridazin-3-yl)-5-(1H-pyrazol-1-yl)phenol

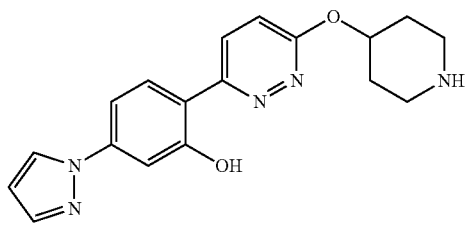 [SMILES: Oc1cc(-n2cccn2)ccc1-c1ccc(OC2CCNCC2)nn1]

Step 1. tert-Butyl 4-((6-(2-methoxy-4-(1H-pyrazol-1-yl)phenyl)pyridazin-3-yl)oxy)-piperidine-1-carboxylate Potassium tert-butoxide (1.0 M in THF, 0.82 mL, 0.82 mmol) was added to tert-butyl 4-hydroxypiperidine-1-carboxylate (0.17 g, 0.82 mmol) in THF (3 mL) at 0° C. and the mixture was stirred for 10 min at 0° C. 3-Chloro-6-(2-methoxy-4-(1H-pyrazol-1-yl)phenyl)pyridazine Intermediate 2-1 (0.13 g, 0.45 mmol) was added to the reaction at 0° C. and the mixture was stirred for 1 h at RT. After evaporation under reduced pressure, the crude material was purified by silica chromatography (70 to 100% EtOAc in heptane) to give tert-butyl 4-((6-(2-methoxy-4-(1H-pyrazol-1-yl)phenyl)pyridazin-3-yl)oxy)piperidine-1-carboxylate (0.18 g, 89%) as a colorless solid.

Step 2: 3-(2-Methoxy-4-(1H-pyrazol-1-yl)phenyl)-6-(piperidin-4-yloxy)pyridazine Trifluoroacetic acid (1 mL) was added to tert-butyl 4-((6-(2-methoxy-4-(1H-pyrazol-1-yl)phenyl)pyridazin-3-yl)oxy)piperidine-1-carboxylate (0.18 g, 0.40 mmol) in DCM (3 mL) at 0° C. The reaction was stirred for 1 h at RT. The reaction mixture was added to an aqueous solution of NaOH (1 M) and the aqueous phase was extracted with chloroform/propan-2-ol (3:1). The combined organic phases were dried over anhydrous $Na_2SO_4$, filtered and concentrated under reduced pressure to afford 3-(2-methoxy-4-(1H-pyrazol-1-yl)phenyl)-6-(piperidin-4-yloxy)pyridazine (0.14 g, 100%) as a colorless solid.

Step 3: 2-(6-(Piperidin-4-yloxy)pyridazin-3-yl)-5-(1H-pyrazol-1-yl)phenol

Following GENERAL METHOD 3-1 for methoxy deprotection with thiophenol, 3-(2-methoxy-4-(1H-pyrazol-1-yl)phenyl)-6-(piperidin-4-yloxy)pyridazine (70 mg, 0.20 mmol) was treated with thiophenol (27 mg, 0.24 mmol) and $K_2CO_3$ (25 mg, 0.18 mmol) in NMP (1.3 mL) for 15 min at 190° C. HPLC purification (0.1% trifluoroacetic acid as modifier) afforded 2-(6-(piperidin-4-yloxy)pyridazin-3-yl)-5-(1H-pyrazol-1-yl)phenol (12 mg, 18%) as a yellow solid. LCMS Rt=0.50 min (LCMS method Q); [M+H]: 338.16; $^1$H NMR (400 MHz, DMSO-d6) δ 13.01 (bs, 1H), 8.53 (d, J=2.5 Hz, 1H), 8.46 (bs, 2H), 8.45 (d, J=9.5 Hz, 1H), 7.50 (d, J=2.0 Hz, 1H), 7.47 (dd, J=8.5, 2.5 Hz, 2H), 7.44 (d, J=9.5 Hz, 1H), 6.51-6.62 (m, 1H), 5.51 (tt, J=7.5, 3.5 Hz, 1H), 3.33 (br. s, 2H), 3.20 (br. s, 2H), 2.18-2.31 (m, 2H), 2.01 (ddt, J=13.5, 8.5, 4.0 Hz, 2H).

Example 17-2

Synthesis of 2-(6-(((2S,4R,6R)-2,6-Dimethylpiperidin-4-yl)oxy)pyridazin-3-yl)-5-(1H-pyrazol-1-yl)phenol

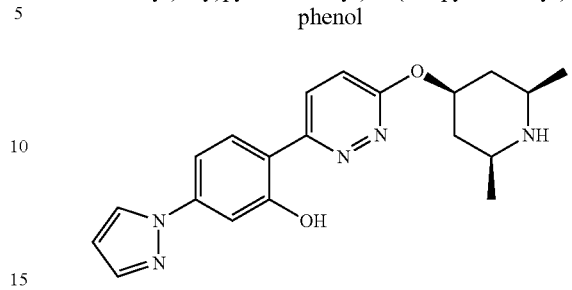

Step 1: 3-(((2S,4R,6R)-2,6-Dimethylpiperidin-4-yl)oxy)-6-(2-methoxy-4-(1H-pyrazol-1-yl)phenyl)pyridazine Potassium tert-butoxide (1.0 M in THF, 0.72 mL, 0.72 mmol) was added to 2,6-dimethylpiperidin-4-ol (0.09 g, 0.66 mmol) in THF (3 mL) at 0° C. and the mixture was stirred for 10 min at 0° C. 3-Chloro-6-(2-methoxy-4-(1H-pyrazol-1-yl)phenyl)pyridazine Intermediate 2-1 (0.15 g, 0.51 mmol) was added to the reaction at 0° C. and the mixture was stirred for 1 h at RT. Water was added and the aqueous phase was extracted with chloroform/propan-2-ol (3:1). The combined organic phases were dried over anhydrous $Na_2SO_4$, filtered and concentrated under reduced pressure. The crude material was purified by silica chromatography (silica gel saturated with $Et_3N$, 1 to 15% MeOH in DCM) to give 3-(((2S,4R,6R)-2,6-dimethylpiperidin-4-yl)oxy)-6-(2-methoxy-4-(1H-pyrazol-1-yl)phenyl)pyridazine (59 mg, 31%) as a colorless solid. A racemic mixture of 3-(((2R,6R)-2,6-dimethylpiperidin-4-yl)oxy)-6-(2-methoxy-4-(1H-pyrazol-1-yl)phenyl)pyridazine and 3-(((2S,6S)-2,6-dimethylpiperidin-4-yl)oxy)-6-(2-methoxy-4-(1H-pyrazol-1-yl)phenyl)pyridazine (91 mg, 47%) was also isolated as a colorless solid (intermediates for Example 17-3, 17-4 below).

Step 2: 2-(6-(((2S,4R,6R)-2,6-Dimethylpiperidin-4-yl)oxy)pyridazin-3-yl)-5-(1H-pyrazol-1-yl)phenol Following the GENERAL METHOD 3-1 for deprotection with thiophenol, 3-(((2S,4r,6R)-2,6-dimethylpiperidin-4-yl)oxy)-6-(2-methoxy-4-(1H-pyrazol-1-yl)phenyl)pyridazine (55 mg, 0.15 mmol) was treated with thiophenol (0.11 M in NMP, 1.5 mL, 0.17 mmol) and $K_2CO_3$ (18 mg, 0.13 mmol) in NMP (1.5 mL) for 15 min at 190° C. After HPLC purification (0.1% trifluoroacetic acid as modifier), the product-containing fractions were free based by catch and release using SiliaBond Propylsulfonic Acid® (2 g, MeOH as eluent and a 2 N ammonia solution in MeOH to release the material). Evaporation under reduced pressure afforded 2-(6-(((2S,4R,6R)-2,6-dimethylpiperidin-4-yl)oxy)pyridazin-3-yl)-5-(1H-pyrazol-1-yl)phenol (9 mg, 17%) as a yellow solid. LCMS Rt=0.50 min (LCMS method Q); [M+H]: 366.191; $^1$H NMR (400 MHz, DMSO-d6) δ 8.66 (bs, 1H), 8.53 (d, J=2.5 Hz, 1H), 8.45 (d, J=9.5 Hz, 1H), 8.12 (bs, 1H), 8.05 (d, J=8.5 Hz, 1H), 7.77 (d, J=2.0 Hz, 1H), 7.49 (d, J=2.0 Hz, 1H), 7.47 (dd, J=8.5, 2.0 Hz, 1H), 7.43 (d, J=9.5 Hz, 1H), 6.56 (dd, J=2.5, 2.0 Hz, 1H), 5-38-5.60 (m, 1H), 3.47 (bs, 3H), 2.45 (bs, 2H), 1.59 (q, J=12.0 Hz, 2H), 1.32 (d, J=6.5 Hz, 6H).

Example 17-3 and 17-4

Synthesis of 2-(6-((-2,6-Dimethylpiperidin-4-yl)oxy)pyridazin-3-yl)-5-(1H-pyrazol-1-yl)phenol, Enantiomer 1 and Enantiomer 2

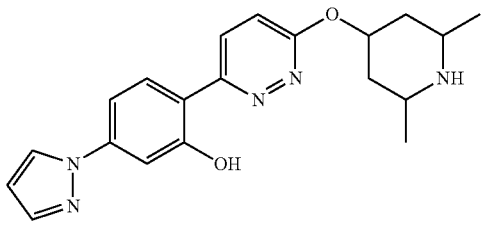 [SMILES: CC1CC(Oc2ccc(-c3ccc(-n4cccn4)cc3O)nn2)CC(C)N1]

The racemic mixture isolated from Step 1 of Example 17-2 was deprotected following GENERAL METHOD 3-1. The racemate (91 mg, 0.24 mmol) was treated with thiophenol (30 mg, 0.27 mmol) and $K_2CO_3$ (30 mg, 0.22 mmol) in NMP (1.6 mL) for 15 min at 190° C. After preparative HPLC purification (0.1% trifluoroacetic acid as modifier), the desired fractions were free based by catch and release using SiliaBond Propylsulfonic Acid® (2 g, MeOH as eluent and a 2 N ammonia solution in MeOH to release the material). Enantiomers 1 and Enantiomer 2 were isolated via normal phase preparative HPLC (AD-H 4.6×250 mm column, 40% EtOH (diethylamine as modifier) in heptane). Two solids (5 mg (6%) and 3 mg (3%)) were afforded. LCMS Rt=0.50 min (LCMS method Q); [M+H]: 366.21; $^1H$ NMR (400 MHz, DMSO-d6) δ 13.16 (bs, 1H), 8.52 (d, J=2.5 Hz, 1H), 8.40 (d, J=9.5 Hz, 1H), 8.03 (d, J=8.5 Hz, 1H), 7.75 (d, J=1.5 Hz, 1H), 7.47 (d, J=2.5 Hz, 1H), 7.45 (dd, J=8.5, 2.5 Hz, 1H), 7.35 (d, J=9.5 Hz, 1H), 6.54 (dd, J=2.5, 1.5 Hz, 1H), 5.52 (td, J=10.0, 5.0 Hz, 1H), 3.29-3.45 (m, 1H), 3.07 (dqd, J=9.5, 6.5, 3.0 Hz, 1H), 2.09-2.22 (m, 1H), 1.86-1.97 (m, 1H), 1.67 (ddd, J=12.0, 10.0, 5.0 Hz, 1H), 1.20-1.28 (m, 1H), 1.18 (d, J=7.0 Hz, 3H), 1.05 (d, J=6.5 Hz, 3H).

Example 17-5

Synthesis of 5-(1H-pyrazol-1-yl)-2-(6-(pyrrolidin-3-yloxy)pyridazin-3-yl)phenol

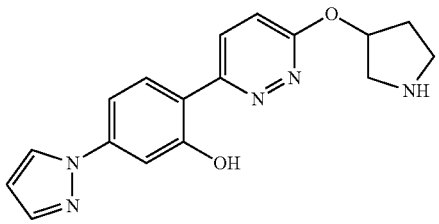 [SMILES: Oc1cc(-n2cccn2)ccc1-c1ccc(OC2CCNC2)nn1]

Step 1. tert-Butyl 3-((6-(2-methoxy-4-(1H-pyrazol-1-yl)phenyl)pyridazin-3-yl)oxy)-pyrrolidine-1-carboxylate Potassium tert-butoxide (1.0 M in THF, 0.98 mL, 0.98 mmol) was added to tert-butyl 3-hydroxypyrrolidine-1-carboxylate (0.18 g, 0.98 mmol) in THF (3.3 mL) at 0° C. and the mixture was stirred for 10 min at 50° C. 3-Chloro-6-(2-methoxy-(1H-pyrazol-1-yl)phenyl)pyridazine Intermediate 2-1 (0.12 g, 0.40 mmol) was added to the reaction at 0° C. and the mixture was stirred for 2 h at RT. Water (0.1 mL) was added and the solvent was concentrated under reduced pressure to afford (0.18 g, 100%) of a brown solid.

Step 2: 3-(2-Methoxy-4-(1H-pyrazol-1-yl)phenyl)-6-(pyrrolidin-3-yloxy)pyridazine Trifluoroacetic acid (1 mL) was added to tert-butyl 3-((6-(2-methoxy-4-(1H-pyrazol-1-yl)phenyl)pyridazin-3-yl)oxy)pyrrolidine-1-carboxylate (0.18 g, 0.40 mmol) in DCM (3 mL) at 0° C. The reaction was stirred for 2 days at RT. The reaction mixture was added to an aqueous solution of NaOH (1 M) and the aqueous phase was extracted with chloroform/propan-2-ol (3:1). The combined organic phases were dried over anhydrous $Na_2SO_4$, filtered and concentrated under reduced pressure to afford 3-(2-methoxy-4-(1H-pyrazol-1-yl)phenyl)-6-(pyrrolidin-3-yloxy)pyridazine (0.14 g, 100%) as a brown solid.

Step 3: 5-(1H-Pyrazol-1-yl)-2-(6-(pyrrolidin-3-yloxy)pyridazin-3-yl)phenol

Following GENERAL METHOD 3-1 for phenol deprotection using thiophenol, 3-(2-methoxy-4-(1H-pyrazol-1-yl)phenyl)-6-(pyrrolidin-3-yloxy)pyridazine (91 mg, 0.24 mmol) was treated with thiophenol (30 mg, 0.27 mmol) and $K_2CO_3$ (30 mg, 0.22 mmol) in NMP (1.6 mL) for 15 min at 190° C. After HPLC purification (0.1% trifluoroacetic acid as modifier), the product-containing fractions were free based by catch and release using SiliaBond Propylsulfonic Acid® (2 g, MeOH as eluent and a 2 N ammonia solution in MeOH to release the material). Solvent was concentrated under reduced pressure and a pale brown solid (83 mg, 68%) was afforded. LCMS Rt=0.48 min (LCMS method Q); [M+H]: 324.1457; $^1H$ NMR (400 MHz, CHLOROFORM-d) δ 13.62 (bs, 1H), 7.97 (d, J=2.5 Hz, 1H), 7.97 (d, J=9.5 Hz, 1H), 7.74 (d, J=1.5 Hz, 1H), 7.70 (d, J=8.5 Hz, 1H), 7.39-7.43 (m, 1H), 7.38 (d, J=2.5 Hz, 1H), 7.12 (d, J=9.5 Hz, 1H), 6.44-6.51 (m, 1H), 5.74 (ddt, J=7.0, 5.0, 2.5 Hz, 1H), 3.24-3.31 (m, 2H), 3.17-3.24 (m, 1H), 3.02 (ddd, J=11.0, 8.5, 5.5 Hz, 1H), 2.20-2.33 (m, 1H), 2.02-2.11 (m, 1H).

Example 17-6 and 17-7

Synthesis of 2-(6-(((2S,4S)-2-Methylpiperidin-4-yl)oxy)pyridazin-3-yl)-5-(1H-pyrazol-1-yl)phenol, Enantiomer 1 and Enantiomer 2

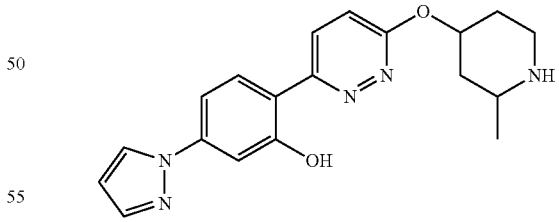

Potassium tert-butoxide (1.0 M in THF, 1.4 mL, 1.4 mmol) was added to cis-2-methylpiperidin-4-ol (0.10 g, 0.68 mmol) in THF (3 mL) and the mixture was stirred for 10 min at 50° C. 2-(6-Chloropyridazin-3-yl)-5-(1H-pyrazol-1-yl)phenol Intermediate 2-2 (0.08 g, 0.28 mmol) was added to the reaction at 0° C. and the mixture was stirred for 2 days at RT. Trifluoroacetic acid (0.3 mL) was added and the solvent was evaporated under reduced pressure. The crude material was purified via preparative HPLC (5 to 95% acetonitrile in water, 0.1% trifluoroacetic acid as modifier).

Enantiomer 1 and Enantiomer 2 were isolated via preparative SFC. Two solids (10 mg (10%) and (15 mg (16%)) were afforded.

Example 17-6, Enantiomer 1 LCMS Rt=0.48 min (LCMS method Q); [M+H]: 352.1; ¹H NMR (400 MHz, METHANOL-d4) 8.28 (d, J=9.5 Hz, 1H), 8.23 (d, J=2.5 Hz, 1H), 7.93 (d, J=8.5 Hz, 1H), 7.73 (d, J=2.0 Hz, 1H), 7.40 (d, J=2.0 Hz, 1H), 7.37 (dd, J=8.5, 2.5 Hz, 1H), 7.26 (d, J=9.5 Hz, 1H), 6.50-6.56 (m, 1H), 5.31 (tt, J=11.0, 4.5 Hz, 1H), 3.20 (ddd, J=13.0, 4.5, 2.5 Hz, 1H), 2.90-2.97 (m, 1H), 2.84 (td, J=13.0, 2.5 Hz, 2H), 2.31 (dddq, J=17.0, 12.0, 4.5, 2.5z Hz, 2H), 1.63 (tdd, J=13.0, 11.0, 4.5 Hz, 1H), 1.32-1.38 (m, 1H), 1.20 (d, J=6.5 Hz, 3H)

Example 17-7, Enantiomer 2 LCMS Rt=0.48 min (LCMS method Q); [M+H]: 352.1; ¹H NMR (400 MHz, DMSO-d6) δ 13.2 (bs, 1H), 8.52 (d, J=2.5 Hz, 1H), 8.40 (d, J=9.5 Hz, 1H), 8.03 (d, J=8.5 Hz, 1H), 7.76 (d, J=1.5 Hz, 1H), 7.48 (d, J=2.0 Hz, 1H), 7.45 (dd, J=8.5, 2.0 Hz, 1H), 7.37 (d, J=9.5 Hz, 1H), 6.51-6.59 (m, 1H), 5.24 (tt, J=11.0, 4.5 Hz, 1H), 3.06 (ddd, J=12.0, 4.5, 2.5 Hz, 1H), 2.70-2.81 (m, 1H), 2.62-2.71 (m, 1H), 2.09-2.23 (m, 2H), 1.47 (qd, J=12.0, 4.5 Hz, 1H), 1.13-1.21 (m, 1H), 1.07 (d, J=6.0 Hz, 3H).

Example 17-8 and 17-9

Synthesis of (5-(1H-pyrazol-1-yl)-2-(6-(pyrrolidin-3-ylmethoxy)pyridazin-3-yl)phenol, Enantiomer 1 and Enantiomer

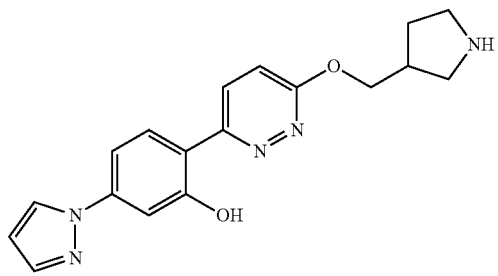 [SMILES: Oc1cc(-n2cccn2)ccc1-c1ccc(OCC2CCNC2)nn1]

Potassium tert-butoxide (1.0 M in THF, 0.7 mL, 0.7 mmol) was added to pyrrolidin-3-ylmethanol (0.06 g, 0.64 mmol) in THF (1.4 mL) and the mixture was stirred for 10 min at 50° C. 2-(6-Chloropyridazin-3-yl)-5-(1H-pyrazol-1-yl)phenol Intermediate 2-2 (0.05 g, 0.18 mmol) was added to the reaction at 0° C. and the mixture was stirred for 1 h at RT. Solvent was evaporated under reduced pressure. The crude material was purified via reverse phase preparative HPLC (5 to 95% acetonitrile in water, 5 mM NH₄OH as modifier). Enantiomer 1 and Enantiomer 2 were isolated via preparative SFC. Two solids (11 mg (17%), and 12 mg (20%) were afforded.

Example 17-8, Enantiomer 1 LCMS Rt=0.48 min (LCMS method Q); [M+H]: 338.161; ¹H NMR (400 MHz, METHANOL-d4) δ 8.31 (d, J=9.5 Hz, 1H), 8.24 (d, J=2.5 Hz, 1H), 7.94 (d, J=8.5 Hz, 1H), 7.73 (d, J=2.0 Hz, 1H), 7.40 (d, J=2.0 Hz, 1H), 7.38 (dd, J=8.5, 2.0 Hz, 1H), 7.34 (d, J=9.5 Hz, 1H), 6.51-6.56 (m, 1H), 4.55-4.66 (m, 2H), 3.39-3.43 (m, 1H), 3.21-3.28 (m, 1H), 3.10-3.19 (m, 1H), 3.04 (dd, J=11.5, 7.0 Hz, 1H), 2.86 (hept, J=7.0 Hz, 1H), 2.20 (dtd, J=13.5, 8.1, 5.5 Hz, 1H), 1.84 (dq, J=13.5, 7.5 Hz, 1H).

Example 17-9, Enantiomer 2 LCMS Rt=0.47 min (LCMS method Q); [M+H]: 338.161; ¹H NMR (400 MHz, DMSO-d6) δ 13.0 (bs, 1H), 8.52 (d, J=2.5 Hz, 1H), 8.44 (d, J=9.5 Hz, 1H), 8.04 (d, J=8.5 Hz, 1H), 7.76 (d, J=2.0 Hz, 1H), 7.49 (d, J=2.0 Hz, 1H), 7.46 (dd, J=8.5, 2.0 Hz, 1H), 7.45 (d, J=9.5 Hz, 1H), 6.52-6.59 (m, 1H), 4.42-4.60 (m, 2H), 3.36 (dd, J=11.5, 8.0 Hz, 1H), 3.22-3.32 (m, 1H), 3.16 (m, 1H), 3.07 (dd, J=11.5, 7.0 Hz, 1H), 2.84 (pentet, J=7.5 Hz, 1H), 2.14 (dtd, J=13.0, 7.5, 5.5 Hz, 1H), 1.81 (dq, J=13.0, 7.5 Hz, 1H).

The following final compounds were prepared using similar procedures as in Examples 17-1 to 17-9, and general methods as outlined in the GENERAL METHODS section when appropriate.

| Example | Compound | LCMS M + 1, Rt, conditions | ¹H NMR 400 MHz |
|---|---|---|---|
| 17-10 | 2-(6-((3-fluoropiperidin-4-yl)oxy)pyridazin-3-yl)-5-(1H-pyrazol-1-yl)-phenol | 356.1 0.46 min Q | METHANOL-d4 δ 8.07-8.14 (m, 1H), 8.00 (d, J = 2.3 Hz, 1H), 7.73-7.80 (m, 1H), 7.66 (d, J = 1.5 Hz, 1H), 7.42 (s, 1H), 7.26 (dq, J = 4.6, 2.3 Hz, 2H), 7.22 (d, J = 9.3 Hz, 1H), 6.41-6.48 (m, 1H), 5.31-5.46 (m, 1H), 4.85-5.09 (m, 1H), 3.27-3.35 (m, 1H), 3.10 (d, J = 14.8 Hz, 1H), 2.79-2.96 (m, 1H), 2.66-2.78 (m, 1H), 1.97-2.07 (m, 2H) |

| Example | Compound | LCMS M + 1, Rt, conditions | ¹H NMR 400 MHz |
|---|---|---|---|
| 17-11 | 2-[6-(1,2,2,6,6-pentamethyl-piperidin-4-yloxy)-pyridazin-3-yl]-5-pyrazol-1-yl-phenol | 408.3 0.51 min Q | CHLOROFORM-d δ 13.69 (br. s, 1H), 7.80-7.90 (m, 2H), 7.63 (d, J = 1.5 Hz, 1H), 7.57-7.62 (m, 1H), 7.25-7.31 (m, 2H), 6.97 (d, J = 9.6 Hz, 1H), 6.38 (t, J = 2.3 Hz, 1H), 5.53 (tt, J = 11.3, 4.1 Hz, 1H), 2.21 (s, 3H), 2.05 (dd, J = 11.9, 3.8 Hz, 2H), 1.56 (t, J = 11.6 Hz, 2H), 1.10 (s, 6H), 1.13 (s, 6H) |
| 17-12 | 5-pyrazol-1-yl-2-[6-(2,2,6,6-tetramethyl-piperidin-4-yloxy)-pyridazin-3-yl]-phenol | 394.2 0.61 min Q | METHANOL-d4 δ ppm 8.20-8.32 (m, 2H), 7.92 (d, J = 8.59 Hz, 1H), 7.73 (d, J = 1.52 Hz, 1H), 7.39-7.40 (m, 1H), 7.34-7.39 (m, 1H), 7.24 (d, J = 9.60 Hz, 1H), 6.51-6.55 (m, 1H), 5.70-5.80 (m, 1H), 2.21 (dd, J = 12.88, 4.29 Hz, 2H), 1.42 (t, J = 11.62 Hz, 2H), 1.33-1.37 (s, 6H), 1.23 (s, 6H) |

Example 17-13

Synthesis of 5-(1H-Pyrazol-4-yl)-2-(6-((2,2,6,6-tetramethylpiperidin-4-yl)oxy)pyridazin-3-yl)phenol hydrochloride salt

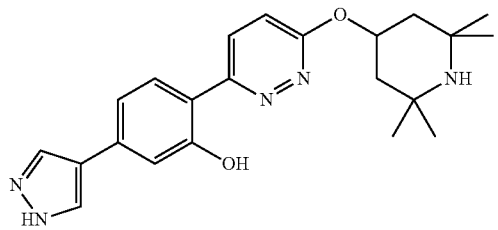 [SMILES: CC1(C)CC(Oc2ccc(-c3ccc(-c4cn[nH]c4)cc3O)nn2)CC(C)(C)N1]

Step 1: 3-(4-Chloro-2-methoxyphenyl)-6-((2,2,6,6-tetramethylpiperidin-4-yl)oxy)pyridazine A mixture of 4-chloro-2-methoxyphenylboronic acid (1.12 g, 6.00 mmol), Intermediate 1-3 (1.94 g, 7.20 mmol), SiliaCat® DPP-Pd (1.15 g, 0.30 mmol) and potassium carbonate in ethanol/water (10:1, 33 mL) was heated at reflux for 5 h. The solvent was evaporated and the resulting brown residue was partitioned between DCM and an 8% aqueous solution of K₂CO₃. After separation, the aqueous layer was extracted with DCM. The combined organic layers were washed with brine, dried over Na₂SO₄, filtered and concentrated to dryness in vacuo. The crude material was purified by flash chromatography (30 uM amine, —(CH₂)₃ NH₂, functionalized silica gel, 30 to 100% Et₂O in heptane) to give a mixture (1.76 g) of the desired product (75%) and Intermediate 1-3 (25%). [M+H]: 376.3; ¹H NMR (400 MHz, DMSO-d6) δ 7.91 (d, J=9.0 Hz, 1H), 7.71 (d, J=8.0 Hz, 1H), 7.27 (d, J=2.0 Hz, 1H), 7.12-7.20 (m, 2H), 5.68 (tt, J=11.0, 4.0 Hz, 1H), 3.85 (s, 3H), 1.99-2.11 (m, 2H), 1.20-1.30 (m, 8H), 1.10 (s, 6H).

Step 2: 3-(2-Methoxy-4-(1H-pyrazol-4-yl)phenyl)-6-((2,6,6-tetramethylpiperidin-4-yl)oxy)pyridazine SiliaCat® DPP-Pd (0.37 g, 0.10 mmol) was added to a microwave vial containing a mixture of 3-(4-chloro-2-methoxyphenyl)-6-((2,2,6,6-tetramethylpiperidin-4-yl)oxy)pyridazine (0.36 g, 0.96 mmol), 4-(4,4,5,5-tetramethyl-1,3,2-dioxaborolan-2-yl)-1H-pyrazole (0.47 g, 2.4 mmol), and K₂CO₃ (0.53 g, 3.8 mmol) in ethanol/water (10:1, 6.6 mL). The reaction mixture was sealed, then heated in a microwave reactor at 160° C. for 1 h. After cooling, the reaction was purified by solid phase extraction (5 g SiliaBond Carbonate®, MeOH as eluent). The filtrate was concentrated in vacuo and the resulting residue was purified by flash chromatography (silica gel saturated with Et₃N, 2 to 25% MeOH in DCM) to give the desired product (0.08 mg, 21%). [M+H]: 408.4; ¹H NMR (400 MHz, DMSO-d6) δ 13.01 (bs, 1H), 8.33 (bs, 1H), 8.05 (bs, 1H), 7.94 (d, J=9.5 Hz, 1H), 7.70 (d, J=8.0 Hz, 1H), 7.38 (d, J=1.5 Hz, 1H), 7.34 (dd, J=8.0, 1.5 Hz, 1H), 7.14 (d, J=9.5 Hz, 1H), 5.57-5.74 (m, 1H), 3.90 (s, 3H), 2.00-2.14 (m, 2H), 1.17-1.31 (m, 8H), 1.11 (s, 6H).

Step 3: 5-(1H-Pyrazol-4-yl)-2-(6-((2,2,6,6-tetramethylpiperidin-4-yl)oxy)pyridazin-3-yl)phenol. Hydrochloride salt Following GENERAL METHOD 3-1 for phenol deprotection using thiophenol, 3-(2-methoxy-4-(1H-pyrazol-4-yl)

phenyl)-6-((2,2,6,6-tetramethylpiperidin-4-yl)oxy) pyridazine (0.58 mg, 1.41 mmol) was treated with thiophenol (0.15 mg, 1.36 mmol) and $K_2CO_3$ (0.23 mg, 1.64 mmol) in NMP (9 mL) for 15 min at 190° C. After purification (0.1% trifluoroacetic acid as modifier), desired fractions were free based by catch and release using SiliaBond Propylsulfonic Acid® (5 g, MeOH as eluent and a 2 N ammonia solution in MeOH to release the material). The solvent was evaporated under reduced pressure. The resulting beige solid was dissolved in $CH_3CN/H_2O/MeOH$ (6/1/6 mL) and SiliaMetS® DMT (2.7 g, 1.4 mmol) was added and the mixture was shaken 18 h. The mixture was then filtered through a small celite plug and the filtrate was purified by catch and release using SiliaBond Propylsulfonic Acid® (5 g, MeOH as eluent and a 2 N ammonia solution in MeOH to release the material). The solvent was concentrated in vacuo and the resulting solid was suspended in $CH_3CN/H_2O$ (4/1 mL). 4 N HCl in 1,4-dioxane (4 equivalents) was added and solvent was concentrated in vacuo to afford a yellow solid (59 mg, 9%). LCMS RT=0.51 min (LCMS method Q); [M+H]: 394.2225; $^1$H NMR (400 MHz, DMSO-d6) δ 9.10 (d, J=12.0 Hz, 1H), 8.49 (d, J=9.5 Hz, 1H), 8.36 (d, J=12.0 Hz, 1H), 8.16 (s, 1H), 7.94 (d, J=8.0 Hz, 1H), 7.47 (d, J=9.5 Hz, 1H), 7.21-7.28 (m, 2H), 5.63-5.87 (m, 1H), 2.34 (dd, J=13.0, 4.0 Hz, 2H), 1.81 (dd, J=13.0, 10.5 Hz, 2H), 1.53 (s, 6H), 1.50 (s, 6H).

Example 18-1

Synthesis of 2-(6-piperazin-1-yl-pyridazin-3-yl)-5-pyrazol-1-yl-phenol HCl salt

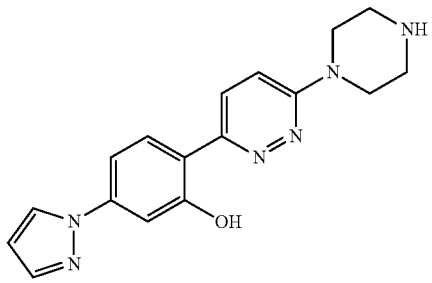 [SMILES: Oc1cc(-n2cccn2)ccc1-c1ccc(N2CCNCC2)nn1]

Step 1 (N-arylation): tert-Butyl 4-(6-(2-methoxy-4-(1H-pyrazol-1-yl)phenyl)pyridazin-3-yl)piperazine-1-carboxylate Following GENERAL METHOD 6-1 for $S_NAr$, Intermediate 2-1 (50 mg, 0.174 mmol), tert-butyl piperazine-1-carboxylate (59 mg, 0.314 mmol), DIPEA (0.06 mL, 0.349 mmol), and n-butanol (0.1 mL) were combined in a 4 mL reaction vial and heated at 120° C. overnight. The reaction was cooled to RT and EtOAc was added. The white solid that formed was filtered off and washed with EtOAc, dissolved in DCM and washed with $H_2O$. The organic layer was dried with sodium sulfate, filtered, and concentrated in vacuo to afford the desired product.

Step 2 tert-Butyl 4-(6-(2-methoxy-4-(1H-pyrazol-1-yl)phenyl)pyridazin-3-yl)piperazine-1-carboxylate (49.2 mg, 0.11 mmol), $K_2CO_3$ (15.6 mg, 0.11 mmol), thiophenol (17.2 uL, 0.17 mmol), and NMP (0.23 mL) were combined in a 2 mL microwave vial and heated in the microwave at 190° C. for 0.5 hrs. The reaction mixture was cooled to RT and acidified with 5% aq. citric acid. EtOAc was added and the resulting product precipitate was isolated by filtration.

Step 3

The Step 2 precipitate was dissolved in 4 M HCl in 1,4-dioxane (2 mL) and stirred at RT for 0.5 hrs then concentrated to provide 2-(6-(piperazin-1-yl)pyridazin-3-yl)-5-(1H-pyrazol-1-yl)phenol, (11.0 mg, 0.03 mmol, 30% yield). LCMS Rt=0.46 min, M+1=323.5 (LCMS method Q). $^1$H NMR (DMSO-d6) δ 9.32 (br. s, 2H), 8.60 (d, J=2.3 Hz, 1H), 8.40 (d, J=10.0 Hz, 1H), 8.01 (d, J=8.8 Hz, 1H), 7.71-7.85 (m, 2H), 7.43-7.56 (m, 2H), 6.54-6.63 (m, 1H), 3.86-4.02 (m, 4H), 3.41-3.78 (m, 2H), 2.60-2.83 (m, 2H).

The following compounds were prepared using similar procedures as in Example 18-1:

| Example | Compound | LCMS M + 1, Rt, conditions | $^1$H NMR 400 MHz |
|---|---|---|---|
| 18-2 | 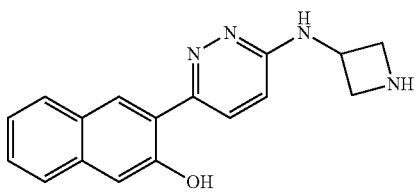<br>3-[6-(azetidin-3-ylamino)-pyridazin-3-yl]-naphthalen-2-ol | 293.2<br>0.37 min<br>Q | DMSO-d6 δ 8.47 (s, 1H), 8.32 (d, J = 9.6 Hz, 1H), 7.85-7.90 (m, 2H), 7.71 (d, J = 8.1 Hz, 1H), 7.27-7.48 (m, 4H), 7.12 (d, J = 9.6 Hz, 1H), 4.75 (quintd, J = 6.9 Hz, 1H), 3.81 (dd, J = 8.6, 7.6 Hz, 2H), 3.53 (dd, J = 8.3, 7.1 Hz, 2H) |

-continued

| Example | Compound | LCMS M + 1, Rt, conditions | ¹H NMR 400 MHz |
|---|---|---|---|
| 18-3 | 2-[6-(azetidin-3-ylamino)-pyridazin-3-yl]-5-pyrazol-1-yl-phenol | 309.1 0.44 min Q | DMSO-d6 δ 8.59 (d, J = 2.5 Hz, 1H), 8.18 (d, J = 9.5 Hz, 1H), 7.95 (d, J = 9.3 Hz, 1H), 7.69-7.84 (m, 2H), 7.39-7.48 (m, 2H), 7.09 (d, J = 9.8 Hz, 1H), 6.56 (dd, J = 2.5, 1.8 Hz, 1H), 4.71 (quint, J = 6.9 Hz, 1H), 3.67-3.82 (m, 2H), 3.43-3.54 (m, 2H) |
| 18-4 | 2-[6-(3,5-dimethyl-piperazin-1-yl)-pyridazin-3-yl]-5-pyrazol-1-yl-phenol | 351.2 0.48 min Q | DMSO-d6 δ 14.11 (br. s, 1H), 8.60 (d, J = 2.0 Hz, 1H), 8.26 (d, J = 10.0 Hz, 1H), 7.95-8.09 (m, 1H), 7.77 (d, J = 1.5 Hz, 1H), 7.58 (d, J = 10.0 Hz, 1H), 7.41-7.48 (m, 2H), 6.56 (dd, J = 2.5, 1.8 Hz, 1H), 4.30 (dd, J = 12.4, 1.9 Hz, 2H), 2.72-2.86 (m, 2H), 2.42 (dd, J = 12.4, 10.7 Hz, 2H), 1.05 (d, J = 6.3 Hz, 6H) |
| 18-5 | 2-[6-(7-methyl-2,7-diaza-spiro[4.4]non-2-yl)-pyridazin-3-yl]-5-pyrazol-1-yl-phenol | 377.1 0.42 min Q | DMSO-d6 δ 8.59 (d, J = 2.3 Hz, 1H), 8.24 (d, J = 9.8 Hz, 1H), 7.95-8.05 (m, 1H), 7.77 (d, J = 1.5 Hz, 1H), 7.38-7.48 (m, 2H), 7.18 (d, J = 9.8 Hz, 1H), 6.56 (dd, J = 2.5, 1.8 Hz, 1H), 3.37-3.72 (m, 4H), 2.53-2.66 (m, 2H), 2.35-2.49 (m, 2H), 2.25 (s, 3H), 1.92-2.10 (m, 2H), 1.72-1.86 (m, 2H) |
| 18-6 | 2-(6-[1,4]diazepan-1-yl-pyridazin-3-yl)-5-pyrazol-1-yl-phenol | 337.2 0.46 min Q | METHANOL-d4 δ 7.91 (d, J = 2.5 Hz, 1H), 7.80 (d, J = 9.6 Hz, 1H), 7.57-7.65 (m, 2H), 7.22 (dq, J = 4.4, 2.4 Hz, 2H), 7.03 (d, J = 10.1 Hz, 1H), 6.40 (t, J = 2.0 Hz, 1H), 3.81-3.89 (m, 2H), 3.74 (t, J = 6.1 Hz, 2H), 3.04-3.13 (m, 2H), 2.87-2.95 (m, 2H), 1.93-2.03 (m, 2H) |

| Example | Compound | LCMS M + 1, Rt, conditions | ¹H NMR 400 MHz |
|---|---|---|---|
| 18-7 | 2-{6-[4-(2-hydroxy-ethyl)-piperazin-1-yl]-pyridazin-3-yl}-5-pyrazol-1-yl-phenol | 367.1 0.44 min Q | DMSO-d6 δ 14.05 (s, 1H), 8.60 (d, J = 2.3 Hz, 1H), 8.29 (d, J = 10.0 Hz, 1H), 8.03 (d, J = 9.3 Hz, 1H), 7.73-7.80 (m, 1H), 7.59 (d, J = 10.0 Hz, 1H), 7.38-7.50 (m, 2H), 6.53-6.60 (m, 1H), 4.49 (t, J = 5.3 Hz, 1H), 3.60-3.72 (m, 4H), 3.55 (q, J = 6.0 Hz, 2H), 2.53-2.60 (m, 4H), 2.45 (t, J = 6.1 Hz, 2H) |
| 18-8 | 2-[6-(3,6-diaza-bicyclo[3.2.1]oct-3-yl)-pyridazin-3-yl]-5-pyrazol-1-yl-phenol | 349.1 0.46 min Q | METHANOL-d4 δ 8.21 (d, J = 2.5 Hz, 1H), 8.07 (d, J = 9.6 Hz, 1H), 7.85 (d, J = 8.1 Hz, 1H), 7.71 (d, J = 1.5 Hz, 1H), 7.28-7.39 (m, 3H), 6.52 (t, J = 2.3 Hz, 1H), 4.13 (dd, J = 11.9, 2.8 Hz, 1H), 4.04 (dd, J = 12.4, 2.8 Hz, 1H), 3.66 (br. s, 1H), 3.22 (d, J = 11.6 Hz, 1H), 3.05-3.16 (m, 2H), 2.97-3.04 (m, 1H), 1.87-1.96 (m, 2H) |
| 18-9 | 2-[6-(2,7-diaza-spiro[3.5]non-7-yl)-pyridazin-3-yl]-5-pyrazol-1-yl-phenol | 363.1 0.47 min Q | METHANOL-d4 δ 8.27 (d, J = 2.3 Hz, 1H), 8.09 (d, J = 10.0 Hz, 1H), 7.86 (d, J = 8.3 Hz, 1H), 7.70-7.75 (m, J = 1.5 Hz, 1H), 7.46 (d, J = 9.8 Hz, 1H), 7.30-7.36 (m, 2H), 6.54 (dd, J = 2.4, 1.9 Hz, 1H), 3.63-3.69 (m, 4H), 3.49 (bs, 4H), 1.87-1.93 (m, 4H) |
| 18-10 | 2-[6-(3-hydroxy-methyl-piperazin-1-yl)-pyridazin-3-yl]-5-pyrazol-1-yl-phenol | 353.1 0.46 min Q | DMSO-d6 δ 14.07 (s, 1H), 8.60 (d, J = 2.5 Hz, 1H), 8.28 (d, J = 10.0 Hz, 1H), 7.96-8.10 (m, 1H), 7.77 (d, J = 1.5 Hz, 1H), 7.56 (d, J = 10.0 Hz, 1H), 7.37-7.49 (m, 2H), 6.56 (dd, J = 2.4, 1.9 Hz, 1H), 4.81 (t, J = 5.3 Hz, 1H), 4.13-4.45 (m, 2H), 3.38-3.49 (m, 2H), 2.89-3.14 (m, 2H), 2.60-2.84 (m, 3H) |

| Example | Compound | LCMS M + 1, Rt, conditions | ¹H NMR 400 MHz |
|---|---|---|---|
| 18-11 | 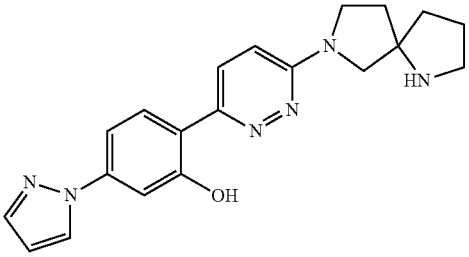<br>2-[6-(1,7-diaza-spiro[4.4]non-7-yl)-pyridazin-3-yl]-5-pyrazol-1-yl-phenol | 363.2<br>0.47 min<br>Q | METHANOL-d4 δ 8.17 (d, J = 2.5 Hz, 1H), 8.04 (d, J = 9.6 Hz, 1H), 7.82 (d, J = 8.6 Hz, 1H), 7.71 (d, J = 1.5 Hz, 1H), 7.28-7.36 (m, 2H), 7.10 (d, J = 10.1 Hz, 1H), 6.47-6.55 (m, 1H), 3.63-3.77 (m, 2H), 3.59 (d, J = 11.1 Hz, 1H), 3.51 (d, J = 10.6 Hz, 1H), 2.93-3.10 (m, 2H), 2.13 (t, J = 7.1 Hz, 2H), 1.81-1.89 (m, 4H) |
| 18-12 | 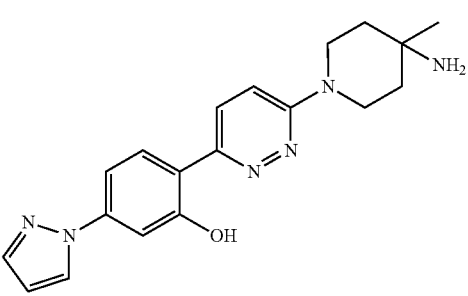<br>2-[6-(4-amino-4-methyl-piperidin-1-yl)-pyridazin-3-yl]-5-pyrazol-1-yl-phenol | 351.1<br>0.49 min<br>Q | METHANOL-d4 δ 8.02 (d, J = 2.5 Hz, 1H), 7.90 (d, J = 10.1 Hz, 1H), 7.69-7.75 (m, 2H), 7.30-7.36 (m, 2H), 7.24 (d, J = 10.1 Hz, 1H), 6.48-6.51 (m, 1H), 3.66-3.82 (m, 5H), 1.72 (ddd, J = 12.9, 8.1, 4.3 Hz, 2H), 1.57-1.66 (m, 2H), 1.25 (s, 3H) |
| 18-13 | 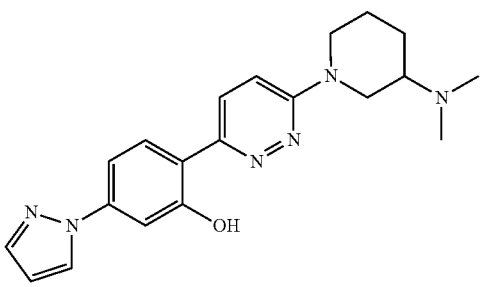<br>2-[6-(3-dimethyl-amino-piperidin-1-yl)-pyridazin-3-yl]-5-pyrazol-1-yl-phenol | 365.2<br>0.43 min<br>Q | CHLOROFORM-d δ 13.71 (br. s, 1H), 7.86 (d, J = 2.5 Hz, 1H), 7.72 (d, J = 10.1 Hz, 1H), 7.63 (d, J = 1.5 Hz, 1H), 7.55 (d, J = 8.1 Hz, 1H), 7.23-7.31 (m, 2H), 7.09 (d, J = 10.1 Hz, 1H), 6.33-6.42 (m, 1H), 4.53 (d, J = 11.6 Hz, 1H), 4.15 (d, J = 13.1 Hz, 1H), 3.10 (t, J = 11.4 Hz, 1H), 2.91-3.02 (m, 1H), 2.58 (br. s, 1H), 2.39-2.53 (br. s, 6H), 2.02-2.14 (m, 1H), 1.83-1.93 (m, 1H), 1.50-1.71 (m, 2H) |
| 18-14 | 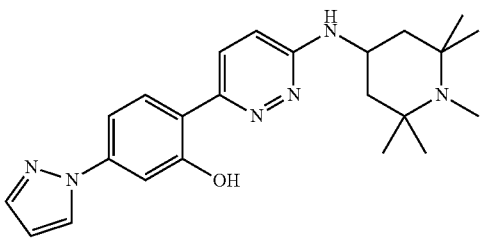<br>2-[6-(1,2,2,6,6-pentamethyl-piperidin-4-ylamino)-pyridazin-3-yl]-5-pyrazol-1-yl-phenol | 407.3<br>0.46 min<br>Q | CHLOROFORM-d δ 13.83 (br. s, 1H), 7.86 (d, J = 2.5 Hz, 1H), 7.65-7.71 (m, 1H), 7.63 (d, J = 1.5 Hz, 1H), 7.54 (d, J = 8.6 Hz, 1H), 7.23-7.30 (m, 1H), 7.17 (s, 1H), 6.73 (d, J = 9.1 Hz, 1H), 6.34-6.40 (m, 1H), 4.54 (br. s, 1H), 4.21 (br., m, 1H), 2.29 (s, 3H), 1.96 (dd, J = 12.4, 3.3 Hz, 2H), 1.49 (br. s, 2H), 1.21 (s, 6H), 1.15 (s, 6H) |

| Example | Compound | LCMS M + 1, Rt, conditions | ¹H NMR 400 MHz |
|---|---|---|---|
| 18-15 | 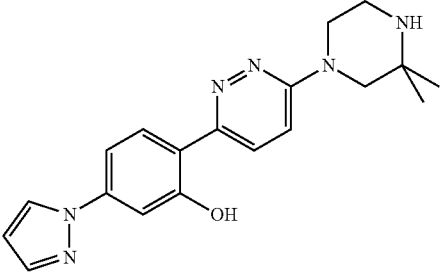<br>2-[6-(3,3-dimethyl-piperazin-1-yl)-pyridazin-3-yl]-5-pyrazol-1-yl-phenol | 351.1<br>0.48 min<br>Q | DMSO-d6 δ 8.59 (d, J = 2.3 Hz, 1H), 8.24 (d, J = 10.3 Hz, 1H), 7.98-8.07 (m, 1H), 7.77 (d, J = 1.5 Hz, 1H), 7.56 (d, J = 10.0 Hz, 1H), 7.39-7.48 (m, 2H), 6.56 (dd, J = 2.4, 1.9 Hz, 1H), 3.54-3.66 (m, 2H), 3.35 (s, 2H), 2.80-2.94 (m, 2H), 1.07 (s, 6H) |
| 18-16 | 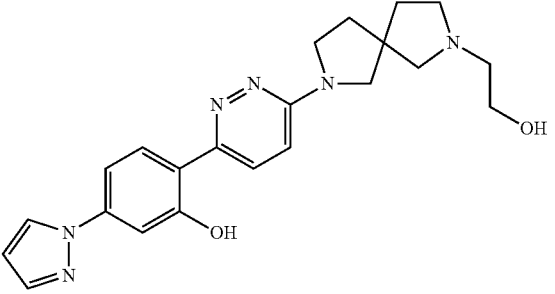<br>2-(6-(7-(2-hydroxyethyl)-2,7-diazaspiro[4.4]nonan-2-yl)pyridazin-3-yl)-5-(1H-pyrazol-1-yl)phenol | 407.1<br>0.46 min<br>Q | METHANOL-d4 δ ppm 8.28 (d, J = 2.51 Hz, 1H), 8.07 (d, J = 9.54 Hz, 1H), 7.83 (d, J = 8.28 Hz, 1H), 7.74 (d, J = 1.76 Hz, 1H), 7.24-7.38 (m, 2H), 7.09 (d, J = 9.29 Hz, 1H), 6.50-6.59 (m, 1H), 3.79 (t, J = 5.52 Hz, 2H), 3.49-3.68 (m, 4H), 3.27-3.32 (m, 2H), 3.21 (q, J = 11.29 Hz, 2H), 3.11 (t, J = 5.40 Hz, 2H), 2.00-2.25 (m, 4H) |
| 18-17 | 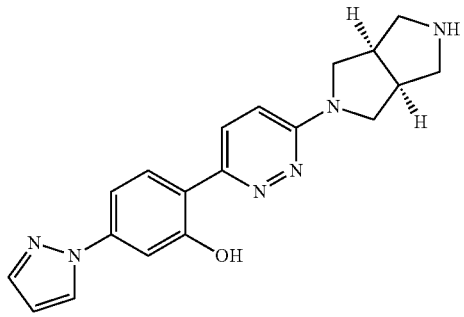<br>2-(6-((3aR,6aS)-hexahydropyrrolo[3,4-c]pyrrol-2(1H)-yl)pyridazin-3-yl)-5-(1H-pyrazol-1-yl)phenol | 349.2<br>0.46 min<br>Q | DMSO-d6 δ ppm 8.49 (d, J = 2.53 Hz, 1H), 8.19 (d, J = 9.60 Hz, 1H), 7.93-7.98 (m, 1H), 7.73 (d, J = 1.52 Hz, 1H), 7.38-7.44 (m, 2H), 7.18 (d, J = 10.11 Hz, 1H), 6.50-6.55 (m, 1H), 3.75 (dd, J = 11.12, 8.08 Hz, 2H), 3.41 (dd, J = 11.2, 8.08 Hz, 2H), 3.04 (dd, J = 10.86, 6.82 Hz, 2H), 2.94 (dd, J = 7.07, 3.54 Hz, 2H), 2.75 (dd, J = 11.12, 3.03 Hz, 2H), 2.63-2.71 (m, 1H) |
| 18-18 | 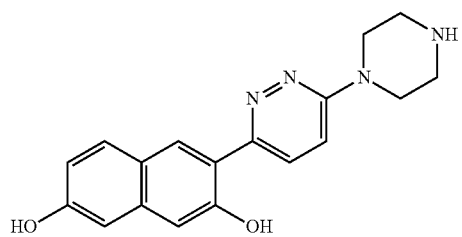<br>3-(6-(piperazin-1-yl)pyridazin-3-yl)naphthalene-2,7-diol-TFA salt | 323.4<br>0.40 min<br>Q | DMSO-d6 δ 9.83 (br. s, 1H), 8.86 (br. s, 2H), 8.30-8.54 (m, 2H), 7.71 (dd, J = 16.1, 9.5 Hz, 2H), 7.06 (s, 1H), 6.81-6.98 (m, 2H), 3.88-3.94 (m, 4H), 3.21-3.33 (m, 4H) |

Example 19-1

Synthesis of 5-pyrazol-1-yl-2-[6-(1,2,3,6-tetrahydro-pyridin-4-yl)-pyridazin-3-yl]-phenol

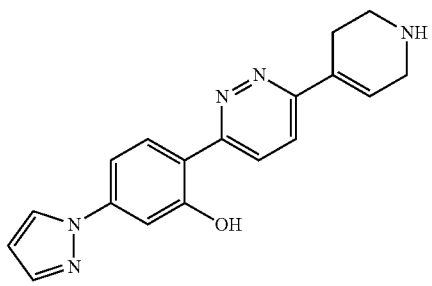 [SMILES: Oc1cc(-n2cccn2)ccc1-c1ccc(C2=CCNCC2)nn1]

Step 1 tert-Butyl 4-(6-(2-methoxy-4-(1H-pyrazol-1-yl)phenyl)pyridazin-3-yl)-5,6-dihydropyridine-1(2H)-carboxylate (151 mg, 0.35 mmol, 100% yield) was prepared from Intermediate 2-1 and tert-butyl 4-(4,4,5,5-tetramethyl-1,3,2-dioxaborolan-2-yl)-5,6-dihydropyridine-1(2H)-carboxylate using General Method 1-4 for Suzuki coupling. LCMS Rt=1.58 min, M+1=434.8 (condition B).

Step 2

5-(1H-Pyrazol-1-yl)-2-(6-(1,2,3,6-tetrahydropyridin-4-yl)pyridazin-3-yl)phenol was prepared following General Method 3-2 for BBr₃ deprotection.

tert-Butyl 4-(6-(2-methoxy-4-(1H-pyrazol-1-yl)phenyl)pyridazin-3-yl)-5,6-dihydropyridine-1(2H)-carboxylate (50 mg, 0.12 mmol) was dissolved in DCM (0.6 mL). The solution was cooled to −78° C. and 1 M BBr₃ in DCM (0.6 mL) was added dropwise. The resulting suspension was removed from the ice bath and stirred at RT overnight. The reaction was quenched with water, diluted with MeOH then adsorbed onto a MeOH conditioned SCX column. The column was washed several times (5-7 column volumes) with MeOH then eluted with 2 N NH₃ in MeOH to provide the desired product, 5-(1H-pyrazol-1-yl)-2-(6-(1,2,3,6-tetrahydropyridin-4-yl)pyridazin-3-yl)phenol, (9.7 mg, 0.03 mmol, 25% yield). LCMS Rt=0.49 min, M+1=320.1 (LCMS method Q). $^1$H NMR (DMSO-d6) δ 8.64 (d, J=2.3 Hz, 1H), 8.52 (d, J=9.5 Hz, 1H), 8.19 (dd, J=9.0, 3.0 Hz, 2H), 7.80 (d, J=1.3 Hz, 1H), 7.43-7.61 (m, 2H), 6.89-7.03 (m, 1H), 6.52-6.66 (m, 1H), 3.56-3.73 (m, 2H), 3.02-3.15 (m, 2H), 2.66-2.74 (m, 2H).

Example 19-2

Synthesis of 2-(6-piperidin-4-yl-pyridazin-3-yl)-5-pyrazol-1-yl-phenol

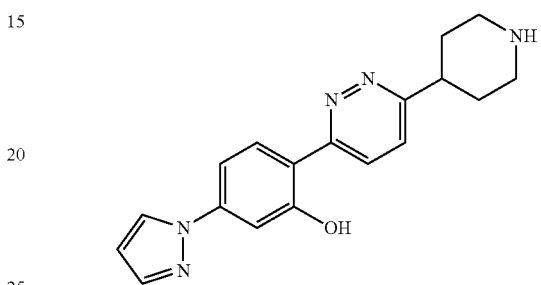

To a round-bottomed flask containing 10% Pd/C (27.7 mg, 0.026 mmol), was added 5-pyrazol-1-yl-2-[6-(1,2,3,6-tetrahydro-pyridin-4-yl)-pyridazin-3-yl]-phenol (Example 19-1) (166 mg, 0.52 mmol) in MeOH (2.5 mL). H₂ was bubbled through the solution for 5 min, then the reaction was stirred under H₂ at 55 psi at RT. After 18 hr, the reaction mixture was filtered through celite and washed with MeOH. The solvent was removed in vacuo and the resulting oil was dissolved in MeOH then adsorbed onto a MeOH conditioned SCX column. The column was washed several times (5-7 column volume) with MeOH then eluted with 2 N NH₃ in MeOH to provide the desired product, 2-(6-(piperidin-4-yl)pyridazin-3-yl)-5-(1H-pyrazol-1-yl)phenol (19.8 mg, 0.06 mmol, 11% yield). LCMS Rt=0.48 min, M+1=322.6 (LCMS method Q). $^1$H NMR (DMSO-d6) δ 8.63 (d, J=2.5 Hz, 1H), 8.50 (d, J=9.3 Hz, 1H), 8.15 (d, J=8.5 Hz, 1H), 7.76-7.92 (m, 2H), 7.47-7.56 (m, 2H), 6.59 (dd, J=2.5, 1.8 Hz, 1H), 3.24 (s, 2H), 3.07-3.19 (m, 1H), 2.84 (td, J=12.2, 2.4 Hz, 2H), 2.00 (s, 2H), 1.77-1.92 (m, 2H).

The following compounds were prepared using similar procedures as in Example 19-1 and 19-2:

| Example | Compound | LCMS M + 1, Rt, conditions | $^1$H NMR 400 MHz |
|---|---|---|---|
| 19-3 | 3-(6-(1,2,3,6-tetra-hydropyridin-4-yl)pyridazin-3-yl)naphthalen-2-ol | 304.1 0.50 min Q | DMSO-d6 δ 12.49 (br. s, 1H), 8.67 (s, 1H), 8.55 (d, J = 9.3 Hz, 1H), 8.18 (d, J = 9.3 Hz, 1H), 7.93 (d, J = 8.0 Hz, 1H), 7.76 (d, J = 8.3 Hz, 1H), 7.49 (s, 1H), 7.26-7.40 (m, 2H), 6.88-7.04 (m, 1H), 3.57-3.66 (m, 2H), 3.02-3.12 (m, 2H), 2.64-2.76 (m, 2H) |

| Example | Compound | LCMS M + 1, Rt, conditions | ¹H NMR 400 MHz |
|---|---|---|---|
| 19-4 | 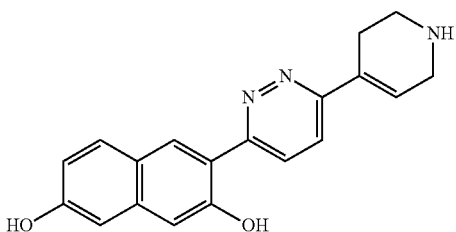<br>3-(6-(1,2,3,6-tetrahydropyridin-4-yl)pyridazin-3-yl)naphthalene-2,7-diol-TFA salt | 320.1<br>0.41 min<br>Q | DMSO-d6 δ 12.47 (br. s, 1H), 9.95 (s, 1H), 8.98 (br. s, 2H), 8.46-8.65 (m, 2H), 8.23 (d, J = 9.5 Hz, 1H), 7.78 (d, J = 8.8 Hz, 1H), 7.12 (s, 1H), 6.84-7.01 (m, J = 8.2, 5.7, 2.1 Hz, 3H), 3.87-3.96 (m, 2H), 3.37-3.46 (m, 2H), 2.90-2.99 (m, 2H) |
| 19-5 | 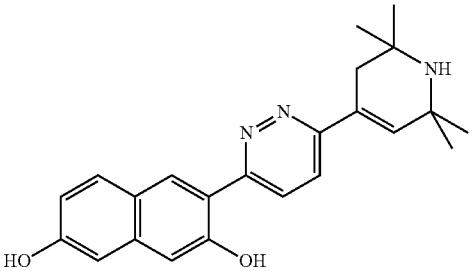<br>3-(6-(2,2,6,6-tetramethyl-1,2,3,6-tetrahydropyridin-4-yl)pyridazin-3-yl)naphthalene-2,7-diol | 376.1<br>0.49 min<br>Q | DMSO-d6 δ 9.95 (br. s, 1H), 8.81 (br. s, 2H), 8.51-8.67 (m, 2H), 8.25 (d, J = 9.3 Hz, 1H), 7.78 (d, J = 8.8 Hz, 1H), 7.12 (s, 1H), 6.83-7.03 (m, 3H), 2.90 (s, 2H), 1.58 (s, 6H), 1.48 (s, 6H) |
| 19-6 | 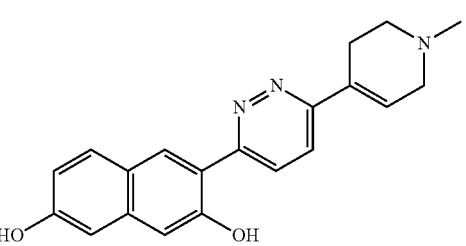<br>3-(6-(1-methyl-1,2,3,6-tetrahydropyridin-4-yl)pyridazin-3-yl)naphthalene-2,7-diol-TFA salt | 334.4<br>0.42 min<br>Q | DMSO-d6 δ 12.39 (br. s, 1H), 10.41 (br. s, 1H), 9.92 (br. s, 1H), 8.41-8.72 (m, 2H), 8.23 (d, J = 9.3 Hz, 1H), 7.78 (d, J = 8.8 Hz, 1H), 7.12 (s, 1H), 6.82-7.01 (m, 3H), 4.05-4.22 (m, 1H), 3.91 (d, J = 16.9 Hz, 1H), 3.68 (br. s., 1H), 3.23-3.31 (m, 1H), 2.96-3.16 (m, 2H), 2.92 (d, J = 4.0 Hz, 3H) |
| 19-7 | 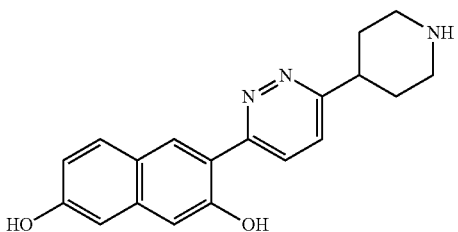<br>3-(6-(piperidin-4-yl)pyridazin-3-yl)naphthalene-2,7-diol-TFA salt | 322.4<br>0.42 min<br>Q | DMSO-d6 δ 8.81-9.16 (m, 1H), 8.59-8.79 (m, 1H), 8.53 (d, J = 9.1 Hz, 1H), 8.47 (s, 1H), 7.86 (d, J = 9.1 Hz, 1H), 7.76 (d, J = 9.1 Hz, 1H), 7.12 (s, 1H), 6.85-7.03 (m, 2H), 3.43 (d, J = 12.6 Hz, 2H), 3.23-3.35 (m, 1H), 3.08 (q, J = 12.0 Hz, 2H), 1.93-2.27 (m, 4H) |

Example 20-1

Synthesis of 3-(6-((2,2,6,6-tetramethylpiperidin-4-yl)oxy)pyridazin-3-yl)naphthalene-2,7-diol

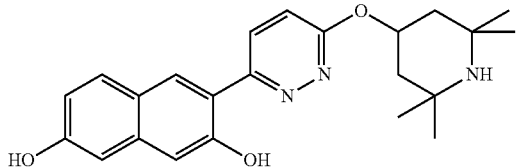 [SMILES: CC1(C)CC(Oc2ccc(-c3cc4ccc(O)cc4cc3O)nn2)CC(C)(C)N1]

Step 1

Following representative procedure GENERAL METHOD 1-1, Suzuki cross-coupling, Intermediate 3-1 and Intermediate 1-3 were reacted to provide 7-(benzyloxy)-6-(6-((2,2,6,6-tetramethylpiperidin-4-yl)oxy)pyridazin-3-yl)naphthalen-2-ol (163 mg, 0.337 mmol). LCMS Rt=1.12 min, M+1=484.3 (condition B).

Step 2: 3-(6-((2,2,6,6-Tetramethylpiperidin-4-yl)oxy)pyridazin-3-yl)naphthalene-2,7-diol (33 mg, 0.084 mmol, 54.1% yield) was prepared from 7-(benzyloxy)-6-(6-((2,2,6,6-tetramethylpiperidin-4-yl)oxy)pyridazin-3-yl)naphthalen-2-ol following GENERAL METHOD 4-1 for hydrogenolysis. LCMS Rt=0.50 min (LCMS method Q); MS (M+1)=394.5. $^1$H NMR (400 MHz, DMSO-d6) δ ppm 12.40 (br. s, 1H), 9.84 (s, 1H), 8.47 (d, J=9.54 Hz, 1H), 8.43 (s, 1H) 7.74 (d, J=8.78 Hz, 1H), 7.40 (d, J=9.54 Hz, 1H), 7.09 (s, 1H), 6.87-6.95 (m, 2H), 5.62-5.73 (m, 1H), 2.11 (d, J=9.29 Hz, 2H), 1.39 (br. s, 2H). 1.25 (br. s, 6H), 1.12 (br. s, 6H).

Example 20-2

Synthesis of 3-(6-(methyl(2,2,6,6-tetramethylpiperidin-4-yl)amino)pyridazin-3-yl)naphthalene-2,7-diol

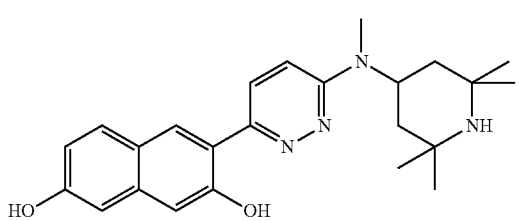 [SMILES: CN(c1ccc(-c2cc3ccc(O)cc3cc2O)nn1)C1CC(C)(C)NC(C)(C)C1]

Step 1

Following representative procedure GENERAL METHOD 1-1, Suzuki cross-coupling, Intermediate 3-1 and Intermediate 1-1 were reacted to provide 7-(benzyloxy)-6-(6-(methyl(2,2,6,6-tetramethylpiperidin-4-yl)amino)pyridazin-3-yl)naphthalen-2-ol (1.25 g, 2.36 mmol, 89% yield). LCMS Rt=0.97 min, M+1=497.8 (condition C). $^1$H NMR (400 MHz, METHANOL-d4) δ ppm 7.91 (s, 1H), 7.76 (d, J=9.54 Hz, 2H), 7.66 (d, J=8.78 Hz, 2H), 7.34-7.40 (m, 2H), 7.31 (s, 2H), 7.18-7.27 (m, 2H), 6.97-7.05 (m, 2H), 6.91 (dd, J=8.78, 2.26 Hz, 1H), 5.18 (m, 3H), 2.92 (s, 3H), 1.60-1.68 (m, 2H), 1.45-1.55 (m, 2H), 1.32 (s, 6H), 1.18 (s, 6H).

Step 2

3-(6-(Methyl(2,2,6,6-tetramethylpiperidin-4-yl)amino)pyridazin-3-yl)naphthalene-2,7-diol (43 mg, 0.097 mmol, 48.2% yield) was prepared from 7-(benzyloxy)-6-(6-(methyl(2,2,6,6-tetramethylpiperidin-4-yl)amino)pyridazin-3-yl)naphthalen-2-ol following GENERAL METHOD 4-1 for hydrogenolysis. LCMS Rt=0.48 min, M+1=407.2 (LCMS method Q). $^1$H NMR (400 MHz, METHANOL-d4) δ ppm 8.27 (d, J=10.04 Hz, 1H), 8.20 (br. s, 3H), 7.71 (d, J=8.78 Hz, 1H), 7.35 (d, J=9.79 Hz, 1H), 7.05 (s, 1H), 6.85-6.94 (m, 2H), 5.27 (br. s, 1H), 3.03 (s, 3H), 1.71-1.91 (m, 4H), 1.54 (s, 6H), 1.39 (s, 6H).

Example 20-3

Synthesis of 3-(6-((2,2,6,6-tetramethylpiperidin-4-yl)amino)pyridazin-3-yl)naphthalene-2,7-diol

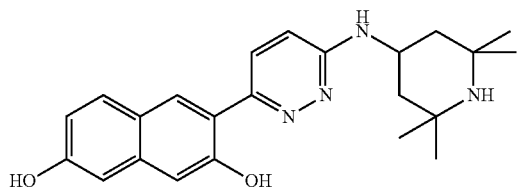 [SMILES: CC1(C)CC(Nc2ccc(-c3cc4ccc(O)cc4cc3O)nn2)CC(C)(C)N1]

Step 1

Following representative procedure GENERAL METHOD 1-1, Suzuki cross-coupling, Intermediate 3-1 and Intermediate 1-2 were reacted to provide 7-(benzyloxy)-6-(6-((2,2,6,6-tetramethylpiperidin-4-yl)amino)pyridazin-3-yl)naphthalen-2-ol (49 mg, 0.096 mmol, 52% yield). LCMS Rt=1.16 min (condition C); MS (M+1)=483.8.

Step 2

3-(6-((2,2,6,6-Tetramethylpiperidin-4-yl)amino)pyridazin-3-yl)naphthalene-2,7-diol (3 mg, 0.007 mmol, 38% yield) was prepared from 7-(benzyloxy)-6-(6-((2,2,6,6-tetramethylpiperidin-4-yl)amino)pyridazin-3-yl)naphthalen-2-ol following GENERAL METHOD 4-1 for hydrogenolysis. LCMS Rt=0.47 min (LCMS method Q); MS (M+1)=393.1. $^1$H NMR (400 MHz, METHANOL-d4) δ ppm 8.42 (d, J=9.29 Hz, 1H), 8.16 (s, 1H), 7.79 (d, J=8.53 Hz, 1H), 7.64 (d, J=9.54 Hz, 1H), 7.15 (s, 1H), 6.96-7.02 (m, 2H), 4.51 (t, J=11.92 Hz, 1H), 2.96-3.04 (m, 1H), 2.68 (s, 1H), 2.35 (dd, J=13.55, 3.01 Hz, 2H), 1.69-1.75 (m, 2H), 1.64 (s, 6H), 1.56 (s, 6H).

Example 20-4

Synthesis of [3-(7-hydroxy-6-{6-[methyl-(2,2,6,6-tetramethyl-piperidin-4-yl)-amino]-pyridazin-3-yl}-naphthalen-2-yloxy)-propyl]-carbamic acid tert-butyl ester

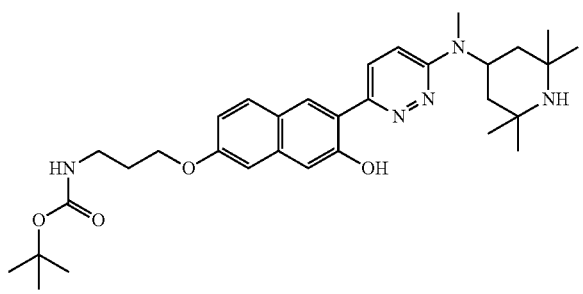 [SMILES: CN(c1ccc(-c2cc3ccc(OCCCNC(=O)OC(C)(C)C)cc3cc2O)nn1)C1CC(C)(C)NC(C)(C)C1]

Step 1: tert-Butyl (3-((7-(benzyloxy)-6-bromonaphthalen-2-yl)oxy)propyl)carbamate Following GENERAL METHOD 5-1 for phenol alkylation using 7-(benzyloxy)-6-bromonaphthalen-2-ol (506.5 mg, 1.54 mmol) and tert-butyl 3-bromopropylcarbamate (409 mg, 1.72 mmol) and after column chromatography (eluting with 3-80% EtOAc/heptane) tert-butyl (3-((7-(benzyloxy)-6-bromonaphthalen-2-yl)oxy)propyl)carbamate was obtained as an off-white solid (706 mg, 94% yield). MS (M-Boc)=388.3. $^1$H NMR (400 MHz, CHLOROFORM-d) δ ppm 7.99 (s, 1H), 7.59 (d, J=9.60 Hz, 1H), 7.54 (d, J=8.08 Hz, 2H), 7.42 (t, J=7.58 Hz, 2H), 7.32-7.37 (m, 1H), 7.13 (s, 1H), 7.05-7.00 (m, 2H), 5.26 (s, 2H), 4.68 (br. s, 1H), 4.14 (t, J=6.06 Hz, 2H), 3.37 (q, J=6.40 Hz, 2H), 2.09-2.01 (m, 2H), 1.47 (s, 9H).

Step 2: tert-Butyl (3-((7-(benzyloxy)-6-(4,4,5,5-tetramethyl-1,3,2-dioxaborolan-2-yl)naphthalen-2-yl)oxy)propyl) carbamate Following GENERAL METHOD 2-1 for boronate ester formation using tert-butyl (3-((7-(benzyloxy)-6-bromonaphthalen-2-yl)oxy)propyl)carbamate (659 mg, 1.36 mmol) affords tert-butyl (3-((7-(benzyloxy)-6-(4,4,5,5-tetramethyl-1,3,2-dioxaborolan-2-yl)naphthalen-2-yl)oxy)propyl)carbamate as an off-white solid (662 mg, 87% yield). MS (M-$^t$Bu)=478.0. $^1$H NMR (400 MHz, CHLOROFORM-d) δ ppm 8.16 (s, 1H), 7.65-7.72 (m, 3H), 7.39 (t, J=7.33 Hz, 2H), 7.29-7.34 (m, 1H), 7.08 (s, 1H), 7.04 (d, J=2.53 Hz, 1H), 6.98 (dd, J=8.84, 2.27 Hz, 1H), 5.23 (s, 2H), 4.70 (br. s, 1H), 4.16 (t, J=6.06 Hz, 2H), 3.38 (q, J=6.57 Hz, 2H), 2.00-2.10 (m, 2H), 1.47 (s, 9H), 1.41 (s, 12H).

Step 3: tert-Butyl (3-((7-(benzyloxy)-6-(6-(methyl (2,2,6,6-tetramethylpiperidin-4-yl)amino)pyridazin-3-yl)naphthalen-2-yl)oxy)propyl)carbamate Intermediate 1-1 (242.5 mg, 0.86 mmol) and tert-butyl (3-((7-(benzyloxy)-6-(4,4,5,5-tetramethyl-1,3,2-dioxaborolan-2-yl)naphthalen-2-yl)oxy)propyl)carbamate (662 mg, 1.18 mmol) were reacted following GENERAL METHOD 1-1 for Suzuki coupling with the following modifications: Instead of SCX purification, the crude material was purified by flash chromatography (eluting with 1-15% 7N NH$_3$ in MeOH/DCM) to afford a yellow oil. The oil was triturated with Et$_2$O then concentrated in vacuo to dryness affording tert-butyl (3-((7-(benzyloxy)-6-(6-(methyl(2,2,6,6-tetramethylpiperidin-4-yl)amino)pyridazin-3-yl)naphthalen-2-yl)oxy)propyl)carbamate a pale-yellow solid (492 mg, 83% yield). MS (M+1)=654.8.

Step 4: tert-Butyl (3-((7-hydroxy-6-(6-(methyl(2,2,6,6-tetramethylpiperidin-4-yl)amino)pyridazin-3-yl)naphthalen-2-yl)oxy) propyl)carbamate Pd/C (10% wt 80 mg, 0.075 mmol) was added to a EtOAc (5 mL)/MeOH (5 mL) solution of tert-butyl (3-((7-(benzyloxy)-6-(6-(methyl(2,2,6,6-tetramethylpiperidin-4-yl)amino)pyridazin-3-yl)naphthalen-2-yl)oxy)propyl)carbamate (492 mg, 0.752 mmol) at RT. The reaction mixture was evacuated and filled with H$_2$ (2×) then stirred at RT under H$_2$ (1 atm) for 16 h. The reaction mixture was filtered through celite washing with MeOH, wash then concentrated in vacuo to dryness affording a tan solid. The solid was dissolved in DCM then adsorbed onto a silica bound amine column (Si—NH$_2$ column 10 g, Varian brand, Bond Elut NH$_2$). The column was then washed with MeOH (150 mL) then the solvent was concentrated in vacuo affording a yellow oil. The oil was dissolved in Et$_2$O then concentrated in vacuo affording the title compound as a beige solid (386 mg, 91% yield). MS (M+1)=564.3; $^1$H NMR (400 MHz, DMSO-d6) δ ppm 13.29 (br. s, 1H), 8.34 (s, 1H), 8.28 (d, J=10.10 Hz, 1H), 7.76 (d, J=9.09 Hz, 1H), 7.34 (d, J=10.11 Hz, 1H), 7.15 (s, 1H), 7.08 (d, J=2.53 Hz, 1H), 6.94 (dd, J=9.09, 2.53 Hz, 1H), 4.89-5.06 (m, 1H), 4.56 (s, 1H), 4.09 (t, J=6.32 Hz, 2H), 3.09-3.16 (m, 2H), 2.98 (s, 3H), 1.80-1.95 (m, 2H), 1.50-1.61 (m, 2H), 1.44 (t, J=12.38 Hz, 2H), 1.38 (s, 9H), 1.27 (s, 6H), 1.10 (s, 6H).

Example 20-5

Synthesis of 7-(3-amino-propoxy)-3-{6-[methyl-(2,2,6,6-tetramethyl-piperidin-4-yl)-amino]-pyridazin-3-yl}-naphthalen-2-ol

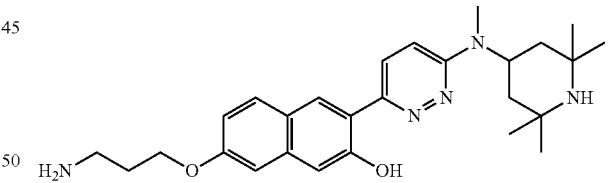

TFA (1.5 ml, 19.47 mmol) was added to a solution of Example 20-4 (289.4 mg, 0.513 mmol) in DCM (6 ml) at RT. The reaction mixture was stirred at RT for 30 min, diluted with MeOH then adsorbed onto a MeOH conditioned SCX column (10 g). The column was washed several times with MeOH then eluted with 3 N NH$_3$ in MeOH. Evaporation of the solvent afforded the title compound as a beige solid (178 mg, 75% yield). LCMS Rt=0.44 min (LCMS method Q); MS (M+1)=464.2. $^1$H NMR (400 MHz, DMSO-d6) δ ppm 8.35 (s, 1H), 8.28 (d, J=9.60 Hz, 1H), 7.77 (d, J=9.09 Hz, 1H), 7.36 (d, J=9.60 Hz, 1H), 7.16-7.18 (m, 1H), 7.11 (d, J=2.53 Hz, 1H), 6.96 (dd, J=8.84, 2.27 Hz, 1H), 4.91-5.04 (m, 1H), 4.56 (s, 1H), 4.17 (t, J=6.32 Hz, 2H), 2.98 (s, 3H), 2.88 (d, J=7.07 Hz, 2H), 1.90-2.05 (m, 2H), 1.46-1.62 (m, 4H), 1.30 (s, 6H), 1.14 (s, 6H).

Example 20-6

Synthesis of N-[3-(7-hydroxy-6-{6-[methyl-(2,2,6,6-tetramethyl-piperidin-4-yl)-amino]-pyridazin-3-yl}-naphthalen-2-yloxy)-propyl]-acetamide

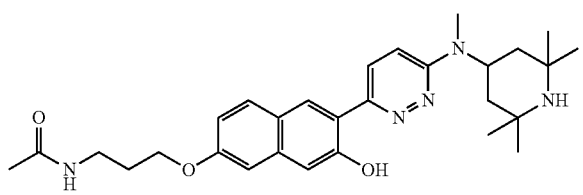 [SMILES: CC(=O)NCCCOc1ccc2cc(-c3ccc(N(C)C4CC(C)(C)NC(C)(C)C4)nn3)c(O)cc2c1]

N-Acetoxysuccinimide (98 mg, 0.624 mmol) was added to a solution of Example 20-5 (50 mg, 0.108 mmol) and TEA (0.747 ml, 5.39 mmol) in DMSO (2 ml) at RT. The reaction mixture was stirred at RT for 30 min then concentrated in vacuo to remove excess Et$_3$N. The resulting residue was purified by preparative HPLC (eluting with 5-80% MeCN/H$_2$O with 0.1% TFA modifier). The appropriate fractions containing product were combined then adsorbed onto a MeOH conditioned SCX column (5 g, BSA Varian brand). The column was washed several times with MeOH then eluted with 3 N NH$_3$ in MeOH. Evaporation of the solvent afforded a yellow oil. Et$_2$O was added to the oil then concentrated to dryness affording the title compound as a yellowish orange solid (30 mg, 55% yield). LCMS Rt=0.52 min (LCMS method Q); MS (M+1)=506.2. $^1$H NMR (400 MHz, DMSO-d6) δ ppm 13.27 (br. s, 1H), 8.35 (s, 1H), 8.28 (d, J=10.10 Hz, 1H), 7.77 (d, J=9.09 Hz, 2H), 7.35 (d, J=9.60 Hz, 1H), 7.17 (s, 1H), 7.09 (d, J=2.02 Hz, 1H), 6.95 (dd, J=9.09, 2.53 Hz, 1H), 4.92-5.04 (m, 1H), 4.11 (t, J=6.32 Hz, 2H), 3.20-3.28 (m, 2H), 2.98 (s, 3H), 1.87-1.96 (m, 2H), 1.82 (s, 3H), 1.55-1.63 (m, 2H), 1.44-1.55 (m, 2H), 1.30 (s, 6H), 1.14 (s, 6H).

Example 20-7

Synthesis of 7-(3-hydroxypropoxy)-3-(6-(methyl(2,2,6,6-tetramethylpiperidin-4-yl)amino)pyridazin-3-yl)naphthalen-2-ol

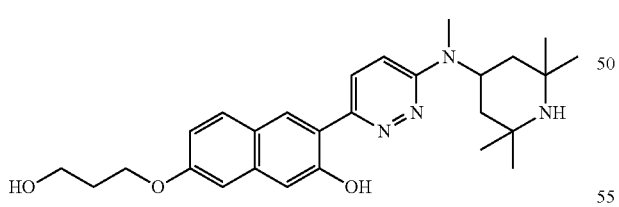

Step 1: 3-(benzyloxy)-6-(3-(benzyloxy)propoxy)-2-bromonaphthalene

Following GENERAL METHOD 5-1 for phenol alkylation, Cs$_2$CO$_3$ (485 mg, 1.489 mmol) was added to a solution of 7-(benzyloxy)-6-bromonaphthalen-2-ol (490 mg, 1.489 mmol) in acetone (14.90 mL) at RT. The reaction mixture was stirred for 5 min then ((3-bromopropoxy)methyl)benzene (682 mg, 2.98 mmol) was added, followed by addition of NaI (446 mg, 2.98 mmol). The reaction mixture was heated to 60° C. and stirred overnight, then filtered, washed with acetone and concentrated in vacuo. The resulting residue was partitioned between Et$_2$O (60 mL) and water (20 mL). After separation, the organic layer was washed with saturated aq. sodium sulfite solution (20 mL), 2 M Na$_2$CO$_3$, and brine. The organic layer was then dried over MgSO$_4$, filtered, and concentrated in vacuo. Silica gel chromatography (10-60% EtOAc/heptane) afforded 3-(benzyloxy)-6-(3-(benzyloxy)propoxy)-2-bromonaphthalene (422 mg, 0.884 mmol, 60% yield) as a white solid (eluting at 30% EtOAc). LCMS Rt=1.81 min (condition C); LCMS (M+1)=479.9.

Step 2

2-(3-(Benzyloxy)-6-(3-(benzyloxy)propoxy)naphthalen-2-yl)-4,4,5,5-tetramethyl-1,3,2-dioxaborolane (355 mg, 0.677 mmol, 81% yield) was prepared from the bromide using following GENERAL METHOD 2-1 for boronate ester formation. LCMS Rt=1.89 min (condition C); MS (M+1)=525.3.

Step 3

6-(3-(benzyloxy)-6-(3-(benzyloxy)propoxy)naphthalen-2-yl)-N-methyl-N-(2,2,6,6-tetramethylpiperidin-4-yl)pyridazin-3-amine (59 mg, 0.091 mmol, 27% yield) was prepared via Suzuki reaction from the boronic ester and Intermediate 1-1 following GENERAL METHOD 1-1.
LCMS Rt=1.50 min (condition C); MS (M+1)=645.3.

Step 4

7-(3-Hydroxy-propoxy)-3-{6-[methyl-(2,2,6,6-tetramethyl-piperidin-4-yl)-amino]-pyridazin-3-yl}-naphthalen-2-ol (10 mg, 0.021 mmol, 23% yield) was prepared from 6-(3-(benzyloxy)-6-(3-(benzyloxy)propoxy)naphthalen-2-yl)-N-methyl-N-(2,2,6,6-tetramethylpiperidin-4-yl)pyridazin-3-amine following GENERAL METHOD 4-1 for hydrogenolysis. LCMS Rt=0.53 min (LCMS method Q); MS (M+1)=465.2. $^1$H NMR (400 MHz, DICHLOROMETHANE-d2) δ ppm 7.97-8.08 (m, 2H), 7.63-7.72 (m, 1H), 7.19 (d, J=9.79 Hz, 1H), 7.04-7.12 (m, 1H), 7.01 (d, J=8.28 Hz, 1H), 6.89-6.97 (m, 1H), 4.99 (br. s, 1H), 4.13-4.24 (m, 2H), 3.74-3.85 (m, 2H), 3.30-3.38 (m, 1H) 2.97 (br. s, 3H), 2.12 (br. s, 1H) 2.01-2.10 (m, 2H), 1.65-1.73 (m, 2H), 1.39-1.50 (m, 2H), 1.34 (br. s, 6H), 1.17 (br. s, 6H).

Example 20-8

Synthesis of 7-(3-methoxypropoxy)-3-(6-(methyl(2,2,6,6-tetramethylpiperidin-4-yl)amino)pyridazin-3-yl)naphthalen-2-ol 7-(3-methoxypropoxy)-3-(6-(methyl(2,2,6,6-tetramethyl-piperidin-4-yl)amino)pyridazin-3-yl)naphthalen-2-ol (15 mg, 0.031 mmol, 27% yield) was prepared in a similar manner to Example 21-7. LCMS Rt=0.53 min (LCMS method Q); MS (M+1)=479.2. ¹H NMR (400 MHz, DICHLOROMETHANE-d2) 6 ppm 8.01-8.07 (m, 2H), 7.69 (d, J=9.09 Hz, 2H), 7.20 (s, 1H), 7.09 (d, J=9.85 Hz, 1H), 7.00 (d, J=2.02 Hz, 1H), 6.95 (d, J=8.84 Hz, 1H), 5.42 (t, J=12.51 Hz, 1H), 4.15 (t, J=6.32 Hz, 2H), 3.58 (t, J=6.19 Hz, 2H), 3.35 (s, 3H), 3.01 (s, 3H), 1.94-2.14 (m, 4H), 1.77 (dd, J=13.39, 3.28 Hz, 2H), 1.58 (s, 6H), 1.51 (s, 6H).

Example 20-9

Synthesis of 7-(2-morpholinoethoxy)-3-(6-((2,2,6,6-tetramethylpiperidin-4-yl)oxy)pyridazin-3-yl)naphthalen-2-ol

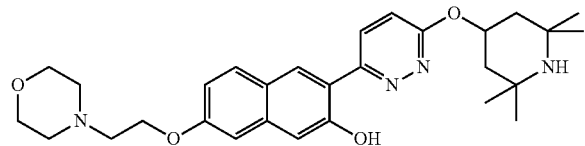 [SMILES: CC1(C)CC(Oc2ccc(-c3cc4ccc(OCCN5CCOCC5)cc4cc3O)nn2)CC(C)(C)N1]

7-(2-morpholinoethoxy)-3-(6-((2,2,6,6-tetramethylpiperidin-4-yl)oxy)pyridazin-3-yl)naphthalen-2-ol was prepared in a similar manner to Example 21-7. LCMS Rt=0.43 min (LCMS method Q); MS (M+1)=507.3. ¹H NMR (400 MHz, METHANOL-d4) ppm 8.49 (d, J=9.79 Hz, 1H), 8.34 (s, 1H) 7.79 (d, J=9.03 Hz, 1H), 7.36 (d, J=9.54 Hz, 1H), 7.24 (s, 1H), 7.12 (d, J=2.26 Hz, 1H), 7.01 (dd, J=9.03, 2.51 Hz, 1H), 5.80-5.91 (m, 1H), 4.29 (t, J=5.40 Hz, 2H), 3.73-3.79 (m, 4H), 2.91 (t, J=5.40 Hz, 2H), 2.63-2.72 (m, 4H), 2.51 (dd, J=13.80, 4.02 Hz, 2H), 1.85 (dd, J=13.43, 10.92 Hz, 2H), 1.64 (s, 6H), 1.56 (s, 6H).

Example 21-1

Synthesis of 3-(6-(piperidin-4-ylmethyl)pyridazin-3-yl)naphthalen-2-ol

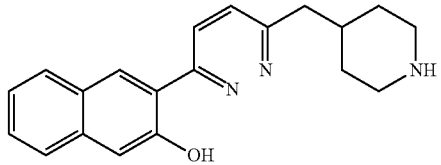 [SMILES: N=C(/C=C\C(=N)c1cc2ccccc2cc1O)CC1CCNCC1]

Step 1: tert-Butyl 4-((6-chloropyridazin-3-yl)methyl)piperidine-1-carboxylate

To a flask containing tert-butyl 4-methylenepiperidine-1-carboxylate (487 mg, 2.47 mmol) was added 0.5 M 9-borabicyclo[3.3.1]nonane in THF (5.4 mL, 2.72 mmol). The reaction was refluxed at 65° C. for 1 h then added to a degassed suspension of 3,6-dichloropyridazine (368 mg, 2.47 mmol), K₂CO₃ (1.0 g, 7.41 mmol), and PdCl₂(dppf) CH₂Cl₂ (101 mg, 0.12 mmol) in 1,4-dioxane (5.2 mL) and water (0.88 mL). The resulting reaction mixture was heated at 60° C. for 3 h then cooled to RT and diluted with EtOAc. The suspension was filtered through celite and concentrated in vacuo. Silica gel chromatography, eluting with 0-100% EtOAc/heptane, afforded the product, tert-butyl 4-((6-chloropyridazin-3-yl)methyl)piperidine-1-carboxylate (376 mg, 1.21 mmol, 49% yield). ¹H NMR (DMSO-d6) δ: 7.85 (d, J=8.8 Hz, 1H), 7.70 (d, J=8.8 Hz, 1H), 3.74-4.05 (m, 2H), 2.85 (d, J=7.3 Hz, 2H), 2.54-2.79 (m, 2H), 1.82-2.01 (m, 1H), 1.48-1.62 (m, 2H), 1.38 (s, 9H), 0.97-1.18 (m, 2H).

Step 2 tert-butyl 4-((6-(3-methoxynaphthalen-2-yl)pyridazin-3-yl)methyl)piperidine-1-carboxylate (63 mg, 0.145 mmol, 45% yield) was prepared from tert-butyl 4-((6-chloropyridazin-3-yl)methyl)piperidine-1-carboxylate and (3-methoxynaphthalen-2-yl)boronic acid using GENERAL METHODS 1-4.

Step 3

3-(6-(Piperidin-4-ylmethyl)pyridazin-3-yl)naphthalen-2-ol (31 mg, 0.097 mmol, 67% yield) was prepared from tert-butyl 4-((6-(3-methoxynaphthalen-2-yl)pyridazin-3-yl)methyl)piperidine-1-carboxylate using GENERAL METHOD3-2. LCMS Rt=0.53 min, M+1=320.2 (LCMS method Q); ¹H NMR (DMSO-d6) δ 8.62 (s, 1H), 8.51 (d, J=9.0 Hz, 1H), 7.93 (d, J=8.0 Hz, 1H), 7.82 (d, J=9.0 Hz, 1H), 7.76 (d, J=8.0 Hz, 1H), 7.48 (ddd, J=8.2, 6.9, 1.3 Hz, 1H), 7.29-7.40 (m, 2H), 2.85-2.99 (m, 4H), 2.41-2.48 (m, 2H), 1.84-1.99 (m, 1H), 1.48-1.65 (m, 2H), 1.10-1.27 (m, 2H).

Example 21-2

Synthesis of 5-(1H-pyrazol-1-yl)-2-(6-((2,2,6,6-tetramethylpiperidin-4-yl)methyl)pyridazin-3-yl)phenol

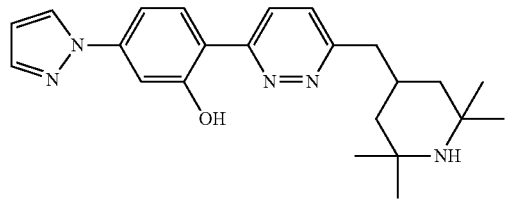 [SMILES: CC1(C)CC(Cc2ccc(-c3ccc(-n4cccn4)cc3O)nn2)CC(C)(C)N1]

Step 1: 2,2,6,6-Tetramethyl-4-methylenepiperidine trifluoroacetate

To a 100 mL flask containing methyltriphenylphosphonium bromide (5.2 g, 14.5 mmol) in ether (8 mL) cooled to 0° C. was added potassium tert-butoxide (2.2 g, 19.3 mmol). The resulting suspension was stirred for 0.5 h at 0° C. followed by the dropwise addition of 2,2,6,6-tetramethylpiperidin-4-one (1.0 g, 6.44 mmol) in ether (5 mL). The resulting mixture was stirred at RT overnight at which time additional potassium tert-butoxide (0.72 g, 6.44 mmol) and methyltriphenylphosphonium bromide (1.7 g, 4.83 mmol) were added. The reaction was stirred at RT for 4 h then cooled to 0° C. and quenched with water, acidified with 1 M HCl aqueous solution and washed with ether (3×). The aqueous mixture was adjusted to pH 10 with 2 M NaOH and extracted with ether (3×). The organic extract was acidified with trifluoracetic acid, dried with sodium sulfate and concentrated in vacuo to afford desired product as a brown oil 2,2,6,6-tetramethyl-4-methylenepiperidine trifluoroacetate salt (1.7 g, 4.46 mmol, 70% yield), $^1$H NMR (DMSO-d6) δ 8.53 (br. s, 2H), 5.00 (s, 2H), 2.20-2.30 (m, 4H), 1.33 (s, 12H).

Step 2: 3-(2-Methoxy-4-(1H-pyrazol-1-yl)phenyl)-6-((2,2,6,6-tetramethylpiperidin-4-yl)methyl)pyridazine To a flask containing 2,2,6,6-tetramethyl-4-methylenepiperidine trifluoroacetate (250 mg, 0.936 mmol) was added 0.5 M 9-borabicyclo[3.3.1]nonane in THF (3.7 mL, 1.87 mmol). The reaction was refluxed at 65° C. for 1 h, then 0.5 M 9-borabicyclo[3.3.1]nonane in THF (0.75 mL, 0.375 mmol) was added and reflux continued for 1 h. The resulting mixture was added to a degassed suspension of Intermediate 2-1 (268 mg, 0.936 mmol), K$_2$CO$_3$ (388 mg, 2.81 mmol), and PdCl$_2$(dppf).CH$_2$Cl$_2$ (38 mg, 0.05 mmol) in 1,4-dioxane (2.7 mL) and water (0.45 mL) and heated at 90° C. overnight then cooled to RT and diluted with EtOAc. The suspension was filtered through celite and concentrated in vacuo. The product was adsorbed onto a methanol-conditioned SCX (5 g) column. The column was washed several times with methanol then eluted with 2 N ammonia in methanol. The product was collected and concentrated in vacuo to afford the crude product. 3-(2-methoxy-4-(1H-pyrazol-1-yl)phenyl)-6-((2,2,6,6-tetramethylpiperidin-4-yl)methyl)pyridazine. LCMS Rt=0.92 min, M+1=406.3.

Step 3

5-(1H-Pyrazol-1-yl)-2-(6-((2,2,6,6-tetramethylpiperidin-4-yl)methyl)pyridazin-3-yl)phenol (56.1 mg, 0.143 mmol, 18% yield) was prepared from 3-(2-methoxy-4-(1H-pyrazol-1-yl)phenyl)-6-((2,2,6,6-tetramethylpiperidin-4-yl)methyl)pyridazine using GENERAL METHOD 3-1. LCMS Rt=0.52 min, M+1=392.3 (LCMS method Q); $^1$H NMR (DMSO-d6) δ 8.64 (d, J=2.5 Hz, 1H), 8.49 (d, J=9.0 Hz, 1H), 8.17 (d, J=8.5 Hz, 1H), 7.87 (d, J=9.0 Hz, 1H), 7.80 (d, J=1.8 Hz, 1H), 7.45-7.59 (m, 2H), 6.59 (dd, J=2.5, 1.8 Hz, 1H), 2.84 (d, J=7.0 Hz, 2H), 2.21-2.42 (m, 1H), 1.46 (d, J=11.8 Hz, 2H), 0.67-1.30 (m, 14H).

Example 22-1

Synthesis of 3-methoxy-2-(6-(methyl(2,2,6-trimethylpiperidin-4-yl)amino)pyridazin-3-yl)-5-(5-methyloxazol-2-yl)phenol

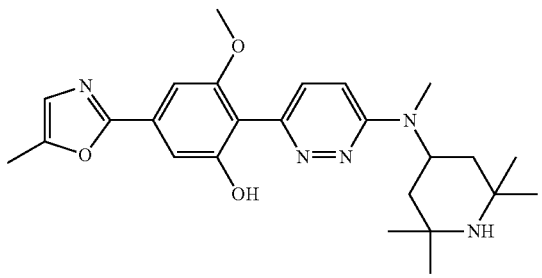

Step 1: Methyl 3-(benzyloxy)-4-bromo-5-hydroxybenzoate

To a mixture of methyl 4-bromo-3,5-dihydroxybenzoate (18.8 g, 76 mmol) and potassium carbonate (5.26 g, 38.1 mmol) in DMF (190 mL) was added benzyl bromide (3.17 mL, 26.6 mmol). The mixture was stirred overnight, diluted with 200 mL water and acidified to pH 1 by slow addition of concentrated hydrochloric acid. The solution was extracted with 1:1 ethyl acetate/ether (6×) and the combined extracts were washed with water (8×), saturated sodium bicarbonate, brine, dried over magnesium sulfate and concentrated to an orange solid. The solids were suspended in DCM (200 mL) and stirred overnight. The solids (primarily unreacted 4-bromo-3,5-dihydroxybenzoate) were removed by filtration and the filtrate was concentrated to an orange oil which was purified by column chromatography (80 g silica gel, 2:1 DCM in heptane elution, followed by DCM elution) to provide methyl 3-(benzyloxy)-4-bromo-5-hydroxybenzoate (4.66 g). MS (M+1)=337.0. $^1$H NMR (400 MHz, CHLOROFORM-d) δ ppm 7.32-7.57 (m, 6H), 7.26 (d, J=1.52 Hz, 1H), 5.77 (s, 1H), 5.22 (s, 2H), 3.93 (s, 3H) as well as the di-benzylated methyl 3,5-bis(benzyloxy)-4-bromobenzoate (1.8 g).

Step 2: Methyl 3-(benzyloxy)-4-bromo-5-methoxybenzoate

To a mixture of methyl 3-(benzyloxy)-4-bromo-5-hydroxybenzoate (3.69 g, 10.94 mmol) and potassium carbonate (3.03 g, 21.98 mmol) in DMF (27 mL) was added methyl iodide (0.753 mL, 12.04 mmol). The mixture was stirred overnight after which time it was diluted with water and extracted with ethyl acetate (4×). The combined extracts were washed with water (8×), brine, dried over magnesium sulfate and concentrated to provide methyl 3-(benzyloxy)-4-bromo-5-methoxybenzoate as a white solid (3.72 g). MS (M+1)=351.1; $^1$H NMR (400 MHz, CHLOROFORM-d) δ ppm 7.31-7.59 (m, 7H), 5.24 (s, 2H), 3.99 (s, 3H), 3.95 (s, 3H).

Step 3: 3-(Benzyloxy)-4-bromo-5-methoxybenzoic acid

To a solution of methyl 3-(benzyloxy)-4-bromo-5-methoxybenzoate (3.72 g, 10.59 mmol) in 1:1 MeOH/THF (50 mL) was added aqueous sodium hydroxide (1 M, 53.0 mL, 53.0 mmol). After 10 minutes the volatiles were removed under reduced pressure and the solution acidified to pH 1 by addition of concentrated hydrochloric acid resulting in formation of a thick white precipitate. The mixture was extracted with ethyl acetate (2×), and DCM (3×). The combined extracts were washed with brine, dried over magnesium sulfate and concentrated to provide 3-(benzyloxy)-4-bromo-5-methoxybenzoic acid as a white solid (3.41 g). MS (M−1)=335.0. $^1$H NMR (400 MHz, CHLOROFORM-d) δ ppm 7.21-7.49 (m, 7H), 5.16 (s, 2H), 3.91 (s, 3H).

Step 4: 3-(Benzyloxy)-4-bromo-5-methoxy-N-(prop-2-yn-1-yl)benzamide

To a suspension of 3-(benzyloxy)-4-bromo-5-methoxybenzoic acid (2.0 g, 5.93 mmol) and 4 drops of DMF in DCM (40 mL) was slowly added oxalyl chloride (0.57 mL, 6.52 mmol). After three hours the solvent was removed and the residue redissolved into DCM (10 mL). To this solution was slowly added a mixture of propargylamine (0.46 mL, 7.12 mmol) and triethylamine (2.5 mL, 17.8 mmol) in DCM (2 mL). After 30 minutes the solution was diluted with ether, washed with water (2×), 1 M hydrochloric acid (2×), water, saturated sodium bicarbonate, brine, dried over magnesium sulfate and concentrated to a yellow solid. The solid was triturated with diethyl ether and dried under vacuum to provide 3-(benzyloxy)-4-bromo-5-methoxy-N-(prop-2-yn-1-yl)benzamide (1.88 g) as an off-white solid. MS=374.0 (M+1).

Step 5. 2-(3-(Benzyloxy)-4-bromo-5-methoxyphenyl)-5-methyloxazole

To a solution of 3-(benzyloxy)-4-bromo-5-methoxy-N-(prop-2-yn-1-yl)benzamide (0.455 g, 1.22 mmol) in dioxane (12 mL) was added sodium hydride (60% wt, 0.146 g, 3.65 mmol) and the mixture heated at reflux for six hours. The mixture was cooled to RT, quenched by slow addition of water and diluted with ethyl acetate. The mixture was washed with water, saturated sodium bicarbonate, brine, dried over magnesium sulfate and concentrated. Flash column chromatography (12 g silica, 2% ethyl acetate in DCM) provided 2-(3-(benzyloxy)-4-bromo-5-methoxyphenyl)-5-methyloxazole (198 mg) as an off-white solid. MS=374 (M+1). $^1$H NMR (400 MHz, CHLOROFORM-d) δ ppm 7.55 (d, J=7.58 Hz, 2H), 7.43 (t, J=7.33 Hz, 2H), 7.32-7.39 (m, 2H), 7.27 (d, J=2.02 Hz, 1H), 6.89 (d, J=1.01 Hz, 1H), 5.27 (s, 2H), 4.02 (s, 3H), 2.44 (d, J=1.52 Hz, 3H).

Step 6: (2-(Benzyloxy)-6-methoxy-4-(5-methyloxazol-2-yl)phenyl)boronic acid

To a stirred solution of 2-(3-(benzyloxy)-4-bromo-5-methoxyphenyl)-5-methyloxazole (197 mg, 0.526 mmol) in THF (1.3 mL) cooled to −78° C. was added n-butyl lithium (2.5 M in hexanes, 232 uL, 0.579 mmol). The solution was stirred for 15 minutes after which time trimethyl borate (235 uL, 2.11 mmol) was added and the solution was allowed to slowly warm to RT overnight. The reaction was quenched by addition of 0.1 M HCl and was diluted with ethyl acetate, washed with water, brine, dried over magnesium sulfate and concentrated. Flash column chromatography (12 g silica, 0-100% ethyl acetate in DCM over 30 column volumes) provided (2-(benzyloxy)-6-methoxy-4-(5-methyloxazol-2-yl)phenyl)boronic acid (63 mg) as a white foam. MS=340.1 (M+1). $^1$H NMR (400 MHz, CHLOROFORM-d) δ ppm 7.28-7.46 (m, 5H), 7.25 (d, J=1.01 Hz, 1H), 7.08 (br. s, 1H), 6.85 (d, J=1.01 Hz, 1H), 5.17 (s, 2H), 3.95 (s, 3H), 2.38 (d, J=1.52 Hz, 3H).

Step 7: 6-(2-(Benzyloxy)-6-methoxy-4-(5-methyloxazol-2-yl)phenyl)-N-methy-N-(2, 2, 6,6-tetramethylpiperidin-4-yl)pyridazin-3-amine A mixture of (2-(benzyloxy)-6-methoxy-4-(5-methyloxazol-2-yl)phenyl)boronic acid (63 mg, 0.186 mmol), 6-chloro-N-methyl-N-(2,2,6,6-tetramethylpiperidin-4-yl)pyridazin-3-amine Intermediate 1-1 (35 mg, 0.124 mmol), sodium carbonate (39.4 mg, 0.371 mmol) in 3:1 DME/water (825 uL) was degassed with a dry stream of nitrogen for five minutes. Tetrakis(triphenylphosphine)palladium(0) (21 mg, 0.019 mmol) was added and the mixture heated via microwave irradiation at 150° C. for fifteen minutes. The crude reaction was filtered, the filtrate was acidified with 2 M HCl in MeOH, and then concentrated to dryness. The residue was redissolved in methanol and adsorbed onto a MeOH conditioned SCX column. The column was washed several times (3-4 column volumes) with MeOH then eluted with 3.5 N ammonia in MeOH. Evaporation of the eluent afforded the product as a light brown foam. Flash column chromatography (4 g silica gel, 0-40% 7 N ammonia in MeOH gradient in DCM over 30 column volumes) provided 6-(2-(benzyloxy)-6-methoxy-4-(5-methyloxazol-2-yl)phenyl)-N-methyl-N-(2,2,6,6-tetramethylpiperidin-4-yl)pyridazin-3-amine as a white solid. MS=542.4 (M+1). $^1$H NMR (400 MHz, METHANOL-d4) ppm 7.45 (d, J=1.01 Hz, 1H), 7.37-7.42 (m, 2H), 7.21-7.33 (m, 5H), 7.14 (d, J=9.60 Hz, 1H), 6.98 (d, J=1.01 Hz, 1H), 5.28 (m, 1H), 5.17 (s, 2H), 3.86 (s, 3H), 3.01 (s, 3H), 2.47 (d, J=1.01 Hz, 3H), 1.71 5 (dd, J=12.1, 3.7 Hz, 2H), 1.62 (t, J=12.1 Hz, 2H), 1.41 (s, 6H), 1.27 (s, 6H).

Step 8. 3-Methoxy-2-(6-(methyl(2,2,6,6-tetramethylpiperidin-4-yl)amino)pyridazin-3-yl)-5-(5-methyloxazol-2-yl)phenol To a solution of 6-(2-(benzyloxy)-6-methoxy-4-(5-methyloxazol-2-yl)phenyl)-N-methyl-N-(2,2,6,6-tetramethylpiperidin-4-yl)pyridazin-3-amine (36 mg, 0.066 mmol) in 1:1 ethyl acetate/MeOH (1.3 mL) under an atmosphere of nitrogen was added palladium on carbon (10% Pd content, 7 mg, 6.6 umol). The atmosphere was replaced by hydrogen (balloon) and the mixture stirred rapidly at RT overnight. The solution was diluted with DCM and filtered through celite. The filtrate was concentrated to a yellow residue and acidified with HCl in MeOH (produced by slow addition of acetyl chloride (14 uL, 0.199 mmol) to 1 mL MeOH). The solution was concentrated under vacuum, the residue redissolved into MeOH, and loaded onto an SCX column preconditioned with MeOH. The column was washed with MeOH (20 mL) and eluted with 3.5 N ammonia in MeOH (20 mL). Evaporation of the eluent afforded the product as a light yellow residue. Sonication with diethyl ether resulted in formation of a light yellow solid. Solvent was removed under reduced pressure to provide 3-methoxy-2-(6-(methyl(2,2,6,6-tetramethylpiperidin-4-yl)amino)pyridazin-3-yl)-5-(5-methyloxazol-2-yl)phenol (22 mg). LCMS Rt=0.54 min (LCMS method Q); MS=352.3 (M+1). $^1$H NMR (400 MHz, METHANOL-d4) δ ppm 8.22 (d, J=10.11 Hz, 1H), 7.18-7.29 (m, 3H), 6.96 (d, J=1.01 Hz, 1H), 5.07-5.20 (m, 1H), 3.98 (s, 3H), 3.03 (s, 3H), 2.46 (d, J=1.52 Hz, 3H), 1.73 (dd, J=12.5, 3.4 Hz, 2H), 1.62 (t, J=12.5 Hz, 2H), 1.42 (s, 6H), 1.26 (s, 6H).

Example 23-1

Synthesis of 2-(6-((6S)-6-((S)-1-hydroxyethyl)-2,2-dimethylpiperidin-4-yloxy)pyridazin-3-yl)-5-(1H-pyrazol-1-yl)phenol

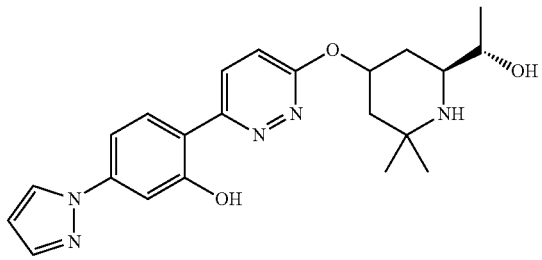 [SMILES: C[C@H](O)[C@@H]1CC(Oc2ccc(-c3ccc(-n4cccn4)cc3O)nn2)CC(C)(C)N1]

Step 1. 3-((6S)-6-((S)-1-(tert-butyldimethylsilyloxy) ethyl)-2,2-dimethylpiperidin-4-yloxy)-6-(2-methoxy-4-(1H-pyrazol-1-yl)phenyl)pyridazine To a solution of 3-chloro-6-(2-methoxy-4-(1H-pyrazol-1-yl)phenyl)pyridazine Intermediate 2-1 (32 mg, 0.11 mmol) and (6S)-6-((S)-1-(tert-butyldimethylsilyloxy)ethyl)-2,2-dimethylpiperidin-4-ol (Intermediate 4-1, 32 mg, 0.11 mmol) in DMF (1 mL) was added potassium tert-butoxide (1 M in THF, 0.45 mL, 0.45 mmol) at 0° C. The reaction mixture was stirred for 1 h at RT. The mixture was then quenched with saturated ammonium chloride solution (10 mL) and extracted with 10% MeOH in dichloromethane (20 mL). The extract was dried over $Na_2SO_4$ and concentrated in vacuo. The residue was purified by column chromatography (EtOAc/Heptane) to afford 56 mg (94%) of 3-((6S)-6-((S)-1-(tert-butyldimethylsilyloxy)ethyl)-2,2-dimethylpiperidin-4-yloxy)-6-(2-methoxy-4-(1H-pyrazol-1-yl)phenyl)pyridazine: LCMS (m/z, MH$^+$): 538.5; $^1$H NMR (400 MHz, CHLOROFORM-d) δ 8.05 (d, J=8.1 Hz, 1H), 8.01 (d, J=2.5 Hz, 1H), 7.97 (d, J=9.1 Hz, 1H), 7.76 (d, J=1.5 Hz, 1H), 7.55 (d, J=2.0 Hz, 1H), 7.30 (dd, J=8.6, 2.0 Hz, 1H), 6.94 (d, J=9.1 Hz, 1H), 6.54-6.47 (m, 1H), 5.79-5.87 (m, 1H), 3.96 (s, 3H), 3.83-3.93 (m, 1H), 3.07-3.17 (m, 1H), 2.13-2.22 (m, 1H), 2.05-2.12 (m, 1H), 1.43-1.57 (m, 2H), 1.27 (s, 3H), 1.16 (d, J=6.6 Hz, 3H), 1.14 (s, 3H), 0.90 (s, 9H), 0.10 (s, 3H), 0.08 (s, 3H).

Step 2. 2-(6-((6S)-6-((S)-1-Hydroxyethyl)-2,2-dimethylpiperidin-4-yloxy)pyridazin-3-yl)-5-(1H-pyrazol-1-yl)phenol To a solution of 3-((6S)-6-((S)-1-(tert-butyldimethylsilyloxy)ethyl)-2,2-dimethylpiperidin-4-yloxy)-6-(2-methoxy-4-(1H-pyrazol-1-yl)phenyl)pyridazine (56 mg, 0.1 mmol) in $CH_2Cl_2$ (2 mL) was added $BBr_3$ (1 M in heptane, 0.13 mL, 0.13 mmol) dropwise at 0° C. The mixture was stirred overnight. The reaction mixture was quenched with water and then basicifed with saturated $NaHCO_3$ solution. The organic layer was extracted with 10% MeOH in dichloromethane (10 mL x 3). The combined extracts were dried over $Na_2SO_4$ and concentrated in vacuo. Purification by HPLC gave 12 mg (28%) of 2-(6-((6S)-6-((S)-1-hydroxyethyl)-2,2-dimethylpiperidin-4-yloxy)pyridazin-3-yl)-5-(1H-pyrazol-1-yl)phenol: LCMS Rt=0.52 min (LCMS method Q); MS=410.3 (M+1); $^1$H NMR (400 MHz, METHANOL-d4) δ 8.23 (d, J=9.6 Hz, 1H), 8.19 (d, J=2.0 Hz, 1H), 7.86 (d, J=8.6 Hz, 1H), 7.65 (d, J=2.0 Hz, 1H), 7.32-7.25 (m, 2H), 7.22 (d, J=9.6 Hz, 1H), 6.47-6.43 (m, 1H), 5.59-5.66 (m, 1H), 3.68-3.77 (m, 1H), 3.02-3.11 (m, 1H), 2.03-2.15 (m, 2H), 1.49-1.59 (m, 2H), 1.24 (s, 3H), 1.11 (d, J=6.4 Hz, 3H), 1.10 (s, 3H).

Preparation 9

Intermediate 5-1: Synthesis of 7-(benzyloxy)-6-(6-(methyl(2,2,6,6-tetramethylpiperidin-4-yl)amino) pyridazin-3-yl)naphthalen-2-ol

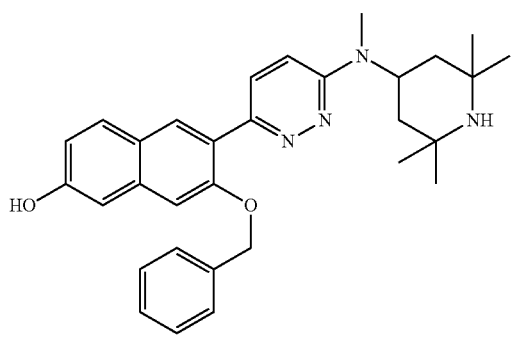 [SMILES: CN(c1ccc(-c2cc3ccc(O)cc3cc2OCc2ccccc2)nn1)C1CC(C)(C)NC(C)(C)C1]

7-(Benzyloxy)-6-(6-(methyl(2,2,6,6-tetramethylpiperidin-4-yl)amino)pyridazin-3-yl)naphthalen-2-ol (1.25 g, 2.366 mmol, 89% yield) was prepared from the 7-(benzyloxy)-6-(4,4,5,5-tetramethyl-1,3,2-dioxaborolan-2-yl)naphthalen-2-ol (1.45 g, 3.85 mmol) and Intermediate 1-1 (0.75 g, 2.65 mmol) using General method 1-1 for Suzuki coupling. M+1=497.8. $^1$H NMR (400 MHz, METHANOL-d$_4$) δ 7.91 (s, 1H), 7.76 (d, J=9.54 Hz, 2H), 7.66 (d, J=8.78 Hz, 2H), 7.34-7.40 (m, 2H), 7.31 (s, 2H), 7.18-7.27 (m, 2H), 6.97-7.05 (m, 2H), 6.91 (dd, J=8.78, 2.26 Hz, 1H), 5.18 (m, 3H), 2.92 (s, 3H), 1.60-1.68 (m, 2H), 1.45-1.55 (m, 2H), 1.32 (s, 6H), 1.18 (s, 6H).

Preparation 10

Intermediate 5-2: Synthesis of 7-(benzyloxy)-6-(6-(methyl(2,2,6,6-tetramethyl-piperidin-4-yl)amino) pyridazin-3-yl)naphthalen-2-yl trifluoromethanesulfonate

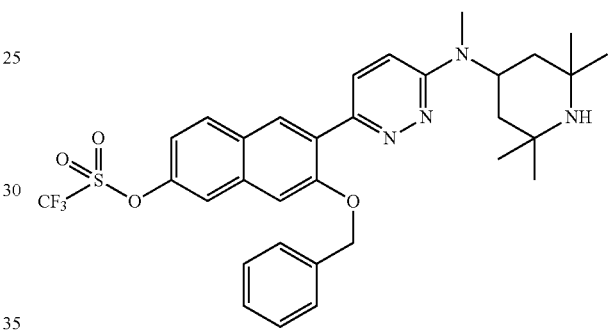

To a reaction mixture of 7-(benzyloxy)-6-(6-(methyl(2,2,6,6-tetramethylpiperidin-4-yl)amino)pyridazin-3-yl)naphthalen-2-ol (Intermediate 5-1, 3 g, 6.04 mmol) in DCM (30 mL) was added Et$_3$N (2.10 mL, 15.10 mmol), and N-phenyltrifluoromethanesulfonimide (2.158 g, 6.04 mmol) in two portions. The mixture was stirred at RT for 3 h and then concentrated in vacuo. The residue was loaded onto two 10 g SCX columns, washed with MeOH, and eluted with 2 M NH$_3$ in MeOH. The product-containing fractions were concentrated to give Intermediate 5-2 as a pale solid (3.47 g, 91% yield). MS (M+1)=629.5.

Preparation 11

Intermediate 5-3: Synthesis of 7-hydroxy-6-(6-(methyl(2,2,6,6-tetramethylpiperidin-4-yl)amino) pyridazin-3-yl)naphthalen-2-yl trifluoromethanesulfonate

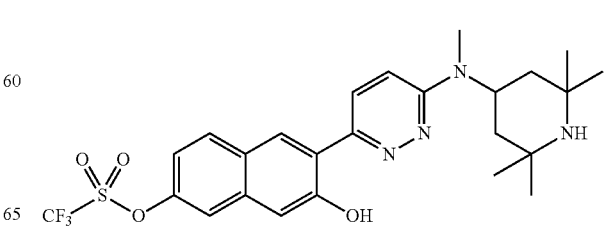

To a mixture of Intermediate 5-2 (500 mg, 0.795 mmol) in DCM (4 mL) was added BBr$_3$ (1 M solution in DCM, 2.4 mL, 2.4 mmol) slowly at −78° C. The mixture was stirred at −78° C. for 10 minutes, then warmed to RT and stirred for 1.5 hours. The reaction was quenched with MeOH and concentrated. The residue was loaded onto an SCX column, washed with MeOH, eluted with 2 M NH$_3$ in MeOH. The product-containing fractions were concentrated to give Intermediate 5-3 as a light yellow solid (382 mg, 89% yield). MS (M+1)=539.3.

Preparation 12

Intermediate 5-4: Synthesis of 6-(3-(benzyloxy)-6-methoxynaphthalen-2-yl)-N-methyl-N-(2,2,6,6-tetramethylpiperidin-4-yl)pyridazin-3-amine

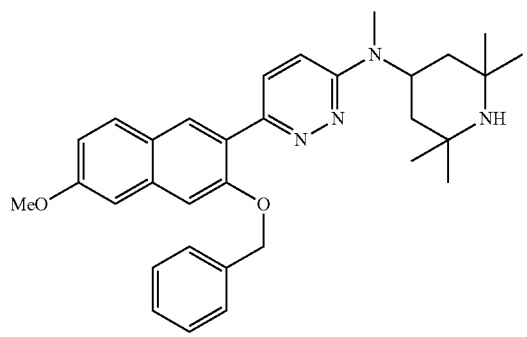 [SMILES: COc1ccc2cc(-c3ccc(N(C)C4CC(C)(C)NC(C)(C)C4)nn3)c(OCc3ccccc3)cc2c1]

To a reaction mixture of 7-(benzyloxy)-6-(6-(methyl(2,2,6,6-tetramethylpiperidin-4-yl)amino)pyridazin-3-yl)naphthalen-2-ol (Intermediate 5-1, 500 mg, 1.01 mmol) in DMF (3 mL) was added 60% wt NaH (48.3 mg, 1.21 mmol) at 0° C. The mixture was stirred for 0.5 h, then methyl iodide (0.063 mL, 1.01 mmol) was added. The mixture was stirred at RT for 1.5 hours, then another portion of methyl iodide (0.063 mL, 1.01 mmol) was added. The reaction mixture was stirred at RT overnight, then slowly quenched with water. The residue was partitioned between water and DCM, and the aqueous layer was further extracted with DCM. The combined organic layers were dried over Na$_2$SO$_4$, and concentrated in vacuo. The residue was purified via silica gel flash column chromatagraphy (0-20% 1.5 M NH$_3$ in MeOH/DCM) to give a mixture of Intermediate 5-4 and 6-(3-(benzyloxy)-6-methoxynaphthalen-2-yl)-N-methyl-N-(1,2,2,6,6-pentamethylpiperidin-4-yl)pyridazin-3-amine which was used without further purification (412 mg, 80% yield). MS (M+1)=511.5.

Preparation 13

Intermediate 6-1: Synthesis of 3-hydroxy-4-(6-(methyl(2,2,6,6-tetramethylpiperidin-4-yl)amino)pyridazin-3-yl)-5-(trifluoromethoxy)phenyl trifluoromethanesulfonate

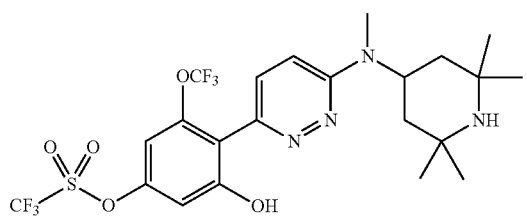 [SMILES: CN(c1ccc(-c2c(O)cc(OS(=O)(=O)C(F)(F)F)cc2OC(F)(F)F)nn1)C1CC(C)(C)NC(C)(C)C1]

Step 1: 6-(4-(Benzyloxy)-2-(trifluoromethoxy)phenyl)-N-methyl-N-(2,2,6,6-tetramethylpiperidin-4-yl)pyridazin-3-amine (4-(Benzyloxy)-2-(trifluoromethoxy)phenyl)boronic acid (1.2 g, 61% pure, 2.307 mmol) and Intermediate 1-1 (246 mg, 0.871 mmol) were reacted according to GENERAL METHOD 1-5 for Suzuki coupling. Compound 6-(4-(benzyloxy)-2-(trifluoromethoxy)phenyl)-N-methyl-N-(2,2,6,6-tetramethylpiperidin-4-yl)pyridazin-3-amine was obtained as a beige solid (405 mg, 90% yield) after flash column chromatography purification. MS (M+1)=515.5.

Step 2: 4-(6-(Methyl(2,2,6,6-tetramethylpiperidin-4-yl)amino)pyridazin-3-yl)-3-(trifluoromethoxy)phenol From compound 6-(4-(benzyloxy)-2-(trifluoromethoxy)phenyl)-N-methyl-N-(2,2,6,6-tetramethylpiperidin-4-yl)pyridazin-3-amine (405 mg, 0.787 mmol), following GENERAL METHOD 4-1 for hydrogenolysis of the benzyl group, compound 4-(6-(methyl(2,2,6,6-tetramethylpiperidin-4-yl)amino)pyridazin-3-yl)-3(trifluoromethoxy)phenol was obtained (335 mg, 100% yield) after SCX column purification. MS (M+1)=425.3.

Step 3: 4-(6-(Methyl(2,2,6,6-tetramethylpiperidin-4-yl)amino)pyridazin-3-yl)-3-(trifluoromethoxy)phenyl trifluoromethanesulfonate To a suspension of 4-(6-(methyl(2,2,6,6-tetramethylpiperidin-4-yl)amino)pyridazin-3-yl)-3-(trifluoromethoxy)phenol (360 mg, 0.848 mmol) in DCM (5 mL) was added Et$_3$N (0.296 ml, 2.120 mmol) and N-phenyltrifluoromethanesulfonimide (364 mg, 1.018 mmol). The mixture was stirred at RT overnight. The reaction mixture was concentrated. The residue was loaded onto a 5 g SCX column, washed with MeOH, eluted with 2 M NH$_3$ in MeOH. The product-containing fractions were concentrated, and the crude product was purified via flash column chromatography to give 4-(6-(methyl(2,2,6,6-tetramethylpiperidin-4-yl)amino) pyridazin-3-yl)-3-(trifluoromethoxy)phenyl trifluoromethanesulfonate as a beige solid (361 mg, 76%). MS (M+1)= 557.5 Step 4: 3-Hydroxy-4-(6-(methyl(2,2,6,6-tetramethylpiperidin-4-yl)amino)pyridazin-3-yl)-5-(trifluoromethoxy) phenyl trifluoromethanesulfonate A mixture of 4-(6-(methyl (2,2,6,6-tetramethylpiperidin-4-yl)amino)pyridazin-3-yl)-3-(trifluoromethoxy)phenyl trifluoromethanesulfonate (360 mg, 0.647 mmol), iodobenzene diacetate (375 mg, 1.164 mmol) and Pd(OAc)$_2$ (7.3 mg, 0.032 mmol) in AcOH (3.0 mL) and Ac$_2$O (3.0 mL) was heated at 60° C. overnight. The reaction mixture was cooled to room temperature and concentrated. The residue was basified with aqueous NaHCO$_3$ solution and extracted with DCM. The combined organic layers were dried over Na$_2$SO$_4$, and concentrated. The crude material was loaded onto a SCX column, washed with MeOH and diluted with 2 M NH$_3$ in MeOH. The product-containing fractions were concentrated. Compound 3-hydroxy-4-(6-(methyl(2,2,6,6-tetramethylpiperidin-4-yl) amino)pyridazin-3-yl)-5-(trifluoromethoxy)phenyl trifluoromethanesulfonate was obtained as a yellow solid (110 mg, 28%) after flash column chromatography and HPLC purification. MS (M+1)=573.2.

Preparation 14

Intermediate 6-2: Synthesis of 3-hydroxy-5-methoxy-4-(6-(methyl(2,2,6,6-tetramethylpiperidin-4-yl)amino)pyridazin-3-yl)phenyl trifluoromethanesulfonate

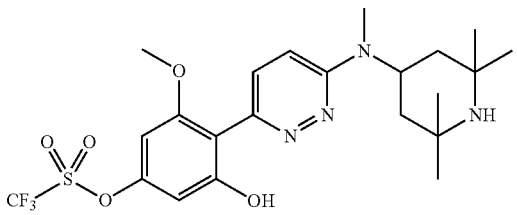

Step 1: 3-Methoxy-4-(4,4,5,5-tetramethyl-1,3,2-dioxaborolan-2-yl)phenol

To a 500 mL pressure vessel was added 4-bromo-3-methoxyphenol (8.12 g, 40 mmol), bis(pinacolato) diboron (22.4 g, 88.0 mmol), potassium acetate (27.4 g, 280 mmol), dppf (2.22 g, 4.00 mmol) and Pd(dppf)Cl$_2$ (2.93 g, 4.00 mmol). Dioxane (120 mL) was added and the reaction mixture was purged with nitrogen for 25 minutes. The reaction mixture was then sealed and stirred at 85° C. for 20 h. The mixture was diluted with ethyl acetate, filtered through celite, and concentrated to a dark brown liquid. The liquid was passed through a plug of silica gel (60 g) eluting with heptane/ethyl acetate to provide 3-methoxy-4-(4,4,5,5-tetramethyl-1,3,2-dioxaborolan-2-yl)phenol as a white solid (4.0 g). $^1$H NMR (400 MHz, CHLOROFORM-d) δ ppm 7.60 (d, J=8.1 Hz, 1H), 6.42 (dd, J=8.1, 2.0 Hz, 1H), 6.33 (d, J=2.0 Hz, 1H), 3.64 (s, 3H), 1.35 (s, 12H).

Step 2: 3-Methoxy-4-(6-(methyl(2,2,6,6-tetramethylpiperidin-4-yl)amino)pyridazin-3-yl)phenol To a 25 mL microwave vial was added 3-methoxy-4-(4,4,5,5-tetramethyl-1,3,2-dioxaborolan-2-yl)phenol (2.90 g, 10.8 mmol), 6-chloro-N-methyl-N-(2,2,6,6-tetramethylpiperidin-4-yl)pyridazin-3-amine (Intermediate 1-1, 2.55 g, 9.00 mmol), NaHCO$_3$ (2.27 g, 27.0 mmol) and tetrakis(triphenylphosphine) palladium(0) (0.520 g, 0.450 mmol). Dioxane (45 mL) and water (15 mL) were added, and the reaction mixture was purged with nitrogen for 10 minutes. The reaction mixture was heated under microwave irradiation at 110° C. for 16 h. After cooling to RT, the mixture was filtered through celite, washing the filter pad sequentially with ethyl acetate, DCM, and MeOH. Concentration of the filtrate afforded a brown solid which was purified by flash chromatography (80 g silica, 0-20% 2 M ammonia in MeOH gradient, in DCM) to provide 3-methoxy-4-(6-(methyl(2,2,6,6-tetramethylpiperidin-4-yl)amino)pyridazin-3-yl)phenol (1.6 g). MS (M+1)=371.3.

Step 3: 3-Methoxy-4-(6-(methyl(2,2,6,6-tetramethylpiperidin-4-yl)amino)pyridazin-3-yl)phenyl trifluoromethanesulfonate N-Phenyltrifluoromethanesulfonimide (2.160 g, 6.05 mmol) was added portionwise to a mixture of 3-methoxy-4-(6-(methyl(2,2,6,6-tetramethylpiperidin-4-yl)amino)pyridazin-3-yl)phenol and triethylamine (1.5 mL, 11 mmol) cooled to 0° C. The mixture was allowed to warm to RT and to stir for 2 h. An additional portion of N-phenyltrifluoromethanesulfonimide (0.30 g, 0.86 mmol) was added and the mixture stirred at RT overnight. The solution was diluted with saturated aqueous NaHCO$_3$ solution and extracted with DCM (2×). The extracts were concentrated and the residue was purified by flash chromatography (40 g silica, 0-25% MeOH gradient in DCM) to provide 3-methoxy-4-(6-(methyl (2,2,6,6-tetramethylpiperidin-4-yl)amino) pyridazin-3-yl)phenyl trifluoromethanesulfonate (1.8 g). MS (M+1)=503.4. $^1$H NMR (400 MHz, METHANOL-d$_4$) δ ppm 7.85 (d, J=9.6 Hz, 1H), 7.78 (d, J=8.6 Hz, 1H), 7.20 (d, J=9.6 Hz, 1H), 7.17 (d, J=2.5 Hz, 1H), 7.12 (dd, J=8.3, 2.3 Hz, 1H), 5.44-5.59 (m, 1H), 3.92 (s, 3H), 3.04 (s, 3H), 1.98 (m, J=8.1 Hz, 4H), 1.65 (s, 6H), 1.53 (s, 6H).

Step 4: 3-Hydroxy-5-methoxy-4-(6-(methyl(2,2,6,6-tetramethylpiperidin-4-yl)amino)pyridazin-3-yl)phenyl trifluoromethanesulfonate A mixture of 3-methoxy-4-(6-(methyl(2,2,6,6-tetramethylpiperidin-4-yl)amino)pyridazin-3-yl)phenyl trifluoromethanesulfonate (2.6 g, 5.17 mmol), Pd(OAc)$_2$ (58 mg, 0.259 mmol), and iodobenzene diacetate (2.33 g, 7.24 mmol) in 1:1 acetic acid/acetic anhydride (42 mL) was heated at 50° C. for 8 h. The mixture was cooled to RT and concentrated under reduced pressure. Flash chromatography (10-100% EtOH in DCM, followed by 7:1 EtOH/7 N ammonia in MeOH elution) provided a mixture of the title compound and the corresponding acetate (3-methoxy-2-(6-(methyl(2,2,6,6-tetramethylpiperidin-4-yl)amino)pyridazin-3-yl)-5-(((trifluoromethyl)sulfonyl)oxy)phenyl acetate). After concentration, the mixture was taken up in methanol and heated at 70° C. for 4 h. The solvent was evaporated to provide 3-hydroxy-5-methoxy-4-(6-(methyl(2,2,6,6-tetramethylpiperidin-4-yl)amino)pyridazin-3-yl)phenyl trifluoromethanesulfonate as a tan-colored solid (1.25 g). MS (M+1)= 519.4. $^1$H NMR (400 MHz, METHANOL-d$_4$) δ ppm 8.08 (d, J=10.1 Hz, 1H), 7.23 (d, J=10.1 Hz, 1H), 6.57 (s, 2H), 5.16 (t, J=12.1 Hz, 1H), 3.89 (s, 3H), 3.02 (s, 3H), 1.69-1.77 (m, 2H), 1.56-1.67 (m, 2H), 1.41 (s, 6H), 1.27 (s, 6H).

Preparation 15

Intermediate 7-1: Synthesis of 6-methoxy-5-(6-(methyl(2,2,6,6-tetramethylpiperidin-4-yl)amino)pyridazin-3-yl)-2,3-dihydro-1H-inden-1-one

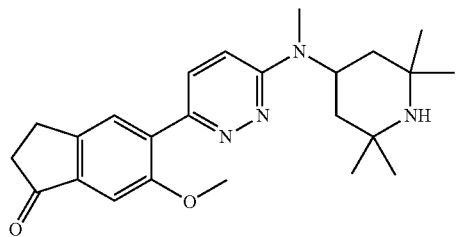 [SMILES: COc1cc2c(cc1-c1ccc(N(C)C3CC(C)(C)NC(C)(C)C3)nn1)CCC2=O]

Step 1: 6-Methoxy-5-(4,4,5,5-tetramethyl-1,3,2-dioxaborolan-2-yl)-2,3-dihydro-1H-inden-1-one Following GENERAL METHOD 2-1 for boronate ester formation using 5-bromo-6-methoxy-2,3-dihydro-1H-inden-1-one (1.0 mg, 4.15 mmol) affords 6-methoxy-5-(4,4, 5,5-tetramethyl-1,3,2-dioxaborolan-2-yl)-2,3-dihydro-1H-inden-1-one (1.16 g) MS [M+H+]=289.2.

Step 2: 6-Methoxy-5-(6-(methyl(2,2,6,6-tetramethylpiperidin-4-yl)amino)pyridazin-3-yl)-2,3-dihydro-1H-inden-1-one Following GENERAL METHOD 1-4 for Suzuki coupling using 6-methoxy-5-(4,4,5,5-tetramethyl-1, 3,2-dioxaborolan-2-yl)-2,3-dihydro-1H-inden-1-one (300 mg, 1.06 mmol) and 6-chloro-N-methyl-N-(2,2,6,6-tetramethylpiperidin-4-yl)pyridazin-3-amine (Intermediate 1-1, 611 mg, 2.12 mmol) affords 6-methoxy-5-(6-(methyl(2,2,6,6-tetramethylpiperidin-4-yl)amino)pyridazin-3-yl)-2,3-dihydro-1H-inden-1-one (433 mg) MS [M+H+]=409.7.

Preparation 16

Intermediate 8-1: Synthesis of 5-bromo-3-fluoro-2-(6-(methyl(2,2,6,6-tetramethylpiperidin-4-yl)amino)pyridazin-3-yl)phenol

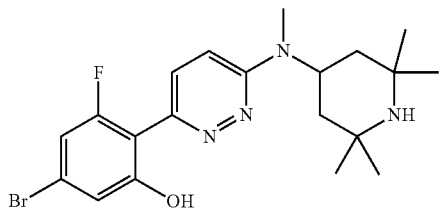 [SMILES: CN(c1ccc(-c2c(O)cc(Br)cc2F)nn1)C1CC(C)(C)NC(C)(C)C1]

Step 1: (2-Fluoro-6-methoxyphenyl)-N-methyl-N-(2,2,6,6-tetramethylpiperidin-4-yl)pyridazin-3-amine Intermediate 1-1 (2.83 g, 10.0 mmol), (2-fluoro-6-methoxyphenyl)boronic acid, and K₃PO₄ (5.52 g, 26.0 mmol) were added to a microwave vial. 2nd Generation XPhos Precatalyst (0.32 g, 0.40 mmol) was then added to the mixture followed by addition of 1:1 THF/water (50 mL). The reaction mixture was sealed and stirred at RT for 4 h then extracted with CH₂Cl₂ (2×). The crude material was purified by catch and release using SiliaBond Propylsulfonic Acid® (3 eq, MeOH as eluent and a 2 N ammonia solution in MeOH to release the material). The solvent was concentrated in vacuo to afford the title compound as a brown gel (2.87 g, 77%). [M+H]: 373.4; ¹H NMR (400 MHz, DMSO) δ 7.43 (td, J=8.5, 7.0 Hz, 1H), 7.36 (d, J=9.5 Hz, 1H), 7.08 (d, J=9.5 Hz, 1H), 6.98 (d, J=8.5 Hz, 1H), 6.92 (td, J=8.5, 1.0 Hz, 1H), 5.07 (bs, 1H), 3.74 (s, 3H), 3.31 (s, 3H), 1.47-1.55 (m, 2H), 1.33-1.48 (m, 2H), 1.24 (s, 6H), 1.09 (s, 6H).

Step 2: 6-(4-Bromo-2-fluoro-6-methoxyphenyl)-N-methyl-N-(2,2,6,6-tetramethylpiperidin-4-yl)pyridazin-3-amine (2-Fluoro-6-methoxyphenyl)-N-methyl-N-(2,2,6,6-tetramethylpiperidin-4-yl)pyridazin-3-amine (1.83 g, 4.91 mmol), [Ir(COD)(OMe)]₂ (0.16 g, 0.24 mmol), dtbpy (0.13 g, 0.24 mmol), and bis(pinacolato)diboron (1.87 g, 7.37 mmol) in dioxane (40 mL) were heated at 80° C. overnight. The volatiles were removed under vacuum. EtOH (20 mL), H₂O (20 mL) and CuBr₂ (3.29 g, 14.7 mmol) were added. The mixture was heated at reflux overnight. The reaction mixture was cooled to RT and the volatiles were removed under vacuum. A 7% aqueous solution of NH₄OH was added and the aqueous phase was extracted with DCM (3×). The product was then purified by silica gel column chromatography (1-10% gradient of 7 N ammonia in MeOH, in CH₂Cl₂) to give an inseparable mixture of the desired product (6-(4-bromo-2-fluoro-6-methoxyphenyl)-N-methyl-N-(2,2,6,6-tetramethylpiperidin-4-yl)pyridazin-3-amine) and 4-bromo-6-(2-fluoro-6-methoxyphenyl)-N-methyl-N-(2,2,6,6-tetramethylpiperidin-4-yl)pyridazin-3-amine (1.26 g). [M+H]: 451.3.

Step 3: 5-Bromo-3-fluoro-2-(6-(methyl(2,2,6,6-tetramethylpiperidin-4-yl)amino)pyridazin-3-yl)phenol 6-(4-Bromo-2-fluoro-6-methoxyphenyl)-N-methyl-N-(2,2,6,6-tetramethylpiperidin-4-yl)pyridazin-3-amine (0.81 g, 1.80 mmol) and pyridine hydrochloride (1.65 g, 14.3 mmol) were heated to 190° C. for 45 min in a Biotage® Initiator microwave reactor. The reaction mixture was diluted in MeOH/DMSO, and purified via reverse phase preparative HPLC (5 to 95% acetonitrile in water, 0.1% trifluoroacetic acid as modifier). The appropriate fractions containing product were free based by catch and release using SiliaBond Propylsulphonic Acid® (4 eq, methanol as eluent and a 2 N ammonia solution in MeOH to release the material). The solvent was concentrated in vacuo to afford 5-bromo-3-fluoro-2-(6-(methyl(2,2,6,6-tetramethylpiperidin-4-yl)amino)pyridazin-3-yl)phenol as a beige solid (0.19 g, 23%). [M+H]: 439.2; ¹H NMR (400 MHz, MeOD) δ 7.96 (d, J=10.0 Hz, 1H), 7.27 (d, J=10.0 Hz, 1H), 6.97 (t, J=2.0 Hz, 1H), 6.89 (dd, J=11.5, 2.0 Hz, 1H), 5.07-5.35 (m, 1H), 3.02 (s, 3H), 1.73 (dd, J=12.5, 3.5 Hz, 2H), 1.62 (t, J=12.5 Hz, 2H), 1.41 (s, 6H), 1.27 (s, 6H).

Preparation 17

Intermediate 9-1: Synthesis of 3-methoxy-4-(6-(methyl(2,2,6,6-tetramethylpiperidin-4-yl)amino)pyridazin-3-yl)phenyl trifluoromethanesulfonate

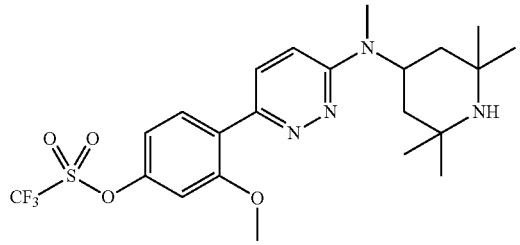 [SMILES: COc1cc(OS(=O)(=O)C(F)(F)F)ccc1-c1ccc(N(C)C2CC(C)(C)NC(C)(C)C2)nn1]

Step 1: (4-Bromo-3-methoxyphenoxy)(tert-butyl)dimethylsilane

To a 5 L round bottom flask fitted with an overhead stirrer, thermocouple and N₂ inlet, was added 4-bromo-3-methoxyphenol (254 g, 1251 mmol), DCM (2500 mL) and DIPEA (437 mL, 2502 mmol). The reaction mixture was cooled in an ice bath, followed by addition of tert-butylchlorodimethylsilane (198 g, 1314 mmol). The reaction mixture was stirred at RT overnight, and then diluted with water. The organic layer was separated, dried over sodium sulfate, filtered and concentrated to provide (4-bromo-3-methoxyphenoxy)(tert-butyl)dimethylsilane (472 g, 1250 mmol, 100% yield). MS (M+1)=319.2.

Step 2: tert-Butyl(3-methoxy-4-(4,4,5,5-tetramethyl-1,3,2-dioxaborolan-2-yl) phenoxy)dimethylsilane To a 500 mL round bottom flask containing (4-bromo-3-methoxyphenoxy)(tert-butyl)dimethylsilane (1.9 g, 6 mmol) and dioxane (60 mL), was added 4,4,4',4',5,5,5',5'-octamethyl-2,2'-bi(1,3,2-dioxaborolane) (3.05 g, 12.00 mmol), potassium acetate (2.35 g, 24.00 mmol), dppf (0.333 g, 0.600 mmol) and PdCl$_2$(dppf).CH$_2$Cl$_2$ adduct (0.49 g, 0.600 mmol). The reaction was evacuated and filled with N$_2$ twice and then stirred at 90° C. overnight. The reaction was then diluted with MeOH, filtered through celite and washed with EtOAc. After concentration in vacuo, the residue was purified by silica gel chromatography using EtOAc/Heptane (0-15%) to provide white solid tert-butyl(3-methoxy-4-(4,4,5,5-tetramethyl-1,3,2-dioxaborolan-2-yl)phenoxy)dimethylsilane (1.6 g, 4.17 mmol, 70% yield), MS (M+1)=365.2.

Step 3: 3-Methoxy-4-(6-(methyl(2,2,6,6-tetramethylpiperidin-4-yl)amino)pyridazin-3-yl)phenol A 20 L jacketed reactor fitted with a reflux condenser, N$_2$ inlet, thermocouple and overhead stirrer was charged with 2.7 L of dioxane followed by tert-butyl(3-methoxy-4-(4,4,5,5-tetramethyl-1,3,2-dioxaborolan-2-yl)phenoxy)dimethylsilane (290 g, 557 mmol), 6-chloro-N-methyl-N-(2,2,6,6-tetramethylpiperidin-4-yl)pyridazin-3-amine (Intermediate 1-1, 113 g, 398 mmol), and sodium bicarbonate (100 g, 1194 mmol). 700 mL of water was added, followed by addition of Pd(PPh$_3$)$_4$ (27.6 g, 23.88 mmol). The reaction mixture was heated at 72° C. overnight. After cooling to RT, the layers were separated. The organic layer was concentrated, and the reside was purified by silica gel chromatography using 5% MeOH (containing 1% TEA) in DCM to provide the desired product, 3-methoxy-4-(6-(methyl(2,2,6,6-tetramethylpiperidin-4-yl)amino)pyridazin-3-yl)phenol (83 g, 211 mmol, 53% yield). MS=371.4.

Step 4: 3-Methoxy-4-(6-(methyl(2,2,6,6-tetramethylpiperidin-4-yl)amino)pyridazin-3-yl)phenyl trifluoromethanesulfonate A mixture of 3-methoxy-4-(6-(methyl(2,2,6,6-tetramethylpiperidin-4-yl)amino)pyridazin-3-yl)phenol (1.6 g, 4.32 mmol) and Et$_3$N (1.50 mL, 10.8 mmol) in DCM (40 mL) was cooled in an ice-water bath, and N-phenyltrifluoromethanesulfonimide (2.16 g, 6.05 mmol) was added dropwise.

After stirring at RT for 2 h, another 0.2 eq of N-phenyltrifluoromethanesulfonimide was added, and the reaction was stirred overnight. The reaction was quenched with an aqueous sodium bicarbonate solution and extracted with DCM. The organic layer was washed with brine, separated and concentrated, and the residue was purified by chromatography column using MeOH/DCM (0-25%) to provide Intermediate 9-1,3-methoxy-4-(6-(methyl(2,2,6,6-tetramethylpiperidin-4-yl)amino)pyridazin-3-yl)phenyl trifluoromethanesulfonate (1.8 g, 3.58 mmol, 83% yield), MS=503.2.

Preparation 18

Intermediate 9-2: Synthesis of 3-hydroxy-4-(6-(methyl(2,2,6,6-tetramethylpiperidin-4-yl)amino)pyridazin-3-yl)phenyl trifluoromethanesulfonate

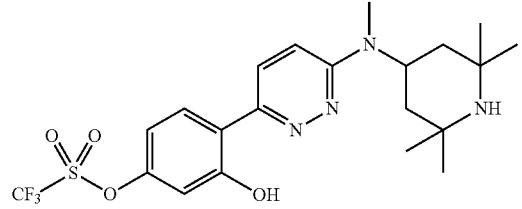 [SMILES: CN(c1ccc(-c2ccc(OS(=O)(=O)C(F)(F)F)cc2O)nn1)C1CC(C)(C)NC(C)(C)C1]

A 1 L round bottom flask fitted with a magnetic stir bar and N$_2$ inlet, was cooled in an ice-water bath, and 3-methoxy-4-(6-(methyl(2,2,6,6-tetramethylpiperidin-4-yl)amino)pyridazin-3-yl)phenyl trifluoromethanesulfonate (37.00 g, 68.6 mmol) and DCM (360 mL) were added. Boron tribromide (1M in DCM, 120 mL) was added slowly via a syringe. After stirring at RT for 4 h, the reaction was quenched with methanol, and stirred at RT for 15 minutes. The reaction mixture was concentrated to provide a sticky glassy solid, which was refluxed in 1M HCl in MeOH (360 mL) overnight. After cooling to RT, the material was concentrated, and the residue was stirred in 4 N HCl in dioxane (18 mL) overnight. Filtration afforded the HCl salt of the desire product, 3-hydroxy-4-(6-(methyl(2,2,6,6-tetramethylpiperidin-4-yl)amino)pyridazin-3-yl)phenyl trifluoromethanesulfonate Intermediate 9-2 (36 g, 68.6 mmol, >100% yield), MS (M+1)=489.3. $^1$H NMR (DMSO-d$_6$) δ 9.06 (d, J=11.6 Hz, 1H), 8.28 (d, J=10.1 Hz, 1H), 8.13 (d, J=12.1 Hz, 1H), 7.99 (d, J=8.1 Hz, 1H), 7.70 (d, J=9.1 Hz, 1H), 7.08-7.12 (m, 1H), 4.99 (br. s., 1H), 3.03 (s, 3H), 2.03 (t, J=12.9 Hz, 2H), 1.80 (d, J=10.6 Hz, 2H), 1.54 (s, 6H), 1.48 (s, 6H).

Preparation 19

Intermediate 9-3: Synthesis of 6-(2-methoxy-4-(4,4,5,5-tetramethyl-1,3,2-dioxaborolan-2-yl)phenyl)-N-methyl-N-(2,2,6,6-tetramethylpiperidin-4-yl)pyridazin-3-amine

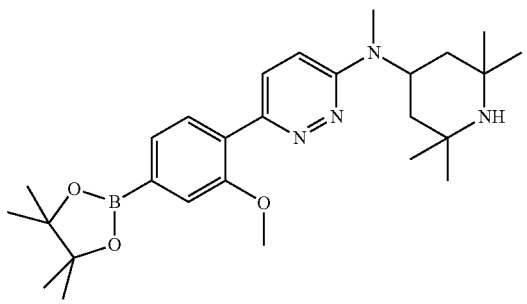

To a microwave vial was added 3-methoxy-4-(6-(methyl(2,2,6,6-tetramethylpiperidin-4-yl)amino)pyridazin-3-yl) phenyl trifluoromethanesulfonate (Intermediate 9-1, 4.0 g, 7.96 mmol), bis(pinacolato)diboron (4.45 g, 17.51 mmol), potassium acetate (4.69 g, 47.8), PdCl$_2$(dppf).CH$_2$Cl$_2$ (0.65 g, 0.79 mmol), dppf (0.44 g, 0.79 mmol), and 1,4-dioxane (10 mL). The reaction solution was purged with nitrogen (3×) and stirred at 90° C. overnight. The reaction mixture was filtered through celite and the filter cake was washed with EtOAc. The filtrate was concentrated in vacuo to give a brown liquid which was purified by silica gel chromotography (10%-60% EtOAc/Heptane) to afford 6-(2-methoxy-4-(4,4,5,5-tetramethyl-1,3,2-dioxaborolan-2-yl)phenyl)-N-methyl-N-(2,2,6,6-tetramethylpiperidin-4-yl)pyridazin-3-amine (1.6 g, MS: 481.5 [M+H$^+$]).

General Method 1-5

Representative procedure for Suzuki Coupling Chloropyridazine intermediate, such as Intermediate 1-1, (1 equivalent), boronic acid reagent (1.2-1.5 equivalents), Pd(PPh$_3$)$_4$ (0.1 equivalents) and Na$_2$CO$_3$ or NaHCO$_3$ (2.5-3 equivalents) were added to a microwave vial followed by addition of 1,4-dioxane and H$_2$O (4:1). The reaction mixture was sealed, then evacuated and filled with N$_2$ (4×) and heated via microwave irradiation at 120° C. for 1 h. The reaction mixture was filtered through celite and washed with EtOAc or 10% MeOH/DCM. The resulting filtrate was concentrated and acidified to pH 3 using 1 M HCl aqueous solution, then loaded on a SCX column, washed with MeOH, and eluted with 2 M NH$_3$ in MeOH. The product-containing fractions were concentrated and purified via flash column chromatography to afford the desired product.

General Method 1-6

Representative Procedure for the Suzuki Coupling

Halo-pyridazine substrate (1 equivalent), boronic acid or ester reagent (2.5 equivalents), and Na$_2$CO$_3$ (3 equivalents) were added to a microwave vial. Pd(PPh$_3$)$_4$(0.1 equivalents) was then added to the reaction mixture followed by addition of dioxane/water (6/1, 0.1 M). The reaction mixture was sealed and heated in a Biotage® Initiator microwave reactor 130° C. for 1 h. The reaction mixture was filtered through celite and the filter cake was washed with methanol. The filtrate was concentrated in vacuo and the crude product was purified via reverse phase preparative HPLC (0.1% trifluoroacetic acid as modifier). The appropriate fractions containing product were free based by catch and release using SiliaBond Propylsulphonic Acid® (4 eq, methanol as eluent and a 2 N ammonia solution in MeOH to release the material). The solvent was concentrated in vacuo and the resulting solid was suspended or dissolved in CH$_3$CN/H$_2$O (3/1 mL). 1 M aqueous HCl (3 equivalents) was added and the solvent was concentrated in vacuo to afford the desired compound as the hydrochloride salt.

General Method 7-1

Representative Procedure for Borylation/Bromination

A mixture of a 2,6-substituted phenylpyridazine intermediate, such as 6-(2,6-dimethoxyphenyl)-N-methyl-N-(2,2,6,6-tetramethylpiperidin-4-yl)pyridazin-3-amine (1 equivalent), bis(pinacolato)diboron (1.5 equivalents), 4,4'-di-tert-butyl bipyridine (dtbpy) (0.2 equivalents) and [Ir(COD)(OMe)]$_2$ (0.2 equivalents) in 1,4-dioxane was evacuated then filled with N$_2$ (4×), then heated at 90° C. overnight. The reaction mixture was cooled to RT and concentrated. To the residue was added CuBr$_2$ (3 equivalents), MeOH and water (1:1). The mixture was heated at 85° C. overnight, then cooled to RT, diluted with EtOAc, filtered through celite and washed with EtOAc. The filtrate was washed with brine, dried over Na$_2$SO$_4$ and concentrated in vacuo. The residue was purified via flash column chromatography (MeOH/DCM) to afford the desired product.

Example 24-1

Synthesis of 7-hydroxy-6-(6-(methyl(2,2,6,6-tetramethylpiperidin-4-yl)amino)pyridazin-3-yl)-2-naphthonitrile

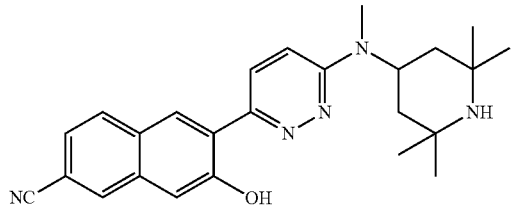 [SMILES: CN(c1ccc(-c2cc3ccc(C#N)cc3cc2O)nn1)C1CC(C)(C)NC(C)(C)C1]

A degassed mixture of 7-hydroxy-6-(6-(methyl (2,2,6,6-tetramethylpiperidin-4-yl)amino)pyridazin-3-yl)naphthalen-2-yl trifluoromethanesulfonate (21 mg, 0.033 mmol), zinc cyanide (5.00 mg, 0.043 mmol) and tetrakis(triphenylphosphine)palladium(0) (1.8 mg, 1.6 µmol) in DMF (0.8 mL) was heated at 120° C. under microwave irradiation for 1 h. The reaction mixture was filtered through celite, washed with EtOAc and concentrated. The residue was loaded on a 1 g SCX column, washed with MeOH, and eluted with 2 M NH$_3$ in MeOH. The product-containing fractions were concentrated. The crude product was purified via HPLC to give the title compound as a light yellow solid (6.9 mg, 50% yield). LCMS Rt=0.55 min [Method Q], MS (M+1)=416.3. $^1$H NMR (METHANOL-d$_4$) δ 8.26 (s, 1H), 8.16 (d, J=9.6 Hz, 1H), 8.04 (s, 1H), 7.86 (d, J=8.6 Hz, 1H), 7.32 (dd, J=8.6, 1.5 Hz, 1H), 7.27 (s, 1H), 7.22 (d, J=9.6 Hz, 1H), 5.05 (t, J=11.9 Hz, 1H), 2.94 (s, 3H), 1.61 (dd, J=13.1, 3.5 Hz, 2H), 1.49 (t, J=12.4 Hz, 2H), 1.30 (s, 6H), 1.14 (s, 6H).

Example 24-2

Synthesis of 3-(6-(methyl(2,2,6,6-tetramethylpiperidin-4-yl)amino)pyridazin-3-yl)-7-(piperidin-1-ylmethyl)naphthalen-2-ol

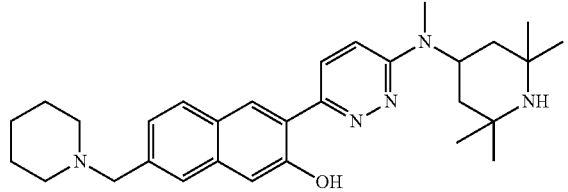 [SMILES: CN(c1ccc(-c2cc3ccc(CN4CCCCC4)cc3cc2O)nn1)C1CC(C)(C)NC(C)(C)C1]

Step 1: 6-(3-(Benzyloxy)-6-(piperidin-1-ylmethyl)naphthalen-2-yl)-N-methyl-N-(2, 2,6,6-tetramethylpiperidin-4-yl)pyridazin-3-amine A degassed reaction mixture of Intermediate 5-2 (125 mg, 0.199 mmol), potassium-1-trifluoroboratomethylpiperidine (44.8 mg, 0.219 mmol), palladium acetate (2.2 mg, 9.9 µmol), X-Phos (9.5 mg, 0.020 mmol) and Cs$_2$CO$_3$ (194 mg, 0.596 mmol) in THF (1 mL) and water (0.1 mL) was heated at 80° C. for 25 h. The reaction mixture was filtered through celite and washed with EtOAc. The filtrate was concentrated and acidified to pH 3 by addition of 1 M aqueous HCl. The residue was loaded onto an SCX column, washed with MeOH and eluted with 2 M NH$_3$ in MeOH. The product-containing fractions were concentrated and the crude product was purified via HPLC to give the title compound (34 mg). MS (M+1)=578.7.

Step 2: 3-(6-(Methyl(2,2,6,6-tetramethylpiperidin-4-yl)amino)pyridazin-3-yl)-7-(piperidin-1-ylmethyl)naphthalen-2-ol A H$_2$ purged mixture of 6-(3-(benzyloxy)-6-(piperidin-1-ylmethyl)naphthalen-2-yl)-N-methyl-N-(2,2,6,6-tetramethylpiperidin-4-yl)pyridazin-3-amine (34 mg, 0.059 mmol) and 10% wt Pd/C (0.3 mg, 3 μmol) in MeOH (3 mL) and EtOAc (3 mL) was stirred under a H$_2$ atmosphere at RT overnight. The reaction mixture was filtered through celite, rinsed with MeOH and concentrated. The crude material was purified via HPLC to give the desired product as a yellow solid (15 mg, 52.3% yield). LCMS Rt=0.45 min [Method Q], MS (M−1)=486.4. $^1$H NMR (METHANOL-d$_4$) δ 8.16 (s, 1H), 8.12 (d, J=10.1 Hz, 1H), 7.69 (d, J=8.6 Hz, 1H), 7.46 (s, 1H), 7.15-7.22 (m, 2H), 7.14 (s, 1H), 4.98 (t, J=12.1 Hz, 1H), 3.49 (s, 2H), 2.89 (s, 3H), 2.37 (br. s., 4H), 1.34-1.60 (m, 10H), 1.29 (s, 6H), 1.13 (s, 6H).

Example 24-3

Synthesis of 3-(6-(methyl(2,2,6,6-tetramethylpiperidin-4-yl)amino)pyridazin-3-yl)-7-(pyrrolidin-1-ylmethyl)naphthalen-2-ol

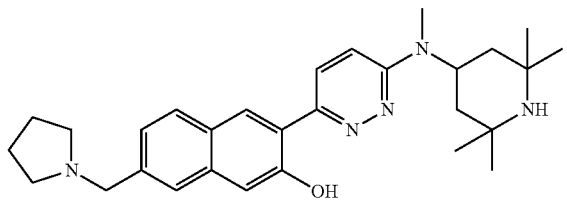 [SMILES: CN(c1ccc(-c2cc3ccc(CN4CCCC4)cc3cc2O)nn1)C1CC(C)(C)NC(C)(C)C1]

A degassed reaction mixture of Intermediate 5-3 (50 mg, 0.093 mmol), potassium-1-trifluoroboratomethylpyrrolidine (26.6 mg, 0.139 mmol), palladium acetate (1.0 mg, 4.6 μmol), X-phos (4.4 mg, 9.3 μmol) and Cs$_2$CO$_3$ (91 mg, 0.28 mmol) in THF (1 mL) and water (0.1 mL) was heated at 100° C. for 1 h under microwave irradiation. The reaction mixture was concentrated, acidified to pH 3 by addition of 1 M aqueous HCl and loaded onto an SCX column, then washed with MeOH, and eluted with 2 M NH$_3$ in MeOH. The product-containing fractions were concentrated and the crude material was purified via HPLC to give the desired product as a white solid (6 mg, 13% yield). MS (M+1)=473.32. $^1$H NMR (METHANOL-d$_4$) δ 8.29 (s, 1H), 8.26 (d, J=10.1 Hz, 1H), 7.81 (d, J=8.6 Hz, 1H), 7.60 (s, 1H), 7.29-7.36 (m, 2H), 7.25 (s, 1H), 5.11 (t, J=12.4 Hz, 1H), 3.76 (s, 2H), 3.01 (s, 3H), 2.56-2.67 (m, 4H), 1.77-1.89 (m, 4H), 1.65-1.74 (m, 2H), 1.52-1.63 (m, 2H), 1.39 (s, 6H), 1.23 (s, 6H).

Example 24-4

Synthesis of 1-bromo-6-(6-(methyl(2,2,6,6-tetramethylpiperidin-4-yl)amino)pyridazin-3-yl)naphthalene-2,7-diol

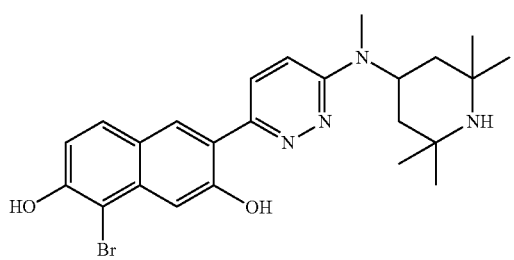

Step 1: 7-(Benzyloxy)-1-bromo-6-(6-(methyl(2,2,6,6-tetramethylpiperidin-4-yl)amino)pyridazin-3-yl)naphthalen-2-ol To a mixture of 7-(benzyloxy)-6-(6-(methyl(2,2,6,6-tetramethylpiperidin-4-yl)amino)pyridazin-3-yl)naphthalen-2-ol (100 mg, 0.201 mmol) in DMF (1 mL) was added N-bromosuccinimide (39.4 mg, 0.221 mmol) at 0° C. The reaction mixture was stirred at RT for 1.5 h, then loaded onto a 2 g SCX column, washed with MeOH, and eluted with 2M NH$_3$ in MeOH. The product-containing fractions were concentrated and the crude material was purified via silica gel flash column chromatography to give the desired product as a brown solid (33.6 mg, 29% yield). MS (M+1)=577.3.

Step 2: 3-(6-(Methyl(2,2,6,6-tetramethylpiperidin-4-yl)amino)pyridazin-3-yl)-7-(piperidin-1-ylmethyl)naphthalen-2-ol To a mixture of 7-(benzyloxy)-1-bromo-6-(6-(methyl(2,2,6,6-tetramethylpiperidin-4-yl)amino)pyridazin-3-yl)naphthalen-2-ol (29 mg, 0.050 mmol) in DCM (1 mL) was added BBr$_3$ (1 M solution in DCM, 0.25 mL, 0.25 mmol) slowly at −78° C. The mixture was stirred at −78° C. for 10 minutes, then warmed to room temperature and stirred at for 2 h. The reaction was quenched with MeOH and concentrated. The residue was loaded onto a 1 g SCX column, washed with MeOH and eluted with 2 M NH$_3$ in MeOH. The product-containing fractions were concentrated to give the desired product as a light brown solid (14 mg, 57% yield). LCMS Rt=0.54 min [Method Q], MS (M+1)=487.2. $^1$H NMR (METHANOL-d$_4$) δ 8.18-8.29 (m, 2H), 7.70 (d, J=8.6 Hz, 1H), 7.50 (s, 1H), 7.33 (d, J=10.1 Hz, 1H), 6.99 (d, J=8.6 Hz, 1H), 5.16 (t, J=11.9 Hz, 1H), 3.03 (s, 3H), 1.72-1.80 (m, 2H), 1.61-1.70 (m, 2H), 1.45 (s, 6H), 1.29 (s, 6H).

Example 24-5

Synthesis of 1-chloro-6-(6-(methyl(2,2,6,6-tetramethylpiperidin-4-yl)amino)pyridazin-3-yl)naphthalene-2,7-diol

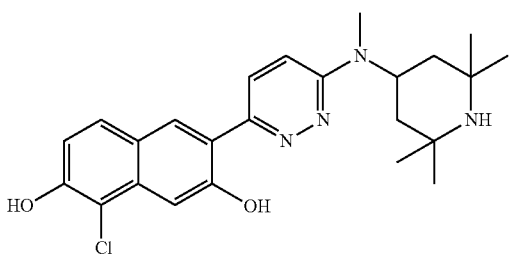 [SMILES: CN(c1ccc(-c2cc3ccc(O)c(Cl)c3cc2O)nn1)C1CC(C)(C)NC(C)(C)C1]

Step 1: 7-(Benzyloxy)-1-chloro-6-(6-(methyl(2,2,6,6-tetramethylpiperidin-4-yl)amino)pyridazin-3-yl)naphthalen-2-ol To a reaction mixture of 7-(benzyloxy)-6-(6-(methyl(2,2,6,6-tetramethylpiperidin-4-yl)amino)pyridazin-3-yl)naphthalen-2-ol (100 mg, 0.201 mmol) in DMF (2 mL) was added N-chlorosuccinimide (32.3 mg, 0.242 mmol) at room temperature. The reaction mixture was stirred overnight then loaded onto an SCX column, washed with MeOH, and eluted with 2 M NH$_3$ in MeOH. The product-containing fractions were concentrated and purified via silica gel flash column chromatography to give the title compound as a light brown solid product (25 mg, 23% yield). MS (M+1)=531.6.

Step 2: 1-Chloro-6-(6-(methyl(2,2,6,6-tetramethyl-piperidin-4-yl)amino)pyridazin-3-yl)naphthalene-2,7-diol To a mixture of 7-(benzyloxy)-1-chloro-6-(6-(methyl(2,2,6,6-tetramethylpiperidin-4-yl)amino)pyridazin-3-yl)naphthalen-2-ol (25 mg, 0.047 mmol) in DCM (1 mL) was added BBr$_3$ (1 M solution in DCM, 0.25 mL, 0.25 mmol) slowly at −78° C. The mixture was stirred at −78° C. for 10 minutes, then warmed to RT and stirred for 1.5 h. The reaction was quenched with MeOH and concentrated. The residue was loaded onto a 1 g SCX column, washed with MeOH and eluted with 2 M NH$_3$ in MeOH. The product-containing fractions were concentrated to give the desired product as a light brown solid (10 mg, 48.2% yield). LCMS Rt=0.54 min [Method Q], MS (M+1)=441.3. $^1$H NMR (METHANOL-d$_4$) δ 8.17-8.27 (m, 2H), 7.66 (d, J=9.1 Hz, 1H), 7.46 (s, 1H), 7.32 (d, J=10.1 Hz, 1H), 7.00 (d, J=9.1 Hz, 1H), 5.13 (t, J=11.9 Hz, 1H), 3.02 (s, 3H), 1.71-1.79 (m, 2H), 1.59-1.68 (m, 2H), 1.44 (s, 6H), 1.28 (s, 6H).

Example 24-6

Synthesis of 7-methoxy-3-(6-(methyl(2,2,6,6-tetramethylpiperidin-4-yl)amino)pyridazin-3-yl)naphthalen-2-ol

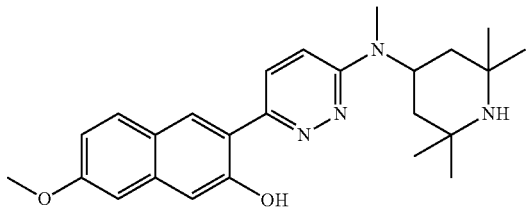

Following GENERAL METHOD 4-1 for hydrogenolysis of the benzyl group, 7-methoxy-3-(6-(methyl (2,2,6,6-tetramethylpiperidin-4-yl)amino)pyridazin-3-yl)naphthalen-2-ol was prepared from Intermediate 5-4 (70 mg, 0.14 mmol). A white solid was obtained after HPLC purification (30 mg, 52% yield). LCMS Rt=0.57 min [Method Q], MS (M+1)=421.3. $^1$H NMR (METHANOL-d$_4$) δ 8.25 (d, J=9.6 Hz, 1H), 8.22 (s, 1H), 7.73 (d, J=8.6 Hz, 1H), 7.33 (d, J=9.6 Hz, 1H), 7.19 (s, 1H), 7.05 (d, J=2.5 Hz, 1H), 6.93 (dd, J=8.6, 2.5 Hz, 1H), 5.10 (t, J=12.1 Hz, 1H), 3.90 (s, 3H), 3.02 (s, 3H), 1.68-1.76 (m, 2H), 1.55-1.65 (m, 2H), 1.41 (s, 6H), 1.25 (s, 6H).

Example 24-7

Synthesis of 7-methoxy-3-(6-(methyl(1,2,2,6,6-pentamethylpiperidin-4-yl)amino)pyridazin-3-yl)naphthalen-2-ol

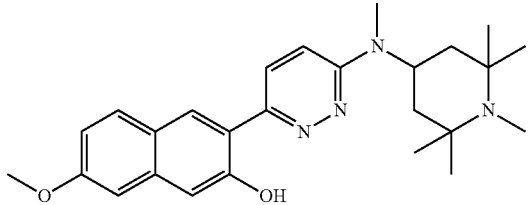

Step 1: 6-(3-(Benzyloxy)-6-methoxynaphthalen-2-yl)-N-methy-N-(1,2,2,6,6-pentamethylpiperidin-4-yl)pyridazin-3-amine To a mixture of Intermediate 5-4 (400 mg, 0.783 mmol) in DMSO (1.5 mL) and water (3 mL) was added 37% wt formaldehyde (0.087 mL, 1.2 mmol) and formic acid (0.060 mL, 1.6 mmol). The mixture was heated at 120° C. under microwave irradiation for 20 mins. The mixture was heated at 120° C. under microwave irradiation for 20 minutes two more times after addition of additional portions of formaldehyde (0.087 mL, 1.28 mmol) and formic acid (0.060 ml, 1.6 mmol) each time. The reaction mixture was concentrated and loaded onto a 5 g SCX column, washed with MeOH, and eluted with 2 M NH$_3$ in MeOH. The product-containing fractions were concentrated and the crude product was purified by flash column chromatography (0-20% 1.5 M NH$_3$ in MeOH/DCM) to give the desired product as beige solid (340 mg, 83% yield). MS (M+1)=525.6.

Step 2: 7-Methoxy-3-(6-(methyl(1,2,2,6,6-pentamethylpiperidin-4-yl)amino)pyridazin-3-yl)naphthalen-2-ol From compound 6-(3-(benzyloxy)-6-methoxynaphthalen-2-yl)-N-methyl-N-(1,2,2,6,6-pentamethylpiperidin-4-yl)pyridazin-3-amine (200 mg, 0.381 mmol), following GENERAL METHOD 4-1 for hydrogenolysis of the benzyl group, compound 7-methoxy-3-(6-(methyl(1,2,2,6,6-pentamethylpiperidin-4-yl)amino)pyridazin-3-yl)naphthalen-2-ol was obtained as a beige solid (150 mg, 91% yield) after flash column chromatography (0-15% 1.5 M of NH$_3$ in MeOH/DCM) purification. The product was converted to the HCl salt by addition of 4 M aqueous HCl (0.2 mL, 2.3 equivalents), followed by lyophilization. LCMS Rt=0.53 min [Method Q], MS (M+1)=435.3. $^1$H NMR (METHANOL-d$_4$) δ 8.52 (d, J=10.1 Hz, 1H), 8.18 (s, 1H), 8.02 (d, J=9.6 Hz, 1H), 7.81 (d, J=9.1 Hz, 1H), 7.30 (s, 1H), 7.12 (d, J=2.5 Hz, 1H), 7.04 (dd, J=9.1, 2.5 Hz, 1H), 5.06 (t, J=11.4 Hz, 1H), 3.93 (s, 3H), 3.20 (s, 3H), 2.90 (s, 3H), 2.38 (t, J=13.1 Hz, 2H), 2.11 (dd, J=13.6, 3.0 Hz, 2H), 1.63 (s, 6H), 1.62 (s, 6H).

Example 24-8

Synthesis of 7-(3,6-dihydro-2H-pyran-4-yl)-3-(6-(methyl(2,2,6,6-tetramethylpiperidin-4-yl)amino)pyridazin-3-yl)naphthalen-2-ol

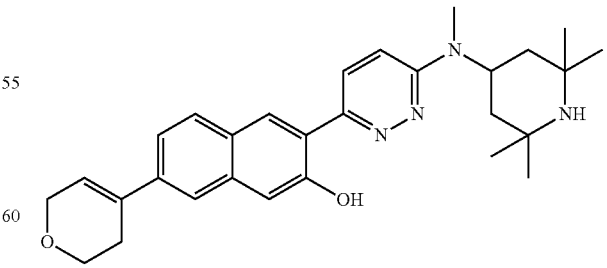

A degassed reaction mixture of Intermediate 5-3 (100 mg, 0.186 mmol), 3,6-dihydro-2H-pyran-4-boronic acid pinacol ester (50.7 mg, 0.241 mmol), and tetrakis(triphenylphosphine)palladium(0) (10.73 mg, 9.28 μmol) in 1,4-dioxane (2 mL) and 1 M aq. Na₂CO₃ solution (0.46 mL, 0.464 mmol) were reacted according to GENERAL METHOD 1-5 for Suzuki coupling. The crude product was purified by HPLC to give the title compound as a light brown solid (65 mg, 73% yield). LCMS Rt=0.60 min [Method Q], MS (M+1)= 473.4. ¹H NMR (METHANOL-d₄) δ 8.20-8.40 (m, 2H), 7.81 (d, J=8.6 Hz, 1H), 7.67 (s, 1H), 7.48 (dd, J=8.8, 1.8 Hz, 1H), 7.35 (d, J=10.1 Hz, 1H), 7.29 (s, 1H), 6.37 (br. s., 1H), 5.13 (t, J=12.0 Hz, 1H), 4.37 (d, J=2.5 Hz, 2H), 3.99 (t, J=5.6 Hz, 2H), 3.04 (s, 3H), 2.67 (s, 2H), 1.68-1.78 (m, 2H), 1.55-1.66 (m, 2H), 1.41 (s, 6H), 1.25 (s, 6H).

Example 24-9

Synthesis of 3-(6-(methyl(2,2,6,6-tetramethylpiperidin-4-yl)amino)pyridazin-3-yl)-7-(tetrahydro-2H-pyran-4-yl)naphthalen-2-ol

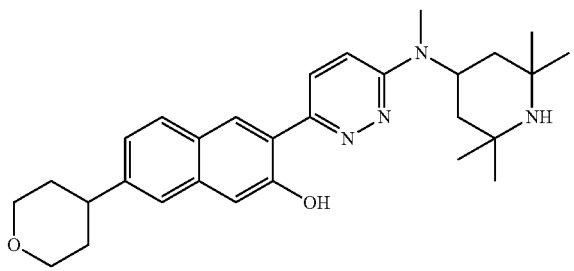 [SMILES: CN(c1ccc(-c2cc3ccc(C4CCOCC4)cc3cc2O)nn1)C1CC(C)(C)NC(C)(C)C1]

From compound 7-(3,6-dihydro-2H-pyran-4-yl)-3-(6-(methyl(2,2,6,6-tetramethylpiperidin-4-yl)amino)pyridazin-3-yl)naphthalen-2-ol (200 mg, 0.381 mmol), following GENERAL METHOD 4-1, compound 3-(6-(methyl(2,2,6,6-tetramethylpiperidin-4-yl)amino)pyridazin-3-yl)-7-(tetrahydro-2H-pyran-4-yl)naphthalen-2-ol was obtained as a white solid after HPLC purification (11 mg, 24% yield). LCMS Rt=0.59 min [Method Q], MS (M+1)=475.4. ¹H NMR (METHANOL-d₄) δ 8.25-8.32 (m, 2H), 7.81 (d, J=8.6 Hz, 1H), 7.52 (s, 1H), 7.35 (d, J=10.1 Hz, 1H), 7.19-7.27 (m, 2H), 5.12 (t, J=12.9 Hz, 1H), 4.09 (dd, J=10.6, 3.0 Hz, 2H), 3.62 (td, J=11.2, 3.3 Hz, 2H), 3.04 (s, 3H), 2.94 (dt, J=10.5, 5.6 Hz, 1H), 1.81-1.97 (m, 4H), 1.68-1.76 (m, 2H), 1.55-1.65 (m, 2H), 1.41 (s, 6H), 1.25 (s, 6H).

Example 24-10

Synthesis of 7-(difluoromethyl)-3-(6-(methyl(2,2,6,6-tetramethylpiperidin-4-yl)amino)pyridazin-3-yl)naphthalen-2-ol

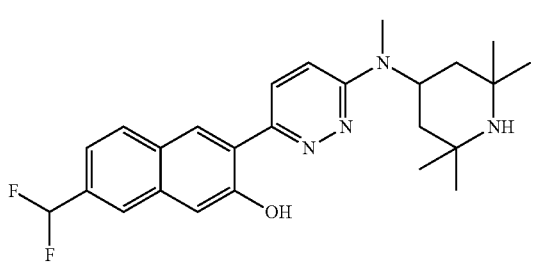 [SMILES: CN(c1ccc(-c2cc3ccc(C(F)F)cc3cc2O)nn1)C1CC(C)(C)NC(C)(C)C1]

Step 1: 6-(3-(Benzyloxy)-6-vinylnaphthalen-2-yl)-N-methyl-N-(1, 2,2,6,6-pentamethylpiperidin-4-yl)pyridazin-3-amine Vinylboronic acid pinacol ester (100 mg, 0.651 mmol) and Intermediate 5-2 (315 mg, 0.501 mmol) were reacted according to GENERAL METHOD 1-5 for Suzuki coupling. A beige solid (250 mg, 98% yield) was obtained after SCX purification. The crude material was carried on without further purification. MS (M+1)=507.5.

Step 2: 7-(Benzyloxy)-6-(6-(methyl(1,2,2,6,6-pentamethylpiperidin-4-yl)amino)pyridazin-3-yl)-2-naphthaldehyde To a mixture of 6-(3-(benzyloxy)-6-vinylnaphthalen-2-yl)-N-methyl-N-(1,2,2,6,6-pentamethylpiperidin-4-yl)pyridazin-3-amine (106 mg, 0.209 mmol) and osmium tetroxide (4% wt aqueous solution, 0.080 mL, 0.013 mmol) in 5:1 THF/water (60 mL) was added sodium periodate (112 mg, 0.523 mmol) at RT. The mixture was stirred at RT overnight and then quenched with 20% Na₂S₂O₃ aqueous solution. The crude mixture was basified with aqueous NaHCO₃ solution and extracted with DCM. The organic layer was dried over Na₂SO₄, filtered and concentrated. The residue was loaded onto a 2 g SCX column, washed with MeOH, eluted with 2 M NH₃ in MeOH. The product-containing fractions were concentrated to give 75 mg of a beige solid which was comprised of a 1:1 mixture of the title compound and the corresponding dimethyl acetal. This mixture was dissolved into DCM (1.5 mL) and TFA (0.22 mL) and stirred at RT for 2 h. The mixture was concentrated, basified with NaHCO₃ aqueous solution and extracted with DCM. The organic layer was dried over Na₂SO₄, filtered and concentrated to give 7-(benzyloxy)-6-(6-(methyl(1,2,2,6,6-pentamethylpiperidin-4-yl)amino)pyridazin-3-yl)-2-naphthaldehyde as a light brown solid. The crude material was carried on without further purification. MS (M+1)=509.4.

Step 3: 6-(3-(Benzyloxy)-6-(difluoromethyl)naphthalen-2-yl)-N-methy-N-(2, 2,6,6-tetramethylpiperidin-4-yl)pyridazin-3-amine To a mixture of 7-(benzyloxy)-6-(6-(methyl(1,2,2,6,6-pentamethylpiperidin-4-yl)amino)pyridazin-3-yl)-2-naphthaldehyde (75 mg, 0.147 mmol) in DCM (1.5 mL) was added diethylaminosulfur trifluoride (DAST) (0.058 mL, 0.44 mmol) at 00° C. The mixture was stirred at 0° C. for 10 minutes then warmed to RT and stirred for 2 days. The reaction mixture was quenched with aqueous NaHCO₃ at 0° C. and extracted with DCM. The organic layer was dried over Na₂SO₄, filtered and concentrated. The crude product was purified by HPLC to give the title compound as white solid (20.6 mg, 26% yield). MS (M+1)=531.1.

Step 4: 7-(Difluoromethyl)-3-(6-(methyl(2,2,6,6-tetramethylpiperidin-4-yl)amino)pyridazin-3-yl)naphthalen-2-ol From compound 6-(3-(benzyloxy)-6-(difluoromethyl)naphthalen-2-yl)-N-methyl-N-(2,2,6,6-tetramethylpiperidin-4-yl)pyridazin-3-amine (15 mg, 0.028 mmol), following GENERAL METHOD 4-1 for hydrogenolysis of the benzyl group, compound 7-(difluoromethyl)-3-(6-(methyl(2,2,6,6-tetramethylpiperidin-4-yl)amino)pyridazin-3-yl)naphthalen-2-ol was obtained after HPLC purification (6 mg, 50% yield). LCMS Rt=0.60 min [Method Q], MS (M+1)=441.3.

¹H NMR (METHANOL-d₄ δ 8.37 (s, 1H), 8.29 (d, J=9.6 Hz, 1H), 7.96 (d, J=8.6 Hz, 1H), 7.85 (s, 1H), 7.41 (d, J=8.6 Hz, 1H), 7.37 (s, 1H), 7.34 (d, J=9.6 Hz, 1H), 6.87 (t, J=58.0 Hz, 1H), 5.23 (t, J=12.1 Hz, 1H), 3.03 (s, 3H), 1.74-1.83 (m, 2H), 1.64-1.74 (m, 2H), 1.47 (s, 6H), 1.28-1.37 (m, 6H).

Example 24-11 and 24-12

Synthesis of 7-((4-hydroxy-2-methylbutan-2-yl) oxy)-3-(6-(methyl(2,2,6,6-tetramethylpiperidin-4-yl) amino)pyridazin-3-yl)naphthalen-2-ol and 7-(3-hydroxy-3-methylbutoxy)-3-(6-(methyl(2,2,6,6-tetramethylpiperidin-4-yl)amino)pyridazin-3-yl) naphthalen-2-ol

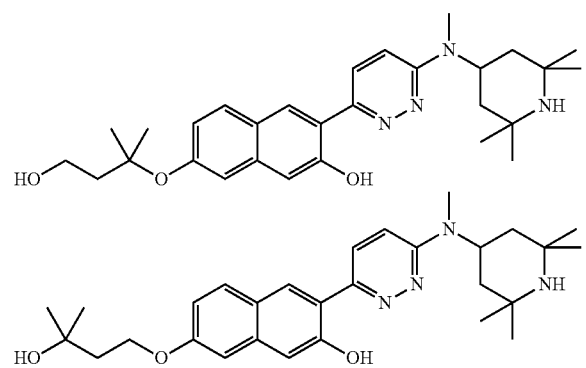

Step 1: 3-((7-(Benzyloxy)-6-(6-(methyl(2,2,6,6-tetramethylpiperidin-4-yl)amino)pyridazin-3-yl) naphthalen-2-yl)oxy)-3-methylbutan-1-ol and 4-((7-(benzyloxy)-6-(6-(methyl(2, 2,6,6-tetramethylpiperidin-4-yl)amino)pyridazin-3-yl) naphthalen-2-yl)oxy)-2-methylbutan-2-ol To a 50 mL round bottom flask was added 7-(benzyloxy)-6-(6-(methyl(2,2,6,6-tetramethylpiperidin-4-yl)amino) pyridazin-3-yl)naphthalen-2-ol (Example 20-2, Step 1, 640 mg, 1.289 mmol) and 3-methylbutane-1,3-diol (550 µL, 5.15 mmol) in THF (8.6 mL) to give a tan solution. Triphenylphosphine (744 mg, 2.84 mmol) and DIAD (560 µl, 2.71 mmol) were added, and the mixture was stirred under nitrogen at room temperature. After stirring overnight, the reaction was concentrated to dryness, then water and EtOAc were added, and the organic layer was separated. The organic layer was extracted with 0.2 N HCl, then sat. NaHCO₃ was added to neutralize the aqueous layer, which was then extracted with EtOAc (2×). The combined organics were dried over MgSO₄, filtered, and concentrated in vacuo. The crude material (a ~1:1 mixture of regioisomers) was taken on to next step without further purification.

Step 2

7-((4-Hydroxy-2-methylbutan-2-yl)oxy)-3-(6-(methyl(2, 2,6,6-tetramethylpiperidin-4-yl)amino)pyridazin-3-yl)naphthalen-2-ol (43 mg, 0.097 mmol, 12% yield, 2 steps) and 7-(3-hydroxy-3-methyl butoxy)-3-(6-(methyl(2,2,6,6-tetramethylpiperidin-4-yl)amino)pyridazin-3-yl)naphthalen-2-ol (29 mg, 0.058 mmol, 9% yield, 2 steps) were prepared from the benzyl adducts following GENERAL METHOD 4-1 for hydrogenolysis. Purification and separation by preparative HPLC (Waters Sunfire 30 mm ID×50 mm, 0.1% TFA, 25-50% ACN/H₂O) provided the regioisomeric products.

7-((4-Hydroxy-2-methylbutan-2-yl)oxy)-3-(6-(methyl(2, 2,6,6-tetramethylpiperidin-4-yl)amino)pyridazin-3-yl)naphthalen-2-ol: LCMS Rt=0.52 min [Method Q], M+1=493.4. ¹H NMR (400 MHz, CHLOROFORM-d) δ 8.04 (s, 1H), 8.00 (d, J=10.04 Hz, 1H), 7.68 (d, J=9.03 Hz, 1H), 7.29 (s, 1H), 7.23-7.27 (m, 2H), 7.04 (d, J=10.04 Hz, 1H), 6.98 (dd, J=2.26, 8.78 Hz, 1H), 4.98 (br. s., 1H), 4.00 (t, J=5.90 Hz, 2H), 3.49 (s, 2H), 3.04 (s, 3H), 2.04 (t, J=5.90 Hz, 2H), 1.73 (dd, J=3.39, 12.42 Hz, 2H), 1.40-1.47 (m, 8H), 1.38 (s, 6H), 1.21 (s, 6H).

7-(3-Hydroxy-3-methylbutoxy)-3-(6-(methyl(2,2,6,6-tetramethylpiperidin-4-yl)amino)pyridazin-3-yl)naphthalen-2-ol: LCMS Rt=0.54 min [Method Q], M+1=493.4. ¹H NMR (400 MHz, CHLOROFORM-d) δ 7.95-8.03 (m, 2H), 7.66 (d, J=8.78 Hz, 1H), 7.28 (s, 1H), 7.26 (s, 1H), 6.99-7.07 (m, 2H), 6.93 (dd, J=2.38, 8.91 Hz, 1H), 4.96 (br. s., 1H), 4.31 (t, J=6.27 Hz, 2H), 3.04 (s, 3H), 2.07 (t, J=6.15 Hz, 2H), 1.72 (dd, J=3.39, 12.42 Hz, 2H), 1.38 (m, 8H), 1.35 (s, 6H), 1.21 (s, 6H).

Example 25-1

Synthesis of 2-(6-(methyl(2,2,6,6-tetramethylpiperidin-4-yl)amino)pyridazin-3-yl)-5-(1H-pyrazol-4-yl) benzene-1,3-diol

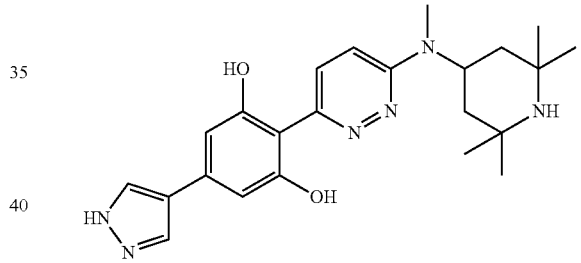

Step 1: 6-(2,6-Dimethoxyphenyl)-N-methyl-N-(2,2, 6,6-tetramethylpiperidin-4-yl)pyridazin-3-amine Intermediate 1-1 (566 mg, 2.0 mmol) and 2,6-dimethoxyphenylboronic acid (437 mg, 2.4 mmol) were reacted according to GENERAL METHOD 1-5 for Suzuki coupling. 6-(2,6-Dimethoxyphenyl)-N-methyl-N-(2,2,6,6-tetramethylpiperidin-4-yl)pyridazin-3-amine was obtained as a beige solid (375 mg, 49% yield) after flash column chromotagraphy purification. MS (M+1)=385.4.

Step 2: 6-(4-Bromo-2,6-dimethoxyphenyl)-N-methyl-N-(2,2,6,6-tetramethylpiperidin-4-yl) pyridazin-3-amine 6-(4-Bromo-2,6-dimethoxyphenyl)-N-methyl-N-(2,2,6,6-tetramethylpiperidin-4-yl)pyridazin-3-amine (240 mg, 0.624 mmol), bis(pinacolato)diboron (238 mg, 0.936 mmol), 4,4'-di-tert-butyl-bipyridine(dtbpy, 3.4 mg, 0.012 mmol) and [Ir(COD)(OMe)]2 (4.1 mg, 6.2 µmol) were reacted following GENERAL METHOD 7-1 for borylation/bromination, and 6-(4-bromo-2,6-dimethoxyphenyl)-N-methyl-N-(2,2,6,6-tetramethylpiperidin-4-yl)pyridazin-3-amine was obtained as a yellow solid (176 mg, 60% yield) after flash column chromatagraphy and HPLC purification. MS (M+1)= 465.4.

Step 3: 6-(2,6-Dimethoxy-4-(1H-pyrazol-4-yl)phenyl)-N-methyl-N-(2,2,6,6-tetramethylpiperidin-4-yl)pyridazin-3-amine 6-(4-Bromo-2,6-dimethoxyphenyl)-N-methyl-N-(2,2,6,6-tetramethylpiperidin-4-yl)pyridazin-3-amine (63 mg, 0.136 mmol) and 4-(4,4,5,5-tetramethyl-1,3,2-dioxaborolan-2-yl)-1H-pyrazole (52.8 mg, 0.272 mmol) were reacted according to GENERAL METHOD 1-5 for Suzuki coupling. The title compound was obtained as a yellow solid after column chromatography (43 mg, 70% yield). MS (M+1)=451.5.

Step 4: 2-(6-(Methyl(2,2,6,6-tetramethylpiperidin-4-yl)amino)pyridazin-3-yl)-5-(1H-pyrazol-4-yl)benzene-1,3-diol From compound 6-(2,6-dimethoxy-4-(1H-pyrazol-4-yl)phenyl)-N-methyl-N-(2,2,6,6-tetramethylpiperidin-4-yl)pyridazin-3-amine (43 mg, 0.095 mmol), following GENERAL METHOD 3-1 for methoxy deprotection using thiophenol (22.1 mg, 0.2 mmol), compound 2-(6-(methyl(2,2,6,6-tetramethylpiperidin-4-yl)amino)pyridazin-3-yl)-5-(1H-pyrazol-4-yl)benzene-1,3-diol was afforded as a pale yellow solid (20 mg, 45% yield) after HPLC purification. LCMS Rt=0.41 min [Method Q], MS (M+1)=423.3. $^1$H NMR (METHANOL-$d_4$) δ 8.60 (d, J=10.1 Hz, 1H), 7.91 (s, 2H), 7.20 (d, J=10.1 Hz, 1H), 6.66 (s, 2H), 5.01 (t, J=12.4 Hz, 1H), 2.90-3.01 (m, 3H), 1.64-1.73 (m, 2H), 1.52-1.61 (m, 2H), 1.38 (s, 6H), 1.23 (s, 6H).

Example 25-2

Synthesis of 3-methoxy-2-(6-(methyl(2,2,6,6-tetramethylpiperidin-4-yl)amino)pyridazin-3-yl)-5-(1H-pyrazol-4-yl)phenol

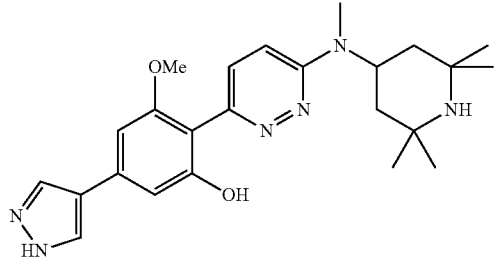 [SMILES: COc1cc(-c2cn[nH]c2)cc(O)c1-c1ccc(N(C)C2CC(C)(C)NC(C)(C)C2)nn1]

Step 1: 1-(Benzyloxy)-2-bromo-3-methoxybenzene

To a mixture of 3-(benzyloxy)-2-bromophenol (2.55 g, 9.14 mmol) in DMF (8 mL) was added $K_2CO_3$ (1.894 g, 13.70 mmol) and MeI (0.63 mL, 10.05 mmol) at RT. The reaction mixture was stirred overnight then quenched with water and diluted with EtOAc. The organic phase was washed with water (3x), brine, dried over $Na_2SO_4$, and concentrated in vacuo. The residue was purified by flash column chromatography (EtOAc/Heptane) to afford the title compound as a colorless oil (2.66 g, 99% yield). $^1$H NMR (CHLOROFORM-d) δ 7.49 (d, J=7.1 Hz, 2H), 7.36-7.43 (m, 2H), 7.30-7.35 (m, 1H), 7.20 (t, J=8.3 Hz, 1H), 6.56-6.65 (m, 2H), 5.18 (s, 2H), 3.92 (s, 3H).

Step 2: (2-(Benzyloxy)-6-methoxyphenyl)boronic acid

To a mixture of 1-(benzyloxy)-2-bromo-3-methoxybenzene (2.66 g, 9.07 mmol) in THF (20 mL) was added butyllithium (2.5 M in THF, 4 mL, 9.98 mmol) at −78° C. dropwise over 15 minutes. The mixture was stirred at −78° C. for 30 minutes, then trimethylborate (4.0 mL, 36.3 mmol) was added. The mixture was allowed to warm to RT and stirred overnight. The mixture was quenched with 1 M aqueous HCl to pH 2 and extracted with DCM. The organic phase was dried over $Na_2SO_4$ and concentrated in vacuo. The residue was purified by flash column chromatography (EtOAc/Heptane) to afford the desired product as a white solid (1.07 g, 46% yield). MS (M+1)=259.4.

Step 3: 6-(2-(Benzyloxy)-6-methoxyphenyl)-N-methyl-N-(2,2,6,6-tetramethylpiperidin-4-yl)pyridazin-3-amine Intermediate 1-1 (391 mg, 1.384 mmol) and (2-(benzyloxy)-6-methoxyphenyl)boronic acid (500 mg, 1.94 mmol) were reacted according to GENERAL METHOD 1-5 for Suzuki coupling. 6-(2-(Benzyloxy)-6-methoxyphenyl)-N-methyl-N-(2,2,6,6-tetramethylpiperidin-4-yl)pyridazin-3-amine was obtained as a beige solid (358 mg, 56% yield) after flash column chromatography purification. MS (M+1)=461.5.

Step 4: 6-(2-(Benzyloxy)-4-bromo-6-methoxyphenyl)-N-methyl-N-(2, 2,6,6-tetramethylpiperidin-4-yl)pyridazin-3-amine From compound 6-(2-(benzyloxy)-6-methoxyphenyl)-N-methyl-N-(2,2,6,6-tetramethylpiperidin-4-yl)pyridazin-3-amine (300 mg, 0.651 mmol), following GENERAL METHOD 7-1 for borylation/bromination, 6-(2-(benzyloxy)-4-bromo-6-methoxyphenyl)-N-methyl-N-(2,2,6,6-tetramethylpiperidin-4-yl)pyridazin-3-amine was obtained after flash column chromatography purification (170 mg, 50% pure, 24% yield). MS (M+1)=541.4.

Step 5: 6-(2-(Benzyloxy)-6-methoxy-4-(1H-pyrazol-4-yl)phenyl)-N-methy-N-(2, 2,6,6-tetramethylpiperidin-4-yl)pyridazin-3-amine 6-(2-(Benzyloxy)-4-bromo-6-methoxyphenyl)-N-methyl-N-(2,2,6,6-tetramethylpiperidin-4-yl)pyridazin-3-amine (129 mg, 50% pure, 0.12 mmol) and 4-(4,4,5,5-tetramethyl-1,3,2-dioxaborolan-2-yl)-1H-pyrazole (46.4 mg, 0.24 mmol) were reacted according to GENERAL METHOD 1-5 for Suzuki coupling. 6-(2-(Benzyloxy)-6-methoxy-4-(1H-pyrazol-4-yl)phenyl)-N-methyl-N-(2,2,6,6-tetramethylpiperidin-4-yl)pyridazin-3-amine was obtained as a yellow solid (14 mg, 22% yield) after HPLC purification. MS (M+1)=527.4.

Step 6: 3-Methoxy-2-(6-(methyl(2,2,6,6-tetramethylpiperidin-4-yl)amino)pyridazin-3-yl)-5-(1H-pyrazol-4-yl)phenol From compound 6-(2-(benzyloxy)-6-methoxy-4-(1H-pyrazol-4-yl)phenyl)-N-methyl-N-(2,2,6,6-tetramethylpiperidin-4-yl)pyridazin-3-amine (14 mg, 0.027 mmol), following GENERAL METHOD 4-1 for hydrogenolysis of the benzyl group, compound 3-methoxy-2-(6-(methyl(2,2,6,6-tetramethylpiperidin-4-yl)amino)pyridazin-3-yl)-5-(1H-pyrazol-4-yl)phenol was obtained after HPLC purification (4.2 mg, 35% yield). LCMS Rt=0.43 min [Method Q], MS (M+1)=437.4. $^1$H NMR (METHANOL-d$_4$) δ 8.23 (d, J=10.1 Hz, 1H), 8.01 (br. s., 2H), 7.22 (d, J=10.1 Hz, 1H), 6.79-6.87 (m, 2H), 5.13 (t, J=12.4 Hz, 1H), 3.94 (s, 3H), 3.00 (s, 3H), 1.72-1.82 (m, 2H), 1.60-1.72 (m, 2H), 1.45 (s, 6H), 1.30 (s, 6H).

Example 25-3

Synthesis of 5-(1H-pyrazol-4-yl)-2-(6-((2,2,6,6-tetramethylpiperidin-4-yl)amino)pyridazin-3-yl)-3-(trifluoromethoxy)phenol

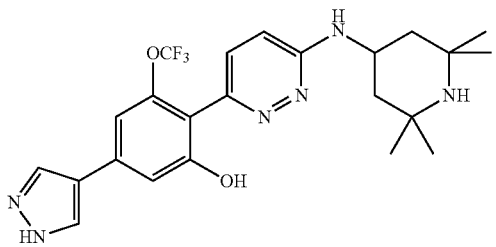 [SMILES: CC1(C)CC(Nc2ccc(-c3c(O)cc(-c4cn[nH]c4)cc3OC(F)(F)F)nn2)CC(C)(C)N1]

Step 1:
4-(Benzyloxy)-1-bromo-2-(trifluoromethoxy)benzene

To a mixture of 4-bromo-3-(trifluoromethoxy)phenol (2.97 g, 11.6 mmol) in DMF (10 mL) was added Cs$_2$CO$_3$ (5.65 g, 17.3 mmol) and benzyl chloride (1.46 mL, 12.7 mmol) at RT. The reaction mixture was stirred overnight then quenched with water and diluted with EtOAc. The organic phase was washed with water (3×), brine, dried over Na$_2$SO$_4$, and concentrated in vacuo. The residue was purified by flash column chromatography (EtOAc/Heptane) to afford the title compound as a colorless oil (3.92 g, 98% yield). $^1$H NMR (METHANOL-d$_4$) 7.51 (d, J=9.1 Hz, 1H), 7.40-7.45 (m, 4H), 7.34-7.40 (m, 1H), 6.97 (dd, J=2.5, 1.5 Hz, 1H), 6.82 (dd, J=9.1, 3.0 Hz, 1H), 5.06 (s, 2H).

Step 2:
(4-(Benzyloxy)-2-(trifluoromethoxy)phenyl)boronic acid

To a mixture of 4-(benzyloxy)-1-bromo-2-(trifluoromethoxy)benzene (1.8 g, 5.19 mmol) in THF (20 mL) was added butyllithium (2.5 M in THF, 2.28 mL, 5.70 mmol) at −78° C. dropwise over 10 minutes. The reaction mixture was stirred at −78° C. for 1 h, then trimethylborate (1.73 mL, 15.6 mmol) was added. The mixture was warmed to room temperature and stirred overnight. The mixture was concentrated from diethyl ether three times and the residue was dried on high vacuum to provide the title compound as a gummy solid (2.2 g, 61% pure, 83% yield). The crude material was carried on without further purification. MS (M−1)=311.3

Step 3: 6-(4-(Benzyloxy)-2-(trifluoromethoxy)phenyl)-N-(2,2,6,6-tetramethylpiperidin-4-yl)pyridazin-3-amine (4-(Benzyloxy)-2-(trifluoromethoxy)phenyl)boronic acid (360 mg, 61% pure, 0.692 mmol) and Intermediate 1-2 (93 mg, 0.346 mmol) were reacted according to GENERAL METHOD 1-5 for Suzuki coupling. 6-(4-(Benzyloxy)-2-(trifluoromethoxy)phenyl)-N-(2,2,6,6-tetramethylpiperidin-4-yl)pyridazin-3-amine was obtained as a white solid (121 mg, 70% yield) after flash column chromatagraphy purification. MS (M+1)=501.3.

Step 4: 4-(6-((2, 2,6,6-Tetramethylpiperidin-4-yl)amino)pyridazin-3-yl)-3-(trifluoromethoxy)phenol From compound 6-(4-(benzyloxy)-2-(trifluoromethoxy)phenyl)-N-(2,2,6,6-tetramethylpiperidin-4-yl)pyridazin-3-amine (120 mg, 0.24 mmol), following GENERAL METHOD 4-1 for hydrogenolysis of the benzyl group, 4-(6-((2,2,6,6-tetramethylpiperidin-4-yl)amino)pyridazin-3-yl)-3-(trifluoromethoxy)phenol
was obtained after SCX column purification (98 mg, 100% yield). MS (M+1)=411.3.

Step 5: 4-(6-((2,2,6,6-Tetramethylpiperidin-4-yl)amino)pyridazin-3-yl)-3-(trifluoromethoxy)phenyl trifluoromethanesulfonate To a suspension of 4-(6-((2,2,6,6-tetramethylpiperidin-4-yl)amino)pyridazin-3-yl)-3-(trifluoromethoxy)phenol (98 mg, 0.239 mmol) in DCM (2 mL) was added Et$_3$N (0.083 mL, 0.597 mmol) and N-phenyltrifluoromethanesulfonimide (172 mg, 0.48 mmol). DMF (0.5 mL) was added to aid in dissolution. The solution was stirred at room temperature overnight then concentrated. The residue was loaded onto a 2 g SCX column, washed with MeOH, eluted with 2 M NH$_3$ in MeOH. The product-containing fractions were concentrated, and the crude material was purified via flash column chromatography to give the title compound as a beige solid (89 mg, 69%). MS (M+1)=543.3.

Step 6: 3-Hydroxy-4-(6-((2,2,6,6-tetramethylpiperidin-4-yl)amino)pyridazin-3-yl)-5-(trifluoromethoxy)phenyl trifluoromethanesulfonate A mixture of 4-(6-((2,2,6,6-tetramethylpiperidin-4-yl)amino)pyridazin-3-yl)-3-(trifluoromethoxy)phenyl trifluoromethanesulfonate (86 mg, 0.16 mmol), iodobenzene diacetate (71.5 mg, 0.222 mmol) and Pd(OAc)$_2$ (3.6 mg, 0.016 mmol) in AcOH (0.6 mL) and Ac$_2$O (0.6 mL) was heated at 75° C. for 3 hours. The mixture was then heated at 80° C. overnight after addition of another 40 mg of iodobenzene diacetate. The reaction mixture was cooled to room temperature and concentrated. The residue was loaded onto an SCX column, washed with MeOH and diluted with 2 M NH$_3$ in MeOH. The product-containing fractions were concentrated. The residue was treated with 7 M NH$_3$/MeOH and stirred at 40° C. for 4 h. The crude material was purified via flash column chromatography to give the title compound as a beige solid (32 mg, 36.1%). MS (M+1)=559.4.

Step 7: 5-(1H-Pyrazol-4-yl)-2-(6-((2,2,6,6-tetramethylpiperidin-4-yl)amino)pyridazin-3-yl)-3-(trifluoromethoxy)phenol 3-Hydroxy-4-(6-((2,2,6,6-tetramethylpiperidin-4-yl)amino)pyridazin-3-yl)-5-(trifluoromethoxy)phenyl trifluoromethanesulfonate (32 mg, 0.043 mmol) and 4-(4,4,5,5-tetramethyl-1,3,2-dioxaborolan-2-yl)-1H-pyrazole (16.68 mg, 0.086 mmol) were reacted according to GENERAL METHOD 1-5 for Suzuki coupling. 5-(1H-Pyrazol-4-yl)-2-(6-((2,2,6,6-tetramethylpiperidin-4-yl)amino)pyridazin-3- yl)-3-(trifluoromethoxy)phenol was obtained as a yellow solid after HPLC purification. The product was converted to the HCl salt by addition of 1 M aqueous HCl (0.1 mL, 2.3 equivalents) followed by lyophilization (10 mg, 45% yield). LCMS Rt=0.48 min [Method Q], MS (M+1)=477.3. $^1$H NMR (METHANOL-d$_4$) δ 8.17 (s, 2H), 8.05 (d, J=9.6 Hz, 1H), 7.68 (d, J=9.6 Hz, 1H), 7.22-7.30 (m, 2H), 4.49 (t, J=12.1 Hz, 1H), 2.33 (dd, J=13.6, 3.5 Hz, 2H), 1.70 (t, J=12.9 Hz, 2H), 1.61 (s, 6H), 1.54 (s, 6H).

Example 25-4

Synthesis of 2-(6-(methyl(2,2,6,6-tetramethylpiperidin-4-yl)amino)pyridazin-3-yl)-5-(1-methyl-1H-pyrazol-4-yl)-3-(trifluoromethoxy)phenol

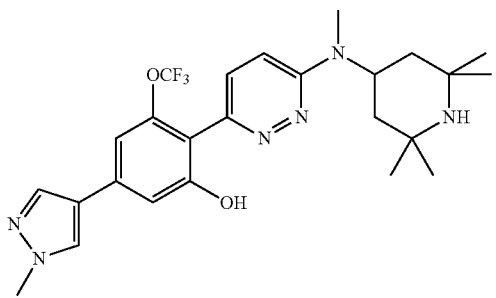 [SMILES: CN(c1ccc(-c2c(O)cc(-c3cnn(C)c3)cc2OC(F)(F)F)nn1)C1CC(C)(C)NC(C)(C)C1]

Intermediate 6-1 (40 mg, 0.070 mmol) and 1-methyl-4-(4,4,5,5-tetramethyl-1,3,2-dioxaborolan-2-yl)-1H-pyrazole (29.1 mg, 0.140 mmol) were reacted according to GENERAL METHOD 1-5 for Suzuki coupling, and 2-(6-(methyl (2,2,6,6-tetramethylpiperidin-4-yl)amino)pyridazin-3-yl)-5-(1-methyl-H-pyrazol-4-yl)-3-(trifluoromethoxy)phenol was obtained as a white solid (7.5 mg, 21% yield). LCMS Rt=0.52 min [Method Q], MS (M+1)=505.4. $^1$H NMR (METHANOL-d$_4$) δ 8.04 (s, 1H), 7.85 (s, 1H), 7.79 (d, J=9.6 Hz, 1H), 7.25 (d, J=9.6 Hz, 1H), 7.11-7.17 (m, 1H), 7.07 (d, J=1.5 Hz, 1H), 5.24 (t, J=11.4 Hz, 1H), 3.94 (s, 3H), 3.02 (s, 3H), 1.72-1.82 (m, 2H), 1.60-1.72 (m, 2H), 1.44 (s, 6H), 1.29 (s, 6H).

Example 25-5

Synthesis of 2-(6-(methyl(2,2,6,6-tetramethylpiperidin-4-yl)amino)pyridazin-3-yl)-5-(1H-pyrazol-4-yl)-3-(trifluoromethoxy)phenol

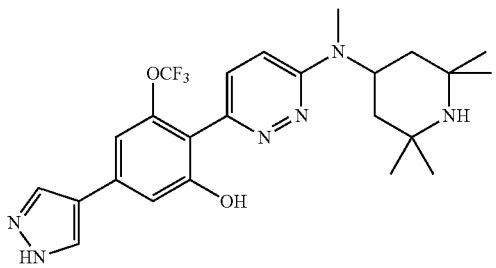 [SMILES: CN(c1ccc(-c2c(O)cc(-c3cn[nH]c3)cc2OC(F)(F)F)nn1)C1CC(C)(C)NC(C)(C)C1]

Intermediate 6-1 (35 mg, 0.061 mmol) and 4-(4,4,5,5-tetramethyl-1,3,2-dioxaborolan-2-yl)-1H-pyrazole (23.72 mg, 0.122 mmol) were reacted according to GENERAL METHOD 1-5 for Suzuki coupling, and 2-(6-(methyl(2,2,6,6-tetramethylpiperidin-4-yl)amino)pyridazin-3-yl)-5-(1H-pyrazol-4-yl)-3-(trifluoromethoxy)phenol was obtained as a white solid (27 mg, 90% yield). LCMS Rt=0.50 min [Method Q], MS (M+1)=491.4. $^1$H NMR (METHANOL-d$_4$) δ 8.02 (br. s., 2H), 7.79 (d, J=9.6 Hz, 1H), 7.25 (d, J=9.6 Hz, 1H), 7.18 (d, J=1.5 Hz, 1H), 7.10-7.13 (m, 1H), 5.26 (t, J=11.9 Hz, 1H), 3.01 (s, 3H), 1.72-1.84 (m, 2H), 1.61-1.72 (m, 2H), 1.45 (s, 6H), 1.30 (s, 6H).

Example 25-6

Synthesis of 4-(3-hydroxy-4-(6-(methyl(2,2,6,6-tetramethylpiperidin-4-yl)amino)pyridazin-3-yl)-5-(trifluoromethoxy)phenyl)-1-methylpyridin-2(1H)-one

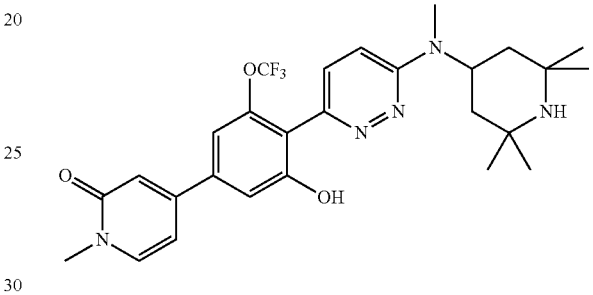

Intermediate 6-1 (40 mg, 0.070 mmol) and 1-methylpyridin-2-one-4-boronic acid pinacol ester (32.8 mg, 0.140 mmol) were reacted according to GENERAL METHOD 1-5 for Suzuki coupling, and 4-(3-hydroxy-4-(6-(methyl(2,2,6,6-tetramethylpiperidin-4-yl)amino)pyridazin-3-yl)-5-(trifluoromethoxy)phenyl)-1-methylpyridin-2(1H)-one was obtained as a white solid. The product was converted to the HCl salt by addition of 4 M HCl in dioxane (0.1 mL, 5.7 equivalents), followed by evaporation of the solvent (14.5 mg, 36% yield). LCMS Rt=0.50 min [Method Q], MS (M+1)=532.3. $^1$H NMR (METHANOL-d$_4$) δ 8.16-8.21 (m, 1H), 8.06-8.13 (m, 1H), 7.81 (d, J=7.1 Hz, 1H), 7.30 (s, 2H), 6.80 (d, J=2.0 Hz, 1H), 6.69 (dd, J=6.8, 2.3 Hz, 1H), 5.02 (br. s., 1H), 3.63 (s, 3H), 3.21 (s, 3H), 2.01-2.13 (m, 4H), 1.64 (s, 6H), 1.57 (s, 6H).

Example 26-1

Synthesis of 3-methoxy-2-(6-(methyl(2,2,6,6-tetramethylpiperidin-4-yl)amino)pyridazin-3-yl)-5-(1-methyl-1H-pyrazol-4-yl)phenol

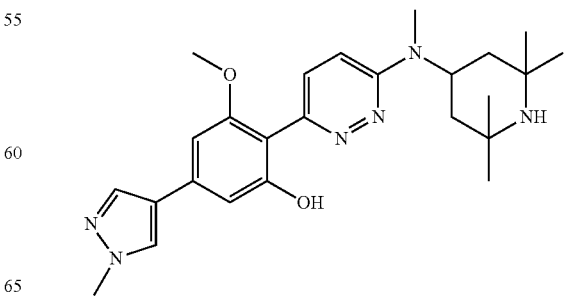

A mixture of 3-hydroxy-5-methoxy-4-(6-(methyl(2,2,6,6-tetramethylpiperidin-4-yl)amino)pyridazin-3-yl)phenyl trifluoromethanesulfonate (Intermediate 6-2, 100 mg, 0.193 mmol), 1-methyl-4-(4,4,5,5-tetramethyl-1,3,2-dioxaborolan-2-yl)-1H-pyrazole (120 mg, 0.579 mmol), and sodium carbonate (102 mg, 0.964 mmol) in 3:1 DME/water (1.9 mL) was degassed with a stream of dry nitrogen for 5 minutes. Tetrakis(triphenylphosphine)palladium(0) (16.7 mg, 0.014 mmol) was added and the mixture was heated under microwave irradiation at 90° C. for one hour. The mixture was partitioned between water and dichloromethane and the organic phase acidified with HCl in MeOH (4 equivalents) and concentrated to dryness. The crude material was loaded onto an SCX column (1 g, preconditioned with MeOH), washed with MeOH, and eluted with 7 N ammonia in MeOH. The eluent was concentrated to dryness and purification by flash chromatography (12 g silica, 1-12% 7 N ammonia in MeOH gradient, in DCM) provided 3-methoxy-2-(6-(methyl(2,2,6,6-tetramethylpiperidin-4-yl)amino)pyridazin-3-yl)-5-(1-methyl-1H-pyrazol-4-yl)-phenol as a light yellow solid (55 mg). LCMS Rt=0.44 min [Method Q], MS (M+1)=451.5. $^1$H NMR (400 MHz, METHANOL-d4) δ 8.25 (d, J=10.11 Hz, 1H), 8.03 (s, 1H), 7.87 (s, 1H), 7.22 (d, J=10.11 Hz, 1H), 6.74-6.85 (m, 2H), 5.05 (t, J=12.38 Hz, 1H), 3.95 (s, 3H), 3.95 (s, 3H), 3.01 (s, 3H), 1.65-1.75 (m, 2H), 1.50-1.64 (m, 2H), 1.39 (s, 6H), 1.24 (s, 6H).

The following compounds were prepared in a manner similar to that of Example 26-1.

| Example | Compound | LCMS Method Q | $^1$H NMR 400 MHz, |
|---|---|---|---|
| 26-2 | 3-methoxy-2-(6-(methyl(2,2,6,6-tetramethylpiperidin-4-yl)amino)pyridazin-3-yl)-5-(5,6,7,8-tetrahydroimidazo[1,2-a]pyridin-3-yl)phenol | M + 1 = 491.4 Rt = 0.48 min | (METHANOL-d4) δ 8.25 (d, J = 10.11 Hz, 1H), 7.76 (s, 1H), 7.23 (d, J = 10.11 Hz, 1H), 6.69 (dd, J = 1.52, 11.12 Hz, 2H), 5.07 (t, J = 12.38 Hz, 1H), 4.19 (t, J = 6.06 Hz, 2H), 3.94 (s, 3H), 3.05 (t, J = 6.32 Hz, 2H), 3.02 (s, 3H), 2.08-2.18 (m, 2H), 1.91-2.02 (m, 2H), 1.67-1.76 (m, 2H), 1.53-1.64 (m, 2H), 1.40 (s, 6H), 1.25 (s, 6H) |
| 26-3 | 3-methoxy-2-(6-(methyl(2,2,6,6-tetramethylpiperidin-4-yl)amino)pyridazin-3-yl)-5-(pyridin-3-yl)phenol | M + 1 = 448.3 Rt = 0.47 min | (METHANOL-d4) δ 8.87 (d, J = 1.52 Hz, 1H), 8.56 (dd, J = 1.26, 4.80 Hz, 1H), 8.25 (d, J = 9.60 Hz, 1H), 8.12-8.20 (m, 1H), 7.55 (dd, J = 5.05, 8.08 Hz, 1H), 7.24 (d, J = 9.60 Hz, 1H), 6.92 (d, J = 1.52 Hz, 1H), 6.88 (d, J = 1.52 Hz, 1H), 5.10 (t, J = 11.87 Hz, 1H), 3.99 (s, 3H), 3.03 (s, 3H), 1.67-1.76 (m, 2H), 1.51-1.65 (m, 2H), 1.40 (s, 6H), 1.25 (s, 6H) |
| 26-4 | 5-(1-cyclopentyl-1H-pyrazol-4-yl)-3-methoxy-2-(6-(methyl(2,2,6,6-tetramethylpiperidin-4-yl)amino)pyridazin-3-yl)phenol | M + 1 = 505.5 Rt = 0.52 min | (METHANOL-d4) δ 8.26 (d, J = 9.60 Hz, 1H), 8.12 (s, 1H), 7.89 (s, 1H), 7.23 (d, J = 10.11 Hz, 1H), 6.77-6.86 (m, 2H), 5.08 (t, J = 12.38 Hz, 1H), 4.75 (quin, J = 7.33 Hz, 1H), 3.96 (s, 3H), 3.02 (s, 3H), 2.17-2.31 (m, 2H), 2.01-2.13 (m, 2H), 1.88-2.01 (m, 2H), 1.68-1.85 (m, 4H), 1.54-1.67 (m, 2H), 1.42 (s, 6H), 1.26 (s, 6H) |

| Example | Compound | LCMS Method Q | $^1$H NMR 400 MHz, |
|---|---|---|---|
| 26-5 | 3',5-Dimethoxy-4-(6-(methyl(2,2,6,6-tetramethylpiperidin-4-yl)amino)pyridazin-3-yl)-[1,1'-biphenyl]-3-ol | M + 1 = 477.4<br>Rt = 0.44 min | (METHANOL-d4) δ ppm 8.25 (d, J = 10.1 Hz, 1H), 7.33-7.43 (m, 1H), 7.16-7.30 (m, 3H), 6.91-7.00 (m, 1H), 6.85 (dd, J = 15.9, 1.8 Hz, 2H), 5.10 (t, J = 12.1 Hz, 1H), 3.97 (s, 3H), 3.88 (s, 3H), 3.02 (s, 3H), 1.67-1.77 (m, 2H), 1.54-1.65 (m, 2H), 1.41 (s, 6H), 1.25 (s, 6H) |

Example 27-1

Synthesis of 3-(benzyloxy)-2-(6-(methyl(2,2,6,6-tetramethylpiperidin-4-yl)amino)pyridazin-3-yl)-5-(5-methyloxazol-2-yl)phenol

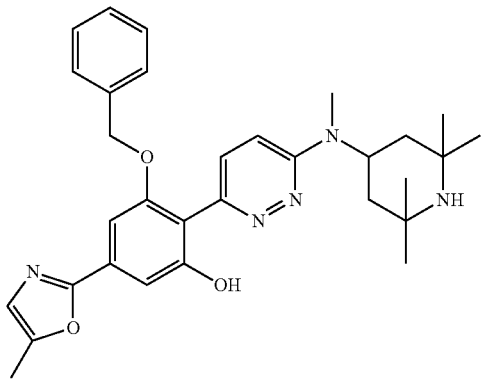

Step 1: 3-(Benzyloxy)-4-bromo-5-((2-(trimethylsilyl)ethoxy)methoxy)benzoic acid (2-(Trimethylsilyl)ethoxymethyl chloride (SEM-Cl, 3.10 mL, 17.5 mmol) was added to a mixture of methyl 3-(benzyloxy)-4-bromo-5-hydroxybenzoate (Example 22-1 Step 1, 5.36 g, 15.9 mmol) and potassium carbonate (5.49 g, 39.7 mmol) in DMF (53.0 mL), and the mixture was allowed to stir at room temperature for two days. An additional portion of SEM-Cl (3.10 mL, 17.5 mmol) was added and the mixture stirred an additional 4 hours. The reaction mixture was partitioned between saturated sodium bicarbonate and 1:1 ethyl acetate/diethyl ether. The organic phase was washed with water (5×), brine, dried over MgSO$_4$, and concentrated to a light orange oil. The crude product was dissolved into 2:1 tetrahydrofuran/methanol (100 mL) and aqueous sodium hydroxide solution (2.0 M, 63.6 mL, 127 mmol) was added. The solution was stirred for 1 hour after which time volatiles were removed via rotary evaporation. The remaining solution was acidified to pH 3 by slow addition of concentrated hydrochloric acid, extracted with dichloromethane (1×), then with 1:1 ether/ethyl acetate (4×). The combined extracts were washed with brine, dried over MgSO$_4$ and concentrated to a solid. The crude product was triturated with heptane and dried under vacuum to provide 3-(benzyloxy)-4-bromo-5-((2-(trimethylsilyl)ethoxy)methoxy)benzoic acid (6.36 g) as a white solid. MS (M+1)= 453.4. $^1$H NMR (400 MHz, CHLOROFORM-d) δ ppm 7.28-7.59 (m, 7H) 5.36 (s, 2H) 5.18-5.28 (m, 2H) 3.75-3.90 (m, 2H) 0.92-1.03 (m, 2H) 0.00 (s, 9H).

Step 2: 3-(Benzyloxy)-4-bromo-N-(prop-2-ynyl)-5-((2-(trimethylsilyl)ethoxy)methoxy)benzamide To a mixture of 3-(benzyloxy)-4-bromo-5-((2-(trimethylsilyl)ethoxy)methoxy)benzoic acid (6.142 g, 13.55 mmol) and Mukaiyama reagent (2-chloro-1-methylpyridinium iodide, 5.19 g, 20.3 mmol) in dichloromethane (135 mL) was added triethylamine (7.55 mL, 54.2 mmol). The solution was stirred for 10 minutes after which time propargylamine (1.74 mL, 27.1 mmol) was added. The solution was stirred overnight. The solution was diluted with 1:1 ethyl acetate/diethyl ether and washed with water, brine, dried over MgSO$_4$ and concentrated. The crude product was purified by flash chromatography (40 g silica gel, gradient of ethyl acetate in dichloromethane) providing 3-(benzyloxy)-4-bromo-N-(prop-2-ynyl)-5-((2-(trimethylsilyl)ethoxy)-methoxy)-benzamide as an orange oil (6.49 g). MS (M+1)= 492.2. $^1$H NMR (400 MHz, CHLOROFORM-d) δ ppm 7.28-7.55 (m, 5H) 7.13 (dd, J=11.37, 1.77 Hz, 2H) 6.23 (br. s., 1H) 5.34 (s, 2H) 5.20 (s, 2H) 4.22 (dd, J=5.05, 2.53 Hz, 2H) 3.81 (dd, J=9.09, 7.58 Hz, 2H) 2.28 (t, J=2.78 Hz, 1H) 0.91-1.00 (m, 2H)-0.03-0.03 (m, 9H).

Step 3: 2-(3-(Benzyloxy)-4-bromo-5-((2-(trimethylsilyl)ethoxy)methoxy)phenyl)-5-methyloxazole Sodium hydride (0.953 g, 39.7 mmol) was added to a solution of 3-(benzyloxy)-4-bromo-N-(prop-2-ynyl)-5-((2-(trimethylsilyl)ethoxy)-methoxy)benzamide (6.49 g, 13.2 mmol) in dioxane (100 mL) and the mixture was heated at reflux overnight. The solution was cooled to room temperature and quenched by slow addition of saturated NaHCO$_3$. The solution was diluted with ethyl acetate/diethyl ether and washed with water (5×), saturated NaHCO$_3$, brine, dried over sodium sulfate and concentrated to a thick brown liquid. Flash chromatography (80 g silica gel, 5-40% EtOAc in heptane) provided 2-(3-(benzyloxy)-4-bromo-5-((2-(trimethylsilyl)ethoxy)methoxy)phenyl)-5-methyloxazole as an orange oil (3.33 g). MS (M+1)=492.21. $^1$H NMR (400 MHz, CHLOROFORM-d) δ ppm 7.30-7.58 (m, 7H), 6.86 (d, J=1.0 Hz, 1H), 5.40 (s, 2H), 5.25 (s, 2H), 3.80-3.92 (m, 2H), 2.41 (s, 3H), 0.95-1.04 (m, 2H), 0.02 (s, 10H).

Step 4: (2-(Benzyloxy)-6-hydroxy-4-(5-methyloxazol-2-yl)phenyl)boronic acid

To a stirred solution of 2-(3-(benzyloxy)-4-bromo-5-((2-(trimethylsilyl)ethoxy)methoxy)phenyl)-5-methyloxazole (1.2 g, 2.447 mmol) in THF (6 mL) cooled to −78° C. was added n-butyl lithium (2.5 M in heptane, 1.17 mL, 2.94 mmol) dropwise. The solution was stirred for 30 minutes after which time trimethyl borate (0.82 mL, 7.34 mmol) was added in a single portion. The cold bath was removed and the solution was allowed to warm to room temperature over two hours. Aqueous HCl (0.1 M) was added followed by 1:1 ethyl acetate/diethyl ether. The solution was washed with 0.1 M HCl, water, brine, dried over magnesium sulfate and concentrated. The resulting solids were washed with DCM to provide 105 mg of a 3:1 mixture of (2-(benzyloxy)-6-hydroxy-4-(5-methyloxazol-2-yl)phenyl)boronic acid (MS (M+1)=326.2) and 3-(benzyloxy)-5-(5-methyloxazol-2-yl)phenol (MS (M+1)=282.2) as an off-white solid. This mixture was taken on without further purification.

Step 5: 3-(Benzyloxy)-2-(6-(methyl(2,2,6,6-tetramethylpiperidin-4-yl)amino)pyridazin-3-yl)-5-(5-methyloxazol-2-yl)phenol A mixture of 6-chloro-N-methyl-N-(2,2,6,6-tetramethylpiperidin-4-yl)pyridazin-3-amine (Intermediate 1-1, 45 mg, 0.16 mmol), the crude (2-(benzyloxy)-6-hydroxy-4-(5-methyloxazol-2-yl)phenyl)boronic acid (103 mg, 0.239 mmol based on 75% purity), and sodium carbonate (51 mg, 0.48 mmol) in 3:1 DME/water was degassed with a stream of dry nitrogen for five minutes. Tetrakis(triphenylphosphine)palladium(0) (18.39 mg, 0.016 mmol) was added and the mixture heated under microwave irradiation at 140° C. for 30 minutes. The mixture was diluted with dichloromethane and washed with water. The organic phase was acidified with HCl in MeOH (3 equivalents) and was concentrated to dryness. The crude material was loaded onto an SCX column (1 g, preconditioned with MeOH), washed with MeOH, and eluted with 7 N ammonia in MeOH. The eluent was concentrated to dryness and purification by flash chromatography (12 g silica, 2-20% 7 N ammonia in MeOH gradient, in DCM) provided 3-(benzyloxy)-2-(6-(methyl(2,2,6,6-tetramethylpiperidin-4-yl)amino)pyridazin-3-yl)-5-(5-methyloxazol-2-yl)phenol as a light yellow solid. LCMS Rt=0.61 min [Method Q], MS (M+1)=528.5. $^1$H NMR (400 MHz, METHANOL-d4) δ ppm 8.18 (d, J=10.10 Hz, 1H), 7.28-7.51 (m, 6H), 7.23 (d, J=1.52 Hz, 1H), 7.13 (d, J=10.11 Hz, 1H), 6.95 (d, J=1.52 Hz, 1H), 5.25 (s, 2H), 5.14 (t, J=11.87 Hz, 1H), 2.99 (s, 3H), 2.45 (d, J=1.01 Hz, 3H), 1.66-1.75 (m, 2H), 1.53-1.64 (m, 2H), 1.40 (s, 6H), 1.25 (s, 6H).

Example 27-2

Synthesis of 3-ethoxy-2-(6-(methyl(2,2,6,6-tetramethylpiperidin-4-yl)amino)pyridazin-3-yl)-5-(5-methyloxazol-2-yl)phenol

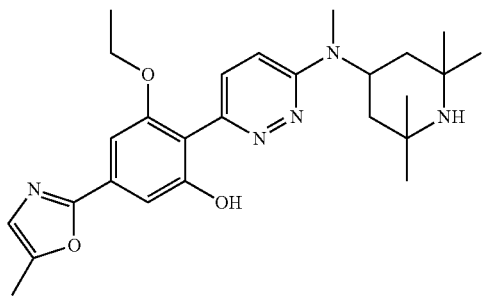

Step 1: 3-(Benzyloxy)-2-bromo-5-(5-methyloxazol-2-yl)phenol

Concentrated hydrochloric acid (3 mL) was added to a solution of 2-(3-(benzyloxy)-4-bromo-5-((2-(trimethylsilyl)ethoxy)methoxy)phenyl)-5-methyloxazole (0.60 g, 1.22 mmol) in THF (8 mL) and stirred at room temperature for three hours. The solution was diluted with water and extracted with 1:1 ethyl acetate/diethyl ether (4×). The extracts were washed with saturated sodium bicarbonate, brine, dried over magnesium sulfate and concentrated to a solid. The solid was triturated with heptane (2×) and dried under vacuum to provide 3-(benzyloxy)-2-bromo-5-(5-methyloxazol-2-yl)phenol as an off white solid (412 mg). MS (M+1)=360.2. $^1$H NMR (400 MHz, CHLOROFORM-d) δ ppm 7.52 (d, J=7.07 Hz, 2H), 7.36-7.43 (m, 2H), 7.28-7.35 (m, 2H), 7.23 (d, J=1.52 Hz, 1H), 6.86 (d, J=1.52 Hz, 1H), 5.24 (s, 2H), 4.21 (q, J=6.74 Hz, 2H), 2.41 (d, J=1.01 Hz, 3H), 1.50 (t, J=6.82 Hz, 3H).

Step 2: 2-(3-(Benzyloxy)-4-bromo-5-ethoxyphenyl)-5-methyloxazole

Iodoethane (111 uL, 1.37 mmol) was added to a mixture of 3-(benzyloxy)-2-bromo-5-(5-methyloxazol-2-yl)phenol (412 mg, 1.14 mmol) and potassium carbonate (632 mg, 4.58 mmol) in DMF (2.8 mL). After stirring for two hours, the solution was diluted with 1:1 ethyl acetate/diethyl ether, washed with water (5×), brine, dried over magnesium sulfate and concentrated to provide 2-(3-(benzyloxy)-4-bromo-5-ethoxyphenyl)-5-methyloxazole as a white crystalline solid (421 mg). MS (M+1)=388.2. $^1$H NMR (400 MHz, CHLOROFORM-d) δ ppm 7.52 (d, J=7.07 Hz, 2H), 7.36-7.43 (m, 2H), 7.28-7.35 (m, 2H), 7.23 (d, J=1.52 Hz, 1H), 6.86 (d, J=1.52 Hz, 1H), 5.24 (s, 2H), 4.21 (q, J=6.74 Hz, 2H), 2.41 (d, J=1.01 Hz, 3H), 1.50 (t, J=6.82 Hz, 3H).

Step 3: (2-(Benzyloxy)-6-ethoxy-4-(5-methyloxazol-2-yl)phenyl)boronic acid

The title compound was prepared in a manner analogous to Example 22-1, Step 6. MS (M+1)=354.3. $^1$H NMR (400 MHz, METHANOL-d$_4$) δ ppm 7.27-7.46 (m, 1H), 7.26 (s, 1H), 7.18 (s, 1H), 6.90 (d, J=1.0 Hz, 1H), 5.14 (s, 2H), 4.11 (q, J=7.1 Hz, 2H), 2.40 (d, J=1.0 Hz, 3H), 1.37 (t, J=6.8 Hz, 3H).

Step 4: 6-(2-(Benzyloxy)-6-ethoxy-4-(5-methyloxazol-2-yl)phenyl)-N-methyl-N-(2, 2, 6,6-tetramethyl-piperidin-4-yl)pyridazin-3-amine The title compound was prepared in a manner analogous to Example 22-1, Step 7. MS (M+1)=556.5

Step 5: 3-Ethoxy-2-(6-(methyl(2,2,6-trimethylpiperidin-4-yl)amino)pyridazin-3-yl)-5-(5-methyloxazol-2-yl)phenol The title compound was prepared in a manner analogous to Example 22-1, Step 8. LCMS Rt=0.53 min [Method Q], MS (M+1)=466.4. $^1$H NMR (400 MHz, METHANOL-d4) δ 8.30 (d, J=9.60 Hz, 1H), 7.26 (d, J=9.60 Hz, 1H), 7.20 (d, J=4.04 Hz, 2H), 6.95 (s, 1H), 5.17 (br. s., 1H), 4.23 (q, J=6.91 Hz, 2H), 3.03 (s, 3H), 2.45 (s, 3H), 1.72-1.81 (m, 2H), 1.59-1.71 (m, 2H), 1.49 (t, J=6.82 Hz, 3H), 1.44 (s, 6H), 1.29 (s, 6H).

141

Example 27-3

Synthesis of 3-(cyclopropylmethoxy)-2-(6-(methyl (2,2,6,6-tetramethylpiperidin-4-yl)amino)-pyridazin-3-yl)-5-(5-methyloxazol-2-yl)phenol

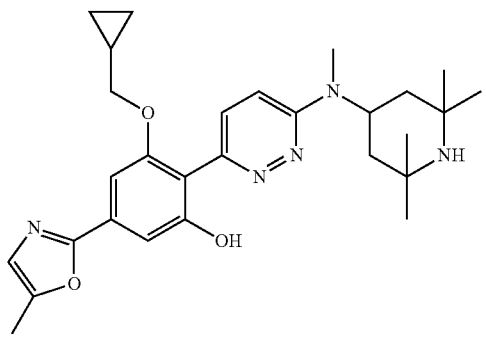

Step 1: 2-(3-(Benzyloxy)-4-bromo-5-(cyclopropylmethoxy)phenyl)-5-methyloxazole

The title compound was synthesized from 3-(benzyloxy)-2-bromo-5-(5-methyloxazol-2-yl)phenol (Example 27-2, Step 1) and bromomethyl)cyclopropane in a manner analogous to Example 27-2, Step 2. MS (M+1)=416.2. $^1$H NMR (400 MHz, CHLOROFORM-d) δ 7.23-7.52 (m, 7H), 6.83 (d, J=1.01 Hz, 1H), 5.19 (s, 2H), 3.94 (d, J=6.70 Hz, 2H), 2.36 (d, J=1.01 Hz, 3H), 1.23-1.35 (m, 1H), 0.53-0.65 (m, 2H), 0.31-0.42 (m, 2H).

Step 2: (2-(Benzyloxy)-6-(cyclopropylmethoxy)-4-(5-methyloxazol-2-yl)phenyl)boronic acid The title compound was prepared in a manner analogous to Example 22-1, Step 6. MS (M+1)=380.3. $^1$H NMR (400 MHz, CHLOROFORM-d) δ ppm 7.30-7.50 (m, 8H), 7.26 (s, 1H), 6.92 (d, J=1.0 Hz, 1H), 5.24 (s, 2H), 4.02 (d, J=7.1 Hz, 2H), 2.45 (d, J=1.0 Hz, 3H), 1.30-1.43 (m, 1H), 0.68-0.78 (m, 2H), 0.38-0.45 (m, 2H).

Step 3: 6-(2-(Benzyloxy)-6-(cyclopropylmethoxy)-4-(5-methyloxazol-2-yl)phenyl)-N-methyl-N-(2,2,6,6-tetramethylpiperidin-4-yl)pyridazin-3-amine The title compound was prepared in a manner analogous to Example 22-1, Step 7. MS (M+1)=582.5.

Step 4: 3-(Cyclopropylmethoxy)-2-(6-(methyl(2,2,6,6-tetramethylpiperidin-4-yl)amino)-pyridazin-3-yl)-5-(5-methyloxazol-2-yl)phenol The title compound was prepared in a manner analogous to Example 22-1, Step 8. LCMS Rt=0.55 min [Method Q], MS (M-1)=489.9. $^1$H NMR (400 MHz, METHANOL-d4) δ 8.43 (d, J=10.11 Hz, 1H), 7.25 (d, J=10.11 Hz, 1H), 7.19 (d, J=1.52 Hz, 1H), 7.14 (d, J=1.52 Hz, 1H), 6.94 (d, J=1.01 Hz, 1H), 5.13 (t, J=12.13 Hz, 1H), 4.01 (d, J=7.07 Hz, 2H), 3.02 (s, 3H), 2.45 (d, J=1.01 Hz, 3H), 1.66-1.75 (m, 2H), 1.52-1.63 (m, 2H), 1.40 (s, 6H), 1.30-1.37 (m, 1H), 1.24 (s, 6H), 0.62-0.74 (m, 2H), 0.35-0.46 (m, 2H).

142

Example 28-1

Synthesis of 2-methyl-5-(6-(methyl(2,2,6,6-tetramethylpiperidin-4-yl)amino)pyridazin-3-yl)-1H-benzo[d]imidazol-6-ol

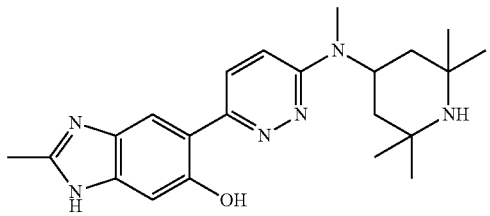

Step 1: 5-Bromo-6-methoxy-2-methyl-1-((2-(trimethylsilyl)ethoxy)methyl)-1H-benzo[d]imidazole To a mixture of 5-bromo-6-methoxy-2-methyl-1H-benzo[d]imidazole (400 mg, 1.659 mmol) in DMF (3 mL) was added 60% wt NaH (80 mg, 1.991 mmol) at 0° C. The mixture was stirred from 0° C. to room temperature for 0.5 hours, then 2-trimethylsilylethoxymethyl chloride (SEMCl, 0.352 mL, 1.991 mmol) was added dropwise. The reaction mixture was stirred at room temperature for 2 hours then quenched with water and extracted with DCM. The organic phase was dried over Na$_2$SO$_4$ and concentrated in vacuo. The residue was purified by flash column chromatography (10-100% EtOAc/Heptane then 0-10% DCM/MeOH) to afford the title compound (310 mg, 50.3% yield) as an oil. MS (M+1)=373.1.

Step 2: 6-Methoxy-2-methyl-5-(4,4,5,5-tetramethyl-1,3,2-dioxaborolan-2-yl)-1-((2-(trimethylsilyl)ethoxy)methyl)-1H-benzo[d]imidazole, and (6-methoxy-2-methyl-1-((2-(trimethylsilyl)ethoxy)methyl)-1H-benzo[d]imidazol-5-yl)boronic acid A degassed reaction mixture of 5-bromo-6-methoxy-2-methyl-1-((2-(trimethylsilyl)ethoxy)methyl)-1H-benzo[d]imidazole (145 mg, 0.390 mmol), bis(pinacolato) diboron (218 mg, 0.859 mmol), Pd(dppf)Cl$_2$ (31.9 mg, 0.039 mmol), dppf (21.7 mg, 0.039 mmol) and potassium acetate (192 mg, 1.95 mmol) in dioxane (1.5 mL) was heated at 90° C. overnight. The reaction mixture was filtered through celite and washed with EtOAc. The filtrate was concentrated to a brown oil. The crude product was purified by flash column chromatography (10-100% EtOAc/Heptane) to afford a mixture of 6-methoxy-2-methyl-5-(4,4,5,5-tetramethyl-1,3,2-dioxaborolan-2-yl)-1-((2-(trimethylsilyl)ethoxy)methyl)-1H-benzo[d]imidazole and (6-methoxy-2-methyl-1-((2-(trimethylsilyl)ethoxy)methyl)-1H-benzo[d]imidazol-5-yl)boronic acid (126.8 mg, 89.3% total yield), which was used in the next step without further purification. MS (M+1)= 419.4 and 337.2, respectively.

Step 3: 6-(6-Methoxy-2-methyl-1-((2-(trimethylsilyl)ethoxy)methyl)-1H-benzo[d]imidazol-5-yl)-N-methyl-N-(2,2,6,6-tetramethylpiperidin-4-yl)pyridazin-3-amine The mixture of (6-methoxy-2-methyl-1-((2-(trimethylsilyl)ethoxy)methyl)-1H-benzo[d]imidazol-5-yl)boronic acid and the pinacol ester (78 mg, 0.139 mmol), and Intermediate 1-1 (26 mg, 0.092 mmol) were reacted according to GENERAL METHOD 1-5 for Suzuki coupling. 6-(6-Methoxy-2-methyl-1-((2-(trimethylsilyl)ethoxy)methyl)-1H-benzo[d]imidazol-5-yl)-N-methyl-N-(2,2,6,6-tetramethylpiperidin-4-yl)pyridazin-3-amine was obtained after flash column chromatography purification (44 mg, 89% yield). MS (M+1)= 539.7.

Step 4: 2-Methyl-5-(6-(methyl(2,2,6,6-tetramethylpiperidin-4-yl)amino)pyridazin-3-yl)-1H-benzo[d]imidazol-6-ol From 6-(6-methoxy-2-methyl-1-((2-(trimethylsilyl)ethoxy)methyl)-1H-benzo[d]imidazol-5-yl)-N-methyl-N-(2,2,6,6-tetramethylpiperidin-4-yl)pyridazin-3-amine (44 mg, 0.082 mmol), following GENERAL METHOD 3.2 for methoxy deprotection using BBr$_3$, 2-methyl-5-(6-(methyl(2,2,6,6-tetramethylpiperidin-4-yl)amino)pyridazin-3-yl)-1H-benzo[d]imidazol-6-ol was obtained as a white solid after HPLC purification (16 mg, 50% yield). LCMS Rt=0.40 min [Method Q], MS (M+1)=395.4. $^1$H NMR (METHANOL-d$_4$) δ 8.15 (d, J=10.1 Hz, 1H), 7.88 (s, 1H), 7.34 (d, J=9.6 Hz, 1H), 6.97 (s, 1H), 5.07 (t, J=11.9 Hz, 1H), 3.02 (s, 3H), 2.55 (s, 3H), 1.65-1.77 (m, 2H), 1.51-1.65 (m, 2H), 1.41 (s, 6H), 1.25 (s, 6H).

Example 29-1

Synthesis of 5-chloro-2-(6-(methyl(2,2,6,6-tetramethylpiperidin-4-yl)amino)pyridazin-3-yl)phenol

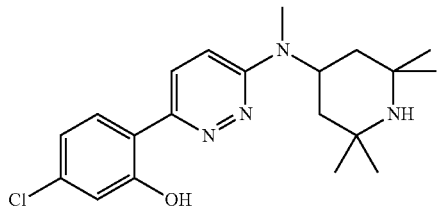 [SMILES: CN(c1ccc(-c2ccc(Cl)cc2O)nn1)C1CC(C)(C)NC(C)(C)C1]

Intermediate 1-1 and 5-chloro-2-(4,4,5,5-tetramethyl-1,3,2-dioxaborolan-2-yl)phenol were reacted according GENERAL METHOD 1-5 for Suzuki coupling. 5-Chloro-2-(6-(methyl(2,2,6,6-tetramethylpiperidin-4-yl)amino)pyridazin-3-yl)phenol was obtained as a yellow solid after HPLC purification. LCMS Rt=0.54 min [Method Q], MS (M+1)= 375.2. $^1$H NMR (METHANOL-d$_4$) δ 8.16 (d, J=9.6 Hz, 1H), 7.74 (d, J=8.6 Hz, 1H), 7.45 (d, J=10.1 Hz, 1H), 6.91-7.05 (m, 2H), 5.28-5.44 (m, 1H), 3.06 (s, 3H), 1.88-2.05 (m, 4H), 1.65 (s, 6H), 1.52 (s, 6H).

Example 30-1

Synthesis of 5-(1H-pyrazol-1-yl)-2-(6-((2,2,6,6-tetramethylpiperidin-4-yl)amino)pyridazin-3-yl)phenol

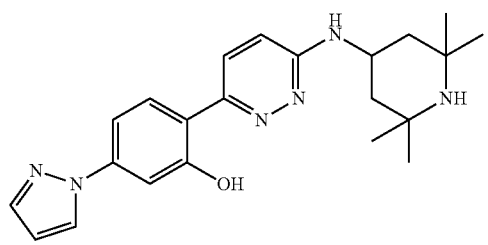 [SMILES: CC1(C)CC(Nc2ccc(-c3ccc(-n4cccn4)cc3O)nn2)CC(C)(C)N1]

Step 1:

6-(2-Methoxy-4-(1H-pyrazol-1-yl)phenyl)-N-(2,2,6,6-tetramethylpiperidin-4-yl)pyridazin-3-amine (148 mg, 0.353 mmol, 48% yield) was prepared following GENERAL METHOD 1-4 for Suzuki coupling from 1-(3-methoxy-4-(4,4,5,5-tetramethyl-1,3,2-dioxaborolan-2-yl)phenyl)-1H-pyrazole (Intermediate 2-1, Step 3, 447 mg, 1.49 mmol) and Intermediate 1-2 (200 mg, 0.744 mmol). LCMS Rt=0.95 min (LCMS condition B); MS (M+1)=407.3. $^1$H NMR (400 MHz, CHLOROFORM-d) δ 7.97-8.06 (m, 2H), 7.73-7.82 (m, 2H), 7.52 (d, J=2.01 Hz, 1H), 7.24-7.31 (m, 1H), 6.64 (d, J=9.29 Hz, 1H), 6.47-6.54 (m, 1H), 4.49 (d, J=8.03 Hz, 1H), 4.27-4.42 (m, 1H), 3.95 (s, 3H), 2.12 (dd, J=3.76, 12.55 Hz, 2H), 1.33 (s, 6H), 1.17 (s, 6H), 1.03 (t, J=12.05 Hz, 2H).

Step 2: 5-(1H-Pyrazol-1-yl)-2-(6-((2,2,6,6-tetramethylpiperidin-4-yl)amino)pyridazin-3-yl)phenol Following GENERAL METHOD 3-1 for methoxy deprotection using thiophenol, the title compound was afforded as pale yellow powder (8 mg). LCMS Rt=0.48 min [Method Q]; MS (M+1)=393.3. $^1$H NMR (400 MHz, METHANOL-d4) δ 8.29 (d, J=2.51 Hz, 1H), 8.05 (d, J=9.79 Hz, 1H), 7.89 (d, J=8.53 Hz, 1H), 7.76 (d, J=1.51 Hz, 1H), 7.32-7.40 (m, 2H), 7.06 (d, J=9.79 Hz, 1H), 6.56 (t, J=2.13 Hz, 1H), 4.41-4.56 (m, 1H), 2.08 (dd, J=3.51, 12.80 Hz, 2H), 1.40 (s, 6H), 1.16-1.27 (m, 8H).

Example 30-2

Synthesis of 3-hydroxy-4-(6-((2,2,6,6-tetramethylpiperidin-4-yl)amino)pyridazin-3-yl)benzonitrile

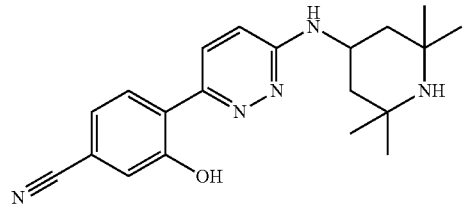 [SMILES: CC1(C)CC(Nc2ccc(-c3ccc(C#N)cc3O)nn2)CC(C)(C)N1]

To a microwave vial was added 3-methoxy-4-(6-(methyl(2,2,6,6-tetramethylpiperidin-4-yl)amino)pyridazin-3-yl)benzonitrile (Example 5-1, Step 1, 100 mg, 0.264 mmol) and pyridine hydrochloride (610 mg, 5.27 mmol), and the mixture was heated at 150° C. for 90 minutes in the microwave. The reaction mixture is dissolved in MeOH/DMSO, and purified by preparative HPLC (Waters Sunfire 30 mm ID×50 mm, 0.1% TFA, 15-40% ACN/H$_2$O) to provide the title compound as a minor product (3 mg, 0.008 mmol). LCMS Rt=0.47 min (Method Q); MS (M+1)=352.2. $^1$H NMR (400 MHz, CHLOROFORM-d) δ 7.81 (d, J=9.54 Hz, 1H), 7.65 (d, J=8.03 Hz, 1H), 7.34 (d, J=1.51 Hz, 1H), 7.18 (dd, J=1.76, 8.28 Hz, 1H), 6.87 (d, J=9.54 Hz, 1H), 4.83 (br. s., 1H), 4.40 (d, J=7.53 Hz, 1H), 2.11 (dd, J=3.64, 12.67 Hz, 2H), 1.59 (td, J=7.72, 15.18 Hz, 1H), 1.33-1.43 (m, 7H), 1.25 (br. s., 6H).

Example 31-1

Synthesis of 2-(6-((2,2-dimethylpiperidin-4-yl)oxy)pyridazin-3-yl)-5-(1H-pyrazol-1-yl)phenol

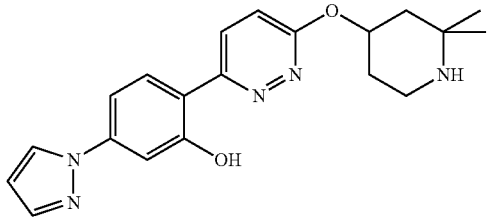 [SMILES: CC1(C)CC(Oc2ccc(-c3ccc(-n4cccn4)cc3O)nn2)CCN1]

Potassium tert-butoxide (1.0 M in THF, 2.2 mL, 2.2 mmol) was added to 2,2-dimethylpiperidin-4-ol (0.22 g, 1.66 mmol) in THF (2.2 mL) and DMF (0.6 mL) and the mixture was stirred for 10 minutes at 50° C. Intermediate 2-2 (0.15 g, 0.55 mmol) was added to the reaction at 0° C. and the mixture was stirred for 4 h at RT. A solution of sodium bicarbonate was added and the aqueous phase was extracted with 3:1 chloroform propan-2-ol (2×). The combined organic phases were dried over anhydrous $Na_2SO_4$, filtered and concentrated under reduced pressure. The crude material was purified via preparative HPLC (10 to 60% acetonitrile in water, 0.1% trifluoroacetic acid as modifier). The appropriate fractions containing product were free based by catch and release using SiliaBond Tosic Acid® (5 g, MeOH as eluent and a 2 N ammonia solution in MeOH to release the material). Evaporation under reduced pressure afforded 2-(6-((2,2-dimethylpiperidin-4-yl)oxy)pyridazin-3-yl)-5-(1H-pyrazol-1-yl)phenol as a beige solid (0.11 g, 53%). LCMS Rt=0.52 min [Method Q]; [M+H]: 366.2; $^1$H NMR (400 MHz, DMSO) δ 13.30 (bs, 1H), 8.60 (d, J=2.5 Hz, 1H), 8.44 (d, J=9.5 Hz, 1H), 8.07 (d, J=8.5 Hz, 1H), 7.78 (d, J=2.0 Hz, 1H), 7.50 (d, J=2.0 Hz, 1H), 7.48 (dd, J=8.5, 2.0 Hz, 1H), 7.40 (d, J=9.5 Hz, 1H), 6.61-6.54 (m, 1H), 5.45 (td, J=10.5, 5.0 Hz, 1H), 2.94-2.76 (m, 2H), 2.16-2.05 (m, 1H), 2.03-1.96 (m, 1H), 1.49-1.30 (m, 2H), 1.13 (s, 3H), 1.10 (s, 3H).

Example 32-1

Synthesis of 2-(6-(methyl(2,2,6,6-tetramethylpiperidin-4-yl)amino)pyridazin-3-yl)-4-(1H-pyrazol-4-yl)phenol

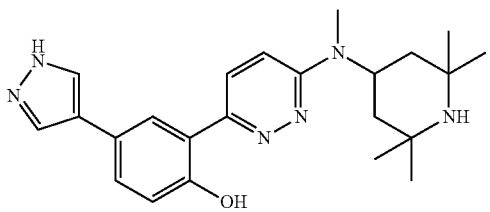 [SMILES: CN(c1ccc(-c2cc(-c3cn[nH]c3)ccc2O)nn1)C1CC(C)(C)NC(C)(C)C1]

Step 1: 4-Methoxy-3-(4,4,5,5-tetramethyl-1,3,2-dioxaborolan-2-yl)phenol

Following GENERAL METHOD 2-1 for boronate ester formation using 3-bromo-4-methoxyphenol (1.0 g, 4.90 mmol) affords 4-methoxy-3-(4,4,5,5-tetramethyl-1,3,2-dioxaborolan-2-yl)phenol (1.23 mg) MS [M+H$^+$]=251.1.

Step 2: 4-Methoxy-3-(6-(methyl(2,2,6,6-tetramethylpiperidin-4-yl)amino)pyridazin-3-yl)phenol To a microwave vial was added 4-methoxy-3-(4,4,5,5-tetramethyl-1,3,2-dioxaborolan-2-yl)phenol (400 mg, 1.60 mmol), 6-chloro-N-methyl-N-(2,2,6,6-tetramethylpiperidin-4-yl)pyridazin-3-amine (Intermediate 1-1, 452 mg, 1.60 mmol), potassium phosphate (1.4 g, 6.40 mmol), $Pd_2(dba)_3$ (146 mg, 0.16 mmol), and SPhos (65.7 mg, 0.16 mmol), followed by addition of 1,4-dioxane (4 mL)/$H_2O$ (0.8 mL). The vial was purged with $N_2$ for 5 minutes and the reaction mixture was heated at 100° C. in the microwave for 2 h. The reaction mixture was concentrated in vacuo. The crude material was adjusted to pH 3 using 12 M HCl aqueous solution and loaded onto an SCX column. The crude material was washed with methanol then eluted with 2 N ammonia in methanol. The product-containing fractions were concentrated to afford 4-methoxy-3-(6-(methyl(2,2,6,6-tetramethylpiperidin-4-yl)amino)pyridazin-3-yl)phenol (491 mg) MS [M+H$^+$]=371.2.

Step 3: 4-Methoxy-3-(6-(methyl(2,2,6,6-tetramethylpiperidin-4-yl)amino)pyridazin-3-yl)phenyl trifluoromethanesulfonate To a solution of 4-methoxy-3-(6-(methyl(2,2,6,6-tetramethylpiperidin-4-yl)amino)pyridazin-3-yl)phenol (490 mg, 1.32 mmol) in DCM (8 mL) was added triethylamine (0.461 mL, 3.31 mmol) at RT. The reaction mixture was cooled to 0° C., followed by addition of N-phenyltrifluoromethanesulfonimide (472 mg, 1.32 mmol). The reaction mixture was warmed to RT and stirred for two hours then quenched with aqueous sodium bicarbonate solution and extracted with DCM. The organic layer was dried over sodium sulfate, filtered and concentrated to give the crude product which was adjusted to pH 3 using 1 M HCl aqueous solution and loaded onto an SCX column. The crude product was washed with methanol then eluted with 2 N ammonia in methanol. The product fractions were collected and dried to afford 4-methoxy-3-(6-(methyl(2,2,6,6-tetramethylpiperidin-4-yl)amino)pyridazin-3-yl)phenyl trifluoromethanesulfonate (665 mg) MS [M+H$^+$]=503.2.

Step 4: 6-(2-Methoxy-5-(1H-pyrazol-4-yl)phenyl)-N-methyl-N-(2,2,6,6-tetramethylpiperidin-4-yl)pyridazin-3-amine To a microwave vial was added 4-methoxy-3-(6-(methyl(2,2,6,6-tetramethylpiperidin-4-yl)amino)pyridazin-3-yl)phenyl trifluoromethanesulfonate (100 mg, 0.20 mmol), 1H-pyrazol-4-ylboronic acid (33.4 mg, 0.30 mmol), potassium phosphate (127 mg, 0.60 mmol), $Pd_2(dba)_3$ (18.22 mg, 0.02 mmol), and SPhos (16.4 mg, 0.04 mmol), followed by addition of 1,4-dioxane (1.6 mL)/$H_2O$ (0.4 mL). The vial was purged with $N_2$ for 5 minutes and the reaction mixture was heated at 100° C. in the microwave for 1 hour. The reaction mixture was concentrated in vacuo. The crude material was adjusted to pH 3 using 1 M HCl aqueous solution and loaded on an SCX column. The crude material was washed with methanol then eluted with 2 N ammonia in methanol. The product-containing fractions were concentrated to afford 6-(2-methoxy-5-(1H-pyrazol-4-yl)phenyl)-N-methyl-N-(2,2,6,6-tetramethylpiperidin-4-yl)pyridazin-3-amine (68 mg) MS [M+H$^+$]=421.3.

Step 5: 2-(6-(Methyl(2,2,6,6-tetramethylpiperidin-4-yl)amino)pyridazin-3-yl)-4-(1H-pyrazol-4-yl)phenol Following standard GENERAL METHOD 3-2 for methoxy deprotection, the title compound was afforded. MS [M+H$^+$]=407.3, LCMS Rt=0.51 min [Method Q]; $^1$H NMR (400 MHz, DMSO-d) ppm 8.42 (d, J=9.79 Hz, 1H), 7.99-

8.12 (m, 3H), 7.48 (d, J=7.78 Hz, 1H), 7.35 (d, J=9.79 Hz, 1H), 6.90 (d, J=8.28 Hz, 1H), 4.84-5.10 (m, 1H), 2.97 (s, 3H), 1.49-1.58 (m, 2H), 1.37-1.49 (m, 2H), 1.23-1.28 (m, 7H), 1.09 (s, 6H).

The following compounds were prepared using similar procedures as described in Example 32-1, followed by methoxy deprotection as outlined in GENERAL METHODS 3-1 and 3-2 when appropriate.

| Example | Compound | LCMS Method Q | $^1$HNMR 400 MHz |
|---|---|---|---|
| 32-2 | 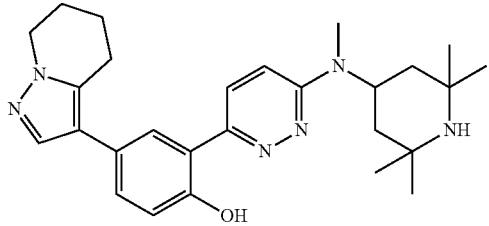<br>2-(6-(methyl(2,2,6,6-tetramethylpiperidin-4-yl)amino)pyridazin-3-yl)-4-(4,5,6,7-tetrahydropyrazolo[1,5-a]pyridin-3-yl)phenol | M + 1 = 461.4<br>Rt = 0.52 min | (DMSO-d$_6$) δ ppm 13.48 (br. s., 1H), 8.30 (d, J = 10.04 Hz, 1H), 7.83 (d, J = 2.01 Hz, 1H), 7.74 (s, 1H), 7.27-7.41 (m, 2H), 6.96 (d, J = 8.53 Hz, 1H), 4.74-5.12 (m, 1H), 4.10 (t, J = 6.02 Hz, 2H), 2.84-3.09 (m, 5H), 1.92-2.09 (m, 2H), 1.75-1.90 (m, 2H), 0.89-1.67 (m, 17H) |
| 32-3 | 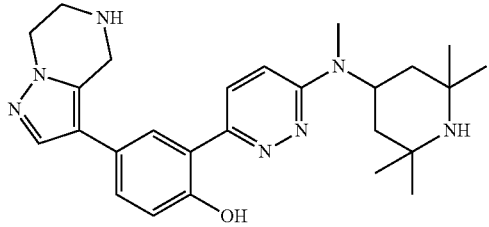<br>2-(6-(methyl(2,2,6,6-tetramethylpiperidin-4-yl)amino)pyridazin-3-yl)-4-(4,5,6,7-tetrahydropyrazolo[1,5-a]pyrazin-3-yl)phenol | M + 1 = 462.4<br>Rt = 0.38 min | (DMSO-d$_6$) δ ppm 13.44-13.57 (m, 1H), 8.28-8.38 (m, 1H), 7.76-7.86 (m, 2H), 7.31-7.41 (m, 1H), 7.20-7.29 (m, 1H), 6.92-7.02 (m, 1H), 4.84-5.08 (m, 1H), 3.90-4.29 (m, 5H), 3.09-3.19 (m, 2H), 2.97 (s, 3H), 1.39-1.58 (m, 4H), 1.24-1.30 (m, 7H), 1.09 (s, 6H) |
| 32-4 | 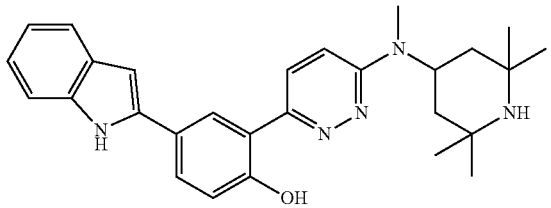<br>4-(1H-indol-2-yl)-2-(6-(methyl(2,2,6,6-tetramethylpiperidin-4-yl)amino)pyridazin-3-yl)phenol | M + 1 = 456.4<br>Rt = 0.58 min | (DMSO-d$_6$) δ ppm 13.77 (s, 1H), 11.48 (s, 1H), 8.41 (d, J = 10.04 Hz, 1H), 8.35 (d, J = 2.01 Hz, 1H), 7.78 (dd, J = 8.53, 2.01 Hz, 1H), 7.33-7.57 (m, 3H), 6.94-7.14 (m, 3H), 6.85-6.92 (m, 1H), 4.74-5.29 (m, 1H), 2.99 (s, 3H), 1.38-1.66 (m, 4H), 1.27 (s, 6H), 1.10 (s, 6H) |
| 32-5 | 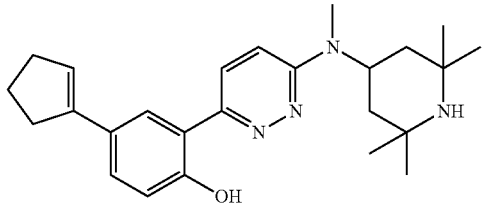<br>4-(cyclopent-1-en-1-yl)-2-(6-(methyl(2,2,6,6-tetramethylpiperidin-4-yl)amino)pyridazin-3-yl)phenol | M + 1 = 407.4<br>Rt = 0.59 min | (METHANOL-d$_4$) δ ppm 8.15 (d, J = 10.04 Hz, 1H), 7.79 (d, J = 2.01 Hz, 1H), 7.42 (dd, J = 8.53, 2.01 Hz, 1H), 7.32 (d, J = 9.79 Hz, 1H), 6.92 (d, J = 8.53 Hz, 1H), 6.15 (t, J = 1.88 Hz, 1H), 5.02-5.19 (m, 1H), 3.02 (s, 3H), 2.70-2.83 (m, 2H), 2.49-2.61 (m, 2H), 1.98-2.15 (m, 2H), 1.67-1.79 (m, 2H), 1.52-1.66 (m, 2H), 1.42 (s, 6H), 1.26 (s, 6H) |

| Example | Compound | LCMS Method Q | ¹HNMR 400 MHz |
|---|---|---|---|
| 32-6 | 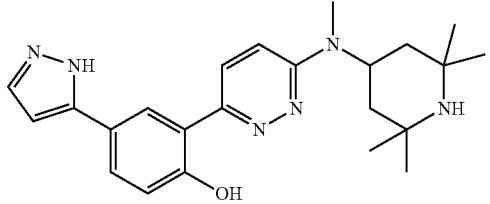<br>2-(6-(methyl(2,2,6,6-tetramethylpiperidin-4-yl)amino)pyridazin-3-yl)-4-(1H-pyrazol-3-yl)phenol | M + 1 = 407.4<br>Rt = 0.48 min | (METHANOL-d4) δ ppm 8.22 (d, J = 9.79 Hz, 2H), 7.68 (d, J = 7.28 Hz, 2H), 7.36 (d, J = 9.79 Hz, 1H), 7.03 (d, J = 8.53 Hz, 1H), 6.69 (d, J = 1.25 Hz, 1H), 5.18 (t, J = 11.29 Hz, 1H), 3.03 (s, 3H), 1.59-1.85 (m, 4H), 1.46 (s, 6H), 1.31 (s, 6H) |
| 32-7 | 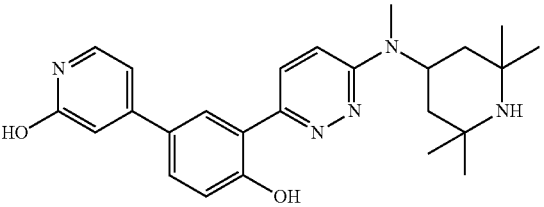<br>4-(4-hydroxy-3-(6-(methyl(2,2,6,6-tetramethylpiperidin-4-yl)amino)pyridazin-3-yl)phenyl)pyridin-2-ol | M + 1 = 434.4<br>Rt = 0.47 min | (METHANOL-d₄) δ ppm 8.13 (d, J = 10.1 Hz, 1H), 7.95 (d, J = 2.5 Hz, 1H), 7.51 (dd, J = 8.6, 2.0 Hz, 1H), 7.35-7.41 (m, 1H), 7.20 (d, J = 10.1 Hz, 1H), 6.98 (d, J = 8.6 Hz, 1H), 6.58-6.76 (m, 2H), 5.01 (m, 1H), 2.93 (s, 3H), 1.64 (dd, J = 12.6, 3.5 Hz, 2H), 1.50 (t, J = 12.4 Hz, 2H), 1.32 (s, 6H), 1.16 (s, 6H) |
| 32-8 | 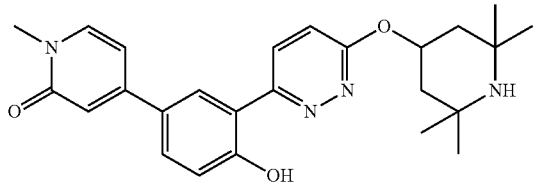<br>4-(4-hydroxy-3-(6-((2,2,6,6-tetramethylpiperidin-4-yl)oxy)pyridazin-3-yl)phenyl)-1-methylpyridin-2(1H)-one | M + 1 = 435.4<br>Rt = 0.48 min | ¹H NMR (DMSO-d₆) δ ppm 13.01 (br. s., 1H), 8.58 (d, J = 9.1 Hz, 1H), 8.19 (d, J = 2.5 Hz, 1H), 7.63-7.72 (m, 2H), 7.33 (d, J = 9.1 Hz, 1H), 7.02 (d, J = 8.6 Hz, 1H), 6.72 (d, J = 2.0 Hz, 1H), 6.62 (dd, J = 7.3, 2.3 Hz, 1H), 5.61 (m, 1H), 3.38 (s, 3H), 2.03 (dd, J = 11.9, 3.8 Hz, 2H), 1.18-1.26 (m, 2H), 1.17 (s, 6H), 1.04 (s, 6H) |
| 32-9 | 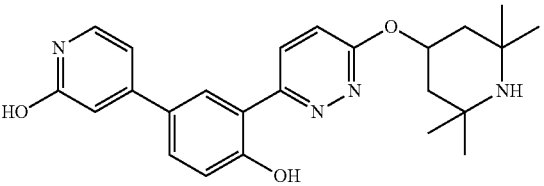<br>4-(4-hydroxy-3-(6-((2,2,6,6-tetramethylpiperidin-4-yl)oxy)pyridazin-3-yl)phenyl)pyridin-2-ol | M + 1 = 421.4<br>Rt = 0.47 min | (METHANOL-d₄) δ ppm 8.36 (d, J = 9.1 Hz, 1H), 8.06 (s, 1H), 7.59 (d, J = 8.1 Hz, 1H), 7.40 (d, J = 6.1 Hz, 1H), 7.18 (d, J = 9.1 Hz, 1H), 7.01 (d, J = 8.6 Hz, 1H), 6.68-6.77 (m, 2H), 5.67 (m, 1H), 2.15 (dd, J = 12.6, 4.0 Hz, 2H), 1.35 (t, J = 11.9 Hz, 2H), 1.28 (s, 6H), 1.16 (s, 6H) |

The following compound was prepared using a similar procedure as described in Example 14-1, utilizing methoxy deprotection as outlined in GENERAL METHOD 3-2:

| NVP | Compound | LCMS Method Q | $^1$HNMR 400 MHz |
|---|---|---|---|
| 33-1 | 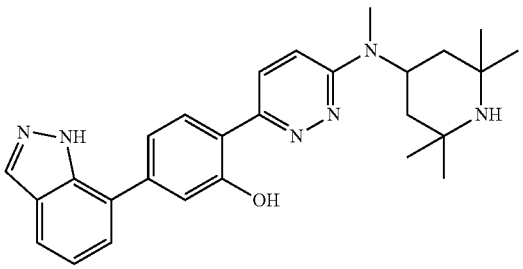<br>5-(1H-indazol-7-yl)-2-(6-(methyl(2,2,6,6-tetramethylpiperidin-4-yl)amino)pyridazin-3-yl)phenol | M + 1 = 457.4<br>Rt = 0.58 min | (DMSO-d$_6$) δ ppm 13.84 (s, 1H), 13.28 (br. s., 1H), 8.31 (d, J = 10.04 Hz, 1H), 8.19 (s, 1H), 8.04 (d, J = 8.82 Hz, 1H), 7.79 (d, J = 8.03 Hz, 1H), 7.46 (dd, J = 7.15, 0.63 Hz, 1H), 7.40 (d, J = 9.79 Hz, 1H), 7.18-7.30 (m, 3H), 4.84-5.11 (m, 1H), 2.98 (s, 3H), 1.39-1.62 (m, 4H), 1.27 (s, 7H) 1.07-1.12 (m, 6H) |

Example 34-1

Synthesis of 4-chloro-2-(6-(methyl(2,2,6,6-tetramethylpiperidin-4-yl)amino)pyridazin-3-yl)-5-(1H-pyrazol-4-yl)phenol

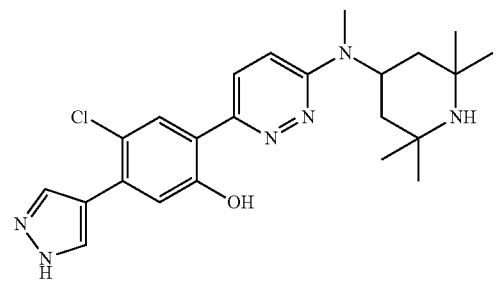 [SMILES: CN(c1ccc(-c2cc(Cl)c(-c3cn[nH]c3)cc2O)nn1)C1CC(C)(C)NC(C)(C)C1]

Step 1:
4-(4-Bromo-2-chloro-5-methoxyphenyl)-1H-pyrazole

Following standard GENERAL METHOD 1-4 for Suzuki coupling using (1H-pyrazol-4-yl)boronic acid (161 mg, 1.44 mmol) and 1-bromo-5-chloro-4-iodo-2-methoxybenzene (500 mg, 1.44 mmol) afforded 4-(4-bromo-2-chloro-5-methoxyphenyl)-1H-pyrazole (300 mg) MS [M+H$^+$]=286.8.

Step 2: 4-(2-Chloro-5-methoxy-4-(4,4,5,5-tetramethyl-1,3,2-dioxaborolan-2-yl)phenyl)-1H-pyrazole Following GENERAL METHOD 2-1 for boronate ester formation using 4-(4-bromo-2-chloro-5-methoxyphenyl)-1H-pyrazole (300 mg, 1.04 mmol) afforded 4-(2-chloro-5-methoxy-4-(4,4,5,5-tetramethyl-1,3,2-dioxaborolan-2-yl)phenyl)-1H-pyrazole (178 mg) MS [M+$^+$]=335.2.

Step 3: 6-(5-Chloro-2-methoxy-4-(1H-pyrazol-4-yl)phenyl)-N-methyl-N-(2, 2,6,6-tetramethylpiperidin-4-yl)pyridazin-3-amine Following standard GENERAL METHOD 1-4 for Suzuki coupling using 4-(2-chloro-5-methoxy-4-(4,4,5,5-tetramethyl-1,3,2-dioxaborolan-2-yl)phenyl)-1H-pyrazole (118 mg, 0.35 mmol) and 6-chloro-N-methyl-N-(2,2,6,6-tetramethylpiperidin-4-yl)pyridazin-3-amine (Intermediate 1-1, 100 mg, 0.35 mmol) afforded 6-(5-chloro-2-methoxy-4-(1H-pyrazol-4-yl)phenyl)-N-methyl-N-(2,2,6,6-tetramethylpiperidin-4-yl)pyridazin-3-amine (138 mg) MS [M+H$^+$]=455.0.

Step 4: 4-Chloro-2-(6-(methyl(2,2,6,6-tetramethylpiperidin-4-yl)amino)pyridazin-3-yl)-5-(1H-pyrazol-4-yl)phenol Following standard GENERAL METHOD 3-2 for methoxy deprotection, the title compound was prepared. MS [M+H$^+$]=441.3, LCMS Rt=0.54 min [Method Q]; $^1$H NMR (400 MHz, DMSO-de) δ ppm 13.72 (br. s., 1H), 13.13 (br. s., 1H), 8.29 (d, J=10.04 Hz, 1H), 8.04-8.26 (m, 2H), 8.01 (s, 1H), 7.35 (d, J=9.79 Hz, 1H), 7.20 (s, 1H), 4.81-5.23 (m, 1H), 2.95 (s, 3H), 1.36-1.63 (m, 4H), 0.96-1.32 (m, 12H).

Example 34-2

Synthesis of 4-fluoro-2-(6-(methyl(2,2,6,6-tetramethylpiperidin-4-yl)amino)pyridazin-3-yl)-5-(1H-pyrazol-4-yl)phenol

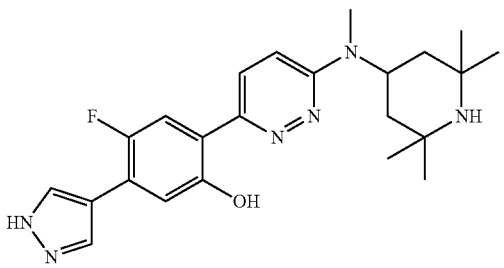 [SMILES: CN(c1ccc(-c2cc(F)c(-c3cn[nH]c3)cc2O)nn1)C1CC(C)(C)NC(C)(C)C1]

Step 1: tert-Butyl 4-(2-fluoro-4-hydroxy-5-methoxyphenyl)-1H-pyrazole-1-carboxylate To a reaction flask was added 4-bromo-5-fluoro-2-methoxyphenol (500 mg, 2.26 mmol), tert-butyl 4-(4,4,5,5-tetramethyl-1,3,2-dioxaborolan-2-yl)-1H-pyrazole-1-carboxylate (998 mg, 3.39 mmol), potassium phosphate (1.4 g, 6.79 mmol), and XPhosPalladacycle (178 mg, 0.23 mmol), followed by addition of DMF (11 mL). The vial was purged with N₂ for 5 minutes and the reaction mixture was heated at 50° C. in the microwave for 16 h. The reaction mixture was concentrated in vacuo and the crude product was purified by silica gel to afford tert-butyl 4-(2-fluoro-4-hydroxy-5-methoxyphenyl)-1H-pyrazole-1-carboxylate (700 mg) MS [M+H⁺]=307.5.

Step 2: tert-Butyl 4-(2-fluoro-5-methoxy-4-(((trifluoromethyl)sulfonyl)oxy)phenyl)-1H-pyrazole-1-carboxylate To a solution of tert-butyl 4-(2-fluoro-4-hydroxy-5-methoxyphenyl)-1H-pyrazole-1-carboxylate (700 mg, 2.27 mmol) in DCM (11.4 mL) was added triethylamine (01.27 mL, 9.08 mmol) at RT. The reaction mixture was cooled to 0° C., followed by addition of N-phenyltrifluoromethanesulfonimide (973 mg, 2.72 mmol). The reaction mixture was warmed to RT and stirred for two hours. The reaction was quenched with aqueous sodium bicarbonate solution and extracted with DCM. The organic layer was dried over sodium sulfate, filtered and concentrated to give the crude product, which was purified on silica gel to afford tert-butyl 4-(2-fluoro-5-methoxy-4-(((trifluoromethyl)sulfonyl)oxy)phenyl)-1H-pyrazole-1-carboxylate (724 mg) MS [M+H⁺−BOC]=341.0.

Step 3: tert-Butyl 4-(2-fluoro-5-methoxy-4-(4,4,5,5-tetramethyl-1, 3,2-dioxaborolan-2-yl)phenyl)-1H-pyrazole-1-carboxylate Following GENERAL METHOD 2-1 for boronate ester formation using tert-butyl 4-(2-fluoro-5-methoxy-4-(((trifluoromethyl)sulfonyl)oxy)phenyl)-1H-pyrazole-1-carboxylate (635 mg, 1.44 mmol) afforded the title compound (170 mg). MS [M+H⁺]=419.3.

Step 4: tert-Butyl 4-(2-fluoro-5-methoxy-4-(6-(methyl(2,2,6,6-tetramethylpiperidin-4-yl)amino)pyridazin-3-yl)phenyl)-1H-pyrazole-1-carboxylate To a microwave vial was added tert-butyl 4-(2-fluoro-5-methoxy-4-(4,4,5,5-tetramethyl-1,3,2-dioxaborolan-2-yl)phenyl)-1H-pyrazole-1-carboxylate (98 mg, 0.23 mmol), 6-chloro-N-methyl-N-(2,2,6,6-tetramethylpiperidin-4-yl)pyridazin-3-amine (Intermediate 1-1, 66.3 mg, 0.23 mmol), potassium phosphate (199 mg, 0.94 mmol), Pd₂(dba)₃ (21.5 mg, 0.02 mmol), and SPhos (9.62 mg, 0.02 mmol), followed by addition of 1,4-dioxane (0.4 mL)/H₂O (0.9 mL). The vial was purged with N₂ for 5 minutes and then heated at 100° C. in the microwave for one hour. The reaction mixture was concentrated in vacuo. The crude material was adjusted to pH 3 using 1 M HCl aqueous solution and loaded on an SCX column. The crude material was washed with methanol then eluted with 2 N ammonia in methanol. The product-containing fractions were concentrated to afford tert-butyl 4-(2-fluoro-5-methoxy-4-(6-(methyl(2,2,6,6-tetramethylpiperidin-4-yl)amino)pyridazin-3-yl)phenyl)-1H-pyrazole-1-carboxylate (126 mg) MS [M+H⁺]=539.2.

Step 5: 4-Fluoro-2-(6-(methyl(2,2,6,6-tetramethylpiperidin-4-yl)amino)pyridazin-3-yl)-5-(1H-pyrazol-4-yl)phenol Following standard GENERAL METHOD 3-2 for methoxy deprotection, the title compound was afforded. MS [M+H⁺]=425.3, LCMS Rt=0.48 min [Method Q]; ¹H NMR (400 MHz, DMSO-de) δ ppm 13.58 (s, 1H), 13.15 (br. s., 1H), 7.90-8.39 (m, 3H), 7.83 (d, J=12.55 Hz, 1H), 7.24-7.41 (m, 2H), 4.80-5.17 (m, 1H), 2.95 (s, 3H), 1.38-1.56 (m, 4H), 1.25 (s, 6H), 1.09 (s, 6H).

Example 34-3

Synthesis of 5-fluoro-4-(1H-imidazol-4-yl)-2-(6-(methyl(2,2,6,6-tetramethylpiperidin-4-yl)amino)pyridazin-3-yl)phenol

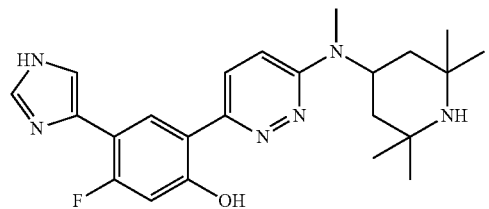 [SMILES: CN(c1ccc(-c2cc(-c3c[nH]cn3)c(F)cc2O)nn1)C1CC(C)(C)NC(C)(C)C1]

Step 1: 6-(4-Fluoro-2-methoxyphenyl)-N-methyl-N-(2,2,6,6-tetramethylpiperidin-4-yl)pyridazin-3-amine To a microwave vial was added 2-(4-fluoro-2-methoxyphenyl)-4,4,5,5-tetramethyl-1,3,2-dioxaborolane (535 mg, 2.12 mmol), 6-chloro-N-methyl-N-(2,2,6,6-tetramethylpiperidin-4-yl)pyridazin-3-amine (Intermediate 1-1, 500 mg, 1.77 mmol), potassium phosphate (1.5 g, 7.07 mmol), Pd₂(dba)₃ (162 mg, 0.18 mmol), and SPhos (72.6 mg, 0.18 mmol), followed by addition of 1,4-dioxane (3.7 mL)/H₂O (0.7 mL). The vial was purged with N₂ for 5 minutes and the reaction mixture was heated at 100° C. in the microwave for one hour. The reaction mixture was concentrated in vacuo. The crude material was adjusted to pH 3 using 1 M HCl aqueous solution, loaded on an SCX column and washed with methanol, then eluted with 2 N ammonia in methanol. The product-containing fractions were concentrated to afford 6-(4-fluoro-2-methoxyphenyl)-N-methyl-N-(2,2,6,6-tetramethylpiperidin-4-yl)pyridazin-3-amine (620 mg) MS [M+⁺]=373.3.

Step 2: (2-Fluoro-4-methoxy-5(6-(methyl(2,2,6,6-tetramethylpiperidin-4-yl)amino)pyridazin-3-yl)phenyl)boronic acid Following GENERAL METHOD 7-1 for Ir Borylation using 6-(4-fluoro-2-methoxyphenyl)-N-methyl-N-(2,2,6,6-tetramethylpiperidin-4-yl)pyridazin-3-amine (100 mg, 0.23 mmol) afforded (2-fluoro-4-methoxy-5-(6-(methyl(2,2,6,6-tetramethylpiperidin-4-yl)amino)pyridazin-3-yl)phenyl)boronic acid (101 mg) MS [M+H⁺]=417.3.

Step 3: 6-(4-Fluoro-5-(1H-imidazol-4-yl)-2-methoxyphenyl)-N-methyl-N-(2,2,6,6-tetramethylpiperidin-4-yl)pyridazin-3-amine Following standard GENERAL METHOD 1-4 for Suzuki coupling using (2-fluoro-4-methoxy-5-(6-(methyl(2,2,6,6-tetramethylpiperidin-4-yl)amino)pyridazin-3-yl)phenyl)boronic acid (50 mg, 0.12 mmol) and 4-bromo-1H-imidazole (35.3 mg, 0.24 mmol) afforded 6-(4-fluoro-5-(1H-imidazol-4-yl)-2-methoxyphenyl)-N-methyl-N-(2,2,6,6-tetramethylpiperidin-4-yl)pyridazin-3-amine (52.7 mg) MS [M+H⁺]=439.3.

Step 4: 5-Fluoro-4-(1H-imidazol-4-yl)-2-(6-(methyl (2,2,6,6-tetramethylpiperidin-4-yl)amino)pyridazin-3-yl)phenol Following standard GENERAL METHOD 3-2 for methoxy deprotection, the title compound was prepared. MS [M+H$^+$]=425.3, LCMS Rt=0.42 min [Method Q]; $^1$H NMR (400 MHz, METHANOL-d$_4$) δ ppm 8.18-8.27 (m, 2H), 8.12 (d, J=10.04 Hz, 1H), 7.49 (d, J=2.26 Hz, 1H), 7.32 (d, J=10.04 Hz, 1H), 6.73 (d, J=12.55 Hz, 1H), 5.23-5.43 (m, 1H), 2.95 (s, 3H), 1.84-1.95 (m, 4H), 1.56 (s, 6H), 1.42 (s, 6H).

The following final compounds were prepared using similar procedures as described in Example 34-3:

Step 2: 6-Methoxy-5-(6-(methyl(2,2,6,6-tetramethylpiperidin-4-yl)amino)pyridazin-3-yl)-2,3-dihydro-1H-inden-1-one: Intermediate 7-1

Following standard GENERAL METHOD 1-4 for Suzuki coupling using 6-methoxy-5-(4,4,5,5-tetramethyl-1,3,2-dioxaborolan-2-yl)-2,3-dihydro-1H-inden-1-one (300 mg, 1.06 mmol) and 6-chloro-N-methyl-N-(2,2,6,6-tetramethylpiperdin-4-yl)pyridazin-3-amine (Intermediate 1-1, 611 mg, 2.12 mmol) afforded 6-methoxy-5-(6-(methyl(2,2,6,6-tetramethylpiperidin-4-yl)amino)pyridazin-3-yl)-2,3-dihydro-1H-inden-1-one (433 mg) MS [M+H$^+$]=409.7.

| NVP | Compound | LCMS Method Q | $^1$HNMR 400 MHz |
|---|---|---|---|
| 34-4 | 5-fluoro-2-(6-(methyl(2,2,6,6-tetramethylpiperidin-4-yl)amino)pyridazin-3-yl)-4-(1H-pyrazol-4-yl)phenol | M + 1 = 425.3 Rt = 0.49 min | (METHANOL-d$_4$) δ ppm 8.13-8.30 (m, 1H), 7.94-8.12 (m, 3H), 7.28-7.39 (m, 1H), 6.77 (d, J = 12.30 Hz, 1H), 5.04-5.18 (m, 1H), 3.02 (s, 3H), 1.53-1.74 (m, 5H), 1.40 (s, 7H), 1.25 (s, 7H) |
| 34-5 | 5-fluoro-2-(6-(methyl(2,2,6,6-tetramethylpiperidin-4-yl)amino)pyridazin-3-yl)-4-(1H-pyrazol-5-yl)phenol | M + 1 = 425.3 Rt = 0.52 min | (METHANOL-d$_4$) δ ppm 8.27 (d, J = 7.53 Hz, 1H), 8.16 (d, J = 10.04 Hz, 1H), 7.71 (s, 1H), 7.36 (d, J = 10.04 Hz, 1H), 6.79 (d, J = 12.80 Hz, 1H), 6.69 (dd, J = 3.51, 2.26 Hz, 1H), 5.05-5.20 (m, 1H), 3.03 (s, 3H), 1.66-1.80 (m, 2H), 1.52-1.66 (m, 2H), 1.41 (s, 6H), 1.25 (s, 6H) |

Example 35-1

Synthesis of 6-hydroxy-5-(6-(methyl(2,2,6,6-tetramethylpiperidin-4-yl)amino)pyridazin-3-yl)-2,3-dihydro-1H-inden-1-one

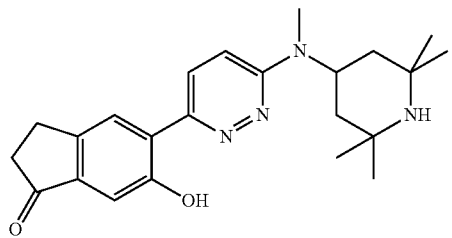 [SMILES: CN(c1ccc(-c2cc3c(cc2O)C(=O)CC3)nn1)C1CC(C)(C)NC(C)(C)C1]

Step 1: 6-Methoxy-5-(4,4,5,5-tetramethyl-1,3,2-dioxaborolan-2-yl)-2,3-dihydro-1H-inden-1-one Following GENERAL METHOD 2-1 for boronate ester formation using 5-bromo-6-methoxy-2,3-dihydro-1H-inden-1-one (1.0 mg, 4.15 mmol) afforded 6-methoxy-5-(4,4,5,5-tetramethyl-1,3,2-dioxaborolan-2-yl)-2,3-dihydro-1H-inden-1-one (1.16 g) MS [M+H$^+$]=289.2.

Step 3: 6-Hydroxy-5-(6-(methyl(2,2,6,6-tetramethylpiperidin-4-yl)amino)pyridazin-3-yl)-2,3-dihydro-1H-inden-1-one Following standard GENERAL METHOD 3-2 for methoxy deprotection, the title compound was prepared. MS [M+H$^+$]=395.2, LCMS Rt=0.47 min [Method Q]; $^1$H NMR (400 MHz, DMSO-de) 6 ppm 13.50 (s, 1H), 8.29 (d, J=10.04 Hz, 1H), 8.10 (s, 1H), 7.37 (d, J=10.04 Hz, 1H), 7.08 (s, 1H), 4.86-5.27 (m, 1H), 3.02-3.11 (m, 2H), 2.97 (s, 3H), 2.62-2.72 (m, 2H), 1.37-1.59 (m, 4H), 1.25 (s, 6H), 1.09 (s, 6H).

Example 35-2

Synthesis of 6-(6-(methyl(2,2,6,6-tetramethylpiperidin-4-yl)amino)pyridazin-3-yl)-1,4-dihydroindeno[1,2-c]pyrazol-7-ol

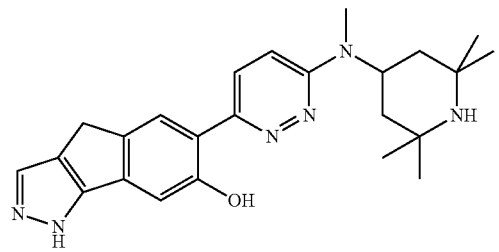 [SMILES: CN(c1ccc(-c2cc3c(cc2O)-c2[nH]ncc2C3)nn1)C1CC(C)(C)NC(C)(C)C1]

Step 1: 6-(7-Methoxy-1,4-dihydroindeno[1,2-c]pyrazol-6-yl)-N-methyl-N-(2,2,6,6-tetramethylpiperidin-4-yl)pyridazin-3-amine To a 100 mL round bottom flask containing toluene (1.0 mL) was added 6-methoxy-5-(6-(methyl(2,2,6,6-tetramethylpiperidin-4-yl)amino)pyridazin-3-yl)-2,3-dihydro-1H-inden-1-one (Intermediate 7-1, 330 mg, 0.81 mmol), ethyl formate (0.13 mL, 1.62 mmol), and sodium hydride (97 mg, 2.42 mmol). The reaction mixture was stirred at RT for 16 h then concentrated in vacuo. Ethanol (5.0 mL), acetic acid (0.51 mL, 8.89 mmol) and hydrazine hydrate (0.53 mL, 10.50 mmol) were added. The mixture was refluxed at 80° C. for 3 h and concentrated in vacuo. The crude material was adjusted to pH 3 using 1 M HCl aqueous solution and loaded onto an SCX column. The crude material was washed with methanol then eluted with 2 N ammonia in methanol. The product-containing fractions were concentrated to afford 6-(7-methoxy-1,4-dihydroindeno[1,2-c]pyrazol-6-yl)-N-methyl-N-(2,2,6,6-tetramethylpiperidin-4-yl)pyridazin-3-amine (75 mg) MS [M+H+]=433.5.

Step 2: 6-(6-(Methyl(2,2,6,6-tetramethylpiperidin-4-yl)amino)pyridazin-3-yl)-1,4-dihydroindeno[1,2-c]pyrazol-7-ol Following standard GENERAL METHOD 3-2 for methoxy deprotection, the title compound was afforded. MS [M+H+]=419.2, LCMS Rt=0.47 min [Method Q]; $^1$H NMR (400 MHz, DMSO-de) δ ppm 13.86 (s, 1H), 12.82 (br. s., 1H), 8.24 (d, J=10.04 Hz, 1H), 8.02 (s, 1H), 7.66 (s, 1H), 7.37 (d, J=10.04 Hz, 1H), 7.13 (s, 1H), 4.78-5.12 (m, 1H), 3.60 (s, 2H), 2.96 (s, 3H), 1.36-1.64 (m, 4H), 1.18-1.35 (m, 7H), 1.09 (br. s., 6H).

Example 35-3

Synthesis of 6-hydroxy-5-(6-(methyl(2,2,6,6-tetramethylpiperidin-4-yl)amino)pyridazin-3-yl)-2,3-dihydro-1H-inden-1-one oxime hydrochloride salt

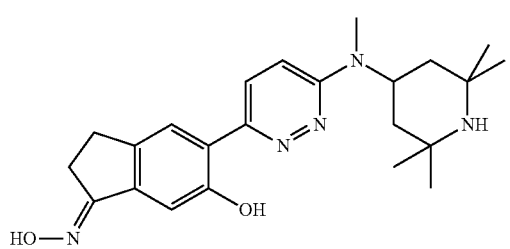 [SMILES: CN(c1ccc(-c2cc3c(cc2O)/C(=N/O)CC3)nn1)C1CC(C)(C)NC(C)(C)C1]

To a microwave vial was added 6-hydroxy-5-(6-(methyl(2,2,6,6-tetramethylpiperidin-4-yl)amino)pyridazin-3-yl)-2,3-dihydro-1H-inden-1-one (Example 35-1,150 mg, 0.38 mmol), hydroxylamine hydrochloride (264 mg, 3.80 mmol), pyridine (0.25 mL, 3.04 mmol) and MeOH (1.0 mL). The resulting suspension was stirred at RT for 1.5 hours. The reaction mixture was acidified with excess acetic acid and loaded onto an SCX column. The crude material was washed with methanol then eluted with 2 N ammonia in methanol. The product-containing fractions were concentrated to afford the title compound. MS [M+H+]=410.2, LCMS Rt=0.48 min [Method Q]; $^1$H NMR (400 MHz, DMSO-de) δppm 10.94-11.13 (m, 1H), 8.91-9.21 (m, 1H), 8.29 (d, J=10.04 Hz, 1H), 8.09-8.21 (m, 1H), 7.83 (s, 1H), 7.52-7.73 (m, 1H), 7.08 (s, 1H), 4.83-5.31 (m, 1H), 2.91-3.04 (m, 5H), 2.74-2.85 (m, 2H), 1.91-2.09 (m, 2H), 1.79 (d, J=10.79 Hz, 2H), 1.53 (s, 6H), 1.47 (s, 6H).

Example 35-4

Synthesis of 5-(6-(methyl(2,2,6,6-tetramethylpiperidin-4-yl)amino)pyridazin-3-yl)-2,3-dihydro-1H-indene-1,6-diol

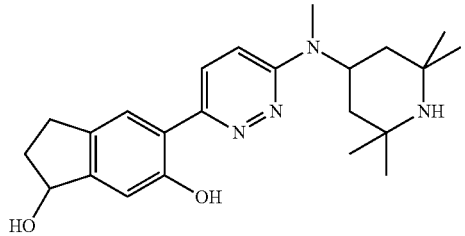 [SMILES: CN(c1ccc(-c2cc3c(cc2O)C(O)CC3)nn1)C1CC(C)(C)NC(C)(C)C1]

To a microwave vial was added 6-hydroxy-5-(6-(methyl(2,2,6,6-tetramethylpiperidin-4-yl)amino)pyridazin-3-yl)-2,3-dihydro-1H-inden-1-one (Example 35-1, 50 mg, 0.13 mmol), sodium borohydride (9.59 mg, 0.25 mmol) and MeOH (1.5 mL). The resulting suspension was stirred at RT for two hours. The reaction mixture was acidified with excess acetic acid and loaded onto an SCX column. The crude material was washed with methanol then eluted with 2 N ammonia in methanol. The product-containing fractions were concentrated to afford the title compound. MS [M+H+]= 397.3, LCMS Rt=0.46 min [LCMS Method Q]; $^1$H NMR (400 MHz, METHANOL-d$_4$) δ ppm 8.11 (d, J=9.54 Hz, 1H), 7.64 (s, 1H), 7.31 (d, J=9.54 Hz, 1H), 6.99 (s, 1H), 5.16 (t, J=6.53 Hz, 1H), 5.01-5.13 (m, 1H), 2.95-3.08 (m, 4H), 2.73-2.86 (m, 1H), 2.41-2.54 (m, 1H), 1.91 (s, 1H), 1.53-1.78 (m, 4H), 1.41 (s, 6H), 1.26 (s, 6H).

Example 35-5

Synthesis of 2-amino-6-(6-(methyl(2,2,6,6-tetramethylpiperidin-4-yl)amino)pyridazin-3-yl)-8H-indeno[1,2-d]thiazol-5-ol hydrochloride salt

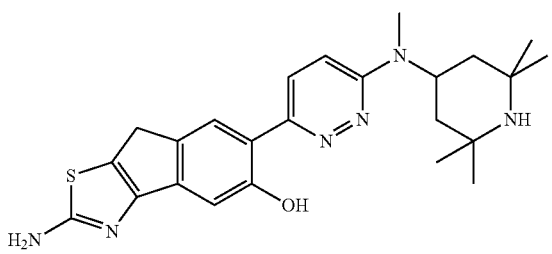 [SMILES: CN(c1ccc(-c2cc3c(cc2O)-c2nc(N)sc2C3)nn1)C1CC(C)(C)NC(C)(C)C1]

Step 1: 5-Methoxy-6-(6-(methyl(2,2,6,6-tetramethylpiperidin-4-yl)amino)pyridazin-3-yl)-8H-indeno[1,2-d]thiazol-2-amine To a microwave vial containing ethanol (1.2 mL) was added 6-methoxy-5-(6-(methyl(2,2,6,6-tetramethylpiperidin-4-yl)amino)pyridazin-3-yl)-2,3-dihydro-1H-inden-1-one (Intermediate 7-1, 100 mg, 0.25 mmol), thiourea (55.9 mL, 0.73 mmol), and iodine (124 mg, 0.49 mmol). The reaction mixture was stirred at 100° C. for 3 hours. The mixture was diluted with MeOH and loaded onto an SCX column. The crude material was washed with methanol then eluted with 2 N ammonia in methanol. The product-containing fractions were concentrated to afford 5-methoxy-6-(6-(methyl(2,2,6,6-tetramethylpiperidin-4-yl)amino)pyridazin-3-yl)-8H-indeno[1,2-d]thiazol-2-amine (114 mg) MS [M+H$^+$]=465.0.

Step 2: 2-Amino-6-(6-(methyl(2,2,6,6-tetramethyl-piperidin-4-yl)amino)pyridazin-3-yl)-8H-indeno[1,2-d]thiazol-5-ol Following standard GENERAL METHOD 3-2 for methoxy deprotection, the title compound was prepared. MS [M+H$^+$]=451.2, LCMS Rt=0.46 min [Method Q]; $^1$H NMR (400 MHz, DMSO-d$_6$) δ ppm 9.25-9.36 (m, 1H), 8.36-8.44 (m, 1H), 8.33 (d, J=9.85 Hz, 1H), 7.89 (s, 1H), 7.75-7.85 (m, 1H), 7.21 (s, 1H), 4.76-5.12 (m, 1H), 3.76 (s, 2H), 3.04 (s, 3H), 2.08 (t, J=12.88 Hz, 2H), 1.72-1.88 (m, 2H), 1.44-1.60 (m, 12H).

Example 35-6

Synthesis of 9-(6-(methyl(2,2,6,6-tetramethylpiperidin-4-yl)amino)pyridazin-3-yl)-5,6-dihydroimidazo[5,1-a]isoquinolin-8-ol hydrochloride salt

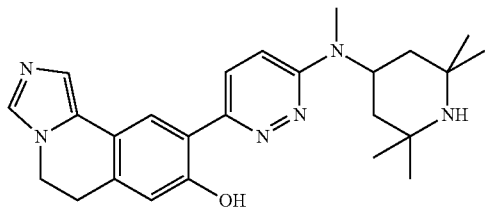 [SMILES: CN(c1ccc(-c2cc3c(cc2O)CCn2cncc2-3)nn1)C1CC(C)(C)NC(C)(C)C1]

Step 1: tert-Butyl 4-hydroxy-3-methoxyphenethylcarbamate

To a 250 mL round bottom flask containing DCM (86 mL) was added 4-(2-aminoethyl)-2-methoxyphenol hydrochloride (3.5 g, 17.19 mmol), TEA (7.2 mL, 51.6 mmol) and Boc-anhydride (3.94 mg, 18.04 mmol). The resulting mixture was stirred at RT for 18 hours then diluted with DCM, washed with H$_2$O, 1 N aqueous HCl, and brine, then the organic layer was dried with sodium sulfate and concentrated in vacuo to afford tert-butyl 4-hydroxy-3-methoxyphenethylcarbamate (4.59 g). $^1$H NMR (400 MHz, DMSO-d) δ ppm 8.71 (s, 1H), 6.85 (t, J=5.52 Hz, 1H), 6.72 (d, J=1.76 Hz, 1H), 6.63-6.68 (m, 1H), 6.55 (dd, J=8.03, 1.76 Hz, 1H), 3.74 (s, 3H), 3.01-3.13 (m, 2H), 2.53-2.62 (m, 2H), 1.37 (s, 9H).

Step 2: tert-Butyl 4-isopropoxy-3-methoxyphenethylcarbamate

To a 250 mL round bottom flask containing acetonitrile (18.7 mL) was added tert-butyl 4-hydroxy-3-methoxyphenethylcarbamate (1.0 g, 3.74 mmol), 2-bromopropane (0.51 g, 4.11 mmol), and potassium carbonate (1.5 g, 11.22 mmol). The resulting suspension was stirred at 65° C. for 18 hours. A second addition of 2-bromopropane (0.51 g, 4.11 mmol) was performed and heating was continued for another 18 hours. The reaction mixture was concentrated reaction in vacuo. The resulting oil was dissolved in EtOAc and washed with H$_2$O, aeqous saturated sodium bicarbonate and brine, then dried with sodium sulfate and concentrated in vacuo. The crude product was purified by silica gel chromatography (0-100% EtOAc in Heptane) to afford tert-butyl 4-isopropoxy-3-methoxyphenethylcarbamate (0.81 g). $^1$H NMR (400 MHz, CHLOROFORM-d) δ ppm 6.84 (d, J=8.03 Hz, 1H), 6.67-6.75 (m, 2H), 4.37-4.70 (m, 2H), 3.86 (s, 3H), 3.27-3.46 (m, 2H), 2.68-2.81 (m, 2H), 1.45 (s, 9H), 1.37 (d, J=6.02 Hz, 6H).

Step 3: 2-(4-Isopropoxy-3-methoxyphenyl)ethanamine hydrochloride

In a 50 mL round bottom flask was combined tert-butyl 4-isopropoxy-3-methoxyphenethylcarbamate (810 mg, 2.62 mmol) and HCl (4M in 1,4-dioxane) (6.5 mL, 26.2 mmol). The suspension was stirred at RT for two hours then concentrated in vacuo to afford 2-(4-isopropoxy-3-methoxyphenyl)ethanamine hydrochloride (643 mg) MS [M+H$^+$]=210.3.

Step 4: 2-Formamido-N-(4-isopropoxy-3-methoxyphenethyl)acetamide 2-(4-isopropoxy-3-methoxyphenyl)ethanamine hydrochloride (487 mg, 2.33 mmol) was taken up in MeOH and loaded onto an SCX column. The crude material was washed with methanol then eluted with 2 N ammonia in methanol. The product-containing fractions were concentrated to afford the free base 2-(4-isopropoxy-3-methoxyphenyl)ethanamine. This material was dissolved in THF (23.3 mL) and 2-formamidoacetic acid (360 mg, 3.49 mmol), DCC (528 mg, 2.56 mmol), HOBt (392 mg, 2.56 mmol), and NMM (1.02 mL, 9.31 mmol) were added. The resulting suspension was stirred at RT for 3 hours, diluted with ether and filtered through celite. The filtrate was purified by silica gel chromatography (25%-50% AcOH in DCM) to afford 2-formamido-N-(4-isopropoxy-3-methoxyphenethyl)acetamide (650 mg) MS [M+H$^+$]=295.3.

Step 5: 9-Isopropoxy-8-methoxy-5,6-dihydroimidazo[5,1-a]isoquinoline

To a 50 mL round bottom flask was added 2-formamido-N-(4-isopropoxy-3-methoxyphenethyl)acetamide (600 mg, 2.04 mmol) followed by acetonitrile (10.2 mL) and POCl$_3$ (0.57 mL, 6.12 mmol). The reaction mixture was heated to 80° C. for one hour then concentrated in vacuo. To the resulting oil was added H$_2$O and aqueous saturated sodium carbonate, then the solution was extracted with EtOAc (2×). The organic extracts were combined, dried with sodium sulfate and concentrated in vacuo. The crude product was purified by silica gel chromatography (0-10% MeOH in DCM) to afford 9-isopropoxy-8-methoxy-5,6-dihydroimidazo[5,1-a]isoquinoline (182 mg) MS [M+H$^+$]=259.2.

Step 6: 8-Methoxy-5,6-dihydroimidazo[5,1-a]isoquinolin-9-ol

To a 50 mL round bottom flask was added 9-isopropoxy-8-methoxy-5,6-dihydroimidazo[5,1-a]isoquinoline (180 mg, 0.70 mmol), chloroform (13 mL), and methanesulfonic acid (1.3 mL, 20.02 mmol). The resulting mixture was heated at 63° C. for 2 h then cooled to RT and concentrated in vacuo. To the resulting oil was added H$_2$O and aqueous saturated sodium carbonate. The solution was extracted with EtOAc (2×), and the organic extracts were combined, dried with sodium sulfate and concentrated in vacuo to afford 8-methoxy-5,6-dihydroimidazo[5,1-a]isoquinolin-9-ol. (151 mg) MS [M+H$^+$]=217.4.

Step 7: 8-Methoxy-5,6-dihydroimidazo[5,1-a]isoquinolin-9-yl trifluoromethanesulfonate To a solution of 8-methoxy-5,6-dihydroimidazo[5,1-a]isoquinolin-9-ol (196 mg, 2.27 mmol) in DCM (5.5 mL) was added triethylamine (0.38 mL, 2.72 mmol) at RT. The reaction mixture was cooled to 0° C., followed by addition of N-phenyltrifluoromethanesulfonimide (356 mg, 0.98 mmol). The reaction mixture was warmed to RT and stirred for 2 h. The reaction was quenched with aqueous sodium bicarbonate solution and extracted with DCM. The organic layer was dried over sodium sulfate, filtered and concentrated to give the crude product, which was purified on silica gel to provide 8-methoxy-5,6-dihydroimidazo[5,1-a]isoquinolin-9-yl trifluoromethanesulfonate (316 mg) MS [M+H$^+$]= 348.9.

Step 8. 8-Methoxy-9-(4,4,5,5-tetramethyl-1,3,2-dioxaborolan-2-yl)-5,6-dihydroimidazo[5,1-a]isoquinoline Following GENERAL METHOD 2-1 for boronate ester formation using 8-methoxy-5,6-dihydroimidazo[5,1-a]isoquinolin-9-yl trifluoromethanesulfonate (316 mg, 1.24 mmol) afforded 8-methoxy-9-(4,4,5,5-tetramethyl-1,3,2-dioxaborolan-2-yl)-5,6-dihydroimidazo[5,1-a]isoquinoline (271 mg) MS [M+H$^+$]=327.4.

Step 9: 6-(8-Methoxy-5,6-dihydroimidazo[5,1-a]isoquinolin-9-yl)-N-methyl-N-(2, 2, 6,6-tetramethylpiperidin-4-yl)pyridazin-3-amine Following standard GENERAL METHOD 1-4 for Suzuki coupling using 8-methoxy-9-(4,4,5,5-tetramethyl-1,3,2-dioxaborolan-2-yl)-5,6-dihydroimidazo[5,1-a]isoquinoline (104 mg, 0.32 mmol) and 6-chloro-N-methyl-N-(2,2,6,6-tetramethylpiperidin-4-yl)pyridazin-3-amine (Intermediate 1-1, 90 mg, 0.32 mmol), afforded 6-(8-methoxy-5,6-dihydroimidazo[5,1-a]isoquinolin-9-yl)-N-methyl-N-(2,2,6,6-tetramethylpiperidin-4-yl)pyridazin-3-amine (140 mg) MS [M+$^+$]=447.6.

Step 10: 9-(6-(Methyl(2,2,6,6-tetramethylpiperidin-4-yl)amino)pyridazin-3-yl)-5,6-dihydroimidazo[5,1-a]isoquinolin-8-ol Following standard GENERAL METHOD 3-2 for methoxy deprotection, the title compound was afforded. MS [M+H$^+$]=433.3, LCMS Rt=0.40 min [Method Q]; $^1$H NMR (400 MHz, METHANOL-d$_4$) δ ppm 8.97 (d, J=1.26 Hz, 1H), 8.46 (d, J=10.04 Hz, 1H), 8.21 (s, 1H), 7.98 (d, J=1.25 Hz, 1H), 7.85 (d, J=10.04 Hz, 1H), 7.10 (s, 1H), 5.08-5.35 (m, 1H), 4.50 (t, J=6.65 Hz, 2H), 3.26-3.31 (m, 2H), 3.17 (s, 3H), 1.99-2.11 (m, 4H), 1.67 (s, 6H), 1.57 (s, 6H).

Example 36-1

Synthesis of 4-hydroxy-3-(6-(methyl(2,2,6,6-tetramethylpiperidin-4-yl)amino)pyridazin-3-yl)-N-((1-methyl-1H-pyrazol-4-yl)methyl)benzamide

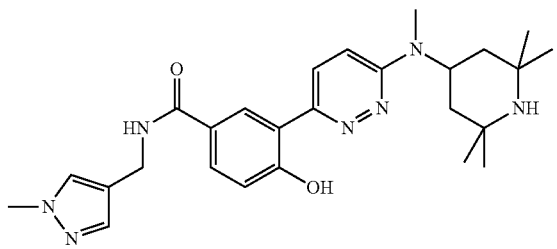

Step 1: 3-Bromo-4-methoxy-N-((1-methyl-1H-pyrazol-4-yl)methyl)benzamide

To a 100 mL round bottom flask containing 3-bromo-4-methoxybenzoic acid (500 mg, 2.16 mmol) and DCM (5 mL) was added oxalyl chloride (0.23 mL, 2.60 mmol) and DMF (0.1 mL, 0.13 mmol). The reaction mixture was stirred at RT for one hour and concentrated in vacuo. The resulting colorless oil was taken up in DCM (2.5 mL) and added to a mixture of (1-methyl-1H-pyrazol-4-yl)methanamine (241 mg, 2.16 mmol), TEA (0.60 mL, 4.33 mmol) and DCM (2.5 mL) at 0° C. The reaction mixture was stirred at RT for 0.5 hours then concentrated in vacuo. The crude material was purified by silica gel chromatography (0-10% MeOH in DCM) to afford 3-bromo-4-methoxy-N-((1-methyl-1H-pyrazol-4-yl)methyl)benzamide (702 mg) MS [M+H$^+$]= 325.9.

Step 2: (2-Methoxy-5-(((1-methyl-1H-pyrazol-4-yl)methyl)carbamoyl)phenyl)boronic acid Following GENERAL METHOD 2-1 for boronate ester formation using 3-bromo-4-methoxy-N-((1-methyl-1H-pyrazol-4-yl)methyl)benzamide (552 mg, 1.70 mmol) afforded (2-methoxy-5-(((1-methyl-1H-pyrazol-4-yl)methyl)carbamoyl)phenyl)boronic acid (492 mg) MS [M+H$^+$]=290.1.

Step 3: 4-Methoxy-3-(6-(methyl(2,2,6,6-tetramethylpiperidin-4-yl)amino)pyridazin-3-yl)-N-((1-methyl-1H-pyrazol-4-yl)methyl)benzamide Following standard GENERAL METHOD 1-4 for Suzuki coupling using (2-methoxy-5-(((1-methyl-1H-pyrazol-4-yl)methyl)carbamoyl)phenyl)boronic acid (613 mg, 2.12 mmol) and 6-chloro-N-methyl-N-(2,2,6,6-tetramethylpiperidin-4-yl)pyridazin-3-amine (Intermediate 1-1, 300 mg, 1.06 mmol) afforded 4-methoxy-3-(6-(methyl(2,2,6,6-tetramethylpiperidin-4-yl)amino)pyridazin-3-yl)-N-((1-methyl-1H-pyrazol-4-yl)methyl)benzamide (522 mg) MS [M+H$^+$]=492.6.

Step 4: 4-Hydroxy-3-(6-(methyl(2,2,6,6-tetramethylpiperidin-4-yl)amino)pyridazin-3-yl)-N-((1-methyl-1H-pyrazol-4-yl)methyl)benzamide Following standard GENERAL METHOD 3-2 for methoxy deprotection, the title compound was prepared. MS

[M+H$^+$]=478.3, LCMS Rt=0.46 min [Method Q]; $^1$H NMR (400 MHz, METHANOL-d$_4$) δ ppm 8.31 (d, J=2.26 Hz, 1H), 8.18 (d, J=10.04 Hz, 1H), 7.78 (dd, J=8.66, 2.13 Hz, 1H), 7.61 (s, 1H), 7.50 (s, 1H), 7.36 (d, J=10.04 Hz, 1H), 7.01 (d, J=8.53 Hz, 1H), 5.06-5.27 (m, 1H), 4.45 (s, 2H), 3.87 (s, 3H), 3.03 (s, 3H), 1.68-1.77 (m, 2H), 1.54-1.67 (m, 2H), 1.42 (s, 6H), 1.27 (s, 6H).

Example 37-1

Synthesis of 4-(4-(hydroxymethyl)-1H-pyrazol-1-yl)-2-(6-(methyl(2,2,6,6-tetramethylpiperidin-4-yl)amino)pyridazin-3-yl)phenol

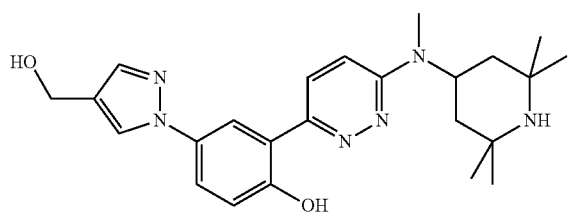 [SMILES: CN(c1ccc(-c2cc(-n3cc(CO)cn3)ccc2O)nn1)C1CC(C)(C)NC(C)(C)C1]

Step 1: (1-(3-Bromo-4-methoxyphenyl)-1H-pyrazol-3-yl)methanol

To a 100 mL round bottom flask was added copper (I) iodide (30.4 mg, 0.16 mmol), 2-(2-pyridyl)benzimidazole (31.2 mg, 0.16 mmol), cesium carbonate (625 mg, 1.92 mmol) and DMF (5.3 mL). The reaction mixture was heated to 60° C. for 1 h then (1H-pyrazol-3-yl)methanol (235 mg, 2.40 mmol) and 2-bromo-4-iodo-1-methoxybenzene (500 mg, 1.60 mmol) were added and the mixture was heated at 100° C. for 18 hours. The reaction was cooled, diluted with EtOAc and filtered through celite. The filtrate was concentrated in vacuo and purified by silica gel chromatography (0-100% EtOAc in Hepane) to afford (1-(3-bromo-4-methoxyphenyl)-1H-pyrazol-3-yl)methanol (353 mg) MS [M+2H$^+$]=285.0.

Step 2: (1-(4-Methoxy-3-(4,4,5,5-tetramethyl-1,3,2-dioxaborolan-2-yl)phenyl)-1H-pyrazol-3-yl) methanol Following GENERAL METHOD 2-1 for boronate ester formation using (1-(3-bromo-4-methoxyphenyl)-1H-pyrazol-3-yl)methanol (353 mg, 1.25 mmol) afforded (1-(4-methoxy-3-(4,4,5,5-tetramethyl-1,3,2-dioxaborolan-2-yl)phenyl)-1H-pyrazol-3-yl)methanol (412 mg) MS [M+H$^+$]=331.2.

Step 3: (1-(4-Methoxy-3-(6-(methyl(2,2,6,6-tetramethylpiperidin-4-yl)amino)pyridazin-3-yl)phenyl)-1H-pyrazol-4-yl)methanol To a microwave vial was added (1-(4-methoxy-3-(4,4,5,5-tetramethyl-1,3,2-dioxaborolan-2-yl)phenyl)-1H-pyrazol-3-yl)methanol (254 mg, 0.77 mmol), 6-chloro-N-methyl-N-(2,2,6,6-tetramethylpiperidin-4-yl)pyridazin-3-amine (Intermediate 1-1, 145 mg, 0.51 mmol), potassium phosphate (435 mg, 2.05 mmol), Pd$_2$(dba)$_3$ (46.9 mg, 0.05 mmol), and SPhos (21.1 mg, 0.05 mmol), followed by addition of 1,4-dioxane (1.3 mL)/H$_2$O (0.3 mL). The vial was purged with N$_2$ for 5 minutes and the reaction mixture was heated at 100° C. in the microwave for 2 h. The reaction mixture was concentrated in vacuo. The crude material was adjusted to pH 3 using 12 M HCl aqueous solution and loaded onto an SCX column. The crude material was washed with methanol then eluted with 2 N ammonia in methanol. The product-containing fractions were concentrated to afford (1-(4-methoxy-3-(6-(methyl(2,2,6,6-tetramethylpiperidin-4-yl)amino)pyridazin-3-yl)phenyl)-1H-pyrazol-4-yl) methanol (231 mg) MS [M+H$^+$]=451.3.

Step 4: 2-(6-(Methyl(2,2,6,6-tetramethylpiperidin-4-yl)amino)pyridazin-3-yl)-4-(1H-pyrazol-4-yl)phenol Following standard GENERAL METHOD 3-1 for methoxy deprotection, the title compound was prepared. MS [M+H$^+$]=437.3, LCMS Rt=0.50 min [Method Q]; $^1$H NMR (400 MHz, CHLOROFORM-d) δ ppm 8.43 (d, J=0.50 Hz, 1H), 8.38 (d, J=10.04 Hz, 1H), 8.19 (d, J=2.76 Hz, 1H), 7.69 (dd, J=8.78, 2.51 Hz, 1H), 7.63 (s, 1H), 7.36 (d, J=10.04 Hz, 1H), 7.04 (d, J=8.78 Hz, 1H), 4.87-5.13 (m, 2H), 4.45 (d, J=5.27 Hz, 2H), 2.97 (s, 3H), 1.36-1.67 (m, 4H), 1.25 (s, 7H), 1.09 (s, 6H).

Example 38-1

Synthesis of 5-(1H-pyrazol-4-yl)-2-(6-((2,2,6,6-tetramethylpiperidin-4-yl)methyl)pyridazin-3-yl)phenol

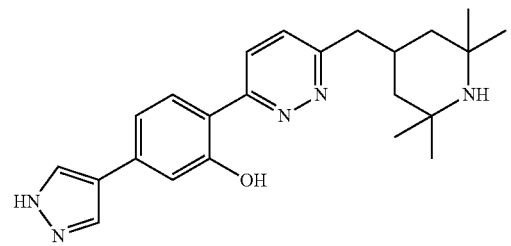 [SMILES: CC1(C)CC(Cc2ccc(-c3ccc(-c4cn[nH]c4)cc3O)nn2)CC(C)(C)N1]

Step 1: 3-Chloro-6-((2,2,6,6-tetramethylpiperidin-4-yl)methyl)pyridazine

To 50 mL flask was added 2,2,6,6-tetramethyl-4-methylenepiperidine 2,2,2-trifluoroacetate (1.1 g, 4.12 mmol) and 9-BBN (0.5 M in THF) (16.5 mL, 8.23 mmol) and the reaction mixture was heated at 65° C. for 1 h. The reaction was cooled to RT and 3,5-dichloropyridazine (0.61 g, 4.12 mmol), K$_2$CO$_3$ (1.7 g, 12.35 mmol), and PdCl$_2$(dppf). CH$_2$Cl$_2$ (0.17 g, 0.21 mmol) in 1,4-dioxane (8.5 mL)/H$_2$O (1.7 mL) were added and heated at 60° C. overnight. The reaction mixture was cooled to RT, diluted with EtOAc, filtered through celite and concentrated in vacuo. The crude material was adjusted to pH 3 using 12 M HCl aqueous solution and loaded onto an SCX column. The crude material was washed with methanol then eluted with 2 N ammonia in methanol. The product-containing fractions were concentrated to afford 3-chloro-6-((2,2,6,6-tetramethylpiperidin-4-yl)methyl)pyridazine (1.1 g) MS [M+$^+$]=268.2.

Step 2: 3-Methoxy-4-(6-((2,2,6,6-tetramethylpiperidin-4-yl)methyl)pyridazin-3-yl)phenol Following standard GENERAL METHOD 1-4 for Suzuki coupling using tert-butyl(3-methoxy-4-(4,4,5,5-tetramethyl- 1,3,2-dioxaborolan-2-yl)phenoxy)dimethylsilane (408 mg, 1.12 mmol) and 3-chloro-6-((2,2,6,6-tetramethylpiperidin-4-yl)methyl)pyridazine (200 mg, 0.75 mmol) affords 3-methoxy-4-(6-((2,2,6,6-tetramethylpiperidin-4-yl)methyl)pyridazin-3-yl)phenol (165 mg) MS [M+H⁺]=356.1.

Step 3: 3-Methoxy-4-(6-((2,2,6,6-tetramethylpiperidin-4-yl)methyl)pyridazin-3-yl)phenyl trifluoromethanesulfonate To a solution of 3-methoxy-4-(6-((2,2,6,6-tetramethylpiperidin-4-yl)methyl)pyridazin-3-yl)phenol (165 mg, 0.46 mmol) in DCM (2.8 mL) was added TEA (0.162 mL, 1.16 mmol) at RT. The reaction mixture was cooled to 00° C., followed by addition of N-phenyltrifluoromethanesulfonimide (174 mg, 0.49 mmol). The reaction mixture was warmed to RT and stirred for 2 h. The reaction was quenched with aqueous sodium bicarbonate solution and extracted with DCM. The organic layer was dried over sodium sulfate, filtered and concentrated in vacuo. The crude product was adjusted to pH 3 using 1 M HCl aqueous solution and loaded on an SCX column, then washed with methanol and eluted with 2 N ammonia in methanol. The product fractions were collected and dried to afford 3-methoxy-4-(6-((2,2,6,6-tetramethylpiperidin-4-yl)methyl)pyridazin-3-yl)phenyl trifluoromethanesulfonate (160 mg) MS [M+H⁺]=488.0.

Step 4: 3-(2-Methoxy-4-(1H-pyrazol-4-yl)phenyl)-6-((2,2,6,6-tetramethylpiperidin-4-yl)methyl)pyridazine To a microwave vial was added 3-methoxy-4-(6-((2,2,6,6-tetramethylpiperidin-4-yl)methyl)pyridazin-3-yl)phenyl trifluoromethanesulfonate (160 mg, 0.33 mmol), 1H-pyrazol-4-ylboronic acid, (73.4 mg, 0.66 mmol), potassium phosphate (209 mg, 0.99 mmol), Pd₂(dba)₃ (30.1 mg, 0.03 mmol), and SPhos (26.9 mg, 0.06 mmol), followed by addition of 1,4-dioxane (2.6 mL)/H₂O (0.7 mL). The vial was purged with N₂ for 5 minutes and the reaction mixture was heated at 100° C. in the microwave for 1 h. The reaction mixture was concentrated in vacuo. The crude material was adjusted to pH 3 using 1 M HCl aqueous solution and loaded on an SCX column. The crude material was washed with methanol then eluted with 2 N ammonia in methanol. The product-containing fractions were concentrated to afford 3-(2-methoxy-4-(1H-pyrazol-4-yl)phenyl)-6-((2,2,6,6-tetramethylpiperidin-4-yl)methyl)pyridazine (133 mg) MS [M+H⁺]=406.2.

Step 5: 5-(1H-Pyrazol-4-yl)-2-(6-((2, 2,6,6-tetramethylpiperidin-4-yl)methyl)pyridazin-3-yl)phenol Following standard GENERAL METHOD 3-2 for methoxy deprotection, the title compound was afforded. MS [M+H⁺]=392.4, LCMS Rt=0.45 min [Method Q]; ¹H NMR (400 MHz, DMSO-d₆) δ ppm 13.65 (br. s., 1H), 13.05 (br. s., 1H), 8.47 (d, J=9.03 Hz, 1H), 8.18 (br. s., 2H), 8.01 (d, J=8.28 Hz, 1H), 7.84 (d, J=9.03 Hz, 1H), 7.24-7.33 (m, 2H), 2.83 (d, J=7.03 Hz, 2H), 2.20-2.37 (m, 1H), 1.44 (dd, J=12.55, 2.76 Hz, 2H), 1.08 (s, 6H), 0.99 (s, 6H), 0.86 (t, J=12.42 Hz, 2H).

Example 39-1

Synthesis of 6-(3-(benzyloxy)isoquinolin-6-yl)-N-methyl-N-(2,2,6,6-tetramethylpiperidin-4-yl) pyridazin-3-amine

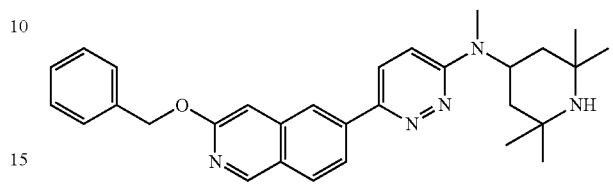

Step 1: 3-(Benzyloxy)-6-bromoisoquinoline

To a 25 mL round-bottomed flask containing 6-bromoisoquinolin-3-ol (500 mg, 2.23 mmol) was added TEA (0.467 mL, 3.35 mmol) and benzyl bromide (0.319 mL, 2.68 mmol) in DMF (10 mL) to give a brown solution. The reaction was heated to 80° C. overnight. After cooling to RT, the reaction mixture was concentrated in vacuo, and taken up in DCM and water. The water was extracted with DCM (2×), and the combined organic fractions were washed with brine, dried over MgSO₄, filtered, and concentrated in vacuo. The residue was purify by flash column chromatography (10-30-50% EtOAc/Heptanes), providing the title compound (132 mg, 0.420 mmol, 19% yield). M+1=316.0. ¹H NMR (400 MHz, CHLOROFORM-d) δ 8.92 (s, 1H), 7.85 (d, J=1.25 Hz, 1H), 7.74 (d, J=8.78 Hz, 1H), 7.31-7.52 (m, 6H), 6.99 (s, 1H), 5.48 (s, 2H).

Step 2: 3-(Benzyloxy)-6-(4,4,5,5-tetramethyl-1,3,2-dioxaborolan-2-yl)isoquinoline Following GENERAL METHOD 2-1 for boronate ester formation using 3-(benzyloxy)-6-bromoisoquinoline (125 mg, 0.398 mmol) the title compound was prepared (115 mg, 0.398 mmol, 80% yield). M+1=362.3. ¹H NMR (400 MHz, CHLOROFORM-d) δ 8.98 (s, 1H), 8.20 (s, 1H), 7.87 (d, J=8.28 Hz, 1H), 7.72 (dd, J=8.28, 1.00 Hz, 1H), 7.50-7.54 (m, 2H), 7.36-7.42 (m, 2H), 7.30-7.35 (m, 1H), 7.12 (s, 1H), 5.48 (s, 2H), 1.40 (s, 12H).

Step 3: 6-(3-(Benzyloxy)isoquinolin-6-yl)-N-methy-N-(2,2,6,6-tetramethylpiperidin-4-yl)pyridazin-3-amine The title compound (38 mg, 0.077 mmol, 49% yield) was prepared following GENERAL METHOD 1-4 for Suzuki coupling from 3-(benzyloxy)-6-(4,4,5,5-tetramethyl-1,3,2-dioxaborolan-2-yl)isoquinoline (115 mg, 0.318 mmol) and Intermediate 1-1 (45 mg, 0.159 mmol). LCMS Rt=0.61 min [Method Q]; MS (M+1)=482.4. ¹H NMR (400 MHz, METHANOL-d4) δ ppm 8.95 (s, 1H), 8.21 (s, 1H), 8.01-8.09 (m, 2H), 7.96 (d, J=9.79 Hz, 1H), 7.49-7.54 (m, 2H), 7.36-7.42 (m, 2H), 7.30-7.35 (m, 1H), 7.23 (s, 1H), 7.16 (d, J=9.79 Hz, 1H), 5.40 (s, 2H), 5.28 (t, J=11.67 Hz, 1H), 3.00 (s, 3H), 1.67-1.73 (m, 2H), 1.56-1.65 (m, 2H), 1.41 (s, 6H), 1.26 (s, 6H).

Example 39-2

Synthesis of 6-(1-(benzyloxy)isoquinolin-7-yl)-N-methyl-N-(2,2,6,6-tetramethylpiperidin-4-yl)pyridazin-3-amine

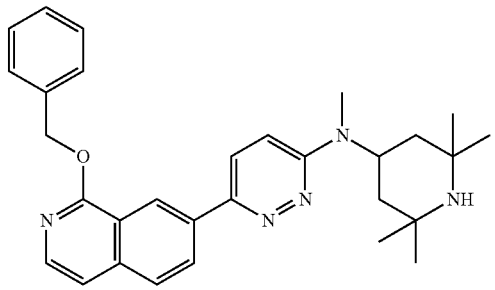 [SMILES: CN(c1ccc(-c2ccc3ccnc(OCc4ccccc4)c3c2)nn1)C1CC(C)(C)NC(C)(C)C1]

Step 1: 1-(Benzyloxy)-7-bromoisoquinoline

To a 25 mL round-bottom flask containing 7-bromoisoquinolin-1-ol (500 mg, 2.23 mmol) was added TEA (0.467 mL, 3.35 mmol) and benzyl bromide (0.319 mL, 2.68 mmol) in DMF (10 mL) to give a brown solution. The reaction was heated to 80° C. overnight. After cooling to RT, the reaction mixture was concentrated in vacuo, and taken up in DCM and water. The aqueous layer was extracted with DCM (2×), and the combined organics fractions were washed with brine, dried over MgSO$_4$, filtered, and concentrated in vacuo. The residue was purify by flash column chromatography (10-30-50% EtOAc/Heptanes), providing the title compound (640 mg, 2.037 mmol, 91% yield). M+1=316.0. $^1$H NMR (400 MHz, CHLOROFORM-d) δ 8.62 (d, J=2.01 Hz, 1H), 7.73 (dd, J=2.13, 8.41 Hz, 1H), 7.39 (d, J=8.28 Hz, 1H), 7.28-7.36 (m, 5H), 7.11 (d, J=7.53 Hz, 1H), 6.46 (d, J=7.28 Hz, 1H), 5.23 (s, 2H).

Step 2: 1-(Benzyloxy)-7-(4,4,5,5-tetramethyl-1,3,2-dioxaborolan-2-yl)isoquinoline Following GENERAL METHOD 2-1 for boronate ester formation using 1-(benzyloxy)-7-bromoisoquinoline (250 mg, 0.796 mmol) afforded the title compound (207 mg, 0.573 mmol, 72% yield). M+1=362.2. $^1$H NMR (400 MHz, CHLOROFORM-d) δ 8.96 (s, 1H), 8.00 (dd, J=7.91, 1.13 Hz, 1H), 7.47 (d, J=7.78 Hz, 1H), 7.27-7.34 (m, 5H), 7.11 (d, J=7.53 Hz, 1H), 6.46 (d, J=7.28 Hz, 1H), 5.23 (s, 2H), 1.36 (s, 12H).

Step 3: 6-(1-(Benzyloxy)isoquinolin-7-yl)-N-methyl-N-(2,2,6,6-tetramethylpiperidin-4-yl)pyridazin-3-amine The title compound (120 mg, 0.249 mmol, 94% yield) was prepared following GENERAL METHOD 1-4 for Suzuki reaction from 1-(benzyloxy)-7-(4,4,5,5-tetramethyl-1,3,2-dioxaborolan-2-yl)isoquinoline (144 mg, 0.398 mmol) and (Intermediate 1-1, 75 mg, 0.265 mmol). LCMS Rt=0.57 min [Method Q]; MS (M+1)=482.4. $^1$H NMR (400 MHz, METHANOL-d4) δ ppm 8.81 (d, J=2.01 Hz, 1H), 8.39 (dd, J=8.41, 1.88 Hz, 1H), 7.99 (d, J=9.79 Hz, 1H), 7.76 (d, J=8.53 Hz, 1H), 7.72-7.74 (m, 1H), 7.46 (d, J=7.28 Hz, 1H), 7.26-7.37 (m, 5H), 7.24 (d, J=9.79 Hz, 1H), 6.76 (d, J=7.53 Hz, 1H), 5.29 (s, 2H), 3.01 (s, 3H), 1.71-1.78 (m, 2H), 1.61-1.70 (m, 2H), 1.44 (s, 6H), 1.29 (s, 6H).

Example 40-1

Synthesis of 3-fluoro-5-(2-methoxypyridin-4-yl)-2-(6-(methyl(2,2,6,6-tetramethylpiperidin-4-yl)amino)pyridazin-3-yl)phenol hydrochloride salt

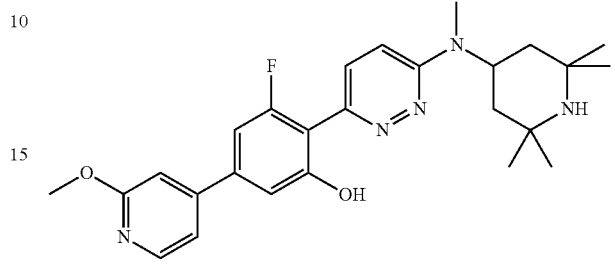

Following GENERAL METHOD 1-6 for Suzuki cross-coupling, 5-bromo-3-fluoro-2-(6-(methyl(2,2,6,6-tetramethylpiperidin-4-yl)amino)pyridazin-3-yl)phenol (Intermediate 8-1) and (2-methoxypyridin-4-yl)boronic acid were reacted and the crude product was purified via reverse phase preparative HPLC (10% CH$_3$CN to 30% in H$_2$O). After salt formation, 3-fluoro-5-(2-methoxypyridin-4-yl)-2-(6-(methyl(2,2,6,6-tetramethylpiperidin-4-yl)amino)pyridazin-3-yl)phenol hydrochloride salt was afforded as a yellow solid (5.7 mg). LCMS Rt=0.56 min [Method Q]; [M+H]: 466.4; $^1$H NMR (400 MHz, MeOD) δ 8.25 (d, J=5.5 Hz, 1H), 8.20 (d, J=10.0 Hz, 1H), 7.71 (d, J=10.0 Hz, 1H), 7.30 (dd, J=5.5, 1.5 Hz, 1H), 7.21 (dd, J=12.0, 1.5 Hz, 1H), 7.21 (s, 1H), 7.13 (d, J=1.0 Hz, 1H), 5.38-5.22 (m, 1H), 4.01 (s, 3H), 3.14 (s, 3H), 2.03 (d, J=8.5 Hz, 4H), 1.67 (s, 6H), 1.56 (s, 6H).

Example 40-2

Synthesis of 4-(3-fluoro-5-hydroxy-4-(6-(methyl(2,2,6,6-tetramethylpiperidin-4-yl)amino)pyridazin-3-yl)phenyl)pyridin-2(1H)-one hydrochloride salt

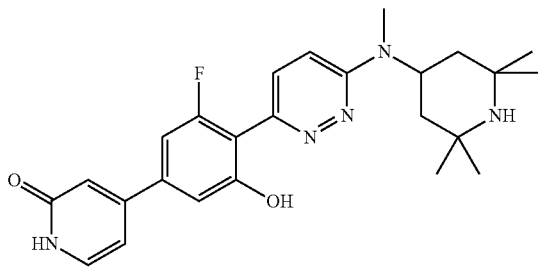 [SMILES: CN(c1ccc(-c2c(O)cc(-c3cc[nH]c(=O)c3)cc2F)nn1)C1CC(C)(C)NC(C)(C)C1]

3-Fluoro-5-(2-methoxypyridin-4-yl)-2-(6-(methyl(2,2,6,6-tetramethylpiperidin-4-yl)amino)pyridazin-3-yl)phenol hydrochloride salt (Example 40-1, 10 mg, 0.02 mmol) and pyridine hydrochloride (50 mg, 0.43 mmol) were heated at 170° C. for 15 minutes in a Biotage® Initiator microwave reactor. The reaction mixture was diluted with MeOH/DMSO, and purified via reverse phase preparative HPLC (10 to 45% acetonitrile in water, 0.1% trifluoroacetic acid as modifier). The appropriate fractions containing product were free based by catch and release using SiliaBond Propylsulphonic Acid® (4 eq, methanol as eluent and a 2 N ammonia solution in MeOH to release the material). The solvent was concentrated in vacuo and the resulting solid was suspended in CH₃CN/H₂O (3/1 mL). 1 M aqueous HCl (3 equivalents) was added and solvent was concentrated in vacuo to afford the title compound as a yellow solid (3 mg, 26%). LCMS Rt=0.47 min [Method Q]; [M+H]: 452.3; ¹H NMR (400 MHz, MeOD) δ 8.28 (d, J=10.0 Hz, 1H), 8.07 (d, J=10.0 Hz, 1H), 7.69 (d, J=6.5 Hz, 1H), 7.25 (dd, J=11.0, 1.5 Hz, 1H), 7.19 (s, 1H), 6.89 (s, 1H), 6.85 (dd, J=6.5, 1.5 Hz, 1H), 5.07 (bs, 1H), 3.21 (s, 3H), 2.20-2.00 (m, 4H), 1.66 (s, 6H), 1.59 (s, 6H).

Example 40-3

Synthesis of 4-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt

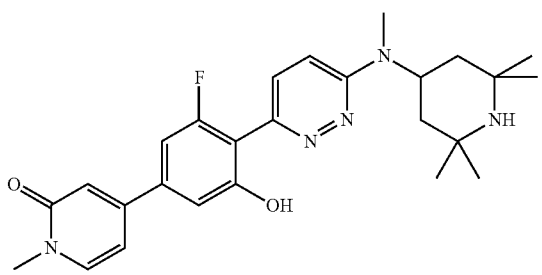 [SMILES: CN(c1ccc(-c2c(O)cc(-c3ccn(C)c(=O)c3)cc2F)nn1)C1CC(C)(C)NC(C)(C)C1]

Following GENERAL METHOD 1-6 for Suzuki cross-coupling, 1-methyl-4-(4,4,5,5-tetramethyl-1,3,2-dioxaborolan-2-yl)pyridin-2(1H)-one and 5-bromo-3-fluoro-2-(6-(methyl(2,2,6,6-tetramethylpiperidin-4-yl)amino)pyridazin-3-yl)phenol (Intermediate 8-1) were reacted and the crude product was purified via reverse phase preparative HPLC (10% CH₃CN to 30% in H₂O). After salt formation, 4-(3-fluoro-5-hydroxy-4-(6-(methy (2,2,6,6-tetramethylpiperidin-4-yl)amino)pyridazin-3-yl)phenyl)-1-methylpyridin-2 (1H)-one hydrochloride salt was afforded as a yellow solid (10 mg, 12%). LCMS Rt=0.49 min [Method Q]; [M+H]: 466.3; ¹H NMR (400 MHz, MeOD) δ 8.22 (d, J=10.0 Hz, 1H), 7.86-7.73 (m, 2H), 7.24-7.13 (m, 2H), 6.82 (d, J=2.0 Hz, 1H), 6.72 (dd, J=7.0, 2.0 Hz, 1H), 5.30-5.15 (m, 1H), 3.64 (s, 3H), 3.16 (s, 3H), 2.04 (d, J=8.0 Hz, 4H), 1.67 (s, 6H), 1.57 (s, 6H).

Example 40-4

Synthesis of 5-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt

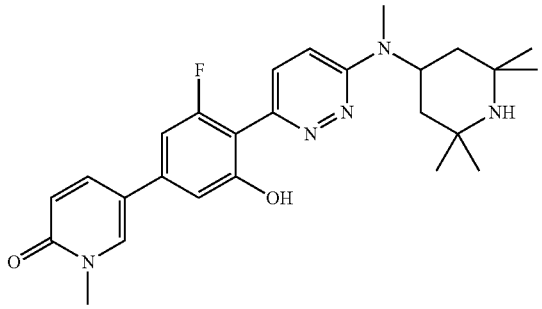 [SMILES: CN(c1ccc(-c2c(O)cc(-c3ccc(=O)n(C)c3)cc2F)nn1)C1CC(C)(C)NC(C)(C)C1]

Following GENERAL METHOD 1-6 for Suzuki cross-coupling, 5-bromo-3-fluoro-2-(6-(methyl(2,2,6,6-tetrameth-ylpiperidin-4-yl)amino)pyridazin-3-yl)phenol and 1-methyl-5-(4,4,5,5-tetramethyl-1,3,2-dioxaborolan-2-yl)pyridin-2(1H)-one were reacted and the crude product was purified via reverse phase preparative HPLC (10% CH₃CN to 30% in H₂O). After salt formation, 5-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt was afforded as a yellow solid (8.0 mg, 11%). LCMS Rt=0.49 min [Method Q]; [M+H]: 466.3; ¹H NMR (400 MHz, MeOD) δ 8.28 (d, J=10.0 Hz, 1H), 8.08 (d, J=10.0 Hz, 1H), 7.83 (d, J=7.0 Hz, 1H), 7.23 (dd, J=11.0, 1.5 Hz, 1H), 7.17 (s, 1H), 6.84 (d, J=2.0 Hz, 1H), 6.75 (dd, J=7.0, 2.0 Hz, 1H), 5.06 (bs, 1H), 3.66 (s, 3H), 3.21 (s, 3H), 2.19-2.01 (m, 4H), 1.66 (s, 6H), 1.59 (s, 6H).

Example 40-5

Synthesis of 3-fluoro-5-(1H-pyrazol-4-yl)-2-(6-((2,2,6,6-tetramethylpiperidin-4-yl)oxy)pyridazin-3-yl)phenol hydrochloride salt

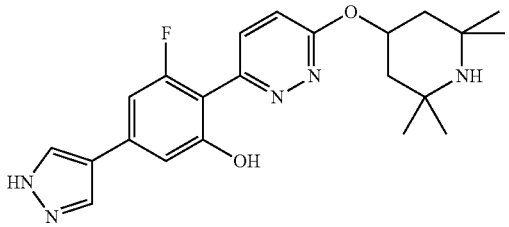 [SMILES: CC1(C)CC(Oc2ccc(-c3c(O)cc(-c4cn[nH]c4)cc3F)nn2)CC(C)(C)N1]

Step 1: 3-(2-Fluoro-4-methoxyphenyl)-6-((2,2,6,6-tetramethylpiperidin-4-yl)oxy)pyridazine Intermediate 1-3 (2.14 g, 7.92 mmol), (2-fluoro-4-methoxyphenyl)boronic acid (2.02 g, 11.9 mmol), and a 0.5 M aqueous solution of K₃PO₄ (32 ml, 16 mmol) were added to a microwave vial. 2nd Generation XPhos Precatalyst (0.19 g, 0.24 mmol) was added to the mixture followed by addition of THF (16 mL). The reaction mixture was sealed and stirred at RT for 2 h then extracted with EtOAc (3×). The combined organic layers were washed with brine, dried over Na₂SO₄, filtered and concentrated in vacuo to provide 3-(2-fluoro-4-methoxyphenyl)-6-((2,2,6,6-tetramethylpiperidin-4-yl)oxy)pyridazine as a brown solid (2.85 g, 90%). [M+H]: 360.3; ¹H NMR (400 MHz, MeOD) δ 7.90 (dd, J=9.5, 2.5 Hz, 1H), 7.81 (t, J=9.0 Hz, 1H), 7.18 (d, J=9.5 Hz, 1H), 6.94 (dd, J=9.0, 2.5 Hz, 1H), 6.88 (dd, J=13.0, 2.5 Hz, 1H), 5.79 (tt, J=11.0, 4.0 Hz, 1H), 3.89 (s, 3H), 2.24 (dd, J=12.0, 4.0 Hz, 2H), 1.43 (t, J=12.0 Hz, 2H), 1.37 (s, 6H), 1.26 (s, 6H).

Step 2: 3-Fluoro-4-(6-((2,2,6,6-tetramethylpiperidin-4-yl)oxy)pyridazin-3-yl)phenol 3-(2-Fluoro-4-methoxyphenyl)-6-((2,2,6,6-tetramethylpiperidin-4-yl)oxy)pyridazine (1.08 g, 3.00 mmol) was dissolved in CH₂Cl₂ (15 mL) and a 1 M solution of BBr₃ in CH₂Cl₂ (7.5 mL, 7.5 mmol) was added dropwise. The reaction mixture was stirred at RT overnight, then diluted with CH₂Cl₂ and a pH 4 buffered aqueous solution. The aqueous phase was washed with 3:1 chloroform/propan-2-ol (2×), then basified to pH 8 with saturated NaHCO₃. The aqueous phase was extracted with 3:1 chloroform/propan-2-ol (4×). The combined organic phases were dried over anhydrous Na₂SO₄, filtered and concentrated under reduced pressure. 3-Fluoro-4-(6-((2,2,6,6-tetramethylpiperidin-4-yl)oxy)pyridazin-3-yl)phenol was afforded as a brown solid (0.59 g, 52%). [M+H]: 346.4; $^1$H NMR (400 MHz, MeOD) δ 7.88 (dd, J=9.0, 2.2 Hz, 1H), 7.69 (t, J=9.0 Hz, 1H), 7.16 (d, J=9.0 Hz, 1H), 6.76 (dd, J=9.0, 2.0 Hz, 1H), 6.65 (dd, J=13.0, 2.0 Hz, 1H), 5.78 (tt, J=11.0, 4.0 Hz, 1H), 2.26 (dd, J=12.5, 4.0 Hz, 2H), 1.47 (t, J=12.0 Hz, 2H), 1.39 (s, 6H), 1.29 (s, 6H).

Step 3: 3-Fluoro-4-(6-((2,2,6,6-tetramethylpiperidin-4-yl)oxy)pyridazin-3-yl)phenyl trifluoromethanesulfonate 3-Fluoro-4-(6-((2,2,6,6-tetramethylpiperidin-4-yl)oxy) pyridazin-3-yl)phenol (0.70 g, 2.03 mmol), N-phenylbis(trifluoromethane-sulfonimide) (0.72 g, 2.03 mmol), $K_2CO_3$ (0.84 g, 6.08 mmol) and THF (10 mL) were mixed in a microwave vial. The reaction mixture was heated to 120° C. for 10 minutes in a Biotage® Initiator microwave reactor. The volatiles were removed under vacuum. A 1 M aqueous solution of NaOH was added and the aqueous phase was extracted with DCM (2×). The combined organic layers were washed with brine, dried over $Na_2SO_4$, filtered and concentrated to dryness in vacuo. The crude material was purified by flash column chromatography using silica gel (elution gradient of 10-50% (3/1) EtOAc/2 N $NH_3$ in EtOH, in heptane) to give 3-fluoro-4-(6-((2,2,6,6-tetramethylpiperidin-4-yl)oxy)pyridazin-3-yl)phenyl trifluoromethanesulfonate as a red gray solid (0.63 g, 66%). [M+H]: 478.2; $^1$H NMR (400 MHz, MeOD) δ 8.09 (t, J=8.6 Hz, 1H), 7.99 (dd, J=9.2, 2.4 Hz, 1H), 7.50 (dd, J=10.6, 2.4 Hz, 1H), 7.45 (dd, J=8.6, 2.4 Hz, 1H), 7.24 (d, J=9.5 Hz, 1H), 5.82 (tt, J=11.2, 4.2 Hz, 1H), 2.24 (dd, J=12.6, 4.1 Hz, 2H), 1.43 (t, J=11.7 Hz, 2H), 1.36 (s, 6H), 1.25 (s, 6H).

Step 4: 3-Fluoro-5-hydroxy-4-(6-((2,2,6,6-tetramethylpiperidin-4-yl)oxy)pyridazin-3-yl)phenyl trifluoromethanesulfonate 3-Fluoro-4-(6-((2,2,6,6-tetramethylpiperidin-4-yl)oxy) pyridazin-3-yl)phenyl trifluoromethanesulfonate (0.48 g, 1.01 mmol), PhI(OAc)$_2$ (0.46 g, 1.41 mmol), and Pd(OAc)$_2$ (68 mg, 0.10 mmol) were dissolved in a mixture of acetic acid (4 mL) and acetic anhydride (4 mL). The mixture was stirred at 80° C. for 3 h. The crude reaction was purified by catch and release using SiliaBond Propylsulfonic Acid® (5 eq, $CH_3CN$ as eluent and a 2 N ammonia solution in MeOH to release the material). The solvent was concentrated in vacuo and 3-fluoro-5-hydroxy-4-(6-((2,2,6,6-tetramethylpiperidin-4-yl)oxy)pyridazin-3-yl)phenyl trifluoromethanesulfonate was afforded as a green solid (0.50 g, 100%). [M+H]: 494.3; $^1$H NMR (400 MHz, MeOD) δ 8.09 (t, J=8.5 Hz, 1H), 7.99 (dd, J=9.5, 2.5 Hz, 1H), 7.50 (dd, J=10.5, 2.5 Hz, 1H), 7.45 (dd, J=8.5, 2.5 Hz, 1H), 7.24 (d, J=9.5 Hz, 1H), 5.82 (tt, J=11.0, 4.0 Hz, 1H), 2.24 (dd, J=12.5, 4.0 Hz, 2H), 1.43 (t, J=12.0 Hz, 2H), 1.36 (s, 6H), 1.25 (s, 6H).

Step 5: 3-Fluoro-5-(1H-pyrazol-4-yl)-2-(6-((2,2,6,6-tetramethylpiperidin-4-yl)oxy)pyridazin-3-yl)phenol hydrochloride salt Following the representative procedure GENERAL METHOD 1-6 for Suzuki cross-coupling, 3-fluoro-5-hydroxy-4-(6-((2,2,6,6-tetramethylpiperidin-4-yl)oxy) pyridazin-3-yl)phenyl trifluoromethanesulfonate and 4-(4,4,5,5-tetramethyl-1,3,2-dioxaborolan-2-yl)-1H-pyrazole-1-carboxylate were reacted and the crude product was purified via reverse phase preparative HPLC (10% $CH_3CN$ to 30% in $H_2O$). After salt formation, the hydrochloride salt of 3-fluoro-5-(1H-pyrazol-4-yl)-2-(6-((2,2,6,6-tetramethylpiperidin-4-yl)oxy)pyridazin-3-yl)phenol hydrate was afforded as a yellow solid (49 mg, 25%). LCMS Rt=0.49 min; [M+H]: 412.3; $^1$H NMR (400 MHz, MeOD) δ 8.51 (d, J=9.5 Hz, 1H), 8.26 (s, 2H), 7.87 (d, J=9.5 Hz, 1H), 7.21 (dd, J=12.0, 1.5 Hz, 1H), 7.16 (s, 1H), 5.77 (tt, J=10.5, 4.0 Hz, 1H), 2.52 (dd, J=14.0, 4.0 Hz, 2H), 1.93 (dd, J=14.0, 10.5 Hz, 2H), 1.64 (s, 6H), 1.59 (s, 6H).

Example 40-6

Synthesis of 5-chloro-3-fluoro-2-(6-(methyl(2,2,6,6-tetramethylpiperidin-4-yl)amino)pyridazin-3-yl)phenol hydrochloride salt

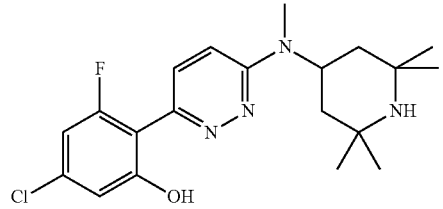 [SMILES: CN(c1ccc(-c2c(O)cc(Cl)cc2F)nn1)C1CC(C)(C)NC(C)(C)C1]

Step 1: 6-(4-Chloro-2-fluorophenyl)-N-methyl-N-(2,2,6,6-tetramethylpiperidin-4-yl)pyridazin-3-amine (4-Chloro-2-fluorophenyl)boronic acid (4.29 g, 24.6 mmol), Intermediate 1-1 (6.63 g, 23.4 mmol) and $Na_2CO_3$ (7.45 g, 70.3 mmol) were degassed for 10 minutes with $N_2$, then PdCl$_2$(dppf)CH$_2$Cl$_2$ (0.96 g, 1.17 mmol) was added. The reaction mixture was heated at 90° C. for 2 h. The reaction mixture was concentrated in vacuo then CH$_2$Cl$_2$ and 1 M HCl were added. The aqueous phase was washed with CH$_2$Cl$_2$, then basified to pH 14 with a 6 M NaOH solution. The aqueous phase was then extracted with CH$_2$Cl$_2$ (3×). The combined organic phases were dried over anhydrous $Na_2SO_4$, filtered and concentrated under reduced pressure to afford 6-(4-chloro-2-fluorophenyl)-N-methyl-N-(2,2,6,6-tetramethylpiperidin-4-yl)pyridazin-3-amine as a brown solid (8.40 g, 95%). [M+H]: 377.2; $^1$H NMR (400 MHz, MeOD) δ 7.87 (t, J=8.5 Hz, 1H), 7.76 (dd, J=9.5, 2.4 Hz, 1H), 7.32-7.40 (m, 2H), 7.17 (d, J=9.5 Hz, 1H), 5.13-5.36 (m, 1H), 1.69 (dd, J=12.5, 3.5 Hz, 2H), 1.57 (t, J=12.5 Hz, 2H), 1.38 (s, 6H), 1.23 (s, 6H).

Step 2: 5-Chloro-3-fluoro-2-(6-(methyl(2,2,6,6-tetramethylpiperidin-4-yl)amino)pyridazin-3-yl)phenol. Hydrochloride salt 6-(4-Chloro-2-fluorophenyl)-N-methyl-N-(2,2,6,6-tetramethylpiperidin-4-yl)pyridazin-3-amine (50 mg, 0.13 mmol), PhI(OAc)$_2$ (60 mg, 0.19 mmol), and Pd(OAc)$_2$ (8.9 mg, 0.013 mmol) were dissolved in a mixture of acetic acid (0.6 mL) and acetic anhydride (0.6 mL). The mixture was stirred at 40° C. overnight. A solution of sodium thiosulfate was added and the mixture was stirred for 8 days at RT. A solution of potassium carbonate was added and the reaction pH was adjusted to 10. The aqueous phase was extracted (2×) with dichloromethane and methanol (9:1). The combined organic phases were dried over anhydrous $Na_2SO_4$, filtered and concentrated under reduced pressure. The crude material was purified via reverse phase preparative HPLC (10 to 30% acetonitrile in water, 0.1% trifluoroacetic acid as modifier). The appropriate fractions containing product were free based by catch and release using SiliaBond Propylsulphonic Acid® (4 eq, CH$_3$CN as eluent and a 2 N ammonia solution in MeOH to release the material). The solvent was concentrated in vacuo and the resulting solid was suspended in CH$_3$CN/H$_2$O (3/1 mL). 1 M aqueous HCl (3 equivalents) was added, and the volatiles were concentrated in vacuo to afford the hydrochloride salt of 5-chloro-3-fluoro-2-(6-(methyl(2,2,6,6-tetramethylpiperidin-4-yl)amino)pyridazin-3-yl)phenol as a yellow solid (19 mg, 33%). LCMS Rt=0.57 min [Method Q]; [M+H]: 393.2; $^1$H NMR (400 MHz, MeOD) δ 8.21 (d, J=10.0 Hz, 1H), 7.99 (d, J=10.0 Hz, 1H), 6.99 (dd, J=10.0, 2.0 Hz, 1H), 6.94 (t, J=2.0 Hz, 1H), 5.09 (bs, 1H), 3.18 (s, 3H), 1.98-2.12 (m, 4H), 1.65 (s, 6H), 1.57 (s, 6H).

Example 40-7

Synthesis of 3-fluoro-2-(6-(methyl(2,2,6,6-tetramethylpiperidin-4-yl)amino)pyridazin-3-yl)-5-(1H-pyrazol-4-yl)phenol hydrochloride salt

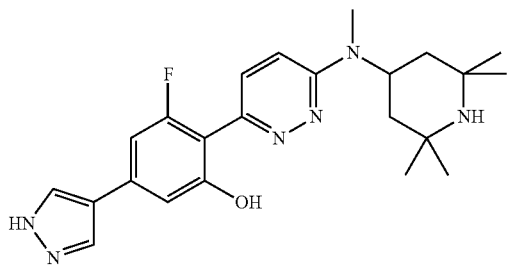 [SMILES: CN(c1ccc(-c2c(O)cc(-c3cn[nH]c3)cc2F)nn1)C1CC(C)(C)NC(C)(C)C1]

5-Chloro-3-fluoro-2-(6-(methyl(2,2,6,6-tetramethylpiperidin-4-yl)amino)pyridazin-3-yl)phenol (Example 40-6, 0.32 g, 0.82 mmol), tert-butyl 4-(4,4,5,5-tetramethyl-1,3,2-dioxaborolan-2-yl)-1H-pyrazole-1-carboxylate (1.00 g, 3.40 mmol), and Cs$_2$CO$_3$ (5.52 g, 26.0 mmol) were added to a microwave vial. XPhos Precatalyst (60 mg, 0.08 mmol) was then added to the mixture followed by dioxane (5 mL) and water (0.9 mL). The reaction mixture was sealed and stirred at 130° C. for 2 h in a Biotage® Initiator microwave reactor. The reaction mixture was filtered through celite and the filter cake was washed with methanol. The filtrate was concentrated in vacuo. The crude product was purified via reverse phase preparative HPLC (10 to 45% acetonitrile in water, 0.1% trifluoroacetic acid as modifier). The appropriate fractions containing product were free based by catch and release using SiliaBond Propylsulphonic Acid® (4 eq, methanol as eluent and a 2 N ammonia solution in MeOH to release the material). The solvent was concentrated in vacuo and the resulting solid was dissolved in MeOH. SiliaMetS® DMT (6 eq.) was added and the mixture was shaken for 18 h. The solid was filtered and the filtrate was concentrated in vacuo. The resulting solid was suspended in CH$_3$CN/H$_2$O (6/2 mL). 1 M HCl aqueous (3 equivalents) was added and volatiles were concentrated in vacuo to provide the hydrochloride salt of 3-fluoro-2-(6-(methyl(2,2,6,6-tetramethylpiperidin-4-yl)amino)pyridazin-3-yl)-5-(1H-pyrazol-4-yl)phenol as a yellow solid (47 mg). LCMS Rt=0.48 min [Method Q]; [M+H]: 425.3; $^1$H NMR (400 MHz, MeOD) δ 8.25-8.32 (m, 1H), 8.14 (s, 2H), 8.04 (d, J=10.0 Hz, 1H), 7.19 (dd, J=11.5, 1.5 Hz, 1H), 7.11 (s, 1H), 5.10 (bs, 1H), 3.19 (s, 3H), 1.91-2.24 (m, 4H), 1.66 (s, 6H), 1.57 (s, 6H).

Example 40-8

Synthesis of 3-fluoro-2-(6-(methyl(2,2,6,6-tetramethylpiperidin-4-yl)amino)pyridazin-3-yl)-5-(1-methyl-1H-pyrazol-4-yl)phenol hydrochloride salt

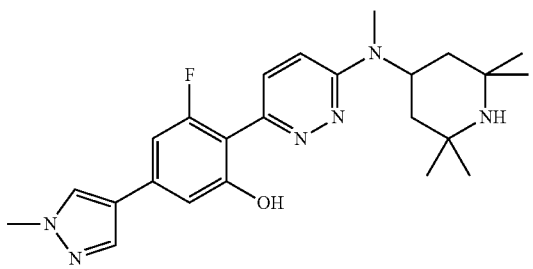

Step 1: 6-(2-Fluoro-6-methoxy-4-(1-methyl-1H-pyrazol-4-yl)phenyl)-N-methyl-N-(2,2,6,6-tetramethylpiperidin-4-yl)pyridazin-3-amine Following GENERAL METHOD 1-6 for Suzuki cross-coupling, a mixture of 6-(4-bromo-2-fluoro-6-methoxyphenyl)-N-methyl-N-(2,2,6,6-tetramethylpiperidin-4-yl) pyridazin-3-amine, 4-bromo-6-(2-fluoro-6-methoxyphenyl)-N-methyl-N-(2,2,6,6-tetramethylpiperidin-4-yl)pyridazin-3-amine (Intermediate 8-1, Step 2, 0.10 g, 0.22 mmol, total amount of the 2 regioisomers) and tert-butyl 4-(4,4,5,5-tetramethyl-1,3,2-dioxaborolan-2-yl)-1H-pyrazole-1-carboxylate (0.14 g, 0.67 mmol) were reacted. The crude product was purified by column chromatography using silica gel and a gradient elution of 1-15% 7 N ammonia in MeOH, in CH$_2$Cl$_2$. An inseparable mixture of the desired product (6-(2-fluoro-6-methoxy-4-(1-methyl-1H-pyrazol-4-yl)phenyl)-N-methyl-N-(2,2,6,6 tetramethylpiperidin-4-yl)pyridazin-3-amine) and 6-(2-fluoro-6-methoxyphenyl)-N-methyl-4-(1-methyl-1H-pyrazol-4-yl)-N-(2,2,6,6-tetramethylpiperidin-4-yl) pyridazin-3-amine was afforded as a colorless solid (80 mg, 80%). [M+H]: 453.4.

Step 2: 3-Fluoro-2-(6-(methyl(2,2,6,6-tetramethylpiperidin-4-yl)amino)pyridazin-3-yl)-5-(1-methyl-1H-pyrazol-4-yl)phenol hydrochloride salt A mixture of 6-(2-fluoro-6-methoxy-4-(1-methyl-1H-pyrazol-4-yl)phenyl)-N-methyl-N-(2,2,6,6-tetramethylpiperidin-4-yl)pyridazin-3-amine and 6-(2-fluoro-6-methoxyphenyl)-N-methyl-4-(1-methyl-1H-pyrazol-4-yl)-N-(2,2,6,6-tetramethylpiperidin-4-yl)pyridazin-3-amine (0.03 g, 0.07 mmol, total amount of the 2 regioisomers) was dissolved in CH$_2$Cl$_2$ (0.2 M). A 1 M solution of BBr$_3$ in CH$_2$Cl$_2$ (0.3 mL, 3.5 mmol) was rapidly added. The reaction mixture was stirred for 3 h. MeOH was added to the reaction at 0° C. then the solvent was concentrated under reduced pressure. The crude material was purified via reverse phase preparative HPLC (15 to 45% acetonitrile in water, 5 mM ammonium hydroxide as modifier). The solvent was concentrated in vacuo and the resulting solid was suspended in CH$_3$CN/H$_2$O (4/1 mL). 1 M aqueous HCl (3 equivalents) was added and the volatiles were concentrated in vacuo to afford the hydrochloride salt of 3-fluoro-2-(6-(methyl(2,2,6,6-tetramethylpiperidin-4-yl)amino)pyridazin-3-yl)-5-(1-methyl-1H-pyrazol-4-yl)phenol as a yellow solid (5 mg, 15%). LCMS Rt=0.50 min [Method Q]; [M+H]: 439.4; $^1$H NMR (400 MHz, DMSO) δ 9.20 (d, J=12.0 Hz, 1H), 8.29 (d, J=12.0 Hz, 1H), 8.23 (s, 1H), 8.04 (d, J=9.5 Hz, 1H), 7.92 (s, 1H), 7.79 (bs, 1H), 7.09 (dd, J=12.0, 1.5 Hz, 1H), 7.04 (s, 1H), 4.92 (bs, 1H), 3.88 (s, 3H), 3.03 (s, 3H), 2.05 (t, J=13.0 Hz, 2H), 1.81 (dd, J=13.0, 3.5 Hz, 2H), 1.53 (s, 6H), 1.49 (s, 6H).

Example 41-1

Synthesis of 5-(5-methoxypyridin-3-yl)-2-(6-(methyl(2,2,6,6-tetramethylpiperidin-4-yl)amino)pyridazin-3-yl)phenol

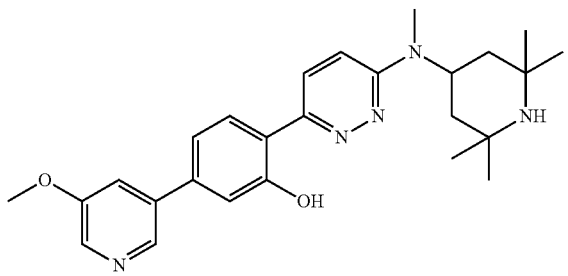

Following GENERAL METHOD 1-3 for Suzuki Coupling, to a 25 mL microwave vial, was added 3-methoxy-5-(4,4,5,5-tetramethyl-1,3,2-dioxaborolan-2-yl)pyridine (94 mg, 0.400 mmol), 3-hydroxy-4-(6-(methyl(2,2,6,6-tetramethylpiperidin-4-yl)amino)pyridazin-3-yl)phenyl trifluoromethanesulfonate (Intermediate 9-2, 105 mg, 0.2 mmol), sodium bicarbonate (50.4 mg, 0.600 mmol) and Pd(PPh$_3$)$_4$ (11.56 mg, 10.00 μmol), followed by dioxane (2 mL) and water (0.5 mL). The reaction mixture was purged with N$_2$ for 10 minutes, and heated in a microwave at 100° C. for 1 h, then diluted with EtOAc and filtered through celite. The filtrate was acidified to pH~3 with 1N HCl, and loaded onto an SCX column. The column was washed with MeOH, and eluted with 2N NH$_3$ in MeOH. After concentration, the residue was purified by preparative HPLC to provide 5-(5-methoxypyridin-3-yl)-2-(6-(methyl(2,2,6,6-tetramethylpiperidin-4-yl)amino)pyridazin-3-yl)phenol (55 mg, 0.120 mmol, 60% yield), LCMS: Rt=0.50 min [Method Q]; MS (M+1)=448.4; $^1$H NMR (METHANOL-d$_4$) δ 8.17 (d, J=5.1 Hz, 1H), 8.11 (d, J=9.1 Hz, 1H), 7.85 (d, J=7.1 Hz, 1H), 7.22-7.33 (m, 4H), 7.06 (s, 1H), 5.10 (m, 1H), 3.97 (s, 3H), 3.03 (s, 3H), 1.74 (dd, J=12.6, 3.0 Hz, 2H), 1.59 (t, J=12.4 Hz, 2H), 1.42 (s, 6H), 1.26 (s, 6H).

The following compounds were prepared using similar procedures as in Examples 41—from Intermediates 1-1, 1-3 or Example 32-1, Step 4, and general methods as outlined in the GENERAL METHOD section.

| Example | Structure | $^1$H NMR, 400 MHz | LCMS Method Q |
|---|---|---|---|
| 41-2 | 5-(3-hydroxy-4-(6-methyl(2,2,6,6-tetramethylpiperidin-4-yl)amino)pyridazin-3-yl)phenyl)pyridin-2-ol | (METHANOL-d$_4$) δ 7.98 (d, J = 9.6 Hz, 1H), 7.86 (dd, J = 9.3, 2.8 Hz, 1H), 7.69 (s, 1H), 7.63 (d, J = 2.0 Hz, 1H), 7.18 (d, J = 10.1 Hz, 1H), 6.99 (d, J = 2.0 Hz, 2H), 6.57 (d, J = 9.6 Hz, 1H), 4.97 (m, 1H), 2.93 (s, 3H), 1.64 (dd, J = 12.6, 3.5 Hz, 2H), 1.49 (t, J = 12.6 Hz, 2H), 1.32 (s, 6H), 1.16 (s, 6H) | Rt = 0.48 min M + 1 = 434.3 |
| 41-3 | 4-(3-hydroxy-4-(6-methyl(2,2,6,6-tetramethylpiperidin-4-yl)amino)pyridazin-3-yl)phenyl)pyridin-2-ol | (METHANOL-d$_4$) δ 8.01 (d, J = 9.6 Hz, 1H), 7.75 (d, J = 8.1 Hz, 1H), 7.39 (d, J = 7.1 Hz, 1H), 7.11-7.21 (m, 3H), 6.71 (d, J = 1.0 Hz, 1H), 6.64 (dd, J = 6.8, 1.8 Hz, 1H), 5.02 (m, 1H), 2.93 (s, 3H), 1.66 (dd, J =12.6, 3.0 Hz, 2H), 1.52 (t, J = 12.4 Hz, 2H), 1.34 (s, 6H), 1.18 (s, 6H) | Rt = 0.49 min M + 1 = 434.3 |

| Example | Structure | ¹H NMR, 400 MHz | LCMS Method Q |
|---|---|---|---|
| 41-4 | 5-(6-methoxypyridin-3-yl)-2-(6-(methyl(2,2,6,6-tetrahydropiperidin-4-yl)amino)pyridazin-3-yl)phenol | (METHANOL-d$_4$) δ 8.42 (s, 1H), 8.10 (br. s., 1H), 7.97 (d, J = 8.1 Hz, 1H), 7.77-7.86 (m, 1H), 7.28 (d, J = 7.1 Hz, 1H), 7.19 (s, 2H), 6.89 (d, J = 8.1 Hz, 1H), 5.06 (m, 1H), 3.97 (s, 3H), 3.02 (s, 3H), 1.72 (dd, J = 12.1, 3.0 Hz, 2H), 1.58 (t, J =12.4 Hz, 2H), 1.41 (s, 6H), 1.25 (s, 6H) | Rt = 0.59 min M + 1 = 448.4 |
| 41-5 | 5-(3-hydroxy-4-(6-(methyl(2,2,6,6-tetramethylpiperidin-4-yl)amino)pyridazin-3-yl)phenyl)-3-(trifluoromethyl)pyridin-2-ol | (METHANOL-d$_4$) δ 8.18-8.24 (m, 1H), 8.05 (d, J = 9.6 Hz, 1H), 7.90 (br. s., 1H), 7.78 (d, J = 8.1 Hz, 1H), 7.24 (d, J = 10.1 Hz, 1H), 7.11 (d, J = 2.0 Hz, 1H), 7.04-7.09 (m, 1H), 5.13 (m, 1H), 3.02 (s, 3H), 1.77 (dd, J = 12.9, 3.3 Hz, 2H), 1.65 (t, J = 12.4 Hz, 2H), 1.45 (s, 6H), 1.27-1.33 (s, 6H) | Rt = 0.54 min M + 1 = 502.3 |
| 41-6 | 5-(3-hydroxy-4-(6-(methyl(2,2,6,6-tetramethylpiperidin-4-yl)amino)pyridazin-3-yl)phenyl)-1-methylpyridin-2(1H)-one | (DMSO-d6) δ 13.90 (br. s., 1H), 8.21-8.29 (m, 2H), 7.85-7.95 (m, 2H), 7.36 (d, J = 10.1 Hz, 1H), 7.17-7.22 (m, 1H), 7.15 (dd, J = 8.3, 1.8 Hz, 1H), 6.48 (d, J = 9.6 Hz, 1H), 4.96 (m, 1H), 3.53 (s, 3H), 2.96 (s, 3H), 1.53 (dd, J = 11.9, 3.3 Hz, 2H), 1.44 (t, J = 12.1 Hz, 2H), 1.26 (s, 6H), 1.10 (s, 6H) | Rt = 0.50 min M + 1 = 448.4 |
| 41-7 | 4-(3-hydroxy-4-(6-(methyl(2,2,6,6-tetramethylpiperidin-4-yl)amino)pyridazin-3-yl)phenyl)-1-methylpyridin-2(1H)-one | (METHANOL-d$_4$) δ 8.16 (d, J = 10.1 Hz, 1H), 7.87-7.93 (m, 1H), 7.74 (d, J = 7.1 Hz, 1H), 7.34 (d, J = 10.1 Hz, 1H), 7.25-7.30 (m, 2H), 6.84 (d, J = 2.0 Hz, 1H), 6.76 (dd, J = 7.1, 2.0 Hz, 1H), 5.17 (m, 1H), 3.63 (s, 3H), 3.04 (s, 3H), 1.76 (dd, J = 12.6, 3.0 Hz, 2H), 1.66 (t, J = 12.6 Hz, 2H), 1.45 (s, 6H), 1.29 (s, 6H) | Rt = 0.51 min M + 1 = 448.4 |

| Example | Structure | ¹H NMR, 400 MHz | LCMS Method Q |
|---|---|---|---|
| 41-8 | 5-(2-methoxypyridin-4-yl)-2-(6-(methyl(2,2,6,6-tetramethylpiperidin-4-yl)amino)pyridazin-3-yl)phenol | (METHANOL-d₄) δ 8.17 (d, J = 5.1 Hz, 1H), 8.11 (d, J = 9.1 Hz, 1H), 7.85 (d, J = 7.1 Hz, 1H), 7.22-7.33 (m, 4H), 7.06 (s, 1H), 5.10 (m, 1H), 3.97 (s, 3H), 3.03 (s, 3H), 1.74 (dd, J = 12.6, 3.0 Hz, 2H), 1.59 (t, J = 12.4 Hz, 2H), 1.42 (s, 6H), 1.26 (s, 6H) | Rt = 0.60 min M + 1 = 448.4 |
| 41-9 | 4-(3-hydroxy-4-(6-((2,2,6,6-tetramethylpiperidin-4-yl)oxy)pyridazin-3-yl)phenyl)pyridin-2-ol | (DMSO-d₆) δ 12.87 (br. s., 1H), 11.64 (br. s., 1H), 8.45 (d, J = 9.6 Hz, 1H), 8.04 (d, J = 8.6 Hz, 1H), 7.46 (d, J = 6.6 Hz, 1H), 7.41 (d, J = 9.6 Hz, 1H), 7.26-7.33 (m, 1H), 6.62 (d, J = 1.0 Hz, 1H), 6.54 (d, J = 7.1 Hz, 1H), 5.69 (m, 1H), 2.13 (d, J = 9.1 Hz, 2H), 1.31-1.42 (m, 2H), 1.27 (s., 6H), 1.15 (s., 6H) | Rt = 0.45 min M + 1 = 421.4 |
| 41-10 | 5-(6-(dimethylamino)pyridin-3-yl)-2-(6-(methyl(2,2,6,6-tetramethylpiperidin-4-yl)amino)pyridazin-3-yl)phenol | (DMSO-d₆) δ 13.80 (s, 1H), 8.50 (d, J = 2.0 Hz, 1H), 8.22 (d, J = 9.6 Hz, 1H), 7.89 (dt, J = 8.8, 2.1 Hz, 2H), 7.36 (d, J = 10.1 Hz, 1H), 7.16-7.23 (m, 2H), 6.73 (d, J = 9.1 Hz, 1H), 4.95 (m, 1H), 3.08 (s, 6H), 2.96 (s, 3H), 1.54 (dd, J = 12.1, 3.5 Hz, 2H), 1.44 (t, J = 12.1 Hz, 2H), 1.26 (s, 6H), 1.10 (s, 6H) | Rt = 0.44 min M + 1 = 461.5 |
| 41-11 | 4-(3-hydroxy-4-(6-((2,2,6,6-tetramethylpiperidin-4-yl)oxy)pyridazin-3-yl)phenyl)-1-methylpyridin-2(1H)-one | (CHLOROFORM-d) δ 8.24 (d, J = 9.6 Hz, 1H), 7.86 (d, J = 8.1 Hz, 1H), 7.64 (d, J = 7.1 Hz, 1H), 7.14-7.25 (m 3H), 6.73 (s, 1H), 6.65 (d, J = 6.6 Hz, 1H), 5.67 (m, 1H), 3.52 (s, 3H), 2.16 (dd, J = 12.6, 3.5 Hz, 2H), 1.37 (t, J = 11.6 Hz, 2H), 1.30 (s, 6H), 1.18 (s, 6H) | Rt = 0.47 min M + 1 = 435.4 |

| Example | Structure | ¹H NMR, 400 MHz | LCMS Method Q |
|---|---|---|---|
| 41-12 | 2-(6-(methyl(2,2,6,6-tetramethylpiperidin-4-yl)amino)pyridazin-3-yl)-5-(pyrimidin-5-yl)phenol | (METHANOL-d₄) δ 9.15 (s, 1H), 9.08 (s, 2H), 8.11 (d, J = 10.1 Hz, 1H), 7.90 (d, J = 8.1 Hz, 1H), 7.23-7.33 (m, 3H), 5.12 (m, 1H), 3.03 (s, 3H), 1.76 (dd, J = 12.6, 3.5 Hz, 2H), 1.61 (t, J = 12.4 Hz, 2H), 1.43 (s, 6H), 1.28 (s, 6H) | Rt = 0.47 min M + 1 = 419.5 |
| 41-13 | 5-(3-hydroxy-4-(6-(methyl(2,2,6,6-tetramethylpiperidin-4-yl)amino)pyridazin-3-yl)phenyl)pyridin-3-ol | (METHANOL-d₄) δ 8.14 (d, J = 1.5 Hz, 1H), 8.03 (d, J = 10.1 Hz, 1H), 7.96 (d, J = 2.0 Hz, 1H), 7.73-7.78 (m, 1H), 7.35 (t, J = 2.0 Hz, 1H), 7.22 (d, J = 10.1 Hz, 1H), 7.08-7.13 (m, 2H), 5.06 (m, 1H), 2.92 (s, 3H), 1.62-1.69 (m, 2H), 1.51-1.60 (m, 2H), 1.35 (s, 6H), 1.19 (s, 6H) | Rt = 0.44 min M + 1 = 434.4 |
| 41-14 | 1-cyclopropyl-4-(3-hydroxy-4-(6-(methyl(2,2,6,6-tetramethylpiperidin-4-yl)amino)pyridazin-3-yl)phenyl)pyridin-2(1H)-one | (METHANOL-d₄) δ 8.04 (d, J = 9.6 Hz, 1H), 7.77 (d, J = 8.6 Hz, 1H), 7.58 (d, J = 7.1 Hz, 1H), 7.22 (d, J = 10.1 Hz, 1H), 7.12-7.17 (m, 2H), 6.70 (d, J = 2.0 Hz, 1H), 6.62 (dd, J = 7.1, 2.0 Hz, 1H), 5.03 (m, 1H), 3.27-3.33 (m, 1H), 2.92 (s, 3H), 1.62 (dd, J = 12.6, 3.0 Hz, 2H), 1.51 (t, J = 12.4 Hz, 2H), 1.31 (s, 6H), 1.16 (s, 6H), 1.01-1.09 (m, 2H), 0.82-0.90 (m, 2H) | Rt = 0.49 min M + 1 = 474.4 |
| 41-15 | 2-(6-(methyl(2,2,6,6-tetramethylpiperidin-4-yl)amino)pyridazin-3-yl)-5-(1,2,3,6-tetrahydropyridin-4-yl)phenol | (METHANOL-d₄) δ 8.06 (d, J = 9.6 Hz, 1H), 7.67-7.72 (m, 1H), 7.27 (d, J = 10.1 Hz, 1H), 7.03 (dd, J = 8.3, 1.8 Hz, 1H), 7.00 (d, J = 1.5 Hz, 1H), 6.23-6.29 (m, 1H), 5.05 (m, 1H), 3.51 (q, J = 2.5 Hz, 2H), 3.09 (t, J = 5.8 Hz, 2H), 3.00 (s, 3H), 2.48-2.56 (m, 2H), 1.69 (dd, J = 12.6, 3.5 Hz, 2H), 1.58 (t, J = 12.4 Hz, 2H), 1.40 (s, 6H), 1.25 (s, 6H) | Rt = 0.37 min M + 1 = 422.6 |

-continued

| Example | Structure | ¹H NMR, 400 MHz | LCMS Method Q |
|---------|-----------|-----------------|---------------|
| 41-16 | 5-(cyclopent-1-en-1-yl)-2-(6-(methyl(2,2,6,6-tetramethylpiperidin-4-yl)amino)pyridazin-3-yl)phenol | (METHANOL-d$_4$) δ 8.07 (d, J = 10.1 Hz, 1H), 7.68 (d, J = 8.1 Hz, 1H), 7.29 (d, J = 10.1 Hz, 1H), 7.08 (dd, J = 8.3, 1.8 Hz, 1H), 7.01 (d, J = 2.0 Hz, 1H), 6.26-6.32 (m, 1H), 5.07 (m, 1H), 3.02 (s, 3H), 2.69-2.76 (m, 2H), 2.52-2.60 (m, 2H), 2.00-2.12 (m, 2H), 1.72 (dd, J = 12.6, 3.5 Hz, 2H), 1.60 (t, J = 12.4 Hz, 2H), 1.42 (s, 6H), 1.26 (s, 6H) | Rt = 0.60 min M + 1 = 407.3 |
| 41-17 | 5-(3,6-dihydro-2H-pyran-4-yl)-2-(6-(methyl(2,2,6,6-tetramethylpiperidin-4-yl)amino)pyridazin-3-yl)phenol | (METHANOL-d$_4$) δ 8.13 (d, J = 10.1 Hz, 1H), 7.71 (d, J = 8.6 Hz, 1H), 7.36 (d, J = 9.6 Hz, 1H), 7.07 (dd, J = 8.3, 1.8 Hz, 1H), 7.04 (d, J = 1.5 Hz, 1H), 6.28 (br. s., 1H), 5.33-5.46 (m, 1H), 4.31-4.37 (m, 2H), 3.95 (t, J = 5.3 Hz, 2H), 3.05 (s, 3H), 2.55 (d, J = 2.0 Hz, 2H), 2.00-2.07 (m, 2H), 1.91-2.00 (m, 2H), 1.67 (s, 6H), 1.55 (s, 6H) | Rt = 0.52 min M + 1 = 423.3 |
| 41-18 | (5-imidazo[1,5-a]pyridin-7-yl)-2-(6-(methyl(2,2,6,6-tetramethylpiperidin-4-yl)amino)pyridazin-3-yl)phenol | (METHANOL-d$_4$) δ 8.40 (d, J = 7.1 Hz, 1H), 8.05 (d, J = 9.6 Hz, 1H), 7.75-7.84 (m, 3H), 7.59 (s, 1H), 7.26-7.34 (m, 2H), 7.19-7.25 (m, 2H), 5.05 (m, 1H), 3.01 (s, 3H), 1.73 (dd, J = 12.6, 3.5 Hz, 2H), 1.56 (t, J = 12.4 Hz, 2H), 1.41 (s, 6H), 1.25 (s, 6H) | Rt = 0.40 min M + 1 = 457.4 |
| 41-19 | 5-(imidazo[1,2-a]pyridin-7-yl)-2-(6-(methyl(2,2,6,6-tetramethylpiperidin-4-yl)amino)pyridazin-3-yl)phenol | (METHANOL-d$_4$) δ 8.39 (d, J = 7.1 Hz, 1H), 8.02 (d, J = 10.1 Hz, 1H), 7.73-7.80 (m, 3H), 7.58 (d, J = 1.5 Hz, 1H), 7.29 (d, J = 2.0 Hz, 1H), 7.26 (dd, J = 8.1, 2.0 Hz, 1H), 7.17-7.23 (m, 2H), 5.02 (m, 1H), 2.99 (s, 3H), 1.70 (dd, J = 12.6, 3.5 Hz, 2H), 1.53 (t, J = 12.6 Hz, 2H), 1.39 (s, 6H), 1.23 (s, 6H) | Rt = 0.41 min M + 1 = 457.3 |

| Example | Structure | ¹H NMR, 400 MHz | LCMS Method Q |
|---|---|---|---|
| 41-20 | 2-(6-(methyl(2,2,6,6-tetramethylpiperidin-4-yl)amino)pyridazin-3-yl)-5-(2-methylpyridin-4-yl)phenol | (METHANOL-$d_4$) δ 8.47 (d, J = 5.1 Hz, 1H), 8.17 (d, J = 10.1 Hz, 1H), 7.91 (d, J = 8.1 Hz, 1H), 7.64 (s, 1H), 7.52-7.59 (m, 1H), 7.29-7.39 (m, 3H), 5.12 (t, J = 12.1 Hz, 1H), 3.04 (s, 3H), 2.63 (s, 3H), 1.67-1.77 (m, 2H), 1.53-1.66 (m, 2H), 1.41 (s, 6H), 1.25 (s, 6H) | Rt = 0.42 min M + 1 = 432.2 |

Example 42-1

Synthesis of 5-(1H-imidazol-2-yl)-2-(6-(methyl(2,2,6,6-tetramethylpiperidin-4-yl)amino)pyridazin-3-yl)phenol

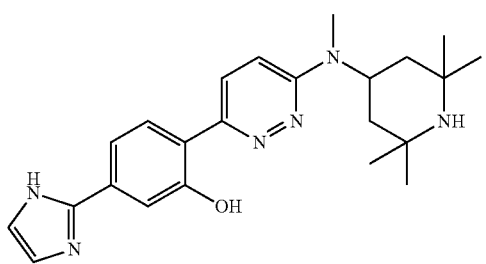 [SMILES: CN(c1ccc(-c2ccc(-c3ncc[nH]3)cc2O)nn1)C1CC(C)(C)NC(C)(C)C1]

Step 1: 6-(4-(1H-Imidazol-2-yl)-2-methoxyphenyl)-N-methyl-N-(2,2,6,6-tetramethylpiperidin-4-yl)pyridazin-3-amine To a microwave vial was added 6-(2-methoxy-4-(4,4,5,5-tetramethyl-1,3,2-dioxaborolan-2-yl)phenyl)-N-methyl-N-(2,2,6,6-tetramethylpiperidin-4-yl)pyridazin-3-amine (Intermediate 9-3, 100 mg, 0.21 mmol), 2-bromo-1H-imidazole (61.2 mg, 0.42 mmol), $Na_2CO_3$ (44 mg, 0.42 mmol), and $Pd(PPh_3)_2Cl_2$ (14 mg, 0.02 mmol), followed by DME (1 mL)/EtOH 0.25 mL)/($H_2O$ (0.25 mL). The vial was purged with $N_2$ for 10 min and the reaction mixture was heated at 150° C. in a microwave reactor for 20 min. The reaction mixture was filtered through celite and the filter cake was washed with EtOAc. The filtrate was concentrated in vacuo to give the crude product which was purified by silica gel chromatography (5%-15% MeOH/DCM) to afford 6-(4-(1H-imidazol-2-yl)-2-methoxyphenyl)-N-methyl-N-(2,2,6,6-tetramethylpiperidin-4-yl)pyridazin-3-amine (40 mg, MS: 421.3 [M+H⁺]).

Step 2: 5-(1H-Imidazol-2-yl)-2-(6-(methyl(2,2,6,6-tetramethylpiperidin-4-yl)amino)pyridazin-3-yl)phenol Following GENERAL METHOD 3-1 for methoxy deprotection using thiophenol, 6-(4-(1H-imidazol-2-yl)-2-methoxyphenyl)-N-methyl-N-(2,2,6,6-tetramethylpiperidin-4-yl)pyridazin-3-amine (40 mg, 0.1 mmol) was treated with thiophenol (0.01 mL, 0.11 mmol) and $K_2CO_3$ (13 mg, 0.1 mmol) in NMP (2 mL) for 30 min at 190° C. to afford 5-(1H-imidazol-2-yl)-2-(6-(methyl(2,2,6,6-tetramethylpiperidin-4-yl)amino)pyridazin-3-yl)phenol as pale yellow powder (6 mg). MS: 407.4 [M+H⁺]; LCMS Rt=0.40 min [Method Q]; ¹H NMR (400 MHz, METHANOL-$d_4$) δ ppm 8.00 (d, J=10.11 Hz, 1H), 7.68-7.78 (m, 1H), 7.32-7.41 (m, 2H), 7.19 (d, J=10.11 Hz, 1H), 7.05 (s, 2H), 4.96 (br. s., 1H), 2.90 (s, 3H), 1.58 (dd, J=12.38, 3.28 Hz, 2H), 1.46 (t, J=12.38 Hz, 2H), 1.28 (s, 6H), 1.12 (s, 6H).

Example 42-2

Synthesis of 5-(1H-imidazol-4-yl)-2-(6-(methyl(2,2,6,6-tetramethylpiperidin-4-yl)amino)pyridazin-3-yl)phenol

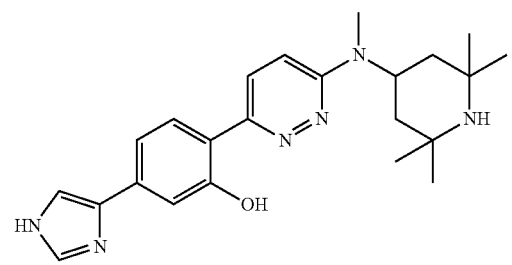 [SMILES: CN(c1ccc(-c2ccc(-c3c[nH]cn3)cc2O)nn1)C1CC(C)(C)NC(C)(C)C1]

Step 1: 4-Bromo-1-((2-(trimethylsilyl)ethoxy)methyl)-1H-imidazole

To a mixture of 4-bromo-1H-imidazole (1.0 g, 6.8 mmol) in THF (15 mL) was added NaH (327 mg, 8.16 mmol) at 0° C. The mixture was stirred at 0° C. to RT for 0.5 h. SEMCl (1.45 mL, 8.16 mmol) was added dropwise and the reaction mixture was stirred at RT for 2 h. The reaction mixture was quenched with water and extracted with DCM. The organic layer was dried ($Na_2SO_4$), filtered and concentrated in vacuo to give the crude product which was purified by silica gel chromatography (10-100% EtOAc/Heptane, then 0-15% MeOH/DCM) to afford 4-bromo-1-((2-(trimethylsilyl)ethoxy)methyl)-1H-imidazole (1.36 g, MS: 279.3 [M+H⁺]).

Step 2: 6-(2-Methoxy-4-(1-((2-(trimethylsilyl)ethoxy)methyl)-1H-imidazol-4-yl)phenyl)-N-methyl-N-(2,2,6,6-tetramethylpiperidin-4-yl)pyridazin-3-amine To a microwave vial was added 6-(2-methoxy-4-(4,4,5,5-tetramethyl-1,3,2-dioxaborolan-2-yl)phenyl)-N-methyl-N-(2,2,6,6-tetramethylpiperidin-4-yl)pyridazin-3-amine (Intermediate 9-3, 50 mg, 0.10 mmol), 4-bromo-1-((2-(trimethylsilyl)ethoxy)methyl)-1H-imidazole (57.7 mg, 0.21 mmol), Na$_2$CO$_3$ (22 mg, 0.21 mmol), and Pd(PPh$_3$)$_2$Cl$_2$ (7.3 mg, 0.01 mmol), followed by DME (1 mL)/EtOH 0.25 mL)/(H2O (0.25 mL). The vial was purged with N$_2$ for 10 minutes and the reaction mixture was heated at 150° C. in a microwave reactor for 20 minutes. The reaction mixture was filtered through celite and the filter cake was washed with EtOAc. The filtrate was concentrated in vacuo to give the crude product which was purified by silica gel chromotography (5%-15% MeOH/DCM) to afford 6-(2-methoxy-4-(1-((2-(trimethylsilyl)ethoxy)methyl)-1H-imidazol-4-yl)phenyl)-N-methyl-N-(2,2,6,6-tetramethylpiperidin-4-yl)pyridazin-3-amine (50 mg). MS: 551.6 [M+H$^+$]).

Step 3: 2-(6-(Methyl(2,2,6,6-tetramethylpiperidin-4-yl)amino)pyridazin-3-yl)-5-(1-((2-(trimethylsilyl)ethoxy)methyl)-1H-imidazol-4-yl)phenol Following GENERAL METHOD 3-1 for methoxy deprotection using thiophenol, 6-(2-methoxy-4-(1-((2-(trimethylsilyl)ethoxy)methyl)-1H-imidazol-4-yl)phenyl)-N-methyl-N-(2,2,6,6-tetramethylpiperidin-4-yl)pyridazin-3-amine (50 mg, 0.09 mmol) was treated with thiophenol (0.01 mL, 0.11 mmol) and K$_2$CO$_3$ (12 mg, 0.09 mmol) in NMP (2 mL) for 30 minutes at 190° C. to afford 2-(6-(methyl(2,2,6,6-tetramethylpiperidin-4-yl)amino)pyridazin-3-yl)-5-(1-((2-(trimethylsilyl)ethoxy)methyl)-1H-imidazol-4-yl)phenol and an impurity (50 mg, MS: 537.6 [M+H$^+$]).

Step 4: 5-(1H-Imidazol-4-yl)-2-(6-(methyl(2,2,6,6-tetramethylpiperidin-4-yl)amino)pyridazin-3-yl)phenol To a microwave vial containing 2-(6-(methyl(2,2,6,6-tetramethylpiperidin-4-yl)amino)pyridazin-3-yl)-5-(1-((2-(trimethylsilyl)ethoxy)methyl)-1H-imidazol-4-yl)phenol (mixture from previous step, 50 mg, 0.09 mmol) in EtOH (1.0 mL)/DCM (1.0 mL) and conc. HCl (8.5 µL) was added BBr$_3$ (0.46 mL, 0.46 mmol). The vial was purged with N$_2$ (2×) and the reaction mixture was heated at 110° C. in a microwave reactor for 30 min. The reaction mixture was filtered through celite (pre-packed filter funnel) with a MeOH wash. The filtrate was acidified to pH 3 using 1N HCl and purified by catch and release using SiliaBond Propylsulfonic Acid® (1 g, MeOH as eluent and a 2 N ammonia solution in MeOH to release the material). After evaporation, the material was purified via reverse phase HPLC to afford 5-(1H-imidazol-4-yl)-2-(6-(methyl(2,2,6,6-tetramethylpiperidin-4-yl)amino)pyridazin-3-yl)phenol (2 mg). MS: 407.4 [M+H$^+$]. LCMS Rt=0.40 min [Method Q]; $^1$H NMR (400 MHz, METHANOL-d$_4$) δ ppm 8.01 (d, J=9.60 Hz, 1H), 7.57-7.74 (m, 2H), 7.39 (s, 1H), 7.14-7.30 (m, 3H), 4.98 (br. s., 1H), 2.92 (s, 3H), 1.62 (d, J=13.14 Hz, 2H), 1.52 (t, J=12.38 Hz, 2H), 1.32 (s, 6H), 1.16 (s, 6H).

Example 42-3

Synthesis of 5-(imidazo[1,2-a]pyrazin-3-yl)-2-(6-(methyl(2,2,6,6-tetramethylpiperidin-4-yl)amino)pyridazin-3-yl)phenol

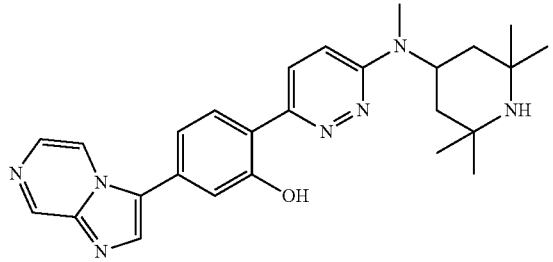 [SMILES: CN(c1ccc(-c2ccc(-c3cnc4cnccn34)cc2O)nn1)C1CC(C)(C)NC(C)(C)C1]

Step 1: 6-(4-(Imidazo[1,2-a]pyrazin-3-yl)-2-methoxyphenyl)-N-methy-N-(2, 2,6,6-tetramethylpiperidin-4-yl)pyridazin-3-amine To a microwave vial was added 6-(2-methoxy-4-(4,4,5,5-tetramethyl-1,3,2-dioxaborolan-2-yl)phenyl)-N-methyl-N-(2,2,6,6-tetramethylpiperidin-4-yl)pyridazin-3-amine (Intermediate 9-3, 50 mg, 0.1 mmol), 3-bromo-5,6,7,8-tetrahydroimidazo[1,2-a]pyrazine (49.6 mg, 0.21 mmol), Na$_2$CO$_3$ (44 mg, 0.42 mmol), and Pd(PPh$_3$)$_2$C$_2$ (7 mg, 0.01 mmol), followed by DME (1 mL)/EtOH 0.25 mL)/(H$_2$O (0.25 mL). The vial was purged with N$_2$ for 10 minutes and the reaction mixture was heated at 150° C. in a microwave reactor for 20 min. The reaction mixture was filtered through celite and the filter cake was washed with EtOAc. The filtrate was concentrated in vacuo to give the crude product which was purified by silica gel chromatography (5%-15% MeOH/DCM) to afford 6-(4-(imidazo[1,2-a]pyrazin-3-yl)-2-methoxyphenyl)-N-methyl-N-(2,2,6,6-tetramethylpiperidin-4-yl)pyridazin-3-amine (49 mg). MS: 476.5 [M+H$^+$]).

Step 2: 5-(Imidazo[1,2-a]pyrazin-3-yl)-2-(6-(methyl(2,2,6,6-tetramethylpiperidin-4-yl)amino)pyridazin-3-yl)phenol Following GENERAL METHOD 3-1 for methoxy deprotection using thiophenol, 6-(4-(imidazo[1,2-a]pyrazin-3-yl)-2-methoxyphenyl)-N-methyl-N-(2,2,6,6-tetramethylpiperidin-4-yl)pyridazin-3-amine (49 mg, 0.1 mmol) was treated with thiophenol (0.01 mL, 0.12 mmol) and K$_2$CO$_3$ (14 mg, 0.11 mmol) in NMP (2 mL) for 30 minutes at 190° C. to afford 5-(imidazo[1,2-a]pyrazin-3-yl)-2-(6-(methyl(2,2,6,6-tetramethylpiperidin-4-yl)amino)pyridazin-3-yl)phenol (8 mg). MS: 458.4 [M+H$^+$]; LCMS Rt=0.47 min [Method Q]; $^1$H NMR (400 MHz, CHLOROFORM-d) δ ppm 9.16 (s, 1H), 8.41 (d, J=5.05 Hz, 1H), 7.92-7.97 (m, 2H), 7.88 (d, J=10.11 Hz, 1H), 7.75 (d, J=8.08 Hz, 1H), 7.31 (s, 1H), 7.13 (s, 1H), 7.05 (d, J=9.60 Hz, 1H), 4.99 (br. s., 1H), 3.05 (s, 3H), 1.72 (d, J=12.13 Hz, 2H), 1.46 (t, J=12.38 Hz, 2H), 1.39 (s, 6H), 1.23 (s, 6H).

Example 42-4

Synthesis of 2-(6-(methyl(2,2,6,6-tetramethylpiperidin-4-yl)amino)pyridazin-3-yl)-5-(5,6,7,8-tetrahydroimidazo[1,2-a]pyrazin-3-yl)phenol

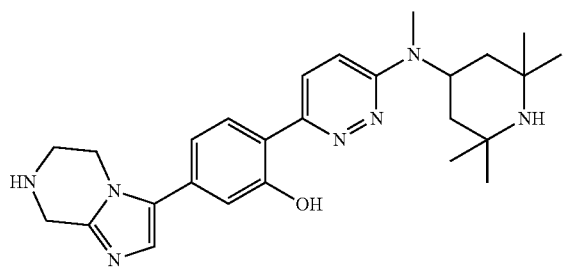 [SMILES: CN(c1ccc(-c2ccc(-c3cnc4n3CCNC4)cc2O)nn1)C1CC(C)(C)NC(C)(C)C1]

To a solution of 6-(4-(imidazo[1,2-a]pyrazin-3-yl)-2-methoxyphenyl)-N-methyl-N-(2,2,6,6-tetramethylpiperidin-4-yl)pyridazin-3-amine (Example 42-3, 50 mg, 0.1 mmol) in DCM (2 mL) was added 1 M solution of BBr$_3$ in DCM (0.52 mL) dropwise at 78° C. The crude reaction mixture was warmed to RT and stirred overnight. The reaction was quenched with NaHCO$_3$ aq solution at 0° C. and extracted with DCM. The organic layer was dried over Na$_2$SO$_4$, filtered and concentrated to give the crude product. The crude product was acidified to pH 3 using 1N HCl and purified by catch and release using SiliaBond Propylsulfonic Acid® (1 g, MeOH as eluent and a 2 N ammonia solution in MeOH to release the material). After evaporation, the material was purified via reverse phase HPLC to afford 2-(6-(methyl(2,2,6,6-tetramethylpiperidin-4-yl)amino)pyridazin-3-yl)-5-(5,6,7,8-tetrahydroimidazo[1,2-a]pyrazin-3-yl)phenol (4 mg). MS: 462.4 [M+H$^+$]; LCMS Rt=0.36 min [Method Q]; $^1$H NMR (400 MHz, METHANOL-d$_4$) ppm 8.03 (d, J=10.11 Hz, 1H), 7.74 (d, J=9.09 Hz, 1H), 7.22 (d, J=10.11 Hz, 1H), 6.96 (s, 2H), 6.99 (s, 1H), 5.02 (br. s., 1H), 3.88-4.09 (m, 4H), 3.11 (t, J=5.31 Hz, 2H), 2.92 (s, 3H), 1.62 (d, J=12.63 Hz, 2H), 1.51 (t, J=12.38 Hz, 2H), 1.31 (s, 6H), 1.16 (s, 6H).

The following compounds were prepared using similar procedures as in Examples 42-1 to 42-4, and general methods as outlined in the GENERAL METHODS section.

| Example | Compound | LCMS Method Q | $^1$H NMR 400 MHz |
|---|---|---|---|
| 42-5 | 2-(6-(methyl(2,2,6,6-tetramethylpiperidin-4-yl)amino)pyridazin-3-yl)-5-(4-methyl-1H-imidazol-2-yl)phenol | M + 1 = 421.4 Rt = 0.39 min | (METHANOL-d$_4$) δ 8.01 (d, J = 10.10 Hz, 1H), 7.71 (d, J = 8.08 Hz, 1H), 7.28-7.38 (m, 2H), 7.20 (d, J = 10.11 Hz, 1H), 6.73 (s, 1H), 5.00 (br. s., 1H), 2.91 (s, 3H), 2.19 (s, 3H), 1.60 (d, J = 3.54 Hz, 2H), 1.53 (d, J = 12.63 Hz, 2H), 1.31 (s, 6H), 1.16 (s, 6H) |
| 42-6 | 2-(6-(methyl(2,2,6,6-tetramethylpiperidin-4-yl)amino)pyridazin-3-yl)-5-(1-methyl-1H-imidazol-4-yl)phenol | M + 1 = 421.4 Rt = 0.39 min | (CHLOROFORM-d) δ ppm 7.77 (d, J = 10.11 Hz, 1H), 7.53 (d, J = 8.08 Hz, 1H), 7.32-7.45 (m, 2H), 7.11-7.23 (m, 2H), 6.91 (d, J = 10.11 Hz, 1H), 4.98 (br. s., 1H), 3.66 (s, 3H), 2.93 (s, 3H), 1.64 (dd, J = 12.38, 3.28 Hz, 2H), 1.48-1.53 (m, 2H), 1.36 (br. s., 6H), 1.20 (br. s., 6H) |

| Example | Compound | LCMS Method Q | ¹H NMR 400 MHz |
|---|---|---|---|
| 42-7 | 2-(6-(methyl(2,2,6,6-tetramethylpiperidin-4-yl)amino)pyridazin-3-yl)-5-(1-methyl-1H-imidazol-5-yl)phenol | M + 1 = 421.4 Rt = 0.37 min | (CHLOROFORM-d) δ 7.77 (d, J = 10.11 Hz, 1H), 7.55 (d, J = 8.08 Hz, 2H), 7.03 (d, J = 1.52 Hz, 2H), 6.94 (d, J = 9.60 Hz, 1H), 6.89 (dd, J = 8.34, 1.77 Hz, 1H), 4.95 (br. s., 1H), 3.67 (s, 3H), 2.95 (s, 3H), 1.64 (dd, J = 12.63, 3.54 Hz, 2H), 1.42-1.52 (m, 2H), 1.34 (s, 6H), 1.17 (s, 6H) |
| 42-8 | 2-(6-(methyl(2,2,6,6-tetramethylpiperidin-4-yl)amino)pyridazin-3-yl)-5-(4-nitro-1H-imidazol-2-yl)phenol | M + 1 = 452.4 Rt = 0.47 min | (METHANOL-d₄) δ 8.03 (d, J = 10.10 Hz, 1H), 7.97 (s, 1H), 7.73 (d, J = 8.59 Hz, 1H), 7.50 (br. s., 2H), 7.21 (d, J = 9.60 Hz, 1H), 5.11 (br. s., 1H), 2.92 (s, 3H), 1.69 (d, J = 4.04 Hz, 2H), 1.57-1.66 (m, 2H), 1.40 (s, 6H), 1.24 (s, 6H) |
| 42-9 | 2-(6-(methyl(2,2,6,6-tetramethylpiperidin-4-yl)amino)pyridazin-3-yl)-5-(2-methyl-1H-imidazol-4-yl)phenol | M + 1 = 421.4 Rt = 0.39 min | (METHANOL-d₄) δ 7.95 (d, J = 10.11 Hz, 1H), 7.61 (d, J = 8.59 Hz, 1H), 7.20 (s, 1H), 7.10-7.18 (m, 3H), 4.93 (br. s., 1H), 2.88 (s, 3H), 2.31 (s, 3H), 1.53-1.62 (m, 2H), 1.39-1.50 (m, 2H), 1.28 (s, 6H), 1.12 (s, 6H) |
| 42-10 | 5-(1,2-dimethyl-1H-imidazol-4-yl)-2-(6-(methyl(2,2,6,6-tetramethylpiperidin-4-yl)amino)pyridazin-3-yl)phenol | M + 1 = 435.4 Rt = 0.38 min | (METHANOL-d₄) δ 7.98 (d, J = 9.60 Hz, 1H), 7.63 (d, J = 8.59 Hz, 1H), 7.28 (s, 1H), 7.14-7.22 (m, 3H), 4.95 (br. s., 1H), 3.56 (s, 3H), 2.90 (s, 3H), 2.31 (s, 3H), 1.60 (d, J = 12.63 Hz, 2H), 1.48 (t, J = 12.38 Hz, 2H), 1.29 (s, 6H), 1.14 (s, 6H) |

| Example | Compound | LCMS Method Q | $^1$H NMR 400 MHz |
|---|---|---|---|
| 42.11 | 1-(3-hydroxy-4-(6-(methyl(2,2,6,6-tetramethylpiperidin-4-yl)amino)pyridazin-3-yl)phenyl)-1H-pyrazole-4-carboxamide | M + 1 = 450.3 Rt = 0.38 min | (METHANOL-d$_4$) δ ppm 8.63 (s, 1H), 7.99-8.08 (m, 2H), 7.81 (d, J = 8.59 Hz, 1H), 7.25-7.31 (m, 2H), 7.23 (d, J = 10.11 Hz, 1H), 5.06 (br. s., 1H), 2.93 (s, 3H), 1.65 (d, J = 12.13 Hz, 2H), 1.55 (t, J = 12.38 Hz, 2H), 1.34 (s, 6H), 1.19 (s, 6H) |

Example 43-1

Synthesis of 2-(6-((3aR,6aS)-5-(2-hydroxyethyl)hexahydropyrrolo[3,4-c]pyrrol-2(1H)-yl)pyridazin-3-yl)-5-(1H-pyrazol-4-yl)phenol

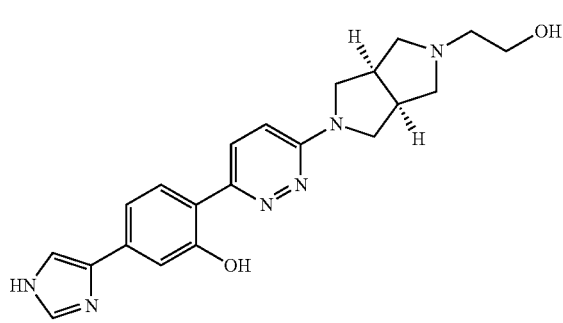 [SMILES: OCCN1C[C@@H]2CN(c3ccc(-c4ccc(-c5c[nH]cn5)cc4O)nn3)C[C@@H]2C1]

Step 1: (3aR,6aS)-tert-Butyl 5-(6-chloropyridazin-3-yl)hexahydropyrrolo[3,4-c]pyrrole-2(1H)-carboxylate To a solution of 3,6-dichloropyridazine (462 mg, 3.10 mmol) in n-butanol (8 mL) was added DIPEA (1.354 ml, 7.75 mmol) and (3aR,6aS)-tert-butyl hexahydropyrrolo[3,4-c]pyrrole-2(1H)-carboxylate (658 mg, 3.1 mmol). The reaction mixture was heated at 120° C. for 2 hour, and then diluted with DCM and water. The organic layer was separated and concentrated to a brownish oil, which was purified by silica gel chromatography (0-25% EtOAc/DCM) to afford (3aR,6aS)-tert-butyl 5-(6-chloropyridazin-3-yl)hexahydropyrrolo[3,4-c]pyrrole-2(1H)-carboxylate (730 mg, 2.180 mmol, 70% yield), MS(M+1)=325.2.

Step 2: (3aR,6aS)-tert-Butyl 5-(6-(4-chloro-2-hydroxyphenyl)pyridazin-3-yl)hexahydropyrrolo[3,4-c]pyrrole-2(1H)-carboxylate The reaction mixture of (3aR,6aS)-tert-butyl 5-(6-chloropyridazin-3-yl)hexahydropyrrolo[3,4-c]pyrrole-2(1H)-carboxylate (325 mg, 1 mmol), 5-chloro-2-(4,4,5,5-tetramethyl-1,3,2-dioxaborolan-2-yl)phenol (280 mg, 1.100 mmol), sodium carbonate (318 mg, 3.00 mmol) and PdCl$_2$(dppf).CH$_2$Cl$_2$ (61.2 mg, 0.075 mmol) in dioxane (5 mL) and water (5.00 mL) was degassed by bubbling N$_2$ for 10 minutes. After heating at 90° C. overnight, the reaction mixture was filtered through celite and washed with EtOAc. The filtrate was concentrated and the residue was purified by silica gel chromatography (0-10% MeOH/DCM) to afford (3aR,6aS)-tert-butyl 5-(6-(4-chloro-2-hydroxyphenyl)pyridazin-3-yl)hexahydropyrrolo[3,4-c]pyrrole-2(1H)-carboxylate (180 mg, 0.432 mmol, 43.2% yield) MS (M+1)= 417.0.

Step 3: (3aR,6aS)-tert-Butyl 5-(6-(2-hydroxy-4-(1H-pyrazol-4-yl)phenyl)pyridazin-3-yl)hexahydropyrrolo[3,4-c]pyrrole-2(1H)-carboxylate To a 10 mL microwave vial, was added (3aR,6aS)-tert-butyl 5-(6-(4-chloro-2-hydroxyphenyl)pyridazin-3-yl)hexahydropyrrolo[3,4-c]pyrrole-2(H)-carboxylate (0.182 g, 0.437 mmol), tert-butyl 4-(4,4,5,5-tetramethyl-1,3,2-dioxaborolan-2-yl)-1H-pyrazole-1-carboxylate (0.385 g, 1.310 mmol), chloro[2-(dicyclohexylphosphino)-3,6-dimethoxy-2',4',6'-triisopropyl-1,1'-biphenyl][2-(2-aminoethyl)phenyl]palladium(II) (0.035 g, 0.044 mmol) and Cs$_2$CO$_3$ (0.427 g, 1.310 mmol), followed by adding 1,4-dioxane (2 mL) and water (0.5 mL). The reaction mixture was evacuated and filled with N$_2$ twice then heated at 90° C. overnight. The reaction mixture was filtered through celite and washed with DMSO and MeOH. The filtrate was acidified with 1N HCl and stirred at RT for 3 hour, then extracted with DCM. The aqueous layer was basified with 2M NH$_2$ in MeOH and a brownish precipitate formed, which was filtered and washed with DMSO to afford a grey solid 2-(6-((3aR,6aS)-hexahydropyrrolo[3,4-c]pyrrol-2(1H)-yl)pyridazin-3-yl)-5-(1H-pyrazol-4-yl)phenol (82 mg, 0.224 mmol, 51.2% yield). MS (M+1)=349.1. The DMSO wash solution was concentrated to afford a DMSO solution of desired (3aR,6aS)-tert-butyl 5-(6-(2-hydroxy-4-(1H-pyrazol-4-yl)phenyl)pyridazin-3-yl)hexahydropyrrolo[3,4-c]pyrrole-2(1H)-carboxylate (75 mg, 0.167 mmol, 38% yield), MS (M+1)=449.1, which was used directly in the next step.

Step 4: 2-(6-((3aR,6aS)-Hexahydropyrrolo[3,4-c]pyrrol-2(1H)-yl)pyridazin 3-yl)-5-(1H-pyrazol-4-yl)phenol To a solution of (3aR,6aS)-tert-butyl 5-(6-(2-hydroxy-4-(1H-pyrazol-4-yl)phenyl)pyridazin-3-yl)hexahydropyrrolo[3,4-c]pyrrole-2(1H)-carboxylate (75 mg, 0.167 mmol) in 1 mL of dioxane was added 4N HCl in dioxane (1 mL, 4.00 mmol). The reaction mixture was stirred at RT overnight, and then basified with 2N NH$_3$ in MeOH to form a precipitate which was separated via centrifugation to provide a dark solid, 2-(6-((3aR,6aS)-hexahydropyrrolo[3,4-c]pyrrol-2(1H)-yl)pyridazin 3-yl)-5-(1H-pyrazol-4-yl)phenol (50 mg, 0.136 mmol, 82% yield) MS(M+1)=349.1.

Step 5: 2-(6-((3aR,6aS)-5-(2-((tert-Butyldimethylsilyl)oxy)ethyl))hexahydropyrrolo[3,4-c]pyrrol-2(1H)-yl)pyridazin-3-yl)-5-(1H-pyrazol-4-yl)phenol To a solution of 2-(6-((3aR,6aS)-hexahydropyrrolo[3,4-c]pyrrol-2(1H)-yl)pyridazin-3-yl)-5-(1H-pyrazol-4-yl)phenol (31.4 mg, 0.09 mmol), 2-((tert-butyldimethylsilyl)oxy)acetaldehyde (47.1 mg, 0.270 mmol), and sodium triacetoxyhydroborate (57.2 mg, 0.270 mmol) in CH$_2$Cl$_2$ (2 mL), was added acetic acid (0.013 mL, 0.225 mmol). The reaction mixture was stirred at RT overnight, then quenched with water and diluted with DCM. The organic layer was acidified with 1N HCl solution to pH-3 and filtered to remove insoluble materials. The filtrate was loaded onto an SCX column, washed with MeOH, then eluted with 7N NH$_3$ in MeOH. Concentration provided a brownish solid, 2-(6-((3aR,6aS)-5-(2-((tert-butyldimethylsilyl)oxy)ethyl)hexahydropyrrolo[3,4-c]pyrrol-2(1H)-yl)pyridazin-3-yl)-5-(1H-pyrazol-4-yl)phenol (23 mg, 0.020 mmol, 51% yield), MS (M+1)=507.1.

Step 6: 2-(6-((3aR,6aS)-5-(2-Hydroxyethyl)hexahydropyrrolo[3,4-c]pyrrol-2(1H)-yl)pyridazin-3-yl)-5-(1H-pyrazol-4-yl)phenol To a solution of 2-(6-((3aR,6aS)-5-(2-((tert-butyldimethylsilyl)oxy)ethyl)hexahydropyrrolo[3,4-c]pyrrol-2(1H)-yl)pyridazin-3-yl)-5-(1H-pyrazol-4-yl)phenol (20 mg, 0.039 mmol) in dioxane (2 mL) was added 4N HCl in dioxane (1 mL, 4.00 mmol). The reaction mixture was stirred at RT overnight, then basified with 2N NH$_3$ in MeOH and concentrated. The crude product was purified via preparative HPLC to give an off-white solid 2-(6-((3aR,6aS)-5-(2-hydroxyethyl)hexahydropyrrolo[3,4-c]pyrrol-2 (1H)-yl)pyridazin-3-yl)-5-(1H-pyrazol-4-yl)phenol (6.5 mg, 0.016 mmol, 41% yield). LCMS Rt=0.87 min [Method Q]; MS (M+1)=393.1. $^1$H NMR (400 MHz, METHANOL-d4) δ ppm 8.01 (d, J=9.60 Hz, 1H), 7.93 (s, 2H), 7.69 (d, J=8.08 Hz, 1H), 7.08-7.19 (m, 3H), 3.67-3.77 (m, 4H), 3.56 (d, J=11.12 Hz, 2H), 3.11 (br. s., 2H), 2.97-3.05 (m, 2H), 2.72 (t, J=5.81 Hz, 2H), 2.63-2.70 (m, 2H).

The following compounds were prepared using similar procedures as in Example 43-1, and general methods as outlined in the GENERAL METHODS section.

| Example | Structure | $^1$H NMR, 400 MHz | LCMS Method Q |
|---|---|---|---|
| 43-2 | 2-(6-((3aR,6aS)-hexahydropyrrolo[3,4-c]pyrrol-2(1H)-yl)pyridazin-3-yl)-5-(1H-pyrazol-4-yl)phenol | (DMSO-d$_6$) δ 8.22 (d, J = 2.5 Hz, 2H), 7.94-8.00 (m, 1H), 7.83 (d, J = 8.1 Hz, 1H), 7.15-7.23 (m, 3H), 3.71-3.86 (m, 2H), 3.45-3.53 (m, 2H), 3.31-3.39 (m, 2H), 3.16-3.23 (m, 1H), 3.00-3.11 (m, 2H), 2.86-2.93 (m, 1H) | Rt = 0.38 min M + 1 = 349.1 |
| 43-3 | 2-(6-((3aR,6aS)-5-methylhexahydropyrrolo[3,4-c]pyrrol-2(1H)-yl)pyridazin-3-yl)-5-(1H-pyrazol-4-yl)phenol | (METHANOL-d$_4$) δ 8.01 (d, J = 10.1 Hz, 1H), 7.93 (s, 2H), 7.68 (d, J = 8.1 Hz, 1H), 7.08-7.17 (m, 3H), 3.72 (dd, J = 10.9, 7.8 Hz, 2H), 3.56 (dd, J = 10.9, 2.3 Hz, 2H), 3.09-3.20 (m, 2H), 2.90-2.99 (m, 2H), 2.67 (dd, J = 9.9, 2.8 Hz, 2H), 2.45 (s, 3H) | Rt = 0.38 min M + 1 = 363.2 |

| Example | Structure | ¹H NMR, 400 MHz | LCMS Method Q |
|---|---|---|---|
| 43-4 | 4-(3-hydroxy-4-(6-(5-methylhexahydropyrrolo[3,4-c]pyrrol-2(1H)-yl)pyridazin-3-yl)phenyl)-1-methylpyridin-2(1H)-one | (METHANOL-$d_4$) δ 7.88 (d, J = 9.6 Hz, 1H), 7.64 (d, J = 8.6 Hz, 1H), 7.38 (d, J = 7.1 Hz, 1H), 7.18 (d, J = 2.0 Hz, 1H), 7.10 (dd, J = 8.3, 1.8 Hz, 1H), 6.97 (d, J = 9.6 Hz, 1H), 6.76 (d, J = 1.5 Hz, 1H), 6.51 (dd, J = 7.1, 2.0 Hz, 1H), 3.66 (d, J = 6.6 Hz, 2H), 3.56-3.63 (m, 2H), 3.52 (s, 3H), 3.20-3.40 (b. s., 2H), 3.05-3.35 (br. s., 2H), 2.73 (br. s., 2H), 2.50 (br. s., 3H) | Rt = 0.41 min<br>M + 1 = 404.3 |
| 43-5 | 4-(3-hydroxy-4-(6-((3aR,6aR)-1-methylhexahydropyrrolo[3,4-b]pyrrol-5(1H)-yl)pyridazin-3-yl)phenyl)-1-methylpyridin-2(1H)-one | (METHANOL-$d_4$) δ 8.03 (d, J = 10.1 Hz, 1H), 7.77 (d, J = 8.6 Hz, 1H), 7.55 (d, J = 7.1 Hz, 1H), 7.24 (d, J = 1.5 Hz, 1H), 7.19 (dd, J = 8.3, 1.8 Hz, 1H), 7.13 (d, J = 9.6 Hz, 1H), 6.82 (d, J = 1.5 Hz, 1H), 6.64 (dd, J = 7.1, 2.0 Hz, 1H), 4.01 (d, J = 12.1 Hz, 1H), 3.74-3.83 (m, 1H), 3.54-3.69 (m, 2H), 3.60 (s, 3H), 3.49 (br. s., 1H), 3.37 (br. s., 1H), 3.20 (br. s., 1H), 2.72 (d, J = 7.6 Hz, 1H), 2.62 (s, 3H), 2.36 (d, J = 9.6 Hz, 1H), 1.89 (d, J = 8.6 Hz, 1H) | Rt = 0.41 min<br>M + 1 = 404.2 |
| 43-6 | 2-(6-(2,7-diazaspiro[4.5]decan-2-yl)pyridazin-3-yl)-5-(1H-pyrazol-4-yl)phenol | (METHANOL-$d_4$) δ 7.83 (d, J = 10.1 Hz, 1H), 7.78-7.81 (m, 2H), 7.55 (d, J = 8.1 Hz, 1H), 7.10 (d, J = 2.0 Hz, 1H), 7.03 (dd, J = 8.1, 1.5 Hz, 1H), 6.90 (d, J = 9.6 Hz, 1H), 3.51-3.62 (m, 2H), 3.47 (d, J = 10.6 Hz, 1H), 3.30 (s, 1H), 2.74-2.84 (m, 1H), 2.61-2.74 (m, 3H), 1.89-2.00 (m, 1H), 1.78-1.89 (m, 1H), 1.59-1.70 (m, 2H), 1.46-1.59 (m, 2H) | Rt = 0.42 min<br>M + 1 = 377.2 |
| 43-7 | 4-(4-(6-(2,7-diazaspiro[4.5]decan-2-yl)pyridazin-3-yl)-3-hydroxyphenyl)-1-methylpyridin-2(1H)-one | (METHANOL-$d_4$) δ 7.97 (d, J = 10.1 Hz, 1H), 7.72 (d, J = 8.1 Hz, 1H), 7.53 (d, J = 7.1 Hz, 1H), 7.16 (d, J = 1.5 Hz, 1H), 7.13 (dd, J = 8.3, 1.8 Hz, 1H), 7.02 (d, J = 9.6 Hz, 1H), 6.75 (d, J = 1.5 Hz, 1H), 6.60 (dd, J = 7.1, 2.0 Hz, 1H), 3.56-3.65 (m, 2H), 3.53 (s, 3H), 3.45-3.50 (m, 1H), 3.30 (d, J = 10.6 Hz, 1H), 2.75-2.84 (m, 1H), 2.62-2.75 (m, 3H), 1.91-2.03 (m, 1H), 1.79-1.90 (m, 1H), 1.60-1.71 (m, 2H), 1.49-1.60 (m, 2H) | Rt = 0.44 min<br>M + 1 = 418.2 |

Example 44

Synthesis of Example 17-13 5-(1H-Pyrazol-4-yl)-2-(6-((2,2,6,6-tetramethylpiperidin-4-yl)oxy)pyridazin-3-yl)phenol hydrochloride

Step 1a: Preparation of 3-chloro-6-((2,2,6,6-tetramethylpiperidin-4-yl)oxy)pyridazine To a 30-L reactor was charged 3,6-dichloropyridazine (1 kg, 6.7 mol), 2,2,6,6-tetramethylpiperidin-4-ol (1.05 kg, 6.7 mol) and THF (5 L). The mixture was stirred and cooled to −5° C. tBuOK (1.13 kg, 10.1 mol) dissolved in THF (10 L) was added slowly to the reactor while keeping the temperature at −5-0° C. The reaction mixture became deep brown during addition. After the addition was complete, the mixture was stirred for 1 hour at −5-0° C., after which time HPLC analysis showed that the reaction was complete. Ice water (1:1, 10 kg) was added slowly to quench the reaction. The mixture was concentrated under reduced pressure to remove most of the THF. The residue was extracted with EtOAc twice (10 L+5 L). The combined organic layer was washed with water (10 L×3), then concentrated under reduced pressure to give a black residue. Petroleum ether (25 L) was added to this residue while stirring. The dark solid that formed was removed by filtration. The pale yellow filtrate was concentrated under reduced pressure to give a yellow solid, which was dried at 50° C. in vacuo to give 3-chloro-6-((2,2,6,6-tetramethylpiperidin-4-yl)oxy)pyridazine (1.3 kg, 4.8 mol), and was used in the next step without further purification. MS m/z 270.1 [M+H]; $^1$H-NMR: (CDCl$_3$, 400 MHz) δ 7.36 (d, J=9.2 Hz, 1H), 6.90 (d, J=9.2 Hz, 1H), 5.74 (m, 1H), 2.20 (dd, J$_a$=4 Hz, J$_b$=12.4 Hz, 2H), 1.30 (m, 14H).

Step 1b: Preparation of 5-chloro-2-(4,4,5,5-tetramethyl-1,3,2-dioxaborolan-2-yl)phenol To a 30-L reactor was charged 2-bromo-5-chlorophenol (2.0 kg, 9.65 mol), B$_2$Pin$_2$ (2.7 kg, 10.6 mol), AcOK (1.9 kg, 19.3 mol) and 1,4-dioxane (15 L). The mixture was stirred and purged with nitrogen 3 times. PdCl$_2$(dppf)-CH$_2$Cl$_2$ (100 g, 0.12 mol) was added under nitrogen and the mixture was heated to 75° C. (the oil bath could be removed in case of strong exotherm). The mixture was heated at 90° C. for 16 hours, after which time HPLC analysis showed that the reaction was complete. After cooling to 35° C., the mixture was filtered through a pad of Celite. The filtrate 5-chloro-2-(4,4,5,5-tetramethyl-1,3,2-dioxaborolan-2-yl)phenol (1.22 kg, 4.8 mol) solution was used in next step without further purification. MS m/z 253.1 [M−H]; $^1$H-NMR: (CDCl$_3$, 400 MHz) δ 9.2 (br, 1H), 7.25 (d, J=8 Hz, 1H), 6.64 (d, J=1.6 Hz, 1H), 6.62 (dd, J$_b$=8 Hz, J$_b$=1.6 Hz, 1H), 1.05 (s, 12H).

Step 2: Preparation of 5-chloro-2-(6-((2,2,6,6-tetramethylpiperidin-4-yl)oxy)pyridazin-3-yl)phenol hydrochloride To the solution containing 5-chloro-2-(4,4,5,5-tetramethyl-1,3,2-dioxaborolan-2-yl)phenol (1.22 kg, 4.8 mol) from the previous step was added 3-chloro-6-((2,2,6,6-tetramethylpiperidin-4-yl)oxy)pyridazine (1.17 kg, 4.4 mol). K$_3$PO$_4$-3H$_2$O (2.34 kg, 8.8 mol) was dissolved in water (5 L) then added to the above solution. The mixture was purged with nitrogen 3 times. Pd(PPh$_3$)$_4$(500 g, 0.42 mol) was added under nitrogen, and the reaction mixture was heated to reflux at 89° C. for 16 hours. After 16 hours, HPLC showed that the reaction was complete. After cooling to room temperature, the mixture was filtered through a pad of celite and the filtrate was concentrated under reduced pressure. CH$_2$Cl$_2$ (10 L×3) and 10% K$_2$CO$_3$ solution (15 L) were added to the above residue. The organic layers were separated and combined, followed by washing with water twice (10 L×2) and concentration under reduced pressure to give yellow oil. MTBE (10 L) was used to dissolve the yellow oil. Petroleum ether (4 L) was added slowly with stirring. A few dark solids precipitated and were removed by filtration. The filtrate was concentrated under reduced pressure and dissolved in CH$_2$Cl$_2$ (20 L). 2N HCl (5 L) was added slowly and a large amount of precipitate formed. After stirring for another 1 hour, the solid was collected by filtration and washed with EtOAc (2 L). The solid was dried in vacuo at 50° C. to give 5-chloro-2-(6-((2,2,6,6-tetramethylpiperidin-4-yl)oxy)pyridazin-3-yl)phenol hydrochloride (0.9 kg, 2.2 mol). MS m/z 362.0 [M+H]$^+$; $^1$H-NMR: (DMSO-d$^6$, 400 MHz) δ 9.26 (d, J=11.6 Hz, 1H), 8.49 (d, J=12 Hz, 1H), 8.38 (d, J=9.6 Hz, 1H), 7.93 (d, J=8.4 Hz, 1H), 7.44 (d, J=9.6 Hz, 1H), 7.07 (d, J=2 Hz, 1H), 7.02 (dd, J$_a$=2 Hz, J$_b$=8.4 Hz, 1H), 5.73 (m, 1H), 2.31 (dd, J$_a$=4 Hz, J$_b$=13.2 Hz, 2H), 1.84 (dd, J$_a$=11.6 Hz, J$_b$=2 Hz, 2H), 1.51 (s, 6H), 1.49 (s, 6H).

Step 3: Preparation of 5-(1H-pyrazol-4-yl)-2-(6-((2,2,6,6-tetramethylpiperidin-4-yl)oxy)pyridazin-3-yl)phenol A 1-L flask was charged with 5-chloro-2-(6-((2,2,6,6-tetramethylpiperidin-4-yl)oxy)pyridazin-3-yl)phenol hydrochloride (9.2 g, 23 mmol), N-Boc-Pyrazole-4-boronic acid pinacol ester (10.2 g, 35 mmol), Cs$_2$CO$_3$ (15 g, 46 mmol), 1,4-dioxane (100 mL) and water (25 mL). The mixture was purged with nitrogen 3 times. X-Phos (0.88 g, 1.85 mmol) and Pd$_2$dba$_3$ (0.845 g, 0.922 mmol) were added. The mixture was purged with nitrogen 3 times, then heated at 80° C. for 3 hrs. By HPLC analysis, the reaction was complete. 37% HCl (10 mL) was added slowly over 20 min. Ethanol (100 mL) and H$_2$O (200 mL) were added and the reaction mixture was heated to 75-80° C. for 16 hours. The reaction mixture was cooled to 50-60° C., and the insoluble black solids were filtered. The filtrate was cooled to 30° C., and 2N NaOH (50 mL) was added to basify the solution to pH 8-9. The resulting precipitate was stirred for 30 min, then filtered and dried under vacuum at 50° C. to give 5-(1H-pyrazol-4-yl)-2-(6-((2,2,6,6-tetramethylpiperidin-4-yl)oxy)pyridazin-3-yl)phenol as yellow solid. HRMS m/z 394.2239 [M+H]; $^1$H-NMR: (DMSO-d$^6$, 400 MHz) δ 13.2 (br, 1H), 13.0 (br, 1H), 8.44 (d, J=8 Hz, 1H), 8.14 (br, 2H), 7.93 (d, J=8 Hz, 1H), 7.39 (d, J=12 Hz, 1H), 7.24 (d, J=8 Hz, 2H), 5.64 (m, 1H), 2.10 (dd, J$_a$=4 Hz, J$_b$=12 Hz, 2H), 1.26-1.30 (m, J=8 Hz, 2H), 1.23 (s, 6H), 1.10 (s, 6H). $^{13}$C-NMR: (DMSO-d$^6$, 100 MHz) b 162.80, 158.55, 155.97, 136.13, 128.30, 127.71, 120.42, 120.01, 116.26, 115.13, 113.44, 71.32, 50.99, 43.20, 34.33, 29.14.

Step 4: Preparation of 5-(1H-pyrazol-4-yl)-2-(6-((2,2,6,6-tetramethylpiperidin-4-yl)oxy)pyridazin-3-yl)phenol hydrochloride To a 2-L flask was added 5-(1H-pyrazol-4-yl)-2-(6-((2,2,6,6-tetramethylpiperidin-4-yl)oxy)pyridazin-3-yl)phenol (50 g, 127 mmol), 37% HCl (21 mL, 254 mmol), H$_2$O (1 L) and EtOH (1 L). SMOPEX-234 (10 g, Pd scavenger) and activated charcoal (10 g) were also added. The mixture was heated at reflux (78° C.) for 3 hours. The resulting black mixture was allowed to cool to 60° C., and the Pd scavenging agents were filtered off at 50-60° C. The filtrate was cooled to 15° C. gradually over 1 h, and a pale yellow precipitate formed. After 2 h, the solid was collected by filtration, washed with EtOH (50 mL), and dried under vacuum at 50° C. to give 5-(1H-pyrazol-4-yl)-2-(6-((2,2,6,6-tetramethylpiperidin-4-yl)oxy)pyridazin-3-yl)phenol hydrochloride (27.2 g, 63 mmol). HRMS m/z 394.2222 [M+H]; $^1$H-NMR: (DMSO-d, 400 MHz) δ 13.09 (br, 2H), 9.41 (d, J=12 Hz, 1H), 8.61 (d, J=12 Hz, 1H), 8.49 (d, J=Hz, 1H), 8.15 (br, 2H), 7.95 (d, J=8 Hz, 1H), 7.46 (d, J=8 Hz, 1H), 7.26 (d, J=8 Hz, 2H), 5.72 (m, 1H), 2.33 (dd, $J_a$=3.2 Hz, $J_b$=13.2 Hz, 2H), 1.86-1.92 (m, $J_a$=8 Hz, 2H), 1.23 (s, 6H), 1.10 (s, 6H); $^{13}$C-NMR: (DMSO-d$^3$, 100 MHz) δ 162.34, 158.51, 156.41, 136.29, 128.72, 127.94, 120.40, 119.95, 116.37, 115.18, 113,45, 67.94, 56.69, 29.23, 25.10; XRPD: 13.47505, 14.29462, 14.99017, 16.55045, 17.60726, 19.69314, 21.89296, 23.89703, 25.82989, 27.13969, 28.47844, 36.94252, 43.77528.

LCMS Conditions:

Condition A:

Column: Acquity BEH 1.7 mm 2.1×50 mm at 50° C.

Neutral system; Gradient: 2 to 98% B in 4.4 min—flow 1 mL/min; Eluent A: Water+3.75 mM ammonium acetate+2% ACN; Eluent B: Acetonitrile+7.5 mM ammonium acetate;

Condition B:

Column: INERTSIL C$_8$-3, 3 μm×33 mm×3.0 mm at 40° C.

Flow rate: 2 mL/min

Mobile phase: A) 5 mM aqueous HCOONH$_4$, B) MeOH/CH$_3$CN (1/1, v/v)

Gradient: linear gradient from 5% A to 95% B in 2 min

Condition Q:

Waters Acquity UPLC system

Waters Acquity UPLC BEH C18 1.7 um, 2.1×30 mm (Part#: 186002349)

Flow rate: 1 mL/min Temperature: 55□C (column temp)

Mobile Phase Compositions:

A. 0.05% formic acid in water.

B. 0.04% formic acid in methanol

Gradient:

| Time (min) | Flow (mL/min) | % A | % B |
|---|---|---|---|
| 0 | 1.000 | 95.0 | 5.0 |
| 0.10 | 1.000 | 95.0 | 5.0 |
| 0.50 | 1.000 | 20.0 | 80.0 |
| 0.60 | 1.000 | 5.0 | 95.0 |
| 0.80 | 1.000 | 5.0 | 95.0 |
| 0.90 | 1.000 | 95.0 | 5.0 |
| 1.15 | 1.000 | 95.0 | 5.0 |

Abbreviations:

| | |
|---|---|
| Ac: Acetyl | aq: aqueous |
| ACN: acetonitrile | B$_2$pin: Bis(pinacolato)diboron |
| BOC, Boc: tertiary butyl carboxy | BOC$_2$O: tertiary butylcarboxyanhydride |
| Bn: benzyl | bs: broad singlet |
| BSA: Bovine Serum Albumin | 9-BBN: 9-Borabicyclo[3.3.1]nonane |
| CH$_3$CN: acetonitrile | CHN: C, H, N elemental analysis |
| d: doublet dd: doublet of doublets | DCM: dichloromethane |
| DIEA: diethylisopropylamine | DMA: dimethylacetamide |
| DIBAL: diisobutylaluminium hydride | DAST: Diethylaminosulfur trifluoride |
| DIPEA: N,N-diisopropylethylamine | DME: 1,2-dimethoxyethane |
| DMF: N,N-dimethylformamide | DMSO: dimethylsulfoxide |
| DIAD: Diisopropyl azodicarboxylate | DCC: N,N'-Dicyclohexylcarbodiimide |
| Dtbpy: 4,4'-di-tert-butyl bipyridine | |
| dppf: 1,1'-bis(diphenylphosphino)ferrocene | EC$_{50}$: half maximal effective concentration |
| ELISA: enzyme-linked immunosorbent assay | Et and EtOAc: ethyl and ethyl acetate |
| Et$_2$O: ether, diethyl ether | EtOH: ethanol |
| g: gram | |
| HATU: O-(7-azobenzotriazol-1-yl)-1,1,3,3-tetramethyluroniumhexafluorophosphate | HPLC: High Pressure Liquid Chromatography |
| HRP: horse radish peroxidase | HOBt: Hydroxybenzotriazole |
| h, hr: hour(s) | |
| LC and LCMS: liquid chromatography and liquid chromatography and mass spectrometry | L: liter |
| M: Molar | Me: methyl |
| M as in M + 1: Molecular Mass | M and mM: Molar and millimolar |
| m: multiplet | mAB: monoclonal antibody |
| MeOD: methanol-d4 | MS: mass spectrometry |
| MeOH: methanol | MTBE: methyl tert-butyl ether |
| min: minutes | m/z: mass to charge ratio |
| mL: milliliter | mm: millimeter |
| mg: milligram | mmol, m: millimole, mole |
| MHz, Hz: mega Hertz; Hertz | N: normal |
| NMP: N-methylpyrrolidone | nM: nanomolar |
| NMM: N-methyl morpholine | |
| NMR: Nuclear Magnetic Resonance Spectroscopy | PBST: Phosphate buffered saline with Tween |
| PdCl$_2$(dppf)•CH$_2$Cl$_2$: 1,1'-Bis(diphenylphosphino)ferrocene-palladium(II)dichloride dichloromethane complex | ppm: parts per million |
| pM: picomolar | |
| PhSH: thiophenol | q: quartet |
| RIPA: radio-immunoprecipitation assay | |
| Rt: retention time | RT: room temperature |
| sat: saturated | s: singlet |
| SFC: Supercritical Fluid Chromatography | SCX: Strong Cation Exchange |

| | |
|---|---|
| SPhos: 2-Dicyclohexylphosphino-2',6'-dimethoxybiphenyl | TFA: trifluoroacetic acid |
| t: triplet | TBAF: tetra-butylammonium fluoride |
| TBSCl: tert-butyldimethylsilyl chloride | tBu: tert-butyl |
| TEA: triethylamine | Tf: triflate |
| THF: tetrahydrofuran | TLC: thin layer chromatography |
| TMB: tertramethylbenzidine | TMSOTf: trimethylsilyl trifluoromethanesulfonate |
| uL, mL and L: microliter, milliliter and liter | UV: ultraviolet |
| wt: weight | |
| XPhos: 2-Dicyclohexylphosphino-2',4',6'-triisopropylbiphenyl | XPhos Palladacycle: Chloro(2-dicyclohexylphosphino-2',4',6'-tri-i-propyl-1,1'-biphenyl)[2-(2-aminoethyl)phenyl] palladium(II) methyl-t-butylether |

Biological Example 1

A cellular SMN ELISA was used to measure the effects of low molecular weight compounds on SMN protein elevation. Cells from a myoblast cell line derived from the SMNdelta7 mouse model (kind gift from Steve Burden, NYU) were seeded into a 384-well plate at a density of 3000 cells/well and treated with compounds for 24 hours. ELISA capture plates were prepared by coating 384-well plates (Immulon 4HBX) with 0.5 ug/mL of anti-SMN mAb (BD Science, Catalog number 610647) at 4° C. overnight. The plates were washed 5 times with 110 uL of PBS-Tween (0.05% Tween-20, PBST), blocked with 100 uL of 1% BSA in PBST for 2 hours and washed (5 times) with 100 uL of PBST. After 24 hours of compound treatment cells were lysed in a modified RIPA-buffer, on ice for 1 hour. 20 uL of lysate and 20 uL of 1% BSA were then added to the ELISA capture plates and incubated at 4° C. overnight. Plates were washed (5 times) with PBST and then incubated with 1:100 dilution of primary rabbit anti-SMN polyclonal antibody (Santa cruz, Catalog number SC-15320) at room temperature for 1 hour and subsequently washed (5 times) with 110 uL of PBST. This was followed by addition of 1:100 Goat anti-Rabbit IgG-HRP linked (Cell Signaling, Catalog number 7074) secondary antibody for 1 hour. Plates were then washed with PBST and incubated with 40 uL TMB substrate (Cell Signaling, Catalog number 7004L) at room temperature for 1-10 minutes with shaking. The reaction was stopped by addition of 40 uL of stop solution (Cell signaling, Catalog number 7002L) and absorption was measured at 450 nm. Data was reported as fold activation over DMSO control, and $EC_{50}$.

ELISA assay condition 1: compound concentration range 20 nM-10 uM; ELISA assay condition 2: compound concentration 100 pM-10 uM.

Activity Table: Data generated in Biological Example 1 using ELISA conditions 1 or 2.

| Example | SMN activity Fold, $EC_{50}$ | ELISA condition |
|---|---|---|
| 1-1 | 2.62, 810 nM | 2 |
| 1-2 | 2.40, 600 nM | 2 |
| 1-3 | 2.45, 726 nM | 2 |
| 1-4 | 2.05, 90 nM | 1 |
| 1-5 | 2.50, 650 nM | 1 |
| 1-6 | 2.00, 2.44 uM | 1 |
| 1-7 | 2.07, 1.55 uM | 1 |
| 1-8 | 2.18, 320 nM | 1 |
| 1-9 | 2.81, 398 nM | 2 |
| 1-10 | 2.75, 1.1 uM | 2 |
| 1-11 | 2.67, 3.90 uM | 2 |
| 1-12 | 2.54, 367 nM | 2 |
| 1-13 | 2.22, 661 nM | 2 |
| 1-14 | 3.13, 252 nM | 2 |
| 1-15 | 2.93, 197 nM | 2 |
| 1-16 | 2.28, 2.98 uM | 2 |
| 1-17 | 2.37, 926 nM | 2 |
| 1-18 | 2.69, 1.13 uM | 1 |
| 1-19 | 3.10, 740 nM | 1 |
| 1-20 | 3.04, 470 nM | 1 |
| 1-21 | 2.49, 630 nM | 1 |
| 1-22 | 2.71, 867 nM | 2 |
| 2-1 | 2.68, 1.37 uM | 1 |
| 2-2 | 2.37, 1.03 uM | 1 |
| 2-3 | 2.46, 1.20 uM | 1 |
| 3-1 | 2.31, 10 nM | 2 |
| 3-2 | 2.06, 1.07 uM | 1 |
| 3-3 | 2.48, 64 nM | 1 |
| 3-4 | 2.03, 620 nM | 1 |
| 3-5 | 2.38, 100 nM | 1 |
| 3-6 | 3.01, 110 nM | 2 |
| 3-7 | 2.67, 4.53 uM | 1 |
| 3-8 | 2.72, 1.58 uM | 2 |
| 3-9 | 2.88, 323 nM | 2 |
| 3-10 | 2.53, 855 nM | 2 |
| 3-11 | 2.47, 220 nM | 2 |
| 3-12 | 2.70, 129 nM | 1 |
| 4-1 | 2.53, 148 nM | 2 |
| 5-1 | 2.97, 54 nM | 2 |
| 6-1 | 2.04, 630 nM | 2 |
| 7-1 | 2.54, 2.73 uM | 1 |
| 8-1 | 2.72, 280 nM | 1 |
| 9-1 | 2.96, 17 nM | 1 |
| 10-1 | 2.99, 31 nM | 2 |
| 11-1 | 2.79, 23 nM | 2 |
| 12-1 | 3.13, 4 nM | 2 |
| 13-1 | 3.46, 20 nM | 2 |
| 14-1 | 2.98, 4 nM | 2 |
| 15-1 | 2.90, 14 nM | 2 |
| 16-1 | 2.66, 77 nM | 2 |
| 16-2 | 3.21, 15 nM | 2 |
| 16-3 | 2.39, 625 nM | 2 |
| 16-4 | 2.71, 94 nM | 2 |
| 16-5 | 2.41, 24 nM | 2 |
| 17-1 | 2.58, 339 nM | 2 |
| 17-2 | 2.62, 70 nM | 1 |
| 17-3 | 2.75, 183 nM | 2 |
| 17-4 | 3.25, 92 nM | 2 |
| 17-5 | 2.78, 2.44 uM | 2 |
| 17-6 | 2.58, 443 nM | 2 |
| 17-7 | 2.50, 617 nM | 2 |
| 17-8 | 2.18, 3.15 uM | 2 |

Activity Table: Data generated in Biological Example 1 using ELISA conditions 1 or 2.

| Example | SMN activity Fold, $EC_{50}$ | ELISA condition |
|---|---|---|
| 17-9 | 2.63, 1.67 uM | 2 |
| 17-10 | 2.03, 945 nM | 2 |
| 17-11 | 3.01, 665 nM | 2 |
| 17-12 | 3.29, 31 nM | 2 |
| 17-13 | 4.00, 17 nM | 2 |
| 18-1 | 3.07, 296 nM | 2 |
| 18-2 | 1.97, 3.23 uM | 2 |
| 18-3 | 1.95, 660 nM | 1 |
| 18-4 | 2.84, 388 nM | 2 |
| 18-5 | 2.66, 151 nM | 2 |
| 18-6 | 2.54, 268 nM | 2 |
| 18-7 | 2.67, 2.66 uM | 2 |
| 18-8 | 2.32, 983 nM | 2 |
| 18-9 | 1.93, 1.18 uM | 1 |
| 18-10 | 2.55, 386 nM | 2 |
| 18-11 | 2.53, 320 nM | 2 |
| 18-12 | 2.62, 792 nM | 2 |
| 18-13 | 2.28, 1.24 uM | 2 |
| 18-14 | 2.62, 17 nM | 1 |
| 18-15 | 2.30, 714 nM | 2 |
| 18-16 | 3.25, 227 nM | 2 |
| 18-17 | 2.85, 158 nM | 2 |
| 18-18 | 2.57, 56 nM | 2 |
| 19-1 | 2.77, 477 nM | 2 |
| 19-2 | 2.73, 402 nM | 2 |
| 19-3 | 2.19, 155 nM | 2 |
| 19-4 | 2.47, 25 nM | 2 |
| 19-5 | 2.58, 402 nM | 2 |
| 19-6 | 2.33, 40 nM | 2 |
| 19-7 | 3.07, 37 nM | 2 |
| 20-1 | 2.75, 18 nM | 2 |
| 20-2 | 2.79, 4 nM | 2 |
| 20-3 | 3.42, 8 nM | 2 |
| 20-4 | 2.32, 310 nM | 1 |
| 20-5 | 2.66, 6 nM | 2 |
| 20-6 | 2.18, 50 nM | 2 |
| 20-7 | 2.75, 7 nM | 2 |
| 20-8 | 2.61, 30 nM | 2 |
| 20-9 | 2.44, 176 nM | 2 |
| 21-1 | 2.35, 959 nM | 2 |
| 21-2 | 2.69, 206 nM | 2 |
| 22-1 | 2.68, 39 nM | 2 |
| 23-1 | 2.32, 3.65 uM | 2 |
| 24-1 | 3.14, 16 nM | 2 |
| 24-2 | 2.33, 157 nM | 2 |
| 24-3 | 2.75, 120 nM | 2 |
| 24-4 | 3.06, 16 nM | 2 |
| 24-5 | 2.99, 47 nM | 2 |
| 24-6 | 2.39, 6 nM | 2 |
| 24-7 | 2.57, 31 nM | 2 |
| 24-8 | 2.39, 7 nM | 2 |
| 24-9 | 2.65, 338 nM | 2 |
| 24-10 | 3.14, 113 nM | 2 |
| 24-11 | 2.54, 133 nM | 2 |
| 24-12 | 2.80, 70 nM | 2 |
| 25-1 | 2.58, 84 nM | 2 |
| 25-2 | 3.44, 8 nM | 2 |
| 25-3 | 2.39, 119 nM | 2 |
| 25-4 | 2.30, 199 nM | 2 |
| 25-5 | 2.36, 96 nM | 2 |
| 25-6 | 2.16, 107 nM | 2 |
| 26-1 | 3.18, 14 nM | 2 |
| 26-2 | 2.61, 97 nM | 2 |
| 26-3 | 2.70, 47 nM | 2 |
| 26-4 | 2.22, 649 nM | 2 |
| 26-5 | 2.14, 313 nM | 2 |
| 27-1 | 2.35, 305 nM | 2 |
| 27-2 | 2.83, 165 nM | 2 |
| 27-3 | 2.75, 619 nM | 2 |
| 28-1 | 3.41, 475 nM | 2 |
| 29-1 | 2.49, 113 nM | 2 |
| 30-1 | 2.99, 8 nM | 2 |
| 30-2 | 2.98, 62 nM | 2 |
| 31-1 | 3.03, 200 nM | 2 |
| 32-1 | 2.67, 125 nM | 2 |
| 32-2 | 2.49, 396 nM | 2 |
| 32-3 | 2.44, 201 nM | 2 |
| 32-4 | 2.09, 168 nM | 2 |
| 32-5 | 2.52, 231 nM | 2 |
| 32-6 | 2.69, 92 nM | 2 |
| 32-7 | 3.27, 551 nM | 2 |
| 32-8 | 2.61, 433 nM | 2 |
| 32-9 | 2.90, 485 nM | 2 |
| 33-1 | 2.29, 349 nM | 2 |
| 34-1 | 2.80, 7 nM | 2 |
| 34-2 | 2.49, 2 nM | 2 |
| 34-3 | 2.56, 27 nM | 2 |
| 34-4 | 2.34, 37 nM | 2 |
| 34-5 | 2.75, 56 nM | 2 |
| 35-1 | 2.79, 27 nM | 2 |
| 35-2 | 2.84, 10 nM | 2 |
| 35-3 | 2.62, 11 nM | 2 |
| 35-4 | 2.11, 131 nM | 2 |
| 35-5 | 2.44, 6 nM | 2 |
| 35-6 | 2.21, 51 nM | 2 |
| 36-1 | 2.04, 652 nM | 2 |
| 37-1 | 2.59, 118 nM | 2 |
| 38-1 | 3.17, 60 nM | 2 |
| 39-1 | 2.65, 1026 nM | 2 |
| 39-2 | 3.04, 408 nM | 2 |
| 40-1 | 2.58, 79 nM | 2 |
| 40-2 | 2.78, 25 nM | 2 |
| 40-3 | 3.03, 11 nM | 2 |
| 40-4 | 2.14, 15 nM | 2 |
| 40-5 | 3.59, 17 nM | 2 |
| 40-6 | 2.16, 208 nM | 2 |
| 40-7 | 2.80, 4 nM | 2 |
| 40-8 | 3.18, 16 nM | 2 |
| 41-1 | 2.78, 125 nM | 2 |
| 41-2 | 2.68, 50 nM | 2 |
| 41-3 | 3.10, 66 nM | 2 |
| 41-4 | 3.29, 80 nM | 2 |
| 41-5 | 2.88, 175 nM | 2 |
| 41-6 | 2.67, 10 nM | 2 |
| 41-7 | 2.87, 7 nM | 2 |
| 41-8 | 3.18, 62 nM | 2 |
| 41-9 | 4.2, 72 nM | 2 |
| 41-10 | 2.80, 59 nM | 2 |
| 41-11 | 2.78, 12 nM | 2 |
| 41-12 | 2.92, 103 nM | 2 |
| 41-13 | 3.50, 308 nM | 2 |
| 41-14 | 3.21, 84 nM | 2 |
| 41-15 | 2.56, 145 nM | 2 |
| 41-16 | 2.30, 62 nM | 2 |
| 41-17 | 2.88, 170 nM | 2 |
| 41-18 | 2.44, 17 nM | 2 |
| 41-19 | 2.62, 17 nM | 2 |
| 41-20 | 2.63, 32 nM | 2 |
| 42-1 | 2.28, 117 nM | 2 |
| 42-2 | 2.06, 26 nM | 2 |
| 42-3 | 2.92, 99 nM | 2 |
| 42-4 | 2.41, 853 nM | 2 |
| 42-5 | 3.22, 202 nM | 2 |
| 42-6 | 2.49, 66 nM | 2 |
| 42-7 | 2.51, 55 nM | 2 |
| 42-8 | 2.82, 756 nM | 2 |
| 42-9 | 2.85, 15 nM | 2 |
| 42-10 | 3.10, 57 nM | 2 |
| 42-11 | 3.37, 239 nM | 2 |
| 43-1 | 3.04, 40 nM | 2 |
| 43-2 | 2.54, 58 nM | 2 |
| 43-3 | 2.39, 19 nM | 2 |
| 43-4 | 2.94, 41 nM | 2 |
| 43-5 | 2.29, 159 nM | 2 |

Activity Table: Data generated in Biological Example 1 using ELISA conditions 1 or 2.

| Example | SMN activity Fold, EC$_{50}$ | ELISA condition |
|---|---|---|
| 43-6 | 2.32, 156 nM | 2 |
| 43-7 | 2.42, 156 nM | 2 |

What is claimed is:

1. A compound or salt thereof according to Formula (I)

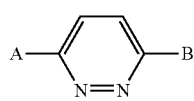

(I)

A is 2-hydroxy-phenyl which is substituted with 1, 2, or 3 substituents independently selected from haloC$_1$-C$_4$alkyl, dihaloC$_1$-C$_4$alkyl, trihaloC$_1$-C$_4$alkyl, C$_1$-C$_4$alkoxy, C$_1$-C$_4$alkoxy-C$_3$-C$_7$cycloalkyl, haloC$_1$-C$_4$alkoxy, dihaloC$_1$-C$_4$alkoxy, trihaloC$_1$-C$_4$alkoxy, hydroxy, cyano, halogen, amino, mono- and di-C$_1$-C$_4$alkylamino, heteroaryl, C$_1$-C$_4$alkyl substituted with hydroxy, C$_1$-C$_4$alkoxy substituted with aryl, amino, —C(O)NH C$_1$-C$_4$alkyl-heteroaryl, —NHC(O)—C$_1$-C$_4$alkyl-heteroaryl, C$_1$-C$_4$alkyl C(O)NH— heteroaryl, C$_1$-C$_4$alkyl NHC(O)-heteroaryl, 3-7 membered cycloalkyl, 5-7 membered cycloalkenyl or 5, 6 or 9 membered heterocycle containing 1 or 2 heteroatoms, independently, selected from S, O and N, wherein heteroaryl has 5, 6 or 9 ring atoms, 1, 2 or 3 ring heteroatoms selected from N, O and S and substituted with 0, 1, or 2 substituents independently selected from oxo, hydroxy, nitro, halogen, C$_1$-C$_4$alkyl, C$_1$-C$_4$alkenyl, C$_1$-C$_4$alkoxy, C$_3$-C$_7$cycloalkyl, C$_1$-C$_4$alkyl-OH, trihaloC$_1$-C$_4$alkyl, mono- and di-C$_1$-C$_4$alkylamino, —C(O)NH$_2$, —NH$_2$, —NO$_2$, hydroxyC$_1$-C$_4$alkylamino, hydroxyC$_1$-C$_4$alkyl, 4-7 member heterocycleC$_1$-C$_4$alkyl, aminoC$_1$-C$_4$alkyl and mono-, di-C$_1$-C$_4$alkylaminoC$_1$-C$_4$alkyl; and C$_1$-C$_4$alkyl, wherein 2 C$_1$-C$_4$alkyl groups can combine with the atoms to which they are bound to form a 5-6 membered ring and is substituted with 0 or 1 substituents selected from oxo, oxime and hydroxy;

B is selected from the group consisting of

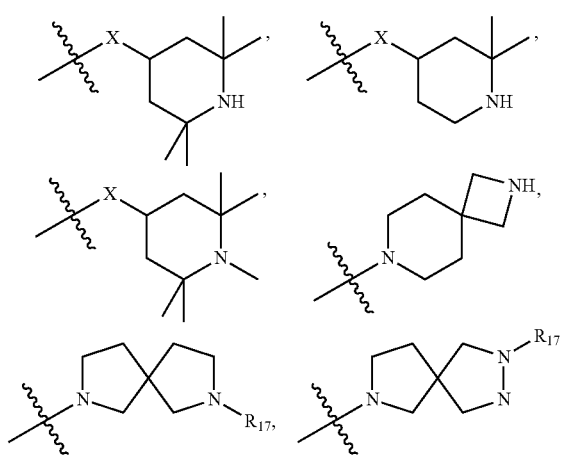

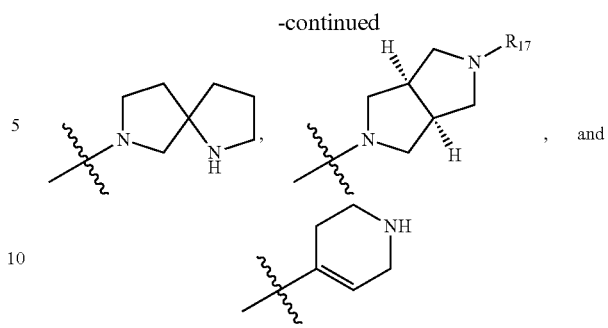

Wherein X is O or N(Me); and
R$_{17}$ is hydrogen or methyl.

2. A compound according to claim 1, or a salt thereof, which compound is represented by Formula (III):

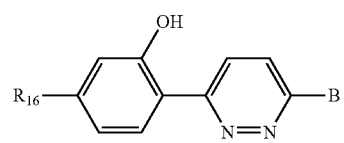

(III)

Wherein R$_{16}$ is a 5 member heteroaryl having one ring nitrogen atom and 0 or 1 additional ring heteroatom selected from N, O or S, wherein the heteroaryl is optionally substituted with C$_1$-C$_4$alkyl.

3. A compound, or salt thereof, according to claim 1, wherein X is —O—.

4. A compound, or salt thereof, according to claim 1, wherein B is:

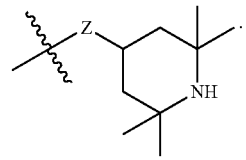

5. The compound, or salt thereof, according to claim 2, wherein R$_{16}$ is:

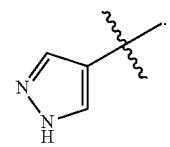

6. A compound, or salt thereof, according to claim 1, wherein the compound is of formula (IV):

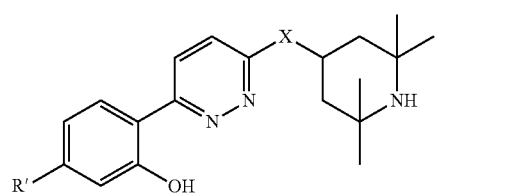

(IV)

wherein
X is —O— or

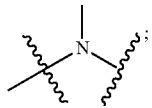

R' is a 5-membered heteroaryl optionally substituted with 0, 1, or 2 groups selected from hydroxy, nitro, halogen, $C_1$-$C_4$alkyl, $C_1$-$C_4$alkenyl, $C_1$-$C_4$alkoxy, $C_3$-$C_7$cycloalkyl, C1-$C_4$alkyl-OH, trihalo$C_1$-$C_4$alkyl, mono- and di-$C_1$-$C_4$alkylamino, —C(O)NH$_2$, —NH$_2$, —NO$_2$, hydroxy$C_1$-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl.

7. A compound, or salt thereof, selected from the group consisting of 2-(6-(2,2,6,6-tetramethylpiperidin-4-ylamino)-pyridazin-3-yl)phenol;
2-(6-(methyl-(2,2,6,6-tetra-methylpiperidin-4-yl)amino)-pyridazin-3-yl)phenol;
5-chloro-2-(6-(methyl(1,2,2,6,6-pentamethylpiperidin-4-yl)amino)pyridazin-3-yl)phenol;
5-chloro-2-(6-(1,2,2,6,6-pentamethylpiperidin-4-ylamino)pyridazin-3-yl)phenol;
4-hydroxy-3-(6-(methyl(2,2,6,6-tetramethylpiperidin-4-yl)amino)pyridazin-3-yl)benzonitrile;
2-{6-[methyl-(2,2,6,6-tetramethyl-piperidin-4-yl)-amino]-pyridazin-3-yl}-4-trifluoromethyl-phenol;
2-fluoro-6-{6-[methyl-(2,2,6,6-tetramethyl-piperidin-4-yl)-amino]-pyridazin-3-yl}-phenol;
3,5-dimethoxy-2-{6-[methyl-(2,2,6,6-tetramethyl-piperidin-4-yl)-amino]-pyridazin-3-yl}-phenol;
4,5-dimethoxy-2-{6-[methyl-(2,2,6,6-tetramethyl-piperidin-4-yl)-amino]-pyridazin-3-yl}-phenol;
5-methoxy-2-{6-[methyl-(2,2,6,6-tetramethyl-piperidin-4-yl)-amino]-pyridazin-3-yl}-phenol;
4,5-difluoro-2-{6-[methyl-(2,2,6,6-tetramethyl-piperidin-4-yl)-amino]-pyridazin-3-yl}-phenol;
5-fluoro-2-{6-[methyl-(2,2,6,6-tetramethyl-piperidin-4-yl)-amino]-pyridazin-3-yl}-phenol;
3-hydroxy-4-(6-(methyl(2,2,6,6-tetramethylpiperidin-4-yl)amino)pyridazin-3-yl)benzonitrile;
N-allyl-3-hydroxy-4-[6-(methyl (2,2,6,6-tetramethylpiperidin-4-yl)amino)pyridazin-3-yl)benzamide;
2-(6-(methyl(2,2,6,6-tetramethylpiperidin-4-yl)amino)pyridazin-3-yl)-5-(1H-pyrazol-1-yl)phenol;
5-(5-methyl-oxazol-2-yl)-2-{6-[methyl-(2,2,6,6-tetramethyl-piperidin-4-yl)-amino]-pyridazin-3-yl}-phenol;
5-(4-hydroxymethyl)-1H-pyrazole-1-yl)-2-(6-(methyl(2,2,6,6-tetramethylpiperidin-4-yl)amino)pyridazin-3-yl)phenol;
5-(1H-imidazole-1-yl)-2-(6-(methyl(2,2,6,6-tetramethyl-piperidin-4-yl)amino)pyridazin-3-yl)phenol;
5-(4-amino-1H-pyrazole-1-yl)-2-(6-(methyl(2,2,6,6-tetramethylpiperidin-4-yl)amino)pyridazin-3-yl)phenol;
5-(4-amino-1H-pyrazol-1-yl)-2-(6-(methyl(2,2,6,6-tetramethylpiperidin-4-yl)amino)pyridazin-3-yl)phenol;
5-(3-amino-pyrazol-1-yl)-2-{6-[methyl-(2,2,6,6-tetramethyl-piperidin-4-yl)-amino]-pyridazin-3-yl}-phenol;
2-(6-(methyl(2,2,6,6-tetramethylpiperidin-4-yl)amino)pyridazin-3-yl)-5-(1-(2-morpholino-ethyl)-1H-pyrazol-4-yl)phenol;
2-(6-(methyl(2,2,6,6-tetramethylpiperidin-4-yl)amino)pyridazin-3-yl)-5-(1-methyl-1H-pyrazol-4-yl)phenol;
5-(5-amino-1H-pyrazol-1-yl)-2-(6-(methyl-(2,2,6,6-tetramethyl-piperidin-4-yl)amino)pyridazin-3-yl)phenol;
2-(6-(methyl(2,2,6,6-tetramethylpiperidin-4-yl)amino)pyridazin-3-yl)-4-(1H-pyrazol-1-yl)phenol;
2-{6-[(2-hydroxy-ethyl)-(2,2,6,6-tetramethyl-piperidin-4-yl)-amino]-pyridazin-3-yl}-5-pyrazol-yl-phenol;
2-(6-(piperidin-4-yloxy)pyridazin-3-yl)-5-(1H-pyrazol-1-yl)phenol;
2-(6-(((2S,4R,6R)-2,6-dimethylpiperidin-4-yl)oxy)pyridazin-3-yl)-5-(1H-pyrazol-1-yl)phenol;
2-(6-((-2,6-dimethylpiperidin-4-yl)oxy)pyridazin-3-yl)-5-(1H-pyrazol-1-yl)phenol;
2-(6-((-2,6-dimethylpiperidin-4-yl)oxy)pyridazin-3-yl)-5-(1H-pyrazol-1-yl)phenol;
5-(1H-pyrazol-1-yl)-2-(6-(pyrrolidin-3-yloxy)pyridazin-3-yl)phenol;
2-(6-((-2-methylpiperidin-4-yl)oxy)pyridazin-3-yl)-5-(1H-pyrazol-1-yl)phenol;
(S)-5-(1H-Pyrazol-1-yl)-2-(6-(pyrrolidin-3-ylmethoxy)pyridazin-3-yl)phenol;
(R)-5-(1H-pyrazol-1-yl)-2-(6-(pyrrolidin-3-ylmethoxy)pyridazin-3-yl)phenol;
2-(6-((3-fluoropiperidin-4-yl)oxy)pyridazin-3-yl)-5-(1H-pyrazol-1-yl)-phenol;
2-[6-(1,2,2,6,6-pentamethyl-piperidin-4-yloxy)-pyridazin-3-yl]-5-pyrazol-1-yl-phenol;
5-pyrazol-1-yl-2-[6-(2,2,6,6-tetramethyl-piperidin-4-yloxy)-pyridazin-3-yl]-phenol;
2-(6-(methyl(2,2,6,6-tetramethylpiperidin-4-yl)amino)pyridazin-3-yl)-5-(1H-pyrazol-4-yl)phenol;
2-(6-piperazin-1-yl-pyridazin-3-yl)-5-pyrazol-1-yl-phenol;
2-[6-(azetidin-3-ylamino)-pyridazin-3-yl]-5-pyrazol-1-yl-phenol;
2-[6-(3,5-dimethyl-piperazin-1-yl)-pyridazin-3-yl]-5-pyrazol-1-yl-phenol;
2-[6-(7-methyl-2,7-diaza-spiro[4.4]non-2-yl)-pyridazin-3-yl]-5-pyrazol-1-yl-phenol;
2-(6-[1,4]diazepan-1-yl-pyridazin-3-yl)-5-pyrazol-1-yl-phenol;
2-{6-[4-(2-hydroxy-ethyl)-piperazin-1-yl]-pyridazin-3-yl}-5-pyrazol-1-yl-phenol;
2-[6-(3,6-diaza-bicyclo[3.2.1]oct-3-yl)-pyridazin-3-yl]-5-pyrazol-1-yl-phenol;
2-[6-(2,7-diaza-spiro[3.5]non-7-yl)-pyridazin-3-yl]-5-pyrazol-1-yl-phenol;
2-[6-(3-hydroxy-methyl-piperazin-1-yl)-pyridazin-3-yl]-5-pyrazol-1-yl-phenol;
2-[6-(1,7-diaza-spiro[4.4]non-7-yl)-pyridazin-3-yl]-5-pyrazol-1-yl-phenol;
2-[6-(4-amino-4-methyl-piperidin-1-yl)-pyridazin-3-yl]-5-pyrazol-1-yl-phenol;
2-[6-(3-dimethyl-amino-piperidin-1-yl)-pyridazin-3-yl]-5-pyrazol-1-yl-phenol;
2-[6-(1,2,2,6,6-pentamethyl-piperidin-4-ylamino)-pyridazin-3-yl]-5-pyrazol-1-yl-phenol;
2-[6-(3,3-dimethyl-piperazin-1-yl)-pyridazin-3-yl]-5-pyrazol-1-yl-phenol;
2-(6-(7-(2-hydroxyethyl)-2,7-diazaspiro[4.4]-nonan-2-yl)pyridazin-3-yl)-5-(1H-pyrazol-1-yl)phenol;
2-(6-((3aR,6aS)-hexahydropyrrolo[3,4-c]pyrrol-2(1H)-yl)pyridazin-3-yl)-5-(1H-pyrazol-1-yl)phenol;
5-pyrazol-1-yl-2-[6-(1,2,3,6-tetrahydro-pyridin-4-yl)-pyridazin-3-yl]-phenol;
2-(6-piperidin-4-yl-pyridazin-3-yl)-5-pyrazol-1-yl-phenol;

5-(1H-pyrazol-1-yl)-2-(6-((2,2,6,6-tetramethylpiperidin-4-yl)methyl)pyridazin-3-yl)phenol;
3-methoxy-2-(6-(methyl(2,2,6-trimethylpiperidin-4-yl)amino)pyridazin-3-yl)-5-(5-methyloxazol-2-yl)phenol;
2-(6-(((6S)-6-((S)-1-hydroxyethyl)-2,2-dimethylpiperidin-4-yloxy)pyridazin-3-yl)-5-(1H-pyrazol-1-yl)phenol;
2-(6-(methyl(2,2,6,6-tetramethylpiperidin-4-yl)amino)pyridazin-3-yl)-5-(1H-pyrazol-4-yl)benzene-1,3-diol;
3-methoxy-2-(6-(methyl(2,2,6,6-tetramethylpiperidin-4-yl)amino)pyridazin-3-yl)-5-(1H-pyrazol-4-yl)phenol;
5-(1H-pyrazol-4-yl)-2-(6-((2,2,6,6-tetramethylpiperidin-4-yl)amino)pyridazin-3-yl)-3-(trifluoromethoxy)phenol;
2-(6-(methyl(2,2,6,6-tetramethylpiperidin-4-yl)amino)pyridazin-3-yl)-5-(1-methyl-1H-pyrazol-4-yl)-3-(trifluoromethoxy)phenol;
2-(6-(methyl(2,2,6,6-tetramethylpiperidin-4-yl)amino)pyridazin-3-yl)-5-(1H-pyrazol-4-yl)-3-(trifluoromethoxy)phenol;
4-(3-hydroxy-4-(6-(methyl(2,2,6,6-tetramethylpiperidin-4-yl)amino)pyridazin-3-yl)-5-(trifluoromethoxy)phenyl)-1-methylpyridin-2(1H)-one;
3-methoxy-2-(6-(methyl(2,2,6,6-tetramethylpiperidin-4-yl)amino)pyridazin-3-yl)-5-(1-methyl-1H-pyrazol-4-yl)phenol;
3-methoxy-2-(6-(methyl(2,2,6,6-tetramethylpiperidin-4-yl)amino)pyridazin-3-yl)-5-(5,6,7,8-tetrahydroimidazo[1,2-a]pyridin-3-yl)phenol;
3-methoxy-2-(6-(methyl(2,2,6,6-tetramethylpiperidin-4-yl)amino)pyridazin-3-yl)-5-(pyridin-3-yl)phenol;
5-(1-cyclopentyl-1H-pyrazol-4-yl)-3-methoxy-2-(6-(methyl(2,2,6,6-tetramethylpiperidin-4-yl)amino)pyridazin-3-yl)phenol;
3',5-dimethoxy-4-(6-(methyl(2,2,6,6-tetramethylpiperidin-4-yl)amino)pyridazin-3-yl)-[1,1'-biphenyl]-3-ol;
3-(benzyloxy)-2-(6-(methyl(2,2,6,6-tetramethylpiperidin-4-yl)amino)pyridazin-3-yl)-5-(5-methyloxazol-2-yl)phenol;
3-ethoxy-2-(6-(methyl(2,2,6,6-tetramethylpiperidin-4-yl)amino)pyridazin-3-yl)-5-(5-methyloxazol-2-yl)phenol;
3-(cyclopropylmethoxy)-2-(6-(methyl(2,2,6,6-tetramethylpiperidin-4-yl)amino)-pyridazin-3-yl)-5-(5-methyloxazol-2-yl)phenol;
2-methyl-5-(6-(methyl(2,2,6,6-tetramethylpiperidin-4-yl)amino)pyridazin-3-yl)-1H-benzo[d]imidazol-6-ol;
5-chloro-2-(6-(methyl(2,2,6,6-tetramethylpiperidin-4-yl)amino)pyridazin-3-yl)phenol;
5-(1H-pyrazol-1-yl)-2-(6-((2,2,6,6-tetramethylpiperidin-4-yl)amino)pyridazin-3-yl)phenol;
3-hydroxy-4-(6-((2,2,6,6-tetramethylpiperidin-4-yl)amino)pyridazin-3-yl)benzonitrile;
2-(6-((2,2-dimethylpiperidin-4-yl)oxy)pyridazin-3-yl)-5-(1H-pyrazol-1-yl)phenol;
2-(6-(methyl(2,2,6,6-tetramethylpiperidin-4-yl)amino)pyridazin-3-yl)-4-(1H-pyrazol-4-yl)phenol;
2-(6-(methyl(2,2,6,6-tetramethylpiperidin-4-yl)amino)pyridazin-3-yl)-4-(4,5,6,7-tetrahydropyrazolo[1,5-a]pyridin-3-yl)phenol;
2-(6-(methyl(2,2,6,6-tetramethylpiperidin-4-yl)amino)pyridazin-3-yl)-4-(4,5,6,7-tetrahydropyrazolo[1,5-a]pyrazin-3-yl)phenol;
4-(1H-indol-2-yl)-2-(6-(methyl(2,2,6,6-tetramethylpiperidin-4-yl)amino)pyridazin-3-yl)phenol;
4-(cyclopent-1-en-1-yl)-2-(6-(methyl(2,2,6,6-tetramethylpiperidin-4-yl)amino)pyridazin-3-yl)phenol;

2-(6-(methyl(2,2,6,6-tetramethylpiperidin-4-yl)amino)pyridazin-3-yl)-4-(1H-pyrazol-3-yl)phenol;
4-(4-hydroxy-3-(6-(methyl(2,2,6,6-tetramethylpiperidin-4-yl)amino)pyridazin-3-yl)phenyl)pyridin-2-ol;
4-(4-hydroxy-3-(6-((2,2,6,6-tetramethylpiperidin-4-yl)oxy)pyridazin-3-yl)phenyl)-1-methylpyridin-2(1H)-one;
4-(4-hydroxy-3-(6-((2,2,6,6-tetramethylpiperidin-4-yl)oxy)pyridazin-3-yl)phenyl)pyridin-2-ol;
5-(1H-indazol-7-yl)-2-(6-(methyl(2,2,6,6-tetramethylpiperidin-4-yl)amino)pyridazin-3-yl)phenol;
4-chloro-2-(6-(methyl(2,2,6,6-tetramethylpiperidin-4-yl)amino)pyridazin-3-yl)-5-(1H-pyrazol-4-yl)phenol;
4-fluoro-2-(6-(methyl(2,2,6,6-tetramethylpiperidin-4-yl)amino)pyridazin-3-yl)-5-(1H-pyrazol-4-yl)phenol;
5-fluoro-4-(1H-imidazol-4-yl)-2-(6-(methyl(2,2,6,6-tetramethylpiperidin-4-yl)amino)pyridazin-3-yl)phenol;
5-fluoro-2-(6-(methyl(2,2,6,6-tetramethylpiperidin-4-yl)amino)pyridazin-3-yl)-4-(1H-pyrazol-4-yl)phenol;
5-fluoro-2-(6-(methyl(2,2,6,6-tetramethylpiperidin-4-yl)amino)pyridazin-3-yl)-4-(1H-pyrazol-5-yl)phenol;
9-(6-(methyl(2,2,6,6-tetramethylpiperidin-4-yl)amino)pyridazin-3-yl)-5,6-dihydroimidazo[5,1-a]isoquinolin-8-ol hydrochloride salt;
4-hydroxy-3-(6-(methyl(2,2,6,6-tetramethylpiperidin-4-yl)amino)pyridazin-3-yl)-N-((1-methyl-1H-pyrazol-4-yl)methyl)benzamide;
4-(4-(hydroxymethyl)-1H-pyrazol-1-yl)-2-(6-(methyl(2,2,6,6-tetramethylpiperidin-4-yl)amino)pyridazin-3-yl)phenol;
5-(1H-pyrazol-4-yl)-2-(6-((2,2,6,6-tetramethylpiperidin-4-yl)methyl)pyridazin-3-yl)phenol;
3-fluoro-5-(2-methoxypyridin-4-yl)-2-(6-(methyl(2,2,6,6-tetramethylpiperidin-4-yl)amino)pyridazin-3-yl)phenol hydrochloride salt;
4-(3-fluoro-5-hydroxy-4-(6-(methyl(2,2,6,6-tetramethylpiperidin-4-yl)amino)pyridazin-3-yl)phenyl)pyridin-2(1H)-one hydrochloride salt;
4-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt;
5-(3-fluoro-5-hydroxy-4-(6-(methyl(2,2,6,6-tetramethylpiperidin-4-yl)amino)pyridazin-3-yl)phenyl)-1-methylpyridin-2(1H)-one hydrochloride salt;
3-fluoro-5-(1H-pyrazol-4-yl)-2-(6-((2,2,6,6-tetramethylpiperidin-4-yl)oxy)pyridazin-3-yl)phenol hydrochloride salt;
5-chloro-3-fluoro-2-(6-(methyl(2,2,6,6-tetramethylpiperidin-4-yl)amino)pyridazin-3-yl)phenol hydrochloride salt;
3-fluoro-2-(6-(methyl(2,2,6,6-tetramethylpiperidin-4-yl)amino)pyridazin-3-yl)-5-(1H-pyrazol-4-yl)phenol hydrochloride salt;
3-fluoro-2-(6-(methyl(2,2,6,6-tetramethylpiperidin-4-yl)amino)pyridazin-3-yl)-5-(1-methyl-1H-pyrazol-4-yl)phenol hydrochloride salt;
5-(5-methoxypyridin-3-yl)-2-(6-(methyl(2,2,6,6-tetramethylpiperidin-4-yl)amino)pyridazin-3-yl)phenol;
5-(3-hydroxy-4-(6-methyl(2,2,6,6-tetramethylpiperidin-4-yl)amino)pyridazin-3-yl)phenyl)pyridin-2-ol;
4-(3-hydroxy-4-(6-methyl(2,2,6,6-tetramethylpiperidin-4-yl)amino)pyridazin-3-yl)phenyl)pyridin-2-ol;
5-(6-methoxypyridin-3-yl)-2-(6-(methyl(2,2,6,6-tetramethylpiperidin-4-yl)amino)pyridazin-3-yl)phenol;
5-(3-hydroxy-4-(6-(methyl(2,2,6,6-tetramethylpiperidin-4-yl)amino)pyridazin-3-yl)phenyl)-3-(trifluoromethyl)pyridin-2-ol;

5-(3-hydroxy-4-(6-(methyl(2,2,6,6-tetramethylpiperidin-4-yl)amino)pyridazin-3-yl)phenyl)-1-methylpyridin-2(1H)-one;
4-(3-hydroxy-4-(6-(methyl(2,2,6,6-tetramethylpiperidin-4-yl)amino)pyridazin-3-yl)phenyl)-1-methylpyridin-2(1H)-one;
5-(2-methoxypyridin-4-yl)-2-(6-(methyl (2,2,6,6-tetramethylpiperidin-4-yl)amino)pyridazin-3-yl)phenol;
4-(3-hydroxy-4-(6-((2,2,6,6-tetramethylpiperidin-4-yl)oxy)pyridazin-3-yl)phenyl)pyridin-2-ol;
5-(6-(dimethylamino)pyridin-3-yl)-2-(6-(methyl(2,2,6,6-tetramethylpiperidin-4-yl)amino)pyridazin-3-yl)phenol;
4-(3-hydroxy-4-(6-((2,2,6,6-tetramethylpiperidin-4-yl)oxy)pyridazin-3-yl)phenyl)-1-methylpyridin-2(1H)-one;
2-(6-(methyl(2,2,6,6-tetramethylpiperidin-4-yl)amino)pyridazin-3-yl)-5-(pyrimidin-5-yl)phenol;
5-(3-hydroxy-4-(6-(methyl(2,2,6,6-tetramethylpiperidin-4-yl)amino)pyridazin-3-yl)phenyl)pyridin-3-ol;
1-cyclopropyl-4-(3-hydroxy-4-(6-(methyl(2,2,6,6-tetramethylpiperidin-4-yl)amino)pyridazin-3-yl)phenyl)pyridin-2(1H)-one;
2-(6-(methyl(2,2,6,6-tetramethylpiperidin-4-yl)amino)pyridazin-3-yl)-5-(1,2,3,6-tetrahydropyridin-4-yl)phenol;
5-(cyclopent-1-en-1-yl)-2-(6-(methyl(2,2,6,6-tetramethylpiperidin-4-yl)amino)pyridazin-3-yl)phenol;
5-(3,6-dihydro-2H-pyran-4-yl)-2-(6-(methyl(2,2,6,6-tetramethylpiperidin-4-yl)amino)pyridazin-3-yl)phenol;
5-(imidazo[1,5-a]pyridin-7-yl)-2-(6-(methyl(2,2,6,6-tetramethylpiperidin-4-yl)amino)pyridazin-3-yl)phenol;
5-(imidazo[1,2-a]pyridin-7-yl)-2-(6-(methyl(2,2,6,6-tetramethylpiperidin-4-yl)amino)pyridazin-3-yl)phenol;
2-(6-(methyl(2,2,6,6-tetramethylpiperidin-4-yl)amino)pyridazin-3-yl)-5-(2-methylpyridin-4-yl)phenol;
5-(1H-imidazol-2-yl)-2-(6-(methyl(2,2,6,6-tetramethylpiperidin-4-yl)amino)pyridazin-3-yl)phenol;
5-(1H-imidazol-4-yl)-2-(6-(methyl(2,2,6,6-tetramethylpiperidin-4-yl)amino)pyridazin-3-yl)phenol;
5-(imidazo[1,2-a]pyrazin-3-yl)-2-(6-(methyl(2,2,6,6-tetramethylpiperidin-4-yl)amino)pyridazin-3-yl)phenol;
2-(6-(methyl(2,2,6,6-tetramethylpiperidin-4-yl)amino)pyridazin-3-yl)-5-(5,6,7,8-tetrahydroimidazo[1,2-a]pyrazin-3-yl)phenol;
2-(6-(methyl(2,2,6,6-tetramethylpiperidin-4-yl)amino)pyridazin-3-yl)-5-(4-methyl-1H-imidazol-2-yl)phenol;
2-(6-(methyl(2,2,6,6-tetramethylpiperidin-4-yl)amino)pyridazin-3-yl)-5-(1-methyl-1H-imidazol-4-yl)phenol;
2-(6-(methyl(2,2,6,6-tetramethylpiperidin-4-yl)amino)pyridazin-3-yl)-5-(1-methyl-1H-imidazol-5-yl)phenol;
2-(6-(methyl(2,2,6,6-tetramethylpiperidin-4-yl)amino)pyridazin-3-yl)-5-(4-nitro-1H-imidazol-2-yl)phenol;
2-(6-(methyl(2,2,6,6-tetramethylpiperidin-4-yl)amino)pyridazin-3-yl)-5-(2-methyl-1H-imidazol-4-yl)phenol;
5-(1,2-dimethyl-1H-imidazol-4-yl)-2-(6-(methyl(2,2,6,6-tetramethylpiperidin-4-yl)amino)pyridazin-3-yl)phenol;
1-(3-hydroxy-4-(6-(methyl(2,2,6,6-tetramethylpiperidin-4-yl)amino)pyridazin-3-yl)phenyl)-1H-pyrazole-4-carboxamide;
2-(6-((3aR,6aS)-5-(2-hydroxyethyl)hexahydropyrrolo[3,4-c]pyrrol-2(1H)-yl)pyridazin-3-yl)-5-(1H-pyrazol-4-yl)phenol;
2-(6-((3aR,6aS)-hexahydropyrrolo[3,4-c]pyrrol-2(1H)-yl)pyridazin-3-yl)-5-(1H-pyrazol-4-yl)phenol;
2-(6-((3aR,6aS)-5-methylhexahydropyrrolo[3,4-c]pyrrol-2(1H)-yl)pyridazin-3-yl)-5-(1H-pyrazol-4-yl)phenol;
4-(3-hydroxy-4-(6-(5-methyl hexahydropyrrolo[3,4-c]pyrrol-2(1H)-yl)pyridazin-3-yl)phenyl)-1-methylpyridin-2(1H)-one;
4-(3-hydroxy-4-(6-((3aR,6aR)-1-methylhexahydropyrrolo[3,4-b]pyrrol-5(1H)-yl)pyridazin-3-yl)phenyl)-1-methylpyridin-2(1H)-one;
2-(6-(2,7-diazaspiro[4.5]decan-2-yl)pyridazin-3-yl)-5-(1H-pyrazol-4-yl)phenol; and
4-(4-(6-(2,7-diazaspiro[4.5]decan-2-yl)pyridazin-3-yl)-3-hydroxyphenyl)-1-methylpyridin-2(1H)-one.

8. A pharmaceutical composition comprising a therapeutically effective amount of a compound according to claim 1, or a pharmaceutically acceptable salt thereof and one or more pharmaceutically acceptable carriers.

9. The compound, or salt thereof, 2-(6-(methyl(2,2,6,6-tetramethylpiperidin-4-yl)amino)pyridazin-3-yl)-5-(1H-pyrazol-4-yl)phenol which is represented by the structure:

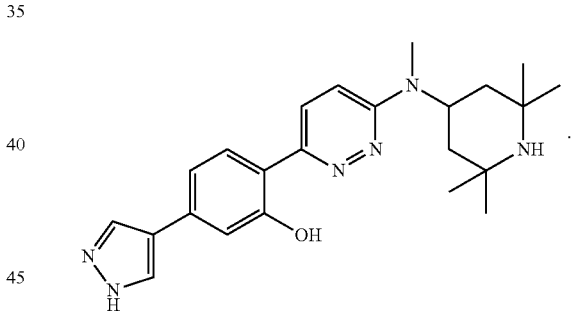

10. A pharmaceutical composition comprising a therapeutically effective amount of a compound according to claim 9, or a pharmaceutically acceptable salt thereof and one or more pharmaceutically acceptable carriers.

* * * * *